(12) United States Patent
Zhang et al.

(10) Patent No.: US 12,331,119 B2
(45) Date of Patent: Jun. 17, 2025

(54) MODIFIED Fc FRAGMENT, ANTIBODY COMPRISING SAME, AND APPLICATION THEREOF

(71) Applicant: Wuhan YZY Biopharma Co., Ltd., Wuhan (CN)

(72) Inventors: Jing Zhang, Wuhan (CN); Lijuan Fang, Wuhan (CN); Yongxiang Yan, Wuhan (CN); Liang Zeng, Wuhan (CN); Pengfei Zhou, Wuhan (CN)

(73) Assignee: Wuhan YZY Biopharma Co., Ltd., Wuhan (CN)

( * ) Notice: Subject to any disclaimer, the term of this patent is extended or adjusted under 35 U.S.C. 154(b) by 0 days.

(21) Appl. No.: 17/432,705

(22) PCT Filed: Feb. 22, 2019

(86) PCT No.: PCT/CN2019/075881
§ 371 (c)(1),
(2) Date: Aug. 20, 2021

(87) PCT Pub. No.: WO2020/168554
PCT Pub. Date: Aug. 27, 2020

(65) Prior Publication Data
US 2022/0098307 A1    Mar. 31, 2022

(51) Int. Cl.
*C07K 16/28* (2006.01)
*C07K 16/30* (2006.01)

(52) U.S. Cl.
CPC ......... *C07K 16/2827* (2013.01); *C07K 16/28* (2013.01); *C07K 16/2809* (2013.01); *C07K 16/2878* (2013.01); *C07K 16/2896* (2013.01); *C07K 16/3007* (2013.01); *C07K 2317/31* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/622* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2009/0042291 A1* 2/2009 Chu .................. C07K 16/2803
435/375
2012/0321626 A1 12/2012 Zhou
2020/0268901 A1 8/2020 Lonberg et al.

FOREIGN PATENT DOCUMENTS

| JP | 2014519322 | | 8/2014 | |
|----|---|---|---|---|
| JP | 2018201208 A | | 1/2018 | |
| WO | WO 99/51642 | * | 10/1999 | ............ C07K 16/00 |
| WO | WO2007024249 A2 | | 3/2007 | |
| WO | WO2010065578 A2 | | 6/2010 | |
| WO | WO2013096221 A1 | | 6/2013 | |
| WO | WO 2015/035215 | * | 3/2015 | ............ C07K 16/00 |
| WO | WO-2016081746 A2 | * | 5/2016 | ......... A61K 39/3955 |
| WO | WO2017052321 A1 | | 3/2017 | |
| WO | WO2018005706 A1 | | 1/2018 | |
| WO | WO2018191438 A1 | | 10/2018 | |

OTHER PUBLICATIONS

Teplyakov et al. 'IgG2 Fc structure and dynamic features of the IgG CH2-CH3 interface.' Molecular Immunology 56:131-139, 2013.*
Idusogie et al. 'Mapping of the C1q Binding Site on Rituxan, a Chimeric Antibody with a Human IgG1 Fc.' J. Immunol. 164(8):4178-4184, 2000.*
International Search Report from PCT/CN2019/075881, Date of MailingJan. 8, 2020 (6 pages).
Writtent Opinion from PCT/CN2019/075881, Date of Mailing Nov. 20, 2019 (5 pages).
Chappel et al., "Identification of the Fc gamma receptor class I binding site in human IgG through the use of recombinant IgG1/IgG2 hybrid and point-mutated antibodies," Proceedings of the National Academy of Sciences of the United States of America, Oct. 1991, vol. 88, Issue 20, pp. 9036-9040.
Tam et al., "Functional, Biophysical, and Structural Characterization of Human IgG1 and IgG4 Fc Variants with Ablated Immune Functionality," Antibodies, Sep. 2017, vol. 6, Issue 12, 34 pages.
Vafa et al., "An engineered Fc variant of an IgG eliminates all immune effector functions via structural perturbations," Methods, Jul. 2013, vol. 62, Issue 1, pp. 114-126.
Wang et al., "IgG Fc engineering to modulate antibody effector functions," Protein & Cell, Jan. 2018, vol. 9, Issue 1, pp. 63-73.

* cited by examiner

*Primary Examiner* — Nora M Rooney
(74) *Attorney, Agent, or Firm* — Sheppard Mullin Richter & Hampton LLP

(57) ABSTRACT

The present disclosure relates to a modified Fc fragment, antibodies containing the same and the use thereof. The Fc fragment is derived from human IgG1, and the constant region CH2 domain of the Fc fragment contains multiple substitutions. Such substitution can significantly reduce the binding ability of Fc fragment to Fcγ receptors (FcγR), and reduce the non-specific activation of T cells by antibodies (such as anti-CD3 antibodies).

8 Claims, 20 Drawing Sheets

Specification includes a Sequence Listing.

MODIFIED Fc FRAGMENT, ANTIBODY COMPRISING SAME, AND APPLICATION THEREOF

CROSS REFERENCE TO RELATED APPLICATIONS

This application is a U.S. National Stage Application under 35 U.S.C. 371 of International Application No. PCT/CN2019/075881, filed Feb. 22, 2019, the content of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on Aug. 20, 2021, is named YZY023_SEQLT.txt and is 197 kb in size.

FIELD OF THE INVENTION

The present disclosure relates to the field of antibodies. Specifically, the present disclosure relates to modified Fc fragments and antibodies containing them.

BACKGROUND OF THE INVENTION

Human natural antibodies, such as IgG1, IgG2, IgG3 and IgG4, have the ability to bind to FcγR. Human FcγR is divided into FcγRI (CD64), FcγRII (CD32) and FcγRIII (CD16), wherein each type of the receptor is correspondingly expressed on the surface of different monocytes, and each type of the receptor is further divided into a, b, c and other subtypes. Through the binding of its own Fc to FcγR, natural antibodies produce the following immunological effect functions: antibody-dependent cell-mediated cytotoxicity (ADCC), antibody-dependent cell-mediated phagocytosis (ADCP), and complement-mediated cytotoxicity (CDC), and the like. In the process of antibody drug research, for some types of antibodies, it is necessary to reduce the ability to bind to FcγR in order to reduce the production of ADCC, ADCP and CDC, thereby reducing the toxicity and side effects of the antibody. In some special cases, such as anti-CD3 antibodies, especially multifunctional antibodies, can target both tumor cells and T lymphocytes expressed by CD3, and it is necessary to remove the binding to FcγR as much as possible in order to reduce the toxic and side effect caused by the release of a large number of cytokines produced by the non-specific activation of T cells.

The multifunctional antibody is an antibody or antibody-like molecule with multiple different binding specificities. The multifunctional antibody can be widely used in biomedicine, particularly in immunotherapy against tumors. Currently, a focus of immunotherapy research is how to use multifunctional antibody-mediated cytotoxicity to kill cells of interest. Multifunctional antibodies can be designed to target both tumor cells and effector cells, and simultaneously stimulate effector cells to kill tumor cells.

Multifunctional antibodies can be prepared by methods such as chemical engineering, cell engineering, and genetic engineering. The advantage of genetic engineering is that antibodies can be easily engineered to design and produce many multifunctional antibody fragments with different formats, including dimers, tanderm ScFv and single-chain dimers and the derivatives thereof (see Jin and Zhu, "The design and engineering of IgG-Like bispecific antibodies", RE Kontermann (eds), Bispecific antibodies). These multifunctional antibodies do not have an IgG Fc domain, and thus their ability to penetrate into tumors is increased due to the small size; however, the multifunctional antibodies have a relatively short half-life in the body and lack ADCC effect, which is related to the constant region of antibodies.

Currently, there are some technologies of Fc modification that can reduce the binding ability of Fc to FcγR, for example: (1) as mentioned in "Curr Opin Biotechnol. 2011 December; 22(6):858-67. Bypassing glycosylation engineering aglycosylated fulllength IgG antibodies for human therapy", the glycosylation of Fc can be effectively removed by mutating the asparagine at position 297 (N297) of human IgG1 Fc, thereby reducing the binding to FcγR; (2) as mentioned in the patent application "WO2009100309A2", the amino acids at position 234 (leucine L234), position 235 (leucine L235) and position 331 (proline P331) of the Fc of human IgG1 were mutated to phenylalanine, glutamine and serine (L234F/L235E/P331S) respectively, thereby reducing the binding to FcγR; (3) as mentioned in the patent application "US20130078249A1", the amino acids at position 234 (leucine L234), position 235 (leucine L235) and position 331 (proline P329) of the Fc of human IgG1 were mutated to alanine, alanine and glycine (L234A/L235A/P329G) respectively, thereby reducing the binding to FcγR; (4) as mentioned in "Protein Eng Des Sel. 2016 October; 29(10):457-466. Novel human IgG1 and IgG4 Fc-engineered antibodies with completely abolished immune effector functions", the leucine at position 234 (L234) and the leucine at position 235 (L235) of the Fc of human IgG1 were mutated to alanine and alanine (L234A/L235A) respectively, thereby reducing the ability to bind to FcγR; (5) as mentioned in the patent application "WO2011066501A1", the amino acids at positions 234 (valine V234), 237 (glycine G237), 238 (proline P238), 268 (histidine H268), 309 (valine V309), 330 (alanine A330) and 331 (proline P331) of the Fc of human IgG2 were mutated to alanine, alanine, serine, alanine, leucine, serine and serine (V234A/G237A/P238S/H268A/V309L/A330S/P331S) respectively, thereby reducing the ability to bind to FcγR.

However, when applied to the structure of multifunctional antibodies, the above-mentioned Fc modification technology cannot completely eliminate the non-specific activation of T cells by anti-CD3 antibodies (such as L234F/L235E/P331S mutation, L234A/L235A/P329G mutation and L234A/L235A mutation in human IgG1), and modification at certain sites may lead to poor stability of the antibody (for example, the mutation of asparagine at position 297 of human IgG1 may remove glycosylation). In addition, as mentioned in "J Immunol 2003 170:3134-3138; Human IgG2 can form covalent dimers", human IgG2 is prone to dimerization to form a tetravalent complex with a molecular weight of 3001(D, and the amino acid mutations at up to 7 positions in human IgG2 (such as V234A/G237A/P238S/H268A/V309L/A330S/P331S) may increase the risk of immunogenicity.

In order to solve the above problems, it is necessary to reduce the binding ability of Fc to FcγR to remove non-specific activation of T cells (such as by anti-CD3 antibodies), and it is also necessary to avoid the deterioration of antibody stability and the increase of immunogenicity. The present disclosure provides a new modification method of Fc, wherein the entire CH2 domain in the Fc of human IgG1 is replaced with the CH2 domain of human IgG2, and the amino acid residue of said domain is mutated, which can significantly reduce the binding ability of antibodies to FcγR, eliminate the non-specific activation of T cells by antibodies (such as anti-CD3 antibodies) more effectively, and maintain good stability of antibodies.

SUMMARY OF THE INVENTION

The present disclosure provides a method of Fc modification, wherein the entire CH2 domain of the constant region of human IgG1 is replaced with the CH2 domain of human IgG2, and preferably several amino acid residues in the replaced CH2 domain are substituted.

The residue substitution of CH2 can effectively reduce the binding ability of the antibody to FcγR. When one binding site of the antibody is CD3, the replacement of CH2 can also significantly reduce the non-specific activation of T cells by the antibody.

The present disclosure provides three kinds of multifunctional antibody and method for preparing thereof, and the specific structures of the multifunctional antibody are shown in FIGS. 1 to 3.

Specifically, the present disclosure relates to the following aspects:

Item 1. A polypeptide comprising or consisting of a modified Fc fragment, wherein the Fc fragment is derived from human IgG1, and a constant region CH2 domain of the Fc fragment is replaced with a CH2 domain of human IgG2, and wherein the CH2 domain of human IgG2 is shown as SEQ ID NO:94.

Item 2. The polypeptide of item 1, wherein the CH2 domain of the Fc fragment further comprises a mutation position selected from the group consisting of C229, D265, D270 or any combination thereof, according to Kabat numbering.

Item 3. The polypeptide of item 2, wherein the mutation is a mutation at position C229, preferably the mutation is selected from the group consisting of C229A, C229G, C229P, C229S, C229V, C229L, C229I, C229T, C229M, C229N, C229Q, C229D, C229E, C229K, C229R, C229F, C229Y, C229W or C229H, preferably C229S, C229A, C229G and C229P.

Item 4. The polypeptide of item 2, wherein the mutation is a mutation at position D265, preferably the mutation is selected from the group consisting of D265A, D265G, D265P, D265S, D265V, D265L, D265I, D265T, D265M, D265N, D265Q, D265E, D265K, D265R, D265F, D265Y, D265W or D265H, preferably D265A.

Item 5. The polypeptide of item 2, wherein the mutation is a mutation at position D270, preferably the mutation is selected from the group consisting of D270A, D270G, D270P, D270S, D270V, D270L, D270I, D270T, D270M, D270N, D270Q, D270E, D270K, D270R, D270F, D270Y, D270W or D270H, preferably D270A.

Item 6. The polypeptide of any one of items 2-5, wherein the mutation is a combination mutation of any two of positions C229, D265 and D270, or a combination mutation of positions C229, D265 and D270, preferably a combination mutation of positions D265 and D270.

Item 7. The polypeptide of any one of items 2-5, wherein the CH2 domain of the Fc fragment further comprises a mutation selected from the group consisting of G327, T339 or a combination thereof.

Item 8. The polypeptide of item 6, wherein the mutation is selected from G327A, G327V, G327L, G327I and/or T339A.

Item 9. The polypeptide of any one of items 2-8, wherein the mutation is selected from C229P/G327A, C229P/T339A, D270A/G327A, D270A/T339A, D270A/G327A/T339A or C229P/D265A/D270A.

Item 10. The polypeptide of any one of items 2-5, wherein the sequence of the CH2 domain of the Fc fragment is selected from the group consisting of SEQ ID NOs: 94 to 101 and 122 to 176.

Item 11. An antibody or antigen-binding fragment thereof comprising the polypeptide of any one of items 1-10, wherein the antibody is selected from a monospecific antibody, a multispecific antibody, more preferably a bispecific antibody; preferably, the antigen binding fragment is selected from Fab, Fab', F(ab')$_2$, Fd, Fv, dAb, Fab/c, a complementary determining region (CDR) fragment, a single-chain antibody (eg, scFv), a diabody or a domain antibody.

Item 12. The antibody of item 11, wherein the antibody specifically binds to an antigen selected from the group consisting of a tumor antigen, a viral or bacterial antigen, an endotoxin, and an immune antigen; preferably, the tumor antigen is selected from PD-L1 (preferably as shown in SEQ ID NO: 118), B7-H3, SLAMF7 (preferably as shown in SEQ ID NO: 119), CD38 (preferably as shown in SEQ ID NO: 116), EpCAM, CEA (preferably as shown in SEQ ID NO: 120), CD19 and BCMA (preferably as shown in SEQ ID NO: 117); the immune antigen is selected from CD3 (preferably as shown in SEQ ID NO: 121), CD16A, CD47 and NKG2D.

Item 13. The antibody of item 12, which is an asymmetric bispecific antibody comprising a light chain, a heavy chain and a fusion peptide 1, wherein the fusion peptide 1 comprises a scFv and an Fc fragment, the antibody has a light chain-heavy chain pair, and a heavy chain-fusion peptide 1 pair, and each pair forms an interchain disulfide bond; the light chain-heavy chain pair targets a tumor antigen, and the ScFv in the fusion peptide 1 targets an immune cell antigen.

Item 14. The antibody of item 12, which is an asymmetric trivalent bispecific antibody comprising two light chains, one heavy chain and one fusion peptide 2, and having a light chain-heavy chain pair, a light chain-fusion peptide 2 pair, and a heavy chain-fusion peptide 2 pair, wherein each pair forms an interchain disulfide bond; the fusion peptide 2 includes a heavy chain variable region VH, a first constant region of heavy chain CH1, ScFv and Fc, wherein the ScFv is located between CH1 and Fc and is linked by a linker, the light chain-heavy chain pair targets a tumor antigen, the pair of VH-CH1 in the fusion peptide 2 and light chain targets the same tumor antigen, and the ScFv targets an immune cell antigen.

Item 15. The antibody of item 12, which is an asymmetric trivalent bispecific antibody comprising a fusion heavy chain, a cross light chain, a heavy chain and a light chain, and having a light chain-heavy chain pair, a light chain-fusion heavy chain pair, a cross light chain-fusion heavy chain pair, and a fusion heavy chain-heavy chain pair, wherein each pair forms an interchain disulfide bond; the light chain includes a first light chain variable region VLm and a light chain constant region CL; the fusion heavy chain includes a first heavy chain variable region VHm, a first constant region of heavy chain CH1, a second heavy chain variable region VHs, a light chain constant region CL and Fc, wherein the VHs and CL are linked by a linker to form a peptide "VHs-linker-CL", and wherein the "VHs-linker-CL" is located between CH1 and Fc and is linked by a linker/hinge; the cross light chain comprises a second light chain variable region VLs and CH1; VLs and CH1 are linked by a linker; the VLm-VHm pair targets a tumor antigen, and the VLs-VHs pair targets an immune cell antigen.

Item 16. The antibody of any one of items 13-15, has two different CH3, and the two CH3 are paired in a form of "knob-in-hole" or/and "salt bridge" to form a heterodimerization, preferably the sequence of CH3 domain is shown in SEQ ID NOs: 102 to 115.

Item 17. The antibody of any one of items 13-16, wherein the light chain-heavy chain pair or the VLm-VHm pair is selected from the group consisting of:
(1) SEQ ID NO: 12 and SEQ ID NO: 11 which target a tumor antigen B7-H3;
(2) SEQ ID NO: 14 and SEQ ID NO: 13 which target a tumor antigen B7-H3;
(3) SEQ ID NO: 16 and SEQ ID NO: 15 which target a tumor antigen CD38;
(4) SEQ ID NO: 18 and SEQ ID NO: 17 which target a tumor antigen CD38;
(5) SEQ ID NO: 20 and SEQ ID NO: 19 which target a tumor antigen CD38;
(6) SEQ ID NO: 22 and SEQ ID NO: 21 which target a tumor antigen EpCAM;
(7) SEQ ID NO: 24 and SEQ ID NO: 23 which target a tumor antigen EpCAM;
(8) SEQ ID NO: 26 and SEQ ID NO: 25 which target a tumor antigen BCMA;
(9) SEQ ID NO: 28 and SEQ ID NO: 27 which target a tumor antigen BCMA;
(10) SEQ ID NO: 30 and SEQ ID NO: 29 which target a tumor antigen BCMA;
(11) SEQ ID NO: 32 and SEQ ID NO: 31 which target a tumor antigen PD-L1;
(12) SEQ ID NO: 34 and SEQ ID NO: 33 which target a tumor antigen PD-L1;
(13) SEQ ID NO: 36 and SEQ ID NO: 35 which target a tumor antigen PD-L1;
(14) SEQ ID NO: 38 and SEQ ID NO: 37 which target a tumor antigen CD19;
(15) SEQ ID NO: 40 and SEQ ID NO: 39 which target a tumor antigen SLAMF7;
(16) SEQ ID NO: 42 and SEQ ID NO: 41 which target a tumor antigen CEA;
(17) SEQ ID NO: 2 and SEQ ID NO: 1 which target an immune antigen CD3;
(18) SEQ ID NO: 4 and SEQ ID NO: 3 which target an immune antigen CD3;
(19) SEQ ID NO: 6 and SEQ ID NO: 5 which target an immune antigen CD3;
(20) SEQ ID NO: 8 and SEQ ID NO: 7 which target an immune antigen CD3; and
(21) SEQ ID NO: 10 and SEQ ID NO: 9 which target an immune antigen CD3.

Item 18. The antibody of any one of items 13-17, wherein the antibody is selected from the group consisting of:
(1) PDL1-M1-G2, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 69, SEQ ID NO: 94 and SEQ ID NO: 109; the heavy chain comprises or consists of SEQ ID NO: 31, SEQ ID NO: 82, SEQ ID NO: 66, SEQ ID NO: 94 and SEQ ID NO: 108; the light chain comprises or consists of SEQ ID NO: 32 and SEQ ID NO: 75;
(2) PDL1-M1-SG2, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 69, SEQ ID NO: 95 and SEQ ID NO: 109; the heavy chain comprises or consists of SEQ ID NO: 31, SEQ ID NO: 82, SEQ ID NO: 66, SEQ ID NO: 95 and SEQ ID NO: 108; the light chain comprises or consists of SEQ ID NO: 32 and SEQ ID NO: 75;
(3) CD38-M1-G2, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 94 and SEQ ID NO: 109; the heavy chain comprises or consists of SEQ ID NO: 15, SEQ ID NO: 82, SEQ ID NO: 66, SEQ ID NO: 94 and SEQ ID NO: 108; the light chain comprises or consists of SEQ ID NO: 16 and SEQ ID NO: 75;
(4) CD38-M1-SG2, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 95 and SEQ ID NO: 109; the heavy chain comprises or consists of SEQ ID NO: 15, SEQ ID NO: 82, SEQ ID NO: 66, SEQ ID NO: 95 and SEQ ID NO: 108; the light chain comprises or consists of SEQ ID NO: 16 and SEQ ID NO: 75;
(5) CD38-M1-SG2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 95 and SEQ ID NO: 109; the heavy chain comprises or consists of SEQ ID NO: 19, SEQ ID NO: 82, SEQ ID NO: 66, SEQ ID NO: 95 and SEQ ID NO: 108; the light chain comprises or consists of SEQ ID NO: 20 and SEQ ID NO: 75;
(6) CD38-M1-G2-3, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 94 and SEQ ID NO: 109; the heavy chain comprises or consists of SEQ ID NO: 19, SEQ ID NO: 82, SEQ ID NO: 66, SEQ ID NO: 94 and SEQ ID NO: 108; the light chain comprises or consists of SEQ ID NO: 20 and SEQ ID NO: 75;
(7) CD38-M1-SG2-2, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 95 and SEQ ID NO: 109; the heavy chain comprises or consists of SEQ ID NO: 17, SEQ ID NO: 82, SEQ ID NO: 66, SEQ ID NO: 95 and SEQ ID NO: 108; the light chain comprises or consists of SEQ ID NO: 18 and SEQ ID NO: 75;
(8) CD38-M1-G2-2, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 94 and SEQ ID NO: 109; the heavy chain comprises or consists of SEQ ID NO: 17, SEQ ID NO: 82, SEQ ID NO: 66, SEQ ID NO: 94 and SEQ ID NO: 108; the light chain comprises or consists of SEQ ID NO: 18 and SEQ ID NO: 75;

(9) CD38-M1-G2-1, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 94 and SEQ ID NO: 109; the heavy chain comprises or consists of SEQ ID NO: 15, SEQ ID NO: 82, SEQ ID NO: 66, SEQ ID NO: 94 and SEQ ID NO: 108; the light chain comprises or consists of SEQ ID NO: 16 and SEQ ID NO: 75;

(10) CD38-M1-SG2-3, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 95 and SEQ ID NO: 109; the heavy chain comprises or consists of SEQ ID NO: 15, SEQ ID NO: 82, SEQ ID NO: 66, SEQ ID NO: 95 and SEQ ID NO: 108; the light chain comprises or consists of SEQ ID NO: 16 and SEQ ID NO: 75;

(11) CD38-M1-AG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 96 and SEQ ID NO: 109; the heavy chain comprises or consists of SEQ ID NO: 15, SEQ ID NO: 82, SEQ ID NO: 66, SEQ ID NO: 96 and SEQ ID NO: 108; the light chain comprises or consists of SEQ ID NO: 16 and SEQ ID NO: 75;

(12) CD38-M1-GG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 97 and SEQ ID NO: 109; the heavy chain comprises or consists of SEQ ID NO: 15, SEQ ID NO: 82, SEQ ID NO: 66, SEQ ID NO: 97 and SEQ ID NO: 108; the light chain comprises or consists of SEQ ID NO: 16 and SEQ ID NO: 75;

(13) CD38-M1-PG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 98 and SEQ ID NO: 109; the heavy chain comprises or consists of SEQ ID NO: 15, SEQ ID NO: 82, SEQ ID NO: 66, SEQ ID NO: 98 and SEQ ID NO: 108; the light chain comprises or consists of SEQ ID NO: 16 and SEQ ID NO: 75;

(14) CD38-M1-DG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 99 and SEQ ID NO: 109; the heavy chain comprises or consists of SEQ ID NO: 15, SEQ ID NO: 82, SEQ ID NO: 66, SEQ ID NO: 99 and SEQ ID NO: 108; the light chain comprises or consists of SEQ ID NO: 16 and SEQ ID NO: 75;

(15) CD38-M1-G2D, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 100 and SEQ ID NO: 109; the heavy chain comprises or consists of SEQ ID NO: 15, SEQ ID NO: 82, SEQ ID NO: 66, SEQ ID NO: 100 and SEQ ID NO: 108; the light chain comprises or consists of SEQ ID NO: 16 and SEQ ID NO: 75;

(16) CD38-M1-DG2D, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 101 and SEQ ID NO: 109; the heavy chain comprises or consists of SEQ ID NO: 15, SEQ ID NO: 82, SEQ ID NO: 66, SEQ ID NO: 101 and SEQ ID NO: 108; the light chain comprises or consists of SEQ ID NO: 16 and SEQ ID NO: 75;

(17) CD38-M1-G2D-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 71, SEQ ID NO: 100 and SEQ ID NO: 109; the heavy chain comprises or consists of SEQ ID NO: 17, SEQ ID NO: 82, SEQ ID NO: 66, SEQ ID NO: 100 and SEQ ID NO: 108; the light chain comprises or consists of SEQ ID NO: 18 and SEQ ID NO: 75;

(18) M1IC-SG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 95 and SEQ ID NO: 109; the heavy chain comprises or consists of SEQ ID NO: 43, SEQ ID NO: 82, SEQ ID NO: 66, SEQ ID NO: 95 and SEQ ID NO: 108; the light chain comprises or consists of SEQ ID NO: 44 and SEQ ID NO: 75;

(19) M1IC-G2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 94 and SEQ ID NO: 109; the heavy chain comprises or consists of SEQ ID NO: 43, SEQ ID NO: 82, SEQ ID NO: 66, SEQ ID NO: 94 and SEQ ID NO: 108; the light chain comprises or consists of SEQ ID NO: 44 and SEQ ID NO: 75;

(20) M1IC-AG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 96 and SEQ ID NO: 109; the heavy chain comprises or consists of SEQ ID NO: 43, SEQ ID NO: 82, SEQ ID NO: 66, SEQ ID NO: 96 and SEQ ID NO: 108; the light chain comprises or consists of SEQ ID NO: 44 and SEQ ID NO: 75;

(21) M1IC-GG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 97 and SEQ ID NO: 109; the heavy chain comprises or consists of SEQ ID NO: 43, SEQ ID NO: 82, SEQ ID NO: 66, SEQ ID NO: 97 and SEQ ID NO: 108; the light chain comprises or consists of SEQ ID NO: 44 and SEQ ID NO: 75;

(22) M1IC-PG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 98 and SEQ ID NO: 109; the heavy chain comprises or consists of SEQ ID NO: 43, SEQ ID NO: 82, SEQ ID NO: 66, SEQ ID NO: 98 and SEQ ID NO: 108; the light chain comprises or consists of SEQ ID NO: 44 and SEQ ID NO: 75;

(23) M1IC-DG2, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 99 and SEQ ID NO: 109; the heavy chain comprises or consists of SEQ ID NO: 43, SEQ ID NO: 82, SEQ ID NO: 66, SEQ ID NO: 99 and SEQ ID NO:

108; the light chain comprises or consists of SEQ ID NO: 44 and SEQ ID NO: 75;
(24) M1IC-G2D, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 100 and SEQ ID NO: 109; the heavy chain comprises or consists of SEQ ID NO: 43, SEQ ID NO: 82, SEQ ID NO: 66, SEQ ID NO: 100 and SEQ ID NO: 108; the light chain comprises or consists of SEQ ID NO: 44 and SEQ ID NO: 75;
(25) M1IC-DG2D, which comprises or consists of a fusion peptide 1, a heavy chain and a light chain; wherein the fusion peptide 1 comprises or consists of SEQ ID NO: 9, SEQ ID NO: 54, SEQ ID NO: 10, SEQ ID NO: 68, SEQ ID NO: 101 and SEQ ID NO: 109; the heavy chain comprises or consists of SEQ ID NO: 43, SEQ ID NO: 82, SEQ ID NO: 66, SEQ ID NO: 101 and SEQ ID NO: 108; the light chain comprises or consists of SEQ ID NO: 44 and SEQ ID NO: 75;
(26) M1IC-G2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 94 and SEQ ID NO: 109; the heavy chain comprises or consists of SEQ ID NO: 43, SEQ ID NO: 82, SEQ ID NO: 66, SEQ ID NO: 94 and SEQ ID NO: 108; the light chain comprises or consists of SEQ ID NO: 44 and SEQ ID NO: 75;
(27) M1IC-SG2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 95 and SEQ ID NO: 109; the heavy chain comprises or consists of SEQ ID NO: 43, SEQ ID NO: 82, SEQ ID NO: 66, SEQ ID NO: 95 and SEQ ID NO: 108; the light chain comprises or consists of SEQ ID NO: 44 and SEQ ID NO: 75;
(28) M1IC-AG2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 96 and SEQ ID NO: 109; the heavy chain comprises or consists of SEQ ID NO: 43, SEQ ID NO: 82, SEQ ID NO: 66, SEQ ID NO: 96 and SEQ ID NO: 108; the light chain comprises or consists of SEQ ID NO: 44 and SEQ ID NO: 75;
(29) M1IC-GG2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 97 and SEQ ID NO: 109; the heavy chain comprises or consists of SEQ ID NO: 43, SEQ ID NO: 82, SEQ ID NO: 66, SEQ ID NO: 97 and SEQ ID NO: 108; the light chain comprises or consists of SEQ ID NO: 44 and SEQ ID NO: 75;
(30) M1IC-PG2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 98 and SEQ ID NO: 109; the heavy chain comprises or consists of SEQ ID NO: 43, SEQ ID NO: 82, SEQ ID NO: 66, SEQ ID NO: 98 and SEQ ID NO: 108; the light chain comprises or consists of SEQ ID NO: 44 and SEQ ID NO: 75;
(31) M1IC-DG2-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 99 and SEQ ID NO: 109; the heavy chain comprises or consists of SEQ ID NO: 43, SEQ ID NO: 82, SEQ ID NO: 66, SEQ ID NO: 99 and SEQ ID NO: 108; the light chain comprises or consists of SEQ ID NO: 44 and SEQ ID NO: 75;
(32) M1IC-G2D-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 100 and SEQ ID NO: 109; the heavy chain comprises or consists of SEQ ID NO: 43, SEQ ID NO: 82, SEQ ID NO: 66, SEQ ID NO: 100 and SEQ ID NO: 108; the light chain comprises or consists of SEQ ID NO: 44 and SEQ ID NO: 75;
(33) M1IC-DG2D-1, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 101 and SEQ ID NO: 109; the heavy chain comprises or consists of SEQ ID NO: 43, SEQ ID NO: 82, SEQ ID NO: 66, SEQ ID NO: 101 and SEQ ID NO: 108; the light chain comprises or consists of SEQ ID NO: 44 and SEQ ID NO: 75;
(34) M1IC-DG2D-1A, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 101 and SEQ ID NO: 107; the heavy chain comprises or consists of SEQ ID NO: 43, SEQ ID NO: 82, SEQ ID NO: 66, SEQ ID NO: 101 and SEQ ID NO: 106; the light chain comprises or consists of SEQ ID NO: 44 and SEQ ID NO: 75;
(35) M1IC-DG2D-1B, which comprises or consists of a fusion peptide 1, a heavy chain and a light chain; wherein the fusion peptide 1 comprises or consists of SEQ ID NO: 1, SEQ ID NO: 54, SEQ ID NO: 2, SEQ ID NO: 68, SEQ ID NO: 101 and SEQ ID NO: 115; the heavy chain comprises or consists of SEQ ID NO: 43, SEQ ID NO: 82, SEQ ID NO: 66, SEQ ID NO: 101 and SEQ ID NO: 114; the light chain comprises or consists of SEQ ID NO: 44 and SEQ ID NO: 75;
(36) BCMA-M2-G2, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 94 and SEQ ID NO: 107; the heavy chain comprises or consists of SEQ ID NO: 29, SEQ ID NO: 82, SEQ ID NO: 66, SEQ ID NO: 94 and SEQ ID NO: 106; the light chain comprises or consists of SEQ ID NO: 30 and SEQ ID NO: 75;
(37) BCMA-M2-SG2, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 95 and SEQ ID NO: 107; the heavy chain comprises or consists of SEQ ID NO: 29, SEQ ID NO: 82, SEQ ID NO: 66, SEQ ID NO: 95 and SEQ ID NO: 106; the light chain comprises or consists of SEQ ID NO: 30 and SEQ ID NO: 75;
(38) BCMA-M2-AG2, which comprises or consists of a fusion peptide 2, a heavy chain and a light chain;

wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 96 and SEQ ID NO: 107; the heavy chain comprises or consists of SEQ ID NO: 29, SEQ ID NO: 82, SEQ ID NO: 66, SEQ ID NO: 96 and SEQ ID NO: 106; the light chain comprises or consists of SEQ ID NO: 30 and SEQ ID NO: 75;

(39) BCMA-M2-GG2, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 97 and SEQ ID NO: 107; the heavy chain comprises or consists of SEQ ID NO: 29, SEQ ID NO: 82, SEQ ID NO: 66, SEQ ID NO: 97 and SEQ ID NO: 106; the light chain comprises or consists of SEQ ID NO: 30 and SEQ ID NO: 75;

(40) BCMA-M2-PG2, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 98 and SEQ ID NO: 107; the heavy chain comprises or consists of SEQ ID NO: 29, SEQ ID NO: 82, SEQ ID NO: 66, SEQ ID NO: 98 and SEQ ID NO: 106; the light chain comprises or consists of SEQ ID NO: 30 and SEQ ID NO: 75;

(41) BCMA-M2-DG2, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 99 and SEQ ID NO: 107; the heavy chain comprises or consists of SEQ ID NO: 29, SEQ ID NO: 82, SEQ ID NO: 66, SEQ ID NO: 99 and SEQ ID NO: 106; the light chain comprises or consists of SEQ ID NO: 30 and SEQ ID NO: 75;

(42) BCMA-M2-G2D, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 100 and SEQ ID NO: 107; the heavy chain comprises or consists of SEQ ID NO: 29, SEQ ID NO: 82, SEQ ID NO: 66, SEQ ID NO: 100 and SEQ ID NO: 106; the light chain comprises or consists of SEQ ID NO: 30 and SEQ ID NO: 75;

(43) BCMA-M2-DG2D, which comprises or consists of a fusion peptide 2, a heavy chain and a light chain; wherein the fusion peptide 2 comprises or consists of SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 101 and SEQ ID NO: 107; the heavy chain comprises or consists of SEQ ID NO: 29, SEQ ID NO: 82, SEQ ID NO: 66, SEQ ID NO: 101 and SEQ ID NO: 106; the light chain comprises or consists of SEQ ID NO: 30 and SEQ ID NO: 75;

(44) M2IC-G2, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 94 and SEQ ID NO: 107; the heavy chain comprises or consists of SEQ ID NO: 43, SEQ ID NO: 82, SEQ ID NO: 66, SEQ ID NO: 94 and SEQ ID NO: 106; the light chain comprises or consists of SEQ ID NO: 44 and SEQ ID NO: 75;

(45) M2IC-SG2, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 95 and SEQ ID NO: 107; the heavy chain comprises or consists of SEQ ID NO: 43, SEQ ID NO: 82, SEQ ID NO: 66, SEQ ID NO: 95 and SEQ ID NO: 106; the light chain comprises or consists of SEQ ID NO: 44 and SEQ ID NO: 75;

(46) M2IC-AG2, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 96 and SEQ ID NO: 107; the heavy chain comprises or consists of SEQ ID NO: 43, SEQ ID NO: 82, SEQ ID NO: 66, SEQ ID NO: 96 and SEQ ID NO: 106; the light chain comprises or consists of SEQ ID NO: 44 and SEQ ID NO: 75;

(47) M2IC-GG2, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 97 and SEQ ID NO: 107; the heavy chain comprises or consists of SEQ ID NO: 43, SEQ ID NO: 82, SEQ ID NO: 66, SEQ ID NO: 97 and SEQ ID NO: 106; the light chain comprises or consists of SEQ ID NO: 44 and SEQ ID NO: 75;

(48) M2IC-PG2, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 98 and SEQ ID NO: 107; the heavy chain comprises or consists of SEQ ID NO: 43, SEQ ID NO: 82, SEQ ID NO: 66, SEQ ID NO: 98 and SEQ ID NO: 106; the light chain comprises or consists of SEQ ID NO: 44 and SEQ ID NO: 75;

(49) M2IC-DG2, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 99 and SEQ ID NO: 107; the heavy chain comprises or consists of SEQ ID NO: 43, SEQ ID NO: 82, SEQ ID NO: 66, SEQ ID NO: 99 and SEQ ID NO: 106; the light chain comprises or consists of SEQ ID NO: 44 and SEQ ID NO: 75;

(50) M2IC-G2D, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 100 and SEQ ID NO: 107; the heavy chain comprises or consists of SEQ ID NO: 43, SEQ ID NO: 82, SEQ ID NO: 66, SEQ ID NO: 100 and SEQ ID NO: 106; the light chain comprises or consists of SEQ ID NO: 44 and SEQ ID NO: 75;

(51) M2IC-DG2D, which comprises or consists of a fusion peptide 2, a heavy chain and a light chain; wherein the fusion peptide 2 comprises or consists of SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 101 and SEQ ID NO: 107; the heavy chain comprises or consists of SEQ ID NO: 43, SEQ ID NO: 82, SEQ ID NO: 66, SEQ ID NO: 101 and SEQ ID NO: 106; the light chain comprises or consists of SEQ ID NO: 44 and SEQ ID NO: 75;

(52) CEA-M3-G2, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 94 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 94 and SEQ ID NO: 106; the light chain comprises or consists of SEQ ID NO: 42 and SEQ ID NO: 75;

(53) CEA-M3-SG2, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 95 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 95 and SEQ ID NO: 106; the light chain comprises or consists of SEQ ID NO: 42 and SEQ ID NO: 75;

(54) CEA-M3-AG2, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 96 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 96 and SEQ ID NO: 106; the light chain comprises or consists of SEQ ID NO: 42 and SEQ ID NO: 75;

(55) CEA-M3-GG2, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 97 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 97 and SEQ ID NO: 106; the light chain comprises or consists of SEQ ID NO: 42 and SEQ ID NO: 75;

(56) CEA-M3-PG2, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 98 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 98 and SEQ ID NO: 106; the light chain comprises or consists of SEQ ID NO: 42 and SEQ ID NO: 75;

(57) CEA-M3-DG2, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 99 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 99 and SEQ ID NO: 106; the light chain comprises or consists of SEQ ID NO: 42 and SEQ ID NO: 75;

(58) CEA-M3-G2D, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 100 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 100 and SEQ ID NO: 106; the light chain comprises or consists of SEQ ID NO: 42 and SEQ ID NO: 75;

(59) CEA-M3-DG2D, which comprises or consists of a fusion heavy chain, a cross light chain, a heavy chain and a light chain; wherein the fusion heavy chain comprises or consists of SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 101 and SEQ ID NO: 107; the cross light chain comprises or consists of SEQ ID NO: 2, SEQ ID NO: 45 and SEQ ID NO: 82; the heavy chain comprises or consists of SEQ ID NO: 41, SEQ ID NO: 82, SEQ ID NO: 66, SEQ ID NO: 101 and SEQ ID NO: 106; the light chain comprises or consists of SEQ ID NO: 42 and SEQ ID NO: 75;

(60) M3IC-G2, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 94 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 94 and SEQ ID NO: 106; the light chain comprises or consists of SEQ ID NO: 44 and SEQ ID NO: 75;

(61) M3IC-SG2, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 95 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 95 and SEQ ID NO: 106; the light chain comprises or consists of SEQ ID NO: 44 and SEQ ID NO: 75;

(62) M3IC-AG2, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 96 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 96 and SEQ ID NO: 106; the light chain comprises or consists of SEQ ID NO: 44 and SEQ ID NO: 75;

(63) M3IC-GG2, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 97 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 97 and SEQ ID NO: 106; the light chain comprises or consists of SEQ ID NO: 44 and SEQ ID NO: 75;

(64) M3IC-PG2, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 98 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 98 and SEQ ID NO: 106; the light chain comprises or consists of SEQ ID NO: 44 and SEQ ID NO: 75;

(65) M3IC-DG2, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 99 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 99 and SEQ ID NO: 106; the light chain comprises or consists of SEQ ID NO: 44 and SEQ ID NO: 75;

(66) M3IC-G2D, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 100 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 100 and SEQ ID NO: 106; the light chain comprises or consists of SEQ ID NO: 44 and SEQ ID NO: 75;

(67) M3IC-DG2D, which comprises or consists of a fusion heavy chain, a cross light chain, a heavy chain and a light chain; wherein the fusion heavy chain comprises or consists of SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 101 and SEQ ID NO: 107; the cross light chain comprises or consists of SEQ ID NO: 2, SEQ ID NO: 45 and SEQ ID NO: 82; the heavy chain comprises or consists of SEQ ID NO: 43, SEQ ID NO: 82, SEQ ID NO: 66, SEQ ID NO: 101 and SEQ ID NO: 106; the light chain comprises or consists of SEQ ID NO: 44 and SEQ ID NO: 75;

(68) CD3mAb-G2, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 94 and SEQ ID NO: 102;

(69) CD3mAb-SG2, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 95 and SEQ ID NO: 102;

(70) CD3mAb-AG2, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 96 and SEQ ID NO: 102;

(71) CD3mAb-GG2, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 97 and SEQ ID NO: 102;

(72) CD3mAb-PG2, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 98 and SEQ ID NO: 102;

(73) CD3mAb-G2-C229L, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 128 and SEQ ID NO: 102;

(74) CD3mAb-G2-C229F, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 129 and SEQ ID NO: 102;

(75) CD3mAb-G2-C229R, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 130 and SEQ ID NO: 102;

(76) CD3mAb-G2-C229V, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 131 and SEQ ID NO: 102;

(77) CD3mAb-G2-C229Q, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 132 and SEQ ID NO: 102;

(78) CD3mAb-G2-C229K, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 133 and SEQ ID NO: 102;

(79) CD3mAb-G2-C229D, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 134 and SEQ ID NO: 102;

(80) CD3mAb-G2-C229I, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 135 and SEQ ID NO: 102;

(81) CD3mAb-G2-C229Y, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 136 and SEQ ID NO: 102;

(82) CD3mAb-G2-C229N, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 137 and SEQ ID NO: 102;

(83) CD3mAb-G2-C229M, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 138 and SEQ ID NO: 102;

(84) CD3mAb-G2-C229T, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 139 and SEQ ID NO: 102;

(85) CD3mAb-G2-C229H, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 140 and SEQ ID NO: 102;

(86) CD3mAb-G2-C229E, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 141 and SEQ ID NO: 102;

(87) CD3mAb-G2-C229W, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 142 and SEQ ID NO: 102;

(88) CD3mAb-G2-C229L, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 128 and SEQ ID NO: 102;

(89) CD3mAb-DG2, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 99 and SEQ ID NO: 102;

(90) CD3mAb-G2-D265P, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 143 and SEQ ID NO: 102;

(91) CD3mAb-G2-D265K, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 144 and SEQ ID NO: 102;

(92) CD3mAb-G2-D265S, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 145 and SEQ ID NO: 102;

(93) CD3mAb-G2-D265F, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 146 and SEQ ID NO: 102;

(94) CD3mAb-G2-D265R, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 147 and SEQ ID NO: 102;

(95) CD3mAb-G2-D265L, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 148 and SEQ ID NO: 102;

(96) CD3mAb-G2-D265G, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 149 and SEQ ID NO: 102;

(97) CD3mAb-G2-D265T, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 150 and SEQ ID NO: 102;

(98) CD3mAb-G2-D265Y, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 151 and SEQ ID NO: 102;

(99) CD3mAb-G2-D265W, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 152 and SEQ ID NO: 102;

(100) CD3mAb-G2-D265H, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 153 and SEQ ID NO: 102;

(101) CD3mAb-G2-D265V, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 154 and SEQ ID NO: 102;

(102) CD3mAb-G2-D265Q, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 155 and SEQ ID NO: 102;

(103) CD3mAb-G2-D265E, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 156 and SEQ ID NO: 102;

(104) CD3mAb-G2-D265M, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 157 and SEQ ID NO: 102;

(105) CD3mAb-G2-D265N, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 158 and SEQ ID NO: 102;

(106) CD3mAb-G2-D265I, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 159 and SEQ ID NO: 102;

(107) CD3mAb-G2D, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 100 and SEQ ID NO: 102;

(108) CD3mAb-G2-D270L, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 160 and SEQ ID NO: 102;

(109) CD3mAb-G2-D270R, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 161 and SEQ ID NO: 102;

(110) CD3mAb-G2-D270P, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 162 and SEQ ID NO: 102;

(111) CD3mAb-G2-D270G, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 163 and SEQ ID NO: 102;

(112) CD3mAb-G2-D270V, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 164 and SEQ ID NO: 102;

(113) CD3mAb-G2-D270H, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 165 and SEQ ID NO: 102;

(114) CD3mAb-G2-D270Y, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 166 and SEQ ID NO: 102;

(115) CD3mAb-G2-D270I, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 167 and SEQ ID NO: 102;

(116) CD3mAb-G2-D270E, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 168 and SEQ ID NO: 102;

(117) CD3mAb-G2-D270F, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 169 and SEQ ID NO: 102;

(118) CD3mAb-G2-D270K, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 170 and SEQ ID NO: 102;

(119) CD3mAb-G2-D270W, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 171 and SEQ ID NO: 102;

(120) CD3mAb-G2-D270S, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 172 and SEQ ID NO: 102;

(121) CD3mAb-G2-D270T, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 173 and SEQ ID NO: 102;

(122) CD3mAb-G2-D270Q, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 174 and SEQ ID NO: 102;

(123) CD3mAb-G2-D270M, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 175 and SEQ ID NO: 102;

(124) CD3mAb-G2-D270N, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 176 and SEQ ID NO: 102;

(125) CD3mAb-PG2-GA, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 122 and SEQ ID NO: 102;

(126) CD3mAb-PG2-TA, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 123 and SEQ ID NO: 102;

(127) CD3mAb-G2D-GA, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 124 and SEQ ID NO: 102;

(128) CD3mAb-G2D-TA, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 125 and SEQ ID NO: 102;

(129) CD3mAb-G2D-GATA, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 126 and SEQ ID NO: 102; or (130) CD3mAb-PDG2D, which comprises or consists of a light chain and a heavy chain, wherein the light chain comprises or consists of SEQ ID NO: 2 and SEQ ID NO: 75; the heavy chain comprises or consists of SEQ ID NO: 1, SEQ ID NO: 82, SEQ ID NO: 66, SEQ ID NO: 127 and SEQ ID NO: 102.

Item 19. A conjugate of the antibody of any one of items 11-18, wherein the conjugate comprises substance A to which the antibody is coupled or fused, and the substance A is selected from therapeutic agents, prodrugs, proteins (such as enzymes), viruses, lipids, biological response modifiers (such as immunomodulators), PEG, hormones, oligonucleotides, diagnostic agents, cytotoxic agents, which can be drugs or toxins, ultrasound enhancers, non-radioactive labels, detectable labels, such as chemiluminescent labeled compounds (such as luminol, isoluminol, thermal acridinium esters, imidazoles, acridinium salts and oxalates), or fluorescent emitting metals (such as 152Eu, or lanthanide marker).

Item 20. A polynucleotide encoding the polypeptide of any one of items 1-10.

Item 21. A cell comprising the polynucleotide of item 20.

Item 22. A composition, preferably a pharmaceutical composition, which comprises the polypeptide of any one of items 1-10, or the antibody of any one of items 11-18.

Item 23. A method for delivering a polypeptide or an antibody to a mammalian (preferably human) subject without inducing antibody-dependent cytotoxicity, comprising administering the polypeptides of any one of items 1-10 or the antibody of any one of items 11-18 to the subject.

Item 24. Use of the polypeptide of any one of items 1-10 or the antibody of any one of items 11-18 in preparation of a drug that does not induce antibody-dependent cytotoxicity after administration to a mammalian (preferably human) subject.

TECHNICAL SOLUTION

The antibody has a Fc fragment of heavy chain constant region, wherein the Fc comprises a hinge, a CH2 and a CH3, and wherein the CH2 domain comprises one or more substitutions, which can significantly reduce the binding ability of Fc fragments to Fcγ receptors (FcγR) and reduce non-specific activation of T cells by the antibody (such as anti-CD3 antibody).

In certain aspects, the Fc of the antibody comprises a CH3 domain, and the CH3 domain comprises one or more substitutions that form knobs-into-holes structure pairing between two different CH3 domains.

After substitution at both CH2 and CH3 in the Fc fragment, the binding ability of the Fc fragment to the FcγR can be significantly reduced and the non-specific activation of T cells by the antibody (such as anti-CD3 antibodies) is reduced.

In certain aspects, the antibody has a light chain-heavy chain pair or a VLm-VHm pair and those pairs are specific for tumor antigens. In one aspect, the tumor antigen is selected from PD-L1, SLAMF7, B7-H3, CEA, CD38, EpCAM, CD19, BCMA and the like. In one aspect, the light chain-heavy chain pair or VLm-VHm pair is specific for proteins that are overexpressed on tumor cells compared to the corresponding non-tumor cells.

In certain aspects, the light chain-heavy chain pair or VLm-VHm pair of the antibody is specific for viruses or bacteria. In one aspect, the light chain-heavy chain pair or VLm-VHm pair is specific for endotoxin.

In some aspects, the antibody has a fusion peptide or light and heavy chain variable region pair (VLs-VHs pair), and the fusion peptide or light and heavy chain variable region pair are specific for immune cell surface antigens, and the surface antigens are CD3, CD16A, CD47, NKG2D, etc.

In certain aspects, the immune cell is selected from a T cell, a CIK cell, a NKT cell, a B cell, a monocyte, a macrophage, a neutrophil, a dendritic cell, a macrophage, a natural killer cell, an eosinophil, a basophil and a mast cell.

In certain aspects, compared to the wild-type antibody fragment, the heavy chain, the fusion heavy chain, and/or the Fc fragment of the fusion peptide comprise one or more substitutions which form a structure pairing of Knobs-into-holes between the heavy chain and the fusion peptide, or between the heavy chain and the fusion heavy chain. This pairing can significantly improve the heterodimer pairing efficiency of the heavy chain and the fusion peptide.

In certain aspects, the heavy chain, the fusion heavy chain, and/or the Fc fragment of the fusion peptide comprise one or more substitutions which form a pairing of salt-bridge between the heavy chain and the fusion peptide, or between the heavy chain and the fusion heavy chain. This pairing can significantly improve the heterodimer pairing efficiency of the heavy chain and the fusion peptide.

In certain aspects, the CH2 domain in the fusion peptide is located between the scFv fragment and the CH3 domain. In one aspect, the fusion peptide does not comprise a CH1 domain.

In certain aspects, there is a light chain constant region between the VH and hinge region of the fused heavy chain.

In certain aspects, the fusion heavy chain and the cross light chain are paired, and the cross light chain has a VL-CH1 structure.

In one embodiment, the present disclosure also provides a composition comprising the antibody in any one of the above embodiments. In one aspect, the composition further comprises a carrier, which is a pharmaceutically acceptable carrier.

In another embodiment, the present disclosure provides a complex which comprises the antibody in any one of the above embodiments that binds to one or more antigens.

The present disclosure further provides a method for preparing the antibody.

Definitions

It is to be noted that an indefinite quantity of "a" or "an" entity refers to one or more of that entity; for example, "a multifunctional antibody" shall be understood to represent one or more multifunctional antibodies. As such, the terms "a" (or "an"), "one or more," and "at least one" defined indefinitely can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are all included within the definition of "polypeptide," and the term "polypeptide" may be used instead of, or interchangeably with any of these terms. The term "polypeptide" is also intended to refer to the post-expression modified products of the polypeptide, including but not limited to glycosylation, acetylation, phosphorylation, amidation, derivatization by known protecting/blocking groups, proteolytic cleavage, or modification by non-naturally occurring amino acids. A polypeptide may be derived from a natural biological source or may be produced by recombinant technology, but is not necessarily translated from a specified nucleic acid sequence. It may be generated by any manner, including by chemical synthesis.

As used herein, the term "recombinant" as it pertains to polypeptides or polynucleotides refers to a form of the polypeptide or polynucleotide that does not exist naturally, a non-limiting example of which can be achieved by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined by using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, which use the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Detailed information of these programs can be found at the following Internet address: http://www.ncbi nlm nih gov/blast/Blast.cgi, last accessed on May 21, 2008. Biologically equivalent polynucleotides are those having the above specified percent homology and encoding a polypeptide having the same or similar biological activity.

The term "encode" as it is applied to polynucleotides refers to a polynucleotide which "encodes" a polypeptide and which, in its native state or when manipulated by methods well known to those skilled in the art, can be transcribed and/or translated to produce the mRNA for the polypeptide and/or a fragment thereof. An antisense strand is a complement of such a nucleic acid, and an encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing a specific molecule, wherein the specific molecule comprises at least a portion of an immunoglobulin molecule having biological activity of binding to an antigen. Examples of such include, but are not limited to a complementary determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody, such as F(ab')$_2$, F(ab)$_2$, Fab', Fab, Fv, Fd, dAb, Fab/c, scFv and the like. Regardless of structure, an antibody fragment that binds to the same antigen is recognized as an intact antibody. The term "antibody fragment" includes aptamers, spiegelmers, and diabodies. The term "antibody fragment" also includes any synthetic or genetically engineered protein that acts like an antibody that can binds to a specific antigen to form a complex.

A "single-chain variable fragment" or "scFv" refers to a fusion protein of the variable regions of the heavy (VH) and light chains (VL) of immunoglobulins. In some aspects, the regions are connected with a short linker peptide of 10 to about 25 amino acids. The linker can be rich in glycine for flexibility, as well as serine or threonine for solubility, and can either connect the N-terminus of the VH to the C-terminus of the VL, or vice versa. This protein retains the specificity of the original immunoglobulin, despite removal of a constant region and introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgD, IgE or IgY, respectively. The immunoglobulin subclasses (isotypes) e.g., IgG1, IgG2, IgG3, IgG4, IgG5, etc. are well characterized and functionally specific. Modified versions of each of these classes and isotypes are readily recognized by those skilled in the art in view of the present disclosure and, accordingly, are within the scope of the present disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides with a molecular weight of approximately 23,000 Daltons, and two identical heavy chain polypeptides with a molecular weight of 53,000-70,000. The four chains are typically joined by disulfide bonds in a "Y" configuration wherein the light chains support the heavy chains starting at the mouth of the "Y" and extend through the variable region.

Antibodies, antigen-binding polypeptides, variants or derivatives thereof in the present disclosure include, but are not limited to, polyclonal antibodies, monoclonal antibodies, multispecific antibodies, human antibodies, humanized antibodies, primatized antibodies, or chimeric antibodies, single chain antibodies, antigen-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to LIGHT antibodies as disclosed herein) Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (κ, λ). Each heavy chain class may be bound to either a kappa or lambda light chain. In general, the light and heavy chains are covalently bonded to each other, and the "tail" portions of the two heavy chains are bonded to each other by covalent disulfide bonds or non-covalent bonds when the immunoglobulins are generated either by hybridomas, B cells or genetically engineered host cells. In the heavy chain, the amino acid sequences extend from an N-terminus at the forked ends of the Y configuration to the C-terminus at the bottom of each chain.

Both the light and heavy chains are divided into structural regions and functional homology regions. The terms "constant" and "variable" are used functionally. In this regard, it will be appreciated that the variable domains of both the light (VL) and heavy (VH) chain determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. Generally, the number of the constant region domains increases as they become more distal from the antigen-binding site or amino-terminus of the antibody. The N-terminal portion is a variable region and the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementary determining regions (CDRs), of an antibody combine to form a variable region that defines a three dimensional antigen-binding site. This tetravalent antibody structure forms an antigen-binding site present at the end of each arm of the Y configuration. More specifically, the antigen-binding site is defined by three CDRs on each of the VH and VL chains (i.e. CDR-H1, CDR-H2, CDR-H3, CDR-L1, CDR-L2 and CDR-L3). In some examples, e.g., for certain immunoglobulin molecules derived from camelid species or engineered based on camelid immunoglobulins, the intact immunoglobulin molecule may consist of heavy chains only, without light chains. See, e.g., Hamers-Casterman et al., Nature 363:446-448 (1993).

In naturally occurring antibodies, the six "complementary determining regions" or "CDRs" present in each antigen-binding domain are short, non-contiguous amino acid sequences that are specifically positioned to form the antigen-binding domain as it is assumed three dimensional configuration of the antibody is located in an aqueous environment. The other amino acids in the antigen-binding domains are referred to as "framework" regions and show less inter-molecular variability. The framework regions largely adopt a β-sheet conformation and the CDRs form loops which connect, and in some cases form part of, the β-sheet structure. Thus, framework regions act to form a scaffold that positions the CDRs in correct orientation by inter-chain, non-covalent interactions. The antigen-binding domain formed by the positioned CDRs defines a surface complementary to the epitope of the immunoreactive antigen. This complementary surface promotes the non-covalent binding of the antibody to its homologous epitope. The amino acids comprising the CDRs and the framework regions, respectively, can be readily identified for any given heavy or light chain variable region by those skilled in the art, since they have been precisely defined (see "Sequences of Proteins of Immunological Interest," Kabat, E., et al., U.S. Department of Health and Human Services, (1983); and Chothia and Lesk, J. Mol. Biol., 196:901-917

(1987), which are incorporated herein by reference in their full text).

In the case where there are two or more definitions of a term which is used and/or accepted within the art, the definition of the term as used herein is intended to include all such meanings unless explicitly stated to the contrary. A specific example is the use of the term "complementary determining region" ("CDR") to describe the non-contiguous antigen-binding sites found within the variable region of both heavy and light chain polypeptides. This particular region has been described in the U.S. Dept. of Health and Human Services, "Sequences of Proteins of Immunological Interest" (1983) and by Chothia et al., J. Mol. Biol. 196: 901-917 (1987), which are incorporated herein by reference in their full text. According to definitions of Kabat and Chothia, the CDR includes overlapping amino acid residues or substructures of amino acid residues when compared with each other. Nevertheless, application of each definition of CDR of an antibody or variants thereof is intended to be within the scope of the term as defined and used herein. The appropriate amino acid residues which encompass the CDRs as defined by each of the above cited references are set forth in the table below as a comparison. The exact number of residues which encompass a particular CDR will vary depending on the sequence and size of the CDR. Those skilled in the art can routinely determine which residues comprise a particular CDR if the variable region amino acid sequence of the antibody is provided.

TABLE 1

Definition of antibody variable region

|        | Kabat  | Chothia |
|--------|--------|---------|
| CDR-H1 | 31-35  | 26-32   |
| CDR-H2 | 50-65  | 52-58   |
| CDR-H3 | 95-102 | 95-102  |
| CDR-L1 | 24-34  | 26-32   |
| CDR-L2 | 50-56  | 50-52   |
| CDR-L3 | 89-97  | 91-96   |

Kabat et al. also defined a numbering system for variable domain sequences that is applicable to any antibody. Those skilled in the art can unambiguously assign this "Kabat numbering" system to any variable domain sequence, without depending on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the CDR regions as described by the Kabat number system are: CDR-H1 begins from the amino acid approximately at position 31 (i.e., approximately 9 residues after the first cysteine residue), includes approximately 5 to 7 amino acids, and ends at the next tryptophan residue. CDR-H2 begins from the fifteenth residue after the end of CDR-H1, includes approximately 16 to 19 amino acids, and ends at the next arginine or lysine residue. CDR-H3 begins from approximately the 33rd amino acid residue after the end of CDR-H2; includes 3 to 25 amino acids; and ends at the sequence W-G-X-G, where X is any amino acid. CDR-L1 begins from the residue approximately at position 24 (i.e., following a cysteine residue); includes approximately 10 to 17 residues; and ends at the next tryptophan residue. CDR-L2 begins from approximately the sixteenth residue after the end of CDR-L1 and includes approximately 7 residues. CDR-L3 begins from approximately the thirty-third residue after the end of CDR-L2 (i.e., following a cysteine residue); includes approximately 7 to 11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be derived from condricthoid (e.g., from sharks).

As used herein, the term "heavy chain constant region" includes amino acid sequences derived from an immunoglobulin heavy chain. A polypeptide comprising a heavy chain constant region comprises at least one of the following: a CH1 domain, a hinge (e.g., upper, middle, and/or lower hinge region) domain, a CH2 domain, a CH3 domain, or a variant or fragment thereof. For example, an antigen-binding polypeptide for use in the present disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the present disclosure comprises a polypeptide chain with a CH3 domain. Further, an antibody for use in the present disclosure may lack at least a portion of a CH2 domain (e.g., all or part of a CH2 domain). As set forth above, it will be understood by those skilled in the art that the heavy chain constant region may be modified such that they differ in amino acid sequence from naturally occurring immunoglobulin molecules.

The heavy chain constant region of an antibody disclosed herein may be derived from different immunoglobulin molecules. For example, a heavy chain constant region of a polypeptide may comprise a CH1 domain derived from an IgG1 molecule and a hinge region derived from an IgG3 molecule. In another embodiment, a heavy chain constant region can comprise a hinge region derived, in part, from an IgG1 molecule and, in part, from an IgG3 molecule. In another embodiment, a heavy chain portion can comprise a chimeric hinge derived, in part, from an IgG1 molecule and, in part, from an IgG4 molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain and the CH1 domain of the light chain.

As previously indicated, the subunit structures and three dimensional configuration of the constant regions of the various classes of immunoglobulin are well known. As used herein, the term "VH domain" includes the amino terminal variable domain of an immunoglobulin heavy chain and the term "CH1 domain" includes the first (mostly amino terminal) constant region of an immunoglobulin heavy chain. The CH1 domain is adjacent to the VH domain and is amino terminal of the hinge region of an immunoglobulin heavy chain molecule.

As used herein the term "CH2 domain" includes a portion of the heavy chain molecule that extends, e.g., from residue at about position 244 to residue at position 360 of an antibody according to conventional numbering system (residues at position 244 to 360, according to Kabat numbering system; and residues at position 231 to 340, according to EU numbering system; see Kabat et al., U.S. Dept. of Health and Human Services, "Sequences of Proteins of Immunological Interest" (1983). The CH2 domain is unique because it is not closely paired with another domain. Rather, two N-linked branched carbohydrate chains are inserted between the two CH2 domains of an intact natural IgG molecule. It is also documented that the CH3 domain extends from the CH2 domain to the C-terminal of an IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol 161:4083 (1998)).

As used herein the term "disulfide bond" includes the covalent bond formed between two sulfur atoms. The amino acid cysteine comprises a sulfydryl group that can form a disulfide bond or bridge with a second sulfydryl group. In most naturally occurring IgG molecules, the CH1 and CL regions are linked by a disulfide bond and the two heavy chains are linked by two disulfide bonds at positions corresponding to positions 239 and 242 under the Kabat numbering system (position 226 or 229, under EU numbering system).

As used herein, the term "chimeric antibody" is intended to refer to any antibody wherein the immunoreactive region or site is obtained or derived from a first species and the constant region (which may be intact, partial or modified in accordance with the present disclosure) is obtained from a second species. In certain examples, the target binding region or site will be derived from a non-human source (e.g. mouse or primate) and the constant region is derived from human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

The term "specifically binds" or "has specificity to" generally means that an antibody binds to an epitope via its antigen-binding domain, and that the binding entails some complementarity between the antigen-binding domain and the epitope. According to this definition, an antibody is said to "specifically bind" to an epitope, and when it binds to the epitope, the binding via its antigen-binding domain is easier than binding via a random, unrelated antigen epitope. The term "specificity" is used herein to determine the relative affinity of a certain antibody binding to a certain epitope. For example, antibody "A" may be deemed to have a higher specificity for a given antigen epitope than that of antibody "B," or antibody "A" may be said to bind to antigen epitope "C" with a higher specificity than it has for related epitope "D."

As used herein, the terms "treat" or "treatment" refer to both therapeutic treatment and prophylactic or preventative measures, wherein the subject is to prevent or slow down (alleviate) an undesired physiological change or disorder, such as the progression of cancer. Beneficial or desired clinical results include, but are not limited to, alleviation of symptoms, diminishment of extent of disease, stabilizing (i.e., not worsening) state of disease, delaying or slowing disease progression, amelioration or palliation of the disease state, and remission (whether partial or total), whether detectable or undetectable. "Treatment" can also mean prolonging survival as compared to expected survival without treatment. Conditions in need of treatment include those already with the condition or disorder as well as those prone to have the condition or disorder or those in which the condition or disorder is to be prevented.

Multifunctional Antibody

Embodiments of the present disclosure provide a variety of multifunctional antibodies, which comprise two different antigen-binding polypeptide units. The antibody domain that binds to the antigen is Fab, or ScFv, or non-covalent pairs between the variable region of the heavy chain (VH) and the variable region of the light chain (VL). In particular, these multifunctional antibodies all have a Fc fragment of heavy chain constant region of antibody. Wherein the Fc contains: (1) a hinge, (2) a heavy chain second constant region (CH2), and/or a heavy chain third constant region (CH3). Both the hinge and CH3 are the corresponding domains of human IgG1 type, and the CH3 undergoes "knob-into-hole" mutation, and the CH2 is the corresponding CH2 domain of human IgG2 type.

Any of the antibodies or polypeptides described above may further include additional polypeptides, thereby constituting a fusion protein or fusion peptide, e.g., an encoded polypeptide as described herein, a signal peptide of the antibody constant region used to direct secretion, or other heterologous polypeptides as described herein.

It will also be understood by those skilled in the art that the antibodies as disclosed herein may be modified such that they vary in amino acid sequence from the naturally occurring binding polypeptide from which they were derived. For example, a polypeptide or amino acid sequence derived from a designated protein may be similar to the original sequence, e.g., having a certain percent identity to the original sequence, e.g., it may be 60%, 70%, 75%, 80%, 85%, 90%, 95%, 98%, or 99% identical to the original sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the original sequence except for one or more independent amino acid substitutions, insertions, or deletions, e.g., 1, 2, 3, 4, 5, 6, 7, 8, 9, 10, 15, 20 or more independent amino acid substitutions, insertions, or deletions. In certain embodiments, a polypeptide or amino acid sequence derived from a designated protein has 1 to 5, 1 to 10, 1 to 15, or 1 to 20 independent amino acid substitutions, insertions, or deletions relative to the original sequence.

In other embodiments, the antigen-binding polypeptides of the present disclosure may contain conservative amino acid substitutions.

A "conservative amino acid substitution" is one in which the amino acid residue is substituted with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably substituted with other amino acid residue from the same side chain family. In another embodiment, a amino acid sequence can be substituted by a structurally similar amino acid sequence that differs in order and/or composition of side chain family members.

Non-limiting examples of conservative amino acid substitutions are provided in the table below, wherein a similarity score of 0 or higher indicates conservative substitution between two amino acids.

TABLE 2

Non-limiting list of conservative amino acid substitutions

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

In some embodiments, the present disclosure provides an antibody conjugate, and the antibody may bind to therapeutic agents, prodrugs, peptides, proteins, enzymes, viruses, lipids, biological response modifiers, pharmaceutical agents, or PEG.

The antibodies may be conjugated or fused to a therapeutic agent, which may include a detectable label such as a radioactive label, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibody can be detectably labeled by coupling it to a chemiluminescent compound. The presence of a chemiluminescent-labeled antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as 152Eu, or other lanthanide series labels. These metals can be attached to the antibody by using metal chelating groups such as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery ($2^{nd}$ Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. (52:119-58 (1982)).

Methods of Preparing Antibodies

Methods of preparing antibodies are well known in the art and described herein. In certain embodiments, both the variable and constant regions of the antigen-binding polypeptides of the present disclosure are fully human. Fully human antibodies can be prepared using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to prepare such antibodies are described in U.S. Pat. Nos: 6,150,584; 6,458,592; 6,420,140 which are incorporated by reference in their full text.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, Science 242:423-442 (1988); Huston et al., Proc. Natl. Acad. Sci. USA 55:5879-5883 (1988); and Ward et al., Nature 334: 544-554 (1989)) can be used to produce single-chain units of the present disclosure. Single-chain units are formed by linking the heavy and light chain fragments of the Fv region via an amino acid bridge, resulting in a single-chain fusion peptide. Techniques for producing functional Fv fragments in E. coli may also be used (Skerra et al., Science 242: 1038-1041 (1988)).

Examples of techniques which can be used to produce single-chain Fvs (scFvs) and antibodies include those described in U.S. Pat. Nos. 4,946,778 and 5,258,498; Huston et al., Methods in Enzymology 203:46-88 (1991); Shu et al., Proc. Natl. Sci. USA 90:1995-1999 (1993); and Skerra et al., Science 240:1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., J. Immunol. Methods 125:191-202 (1989); U.S. Pat. Nos. 5,807, 715; 4,816,567; and 4,816397, which are incorporated herein by reference in their entities.

A humanized antibody is an antibody molecule that is derived from a non-human species antibody and binds the desired antigen, and the antibody molecule has one or more complementary determining regions (CDRs) from the non-human species and a framework region from a human immunoglobulin molecule. Often, framework residues in a human framework region will be changed by substitution with corresponding residues from a CDR donor antibody, preferably to improve, antigen-binding ability. These framework substitutions are identified by methods well known in the art, e.g., by modeling interactions between the CDR and framework residues to identify framework residues important for antigen-binding and sequence comparison in order to identify unusual framework residues at particular positions. (See, e.g., Queen et al., U.S. Pat. No. 5,585,089; Riechmann et al., Nature 332:323 (1988), which are incorporated herein by reference in their entities) Antibodies can be humanized by using a variety of techniques known in the art including, for example, CDR-grafting (EP 239,400; PCT publication No. WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., Proc. Natl. Sci. USA 91:969-973 (1994)), and chain shuffling (U.S. Pat. No. 5,565,332, which is incorporated by reference in its entity).

By using routine recombinant DNA techniques, one or more CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., J. Mol. Biol. 278:457-479 (1998) for a listing of human framework regions). Preferably, the polynucleotide generated by the combination of the framework regions and CDRs encodes a polypeptide that specifically binds to at least one antigen epitope of a desired polypeptide, e.g., LIGHT. Preferably, one or more amino acid substitutions may be performed within the framework regions, and, preferably, the amino acid substitutions improve binding ability of an antibody to an antigen. Additionally, such methods may be used to obtain amino acid substitutions or deletions of one or more variable region cysteine residues participating in forming an intrachain disulfide bond, thereby generating antibody molecules lacking one or more intrachain disulfide bonds. Other alterations to the polynucleotide are encompassed by the present disclosure and within the scope of the prior art.

In addition, techniques developed for the production of "chimeric antibodies" (Morrison et al., Proc. Natl. Acad. Sci. USA: 851-855 (1984); Neuberger et al., Nature 372:604-608 (1984); Takeda et al., Nature 314:452-454 (1985)) by splicing genes from a mouse antibody molecule can be used to link a human antibody molecule of appropriate antigen specificity together with genes from a human antibody molecule of appropriate biological activity. As used herein, a chimeric antibody is a molecule in which different portions are derived from different animal species, such as antibodies having a variable region derived from a murine monoclonal antibody and a human immunoglobulin constant region.

Yet another highly efficient means for generating recombinant antibodies is disclosed by Newman, Biotechnology 10: 1455-1460 (1992). Specifically, this technique results in the generation of primatized antibodies that contain monkey variable domains and human constant sequences. This reference is incorporated by reference in its full text herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to those skilled in the art. Such techniques are described in a variety of laboratory manuals and primary publications. In this respect, techniques suitable for use in the disclosure are described in Current Protocols in Immunology, Coligan et al., Eds., Green Publishing Associates and Wiley-Interscience, John Wiley and Sons, New York (1991) which is herein incorporated by reference in its full text, including supplement reference.

Additionally, standard techniques known to those skilled in the art can be used to introduce mutations in the nucleotide sequence encoding an antibody of the present disclosure, including, but not limited to, site-directed mutagenesis and PCR-mediated mutations which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

Structure Information of the Antibody

Monospecific antibodies are symmetrical antibodies including two identical light chains and two identical heavy chains. The light chain and the heavy chain are connected by a disulfide bond and target a corresponding antigen, and the heavy chain and the heavy chain are connected by a disulfide bond; the entire antibody has a "Y" structure. The light chain includes a light chain variable region (VL) and a light chain constant region (Lc); and the heavy chain includes a heavy chain variable region (VH) and a heavy chain constant region, wherein the heavy chain constant region includes a CH1 and a Fc, and the Fc includes a hinge, a CH2 and a CH3.

Multifunctional antibody structure 1 is an asymmetric bispecific antibody including a light chain, a heavy chain and a fusion peptide 1, wherein the fusion peptide 1 includes a scFv and a Fc fragment; such diabody has a light-heavy chain pair, and a heavy chain-fusion peptide 1 pair, wherein each pair forms an interchain disulfide bond; the light chain-heavy chain pair targets the tumor antigen, and the ScFv in the fusion peptide 1 targets an immune cell antigen.

FIG. 1A is a structural schematic diagram of multifunctional antibody structure 1, and FIG. 1B is a schematic diagram of the primary protein structure of each component of the antibody.

Multifunctional antibody structure 2 is an asymmetric trivalent bispecific antibody comprising two light chains, one heavy chain and one fusion peptide 2, and having a light chain-heavy chain pair, a light chain-fusion peptide 2 pair, and a heavy chain-fusion peptide 2 pair, wherein each pair forms an interchain disulfide bond; the fusion peptide 2 includes a heavy chain variable region (VH), a first constant region of heavy chain (CH1), ScFv and Fc, wherein the ScFv is located between CH1 and Fc and is connected by a linker; the light chain-heavy chain pair targets the tumor antigen, the pairing of VH-CH1 in the fusion peptide 2 and light chain targets the same tumor antigen, and the ScFv targets an immune cell antigen.

FIG. 2A is a structural schematic diagram of multifunctional antibody structure 2, and FIG. 2B is a schematic diagram of the primary protein structure of each component of the antibody.

Multifunctional antibody structure 3 is an asymmetric trivalent bispecific antibody comprising a fusion heavy chain, a cross light chain, a heavy chain and a light chain, and having a light chain-heavy chain pair, a light chain-fusion heavy chain pair, a cross light chain-fusion heavy chain pair, and a fusion heavy chain-heavy chain pair, wherein each pair forms an interchain disulfide bond; the light chain includes a first light chain variable region (VLm) and a light chain constant region (CL); the fusion heavy chain includes a first heavy chain variable region (VHm), a first constant region of heavy chain (CH1), a second heavy chain variable region (VHs), a light chain constant region (CL) and an Fc, wherein the VHs and CL are connected by a linker to form a peptide "VHs-linker-CL", and the "VHs-linker-CL" is located between CH1 and Fc and is connected by a linker/hinge; the cross light chain contains a second light chain variable region (VLs) and a CH1, the VLs and the CH1 are connected by a linker; the VLm-VHm pair targets a tumor antigen, and the VLs-VHs pair targets an immune cell antigen.

FIG. 3A is a structural schematic diagram of multifunctional antibody structure 3, and FIG. 3B is a schematic diagram of the primary protein structure of each component of the antibody.

The above three multifunctional antibody structures all have an Fc fragment comprising a CH2 and/or a CH3, wherein the CH2 is the natural sequence of CH2 of human IgG2 or the sequence modified by amino acid point mutations, and the specific sequences of some CH2 are shown in SEQ ID NOs: 83 to 101 and 122 to 176; each multifunctional antibody has two different CH3, and the two CH3 are paired with a form of "knob-into-hole" or/and "salt bridge" to form a heterodimer, and the seqence of CH3 is shown in SEQ ID NOs: 102 to 115.

The Variable Regions of Antibody equence

TABLE 3

Variable region sequence of anti-CD3 antibody

| Antibody code (Sequence source) | Variable region amino acid sequence of antibody variable region of anti-CD3 (The amino acids underlined in bold are CDR regions) | | | |
|---|---|---|---|---|
| | VHs | SEQ ID NO | VLs | SEQ ID NO |
| 2a5 | QVQLVESGGGVVQPGRSLRLSCAASGFTFSTYAMNWVRQAP GKGLEWVARIRSKYNNYATYYADSVKDRFTISRDDSKNTLY LQMNSLRAEDTAVYYCARHGNFGNSYVSWFAYWGQGTLV TVSS | 1 | QTVVTQEPSLTVSPGGTVTLTCRSSTGAVTTSNYAN WVQQKPGQAPRGLIGGTNKRAPGVPARFSGSLLGGK AALTLSGVQPEDEAEYYCALWYSNLWVFGGGTKVE IK | 2 |
| 2j5a | QVQLVESGGGVVQPGRSLRLSCAASGFTFSTYAMNWVRQAP GKGLEWVARIRSKYNNYATYYADSVKDRFTISRDDSKNTLY LQMNSLRAEDTAVYYCARHGNFGNSYVSWAAYWGQGTLV TVSS | 3 | QTVVTQEPSLTVSPGGTVTLTCRSSTGAVTTSNYAN WFQQKPGQAPRGLIGGTNKRAPGVPARFSGSLLGGK AALTLSGVQPEDEAEYYCALWYSNLWVFGGGTKVE IK | 4 |
| OKT3 | QVQLQQSGAELARPGASVKMSCKASGYTFTRYTMHWVKQR PGQGLEWIGYINPSRGYTNYNQKFKDKATLTTDKSSSTAYM QLSSLTSEDSAVYYCARYYDDHYCLDYWGQGTTLTVSS | 5 | QIVLTQSPAIMSASPGEKVTMTCSASSSVSYMNWYQ QKSGTSPKRWIYDTSKLASGVPAHFRGSGSGTSYSLT ISGMEAEDAATYYCQQWSSNPFTFGSGTKLEIN | 6 |
| L2K | DIKLQQSGAELARPGASVKMSCKTSGYTFTRYTMHWVKQRP GQGLEWIGYINPSRGYTNYNQKFKDKATLTTDKSSSTAYMQ LSSLTSEDSAVYYCARYYDDHYCLDYWGQGTTLTVSS | 7 | DIQLTQSPAIMSASPGEKVTMTCRASSSVSYMNWYQ QKSGTSPKRWIYDTSKVASGVPYRFSGSGSGTSYSLTI SSMEAEDAATYYCQQWSSNPLTFGAGTKLELK | 8 |
| I2C | EVQLVESGGGLVQPGGSLKLSCAASGFTFNKYAMNWVRQAP GKGLEWVARIRSKYNNYATYYADSVKDRFTISRDDSKNTAY LQMNNLKTEDTAVYYCVRHGNFGNSYISYWAYWGQGTLVT VSS | 9 | QTVVTQEPSLTVSPGGTVTLTCGSSTGAVTSGNYPN WVQQKPGQAPRGLIGGTKFLAPGTPARFSGSLLGGK AALTLSGVQPEDEAEYYCVLWYSNRWVFGGGTKLT VL | 10 |

(1) Antibodies Targeting Tumor-Associated Antigens

TABLE 4

Variable region sequence of anti-B7-H3 antibody

| Antibody code (Sequence source) | Variable region amino acid sequence of anti-B7-H3 antibody (The amino acids underlined in bold are CDR regions | | | |
|---|---|---|---|---|
| | VHm | SEQ ID NO | VLm | SEQ ID NO |
| 8H9 | QVQLQQSGAELVKPGASVKLSCKASGYTFTNYDINWVRQRPEQGLEWIGWIFPGDGSTQYNEKFKGKATLTTDTSSSTAYMQLSRLTSEDSAVYFCARQTTATWFAYWGQGTLVTVSS | 11 | DIVMTQSPATLSVTPGDRVSLSCRASQSISDYLHWYQQKSHESPRLLIKYASQSISGIPSRFSGSGSGSDFTLSINSVEPEDVGVYYCQNGHSFPLTFGAGTKLELK | 12 |
| BRCA69D | QVQLQQSGAELARPGASVKLSCKASGYTFTSYWMQWVKQRPGQGLEWIGTIYPGDGDTRYTQKFKGKATLTADKSSSTAYMQLSSLASEDSAVYYCARRGIPRLWYFDVWGAGTTVTVSS | 13 | DIQMTQTTSSLSASLGDRVTISCRASQDISNYLNWYQQKPDGTVKLLIYYTSRLHSGVPSRFSGSGSGTDYSLTIDNLEQEDIATYFCQQGNTLPPTFGGGTKLEIK | 14 |

TABLE 5

Variable region sequences of anti-CD38 antibody

| Antibody code (Sequence source) | Variable region amino acid sequences of anti-CD38 antibody (The amino acids underlined in bold are CDR regions | | | |
|---|---|---|---|---|
| | VHm | SEQ ID NO | VLm | SEQ ID NO |
| Dara | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 15 | EIVLTQSPATLSLSPGERATLSCRASQSVSSYLAWYQQKPGQAPRLLIYDASNRATGIPARFSGSGSGTDFTLTISSLEPEDFAVYYCQQRSNWPPTFGQGTKVEIK | 16 |
| MOR | QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTVSS | 17 | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ | 18 |
| 2F5 | QVQLVQSGAEVKKPGSSVKVSCKASGGTFSSYAFSWVRQAPGQGLEWMGRVIPFLGIANSAQKFQGRVTITADKSTSTAYMDLSSLRSEDTAVYYCARDDIAALGPFDYWGQGTLVTVSS | 19 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPRTFGQGTKVEIK | 20 |

TABLE 6

Variable region sequences of anti-EpCAM antibody

| Antibody code (Sequence source) | Variable region amino acid sequences of anti-EpCAM antibody (The amino acids underlined in bold are CDR regions | | | |
|---|---|---|---|---|
| | VHm | SEQ ID NO | VLm | SEQ ID NO |
| 3-17I | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGLLWNYWGQGTLVTVSS | 21 | EIVMTQSPATLSVSPGERATLSCRASQSVSSNLAWYQQKPGQAPRLIIYGASTTASGIPARFSASGSGTDFTLTISSLQSEDFAVYYCQQYNNWPPAYTFGQGTKLEIK | 22 |
| 2-6 | EVQLVESGPELKKPGETVKISCKASGYTFTDYSMHWVKQAPGKGLKWMGWINTETGEPTYADDFKGRFAFSLETSASTAYLQINNLKNEDTATYFCARTAVYWGQGTTVTVSS | 23 | DIQMTQSPSSLSASLGERVSLTCRASQEISVSLSWQEPDGTIKRLIYATSTLDSGVPKRFSGSRSGSDYSLTISSLESEDFVDYYCLQYASYPWTFGGGTKLEIK | 24 |

TABLE 7

Variable region sequences of anti-BCMA antibody

Variable region amino acid sequences of anti-BCMA antibody (The amino acids underlined in bold are CDR regions)

| Antibody code (Sequence source) | VHm | SEQ ID NO | VLm | SEQ ID NO |
|---|---|---|---|---|
| B50 | QVQLVQSGAEVKKPGASVKVSCKASGYSFPDYYINWVRQAPGQGLEWMGWIYFASGNSEYNQKFTGRVTMTRDTSINTAYMELSSLTSEDTAVYFCASLYDYDWYFDVWGQGTMVTVSS | 25 | DIVMTQTPLSLSVTPGQPASISCKSSQSLVHSNGNTYLHWYLQKPGQSPQLLIYKVSNRFSGVPDRFSGSGSGTDFTLKISRVEAEDVGIYYCSQSSIYPWTFGQGTKLEIK | 26 |
| B140153 | QVQLVQSGAEVKKPGSSVKVSCKASGGTFSSYAISWVRQAPGQGLEWMGRIIPILGIANYAQKFQGRVTITADKSTSTAYMELSSLRSEDTAVYYCARGGYYSHDMWSEDWGQGTLVTVSS | 27 | LPVLTQPPSASGTPGQRVTISCSGSRSSNIGSNSVNWYRQLPGAAPKLLIYSNNQRPPGVPVRFSGSKSGTSASLAISGLQSEDEATYYCATWDDNLNVHYVFGTGTKVTVLG | 28 |
| B69 | QLQLQESGPGLVKPSETLSLTCTVSGGSISSGSYFWGWIRQPPGKGLEWIGSIYYSGITYYNPSLKSRVTISVDTSKNQFSLKLSSVTAADTAVYYCARHDGAVAGLFDYWGQGTLVTVSS | 29 | SYVLTQPPSVSVAPGQTARITCGGNNIGSKSVHWYQQPPGQAPVVVVYDDSDRPSGIPERFSGNSNGNTALTLTISRVEAGDEAVYYCQVWDSSSDHVVFGGGTKLTVL | 30 |

TABLE 8

Variable region sequences of anti-PD-L1 antibody

Variable region amino acid sequences of anti-PD-L1 antibody (The amino acids underlined in bold are CDR regions)

| Antibody code (Sequence source) | VHm | SEQ ID NO | VLm | SEQ ID NO |
|---|---|---|---|---|
| S70 | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGFDYWGQGTLVTVSS | 31 | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIK | 32 |
| Avelumab | EVQLLESGGGLVQPGGSLRLSCAASGFTFSSYIMMWVRQAPGKGLEWVSSIYPSGGITFYADTVKGRFTISRDNSKNTLYLQMNSLRAEDTAVYYCARIKLGTVTTVDYWGQGTLVTVSS | 33 | QSALTQPASVSGSPGQSITISCTGTSSDVGGYNYVSWYQQHPGKAPKLMIYDVSNRPSGVSNRFSGSKSGNTASLTISGLQAEDEADYYCSSYTSSSTRVFGTGTKVTVL | 34 |
| 12A4 | QVQLVQSGAEVKKPGSSVKVSCKTSGDTFSTYAISWVRQAPGQGLEWMGGIIPIFGKAHYAQKFQGRVTITADESTSTAYMELSSLRSEDTAVYFCARKFHFVSGSPFGMDVWGQGTTVTVSS | 35 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK | 36 |

TABLE 9

Variable region sequences of anti-CD 19 antibody

Variable region amino acid sequences of anti-CD 19 antibody (The amino acids underlined in bold are CDR regions)

| Antibody code (Sequence source) | VHm | SEQ ID NO | VLm | SEQ ID NO |
|---|---|---|---|---|
| M208 | EVQLVESGGGLVKPGGSLKLSCAASGYTFTSYVMHWVRQAPGKGLEWIGYINPYNDGTKYNEKFQGRVTISSDKSISTAYMELSSLRSEDTAMYYCARGTYYYCTRVFDYWGQGTLVTVS | 37 | DIVMTQSPATLSLSPGERATLSCRSSKSLQNVNGNTYLYWFQQKPGQSPQLLIYRMSNLNSGVPDRFSGSGSGTEFTLTISSLEPEDFAVYYCMQHLEYPITFGAGTKLEIK | 38 |

TABLE 10

Variable region sequences of anti-SLAMF7 antibody

Variable region amino acid sequences of anti-SLAMF7 antibody (The amino acids underlined in bold are CDR regions)

| Antibody code (Sequence source) | VHm | SEQ ID NO | VLm | SEQ ID NO |
|---|---|---|---|---|
| Elotuzumab | HVQLVESGGG LVQPGGSLRL SCAASGFDFS RYWMSWVRQA PGKGLEWIGE INPDSSTINY APSLKDKFII SRDNAKNSLY LQMNSLRAED TAVYYCARPD GNYWYFDVWG QGTLVTVSS | 39 | DIQMTQSPSS LSASVGDRVT ITCKASQDVG IAVAWYQQKP GKVPKLLIYW ASTRHTGVPD RFSGSGSGTD FTLTISSLQP EPVATYYCQQ YSSYPYTFGQ GTKVEIK | 40 |

TABLE 11

Variable region sequences of anti-CEA antibody

Variable region amino acid sequences of anti-CEA antibody (The amino acids Underlined in bold are CDR regions)

| Antibody code (Sequence source) | VHm | SEQ ID NO | VLm | SEQ ID NO |
|---|---|---|---|---|
| HPRIA3 | QVQLVQSGSE LKKPGASVKV SCKASGYTFT VFGMNWVRQA PGQGLEWMGW INTKTGKATY VKKFKGRFVF SLDTSVSTAY LQISSLKADD TAVYYCARWD FYDYVKAMDY WGQGTTVTVS S | 41 | DIQMTQSPSS LSASVGDRVT ITCKASQNVG TNVAWYQQKP GKAPKLLIYS ASYRYSGVPS RFSGSGSGTD FTFTISSLQP EDIATYYCHQ YYTYPLFTFG QGTKVEIK | 42 |

(2) Antibodies that target other antigens

TABLE 12

Variable region sequences of anti-luciferase antibody

Variable region amino acid sequences of anti-luciferase antibody (The amino acids underlined in bold are CDR regions)

| Antibody code (Sequence source) | VHm | SEQ ID NO | VLm | SEQ ID NO |
|---|---|---|---|---|
| 4420 | EVKLDETGGG LVQPGRPMKL SCVASGFTFS DYWMNWVRQS PEKGLEWVAQ IRNKPYNYET YYSDSVKGRF TISRDDSKSS VYLQMNNLRV EDMGIYYCTG SYYGMDYWGQ GTSVTVSS | 43 | DVVMTQTPLS LPVSLGDQAS ISCRSSQSLV HSNGNTYLRW YLQKPGQSPK VLIYKVSNRF SGVPDRFSGS GSGTDFTLKI SRVEAEDLGV YFCSQSTHVP WTFGGGTKLE IK | 44 |

Sequences of Other Domains (1) Amino acid sequences of linker domains

TABLE 13

Amino acid sequences of linkers

| Domain | Code | Amino acid sequence | SEQ ID NO |
|---|---|---|---|
| Linker | Lin1 | SS | 45 |
| | Lin2 | AS | 46 |
| | Lin3 | GGGGS | 47 |
| | Lin4 | GGGSAAA | 48 |
| | Lin5 | GGGGSAS | 49 |
| | Lin6 | GRPGSRPGS | 50 |
| | Lin7 | GGGGSGGGGS | 51 |
| | Lin8 | GKSSGSGSESKS | 52 |
| | Lin9 | GSTSGSGKSSEGKG | 53 |
| | Lin10 | GGGGSGGGGSGGGGS | 54 |
| | Lin11 | GGGGSDKTHTSPPS | 55 |
| | Lin12 | EPKSSDKTHTSPPS | 56 |
| | Lin13 | GGGGSGGGGSGGGGSAS | 57 |
| | Lin14 | GSTSGSGKSSEGSGSTKG | 58 |
| | Lin15 | GSTSGSGKPGSGEGSTKG | 59 |
| | Lin16 | GGGGSGGGGSGGGGSGGGGS | 60 |
| | Lin15 | DKTHTSPPSGGGGSGGGGS | 61 |
| | Lin16 | APAPAPAPAPAP | 62 |
| | Lin17 | AEAAAKEAAAKA | 63 |
| | Lin18 | GGGGSGGGGSGGGGSGGGGS GGGGSGGGGSAS | 64 |

TABLE 13-continued

Amino acid sequences of linkers

| Domain | Code | Amino acid sequence | SEQ ID NO |
|---|---|---|---|
|  | Lin19 | AGGGSGGGGSGGGGSGGGGS GGGGSGGGGSGGGGSAS | 65 |

(2) Amino acid sequences of hinge domains

TABLE 14

Amino acid sequences of hinges

| Domain | Code | Amino acid sequence | SEQ ID NO |
|---|---|---|---|
| Hinge | Hin1 | DKTHTCP | 66 |
|  | Hin2 | EPKSSDKTHTCP | 67 |
|  | Hin3 | GGGGSDKTHTCP | 68 |
|  | Hin4 | RGRGSDKTHTCP | 69 |
|  | Hin5 | DGDGSDKTHTCP | 70 |
|  | Hin6 | GRGRGSDKTHTCP | 71 |
|  | Hin7 | ASTRGRGSDKTHTCP | 72 |
|  | Hin8 | GQPDGDASDKTHTCP | 73 |
|  | Hin9 | DKTHT | 74 |

(3) Amino acid sequences of CL domain of light chain constant region

TABLE 15

Amino acid sequences of CL

| Domain | NO | Amino acid sequence | SEQ ID NO |
|---|---|---|---|
| CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
|  | Lc2 | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | 76 |
|  | Lc3 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS | 77 |
|  | Lc4 | GQPKAAPSVTLFPPSSEELQANKATLVCLISDFYPGAVTVAWKADSSPAKAGVETTTPSKQSNNKYAASSYLSLTPEQWKSHKSYSCQVTHEGSTVEKTVAPTECS | 78 |
|  | Lc5 | GQPKAAPSVTLFPPSSEELQANKATLVCLISDFYPGAVKVAWKADGSPVNTGVETTTPSKQSNNKYAASSYLSLTPEQWKSHRSYSCQVTHEGSTVEKTVAPAECS | 79 |
|  | Lc6 | GQPKAAPTVTLFPPSSEELQANKATLVCLISDFYPGAVKVAWKADSSPAKAGVETTTPSKQSNNKYAASSYLSLTPEQWKSHKSYSCQVTHEGSTVEKTVAPTECS | 80 |
|  | Lc7 | VAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 81 |

(4) Amino acid sequences of CH1 domain of heavy chain constant region

TABLE 16

Amino acid sequences of CH1

| Domain | Code | Amino acid sequence | SEQ ID NO |
|---|---|---|---|
| CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |

Specific Information of Fc Modification

Fc amino acids are numbered according to the Kabat numbering. The "Kabat numbering" refers to the numbering system set forth by Kabat et al., U.S. Dept. of Health and Human Services, "Sequence of Proteins of Immunological Interest" (1983). The specific numbering is shown in the table below:

TABLE 17

Fc amino acid numbering based on Kabat numbering system

| 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 |
|---|---|---|---|---|---|---|---|---|---|---|---|---|---|---|---|---|---|---|---|---|---|---|---|---|---|
| E | P | K | S | C | D | K | T | H | T | C | P | P | C | P | A | P | E | L | L | G | G | P | S | V | F |
| 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 |
| L | F | P | P | K | P | K | D | T | L | M | I | S | R | T | P | E | V | T | C | V | V | V | D | V | S |
| 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 |
| H | E | D | P | E | V | K | F | N | W | Y | V | D | G | V | E | V | H | N | A | K | T | K | P | R | E |
| 294 | 295 | 296 | 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 |
| E | Q | Y | N | S | T | Y | R | V | V | S | V | L | T | V | L | H | Q | D | W | L | N | G | K | E | Y |
| 320 | 321 | 322 | 323 | 324 | 325 | 326 | 327 | 328 | 329 | 330 | 331 | 332 | 333 | 334 | 335 | 336 | 337 | 338 | 339 | 340 | 341 | 342 | 343 | 344 | 345 |
| K | C | K | V | S | N | K | A | L | P | A | P | I | E | K | T | I | S | K | A | K | G | Q | P | R | E |
| 346 | 347 | 348 | 349 | 350 | 351 | 352 | 353 | 354 | 355 | 356 | 357 | 358 | 359 | 360 | 361 | 362 | 363 | 364 | 365 | 366 | 367 | 368 | 369 | 370 | 371 |
| P | Q | V | Y | T | L | P | P | S | R | D | E | L | T | K | N | Q | V | S | L | T | C | L | V | K | G |
| 372 | 373 | 374 | 375 | 376 | 377 | 378 | 379 | 380 | 381 | 382 | 383 | 384 | 385 | 386 | 387 | 388 | 389 | 390 | 391 | 392 | 393 | 394 | 395 | 396 | 397 |
| F | Y | P | S | D | I | A | V | E | W | E | S | N | G | Q | P | E | N | N | Y | K | T | T | P | P | V |
| 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 |
| L | D | S | D | G | S | F | F | L | Y | S | K | L | T | V | D | K | S | R | W | Q | Q | G | N | V | F |
| 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | |
| S | C | S | V | M | H | E | A | L | H | N | H | Y | T | Q | K | S | L | S | L | S | P | G | K | — | | wherein,
amino acids at positions 221 to 227 are the hinge domain,
amino acids at positions 228 to 340 are the CH2 domain of the second constant region of the heavy chain,
amino acids at positions 341 to 447 are the CH3 domain of the third constant region of the heavy chain.

In one aspect, the CH2 domain contains one or more substitutions to reduce the binding ability of Fc to FcγR. The amino acid residues that can be substituted include, but are not limited to, E233, L234, L235, G236, D265, D270, K274, Y296, N297, Y300, L309, A327, P329, P331, A339. Non-limiting examples of these substitution combinations are listed in the table below:

TABLE 18

CH2 amino acid substitution combination that reduces the binding ability of Fc to FcγR

| Combination No. | Substitutions on CH2 |
|---|---|
| CH2-1 | L234A, L235A |
| CH2-2 | L234A, L235A, P329G |
| CH2-3 | L234F, L235E, P331S |
| CH2-4 | L234F, L235E, P331A |
| CH2-5 | N297A |
| CH2-6 | N297G |
| CH2-7 | N297Q |
| CH2-8 | D265A, N297Q, A327Q |
| CH2-9 | Completely deletion of CH2 domain |
| CH2-10 | E233P, L234V, L235A, G236-*, K274Q, Y296F, Y300F, L309V, A327G, A339T |
| CH2-11 | C229S, E233P, L234V, L235A, G236-*, K274Q, Y296F, Y300F, L309V, A327G, A339T |
| CH2-12 | C229A, E233P, L234V, L235A, G236-*, K274Q, Y296F, Y300F, L309V, A327G, A339T |
| CH2-13 | C229G, E233P, L234V, L235A, G236-*, K274Q, Y296F, Y300F, L309V, A327G, A339T |
| CH2-14 | C229P, E233P, L234V, L235A, G236-*, K274Q, Y296F, Y300F, L309V, A327G, A339T |
| CH2-15 | E233P, L234V, L235A, G236-*, D265A, K274Q, Y296F, Y300F, L309V, A327G, A339T |
| CH2-16 | E233P, L234V, L235A, G236-*, D270A, K274Q, Y296F, Y300F, L309V, A327G, A339T |
| CH2-17 | E233P, L234V, L235A, G236-*, D265A, D270A, K274Q, Y296F, Y300F, L309V, A327G, A339T |

*Represents that the residue at that position is deleted.

The sequence and numbering of the Fc after deleting the glycine residue at position 236 in combination 10 in the above table are as follows:

TABLE 19

Fc (combination 10 of table 6) amino acid numbering after residue deletion based on kabat numbering system

| 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 |
|---|---|---|---|---|---|---|---|---|---|---|---|---|---|---|---|---|---|---|---|---|---|---|---|---|---|
| E | P | K | S | C | D | K | T | H | T | C | P | P | C | P | A | P | P | V | A | — | G | P | S | V | F |
| 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 |
| L | F | P | P | K | P | K | D | T | L | M | I | S | R | T | P | E | V | T | C | V | V | V | D | V | S |
| 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 |
| H | E | D | P | E | V | Q | F | N | W | Y | V | D | G | V | E | V | H | N | A | K | T | K | P | R | E |
| 294 | 295 | 296 | 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 |
| E | Q | F | N | S | T | F | R | V | V | S | V | L | T | V | V | H | Q | D | W | L | N | G | K | E | Y |
| 320 | 321 | 322 | 323 | 324 | 325 | 326 | 327 | 328 | 329 | 330 | 331 | 332 | 333 | 334 | 335 | 336 | 337 | 338 | 339 | 340 | 341 | 342 | 343 | 344 | 345 |
| K | C | K | V | S | N | K | G | L | P | A | P | I | E | K | T | I | S | K | T | K | G | Q | P | R | E |
| 346 | 347 | 348 | 349 | 350 | 351 | 352 | 353 | 354 | 355 | 356 | 357 | 358 | 359 | 360 | 361 | 362 | 363 | 364 | 365 | 366 | 367 | 368 | 369 | 370 | 371 |
| P | Q | V | Y | T | L | P | P | S | R | D | E | L | T | K | N | Q | V | S | L | T | C | L | V | K | G |
| 372 | 373 | 374 | 375 | 376 | 377 | 378 | 379 | 380 | 381 | 382 | 383 | 384 | 385 | 386 | 387 | 388 | 389 | 390 | 391 | 392 | 393 | 394 | 395 | 396 | 397 |
| F | Y | P | S | D | I | A | V | E | W | E | S | N | G | Q | P | E | N | N | Y | K | T | T | P | P | V |

TABLE 19-continued

Fc (combination 10 of table 6) amino acid numbering after residue deletion based on kabat numbering system

| 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 |
|---|---|---|---|---|---|---|---|---|---|---|---|---|---|---|---|---|---|---|---|---|---|---|---|---|---|
| L | D | S | D | G | S | F | F | L | Y | S | K | L | T | V | D | K | S | R | W | Q | Q | G | N | V | F |
| 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 | 448 | |
| S | C | S | V | M | H | E | A | L | H | N | H | Y | T | Q | K | S | L | S | L | S | P | G | K | — | |

In the above table, the glycine at position 236 (G236) is deleted, but the amino acid numbering "236" is retained, which is represented by "–".

The CH3 domain of the antibody can be modified to improve the efficiency of heterodimer pairing. For example, in some aspects, compared with the wild-type antibody fragments, the Fc fragment of the heavy chain of the monovalent unit and/or the Fc fragment of the fusion peptide may contain one or more substitutions, which form a knob-into-hole. The knob-into-hole configuration is known in the art. See, for example, Ridgway et al., "'Knob-into-holes' engineering of antibody CH3 domains for heavy chain heterodimerization," Protein Engineering 9(7):617-21 (1996).

On the one hand, T366 on a CH3 domain is substituted with a relatively large amino acid residue, such as tyrosine (Y) or tryptophan (W). Then, Y407 on the other CH3 domain can be substituted with a relatively small amino acid residue, such as threonine (T), alanine (A) or valine (V). Some non-limiting examples of these substitution combinations are shown in table 20 below.

TABLE 20

Fc amino acid substitution combinations forms a knob-in-hole structure between different fc to improve the efficiency of heterodimer pairing

| Combination No. | Substitutions on one CH3 | Substitutions on another CH3 |
|---|---|---|
| CH3-1 | T366W | Y407A |
| CH3-2 | T366W | Y407V |
| CH3-3 | T366Y | Y407A |
| CH3-4 | T366Y | Y407V |
| CH3-5 | T366W | T366S, L368A, Y407V |

In one aspect, one of the CH3 domains contains one or more substitutions, which are substituted with positively charged amino acid residues under physiological conditions, while another CH3 domain contains one or more substitutions, which are substituted with one or more negatively charged amino acid residues under physiological conditions. In one aspect, the positively charged amino acid residues may be arginine (R), histidine (H) or lysine (K). On the other hand, the negatively charged amino acid residues may be aspartic acid (D) or glutamic acid (E). The amino acid residues that can be substituted include, but are not limited to, D356, L368, K392, D399, and K409. Non-limiting examples of these substitution combinations are listed in Table 21 below.

TABLE 21

CH3 amino acid substitution combinations forms an ionic bond between different Fc to improve the efficiency of heterodimer pairing

| Combination No. | Substitutions on one CH3 | Substitutions on another CH3 |
|---|---|---|
| CH3-6 | D356K D399K | K392D K409D |
| CH3-7 | L368R D399K | K392D K409D |
| CH3-8 | L368K D399K | K392D K409D |
| CH3-9 | L368R D399K | K409D |
| CH3-10 | L368K D399K | K409D |
| CH3-11 | L368R | K409D |
| CH3-12 | L368K | K409D |

On one hand, 5354 on one CH3 domain is substituted with cysteine, and Y349 on another CH3 domain is also substituted with cysteine. The two residues at the substituted position form a disulfide bond. The following table shows an example of this substitution combination.

TABLE 22

CH3 amino acid substitution combinations forms a disulfide bond between different Fc to improve the efficiency of heterodimer pairing

| Combination No. | Substitutions on one CH3 | Substitutions on another CH3 |
|---|---|---|
| CH3-13 | S354C | Y349C |

In certain aspects, the antibody may comprise a CH2 that reduces the binding to FcγR or a CH3 that improves the heterodimer pairing, or both.

On one hand, H435 and Y436 on one CH3 domain are substituted with arginine and phenylalanine, respectively. Such substitution results in a significant reduction of the binding ability of Fc to protein A, thereby leading to different protein A-binding activities between heterodimers and homodimers, and thus it is easy to separate the two components in the process of affinity chromatography. An example of this substitution combination is shown in the following table.

TABLE 23

One amino acid substitution on CH3 leads to a decrease in binding ability to protein a

| Combination No. | Substitution on CH3 |
|---|---|
| CH3-14 | H435R, Y436F |

In the above Table 18 to Table 23, amino acid substitution combination in different domains can be constructed according to the "hinge-CH2-CH3" to form an intact Fc fragment, which satisfies the following requirements: (1) reducing the binding ability to FcγR, (2) facilitating the formation of heterodimers, (3) changing the binding ability to protein A.

Examples of Some Specific Fc Sequences

TABLE 24

CH2 amino acid sequence of Fc with reduced FcγR binding ability

| Combination No. | Amino acid sequence of CH2 | SEQ ID NO |
|---|---|---|
| WT | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 83 |
| AAG | PCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAK | 84 |
| FES | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 85 |
| FEG | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAGIEKTISKAK | 86 |
| N297A | PCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAK | 87 |
| N297G | PCPAPELLGGPSVFLFPPKPKDTLMISRTPEVTCVVVDVSHEDPEVKFNVVYVDGVEVHNAKTKPREEQYGSTYRVVSVLTVLHQDWLNGKEYKCKVSNKALPAPIEKTISKAK | 88 |
| N297Q | PCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAK | 89 |
| LALA | PCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 90 |
| LALANQ | PCPAPEAAGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAK | 91 |
| AAQ | PCPAPELLGGPSVFLFPPKPKDTLMISRTPEVTCVVVAVSHEDPEVKFNWYVDGVEVHNAKTKPREEQYASTYRVVSVLTVLHQDWLNGKEYKCKVSNKQLPAPIEKTISKAK | 92 |
| AQQ | PCPAPELLGGPSVFLFPPKPKDTLMISRTPEVTCVVVAVSHEDPEVKFNWYVDGVEVHNAKTKPREEQYQSTYRVVSVLTVLHQDWLNGKEYKCKVSNKQLPAPIEKTISKAK | 93 |
| G2CH2 | PCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 94 |
| SG2CH2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 95 |
| AG2CH2 | PAPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 96 |
| GG2CH2 | PGPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 97 |
| PG2CH2 | PPPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 98 |
| DG2CH2 | PCPAPPVAGPSVFLFPPKPKDTLMISRTPEVTCVVVAVSHEDPEVQFNWYVDGVEVHNAKTKPREEQFNSTFRVVSVLTVVHQDWLNGKEYKCKVSNKGLPAPIEKTISKTK | 99 |
| G2DCH2 | PCPAPPVAGPSVFLFPPKPKDTLMISRTPEVTCVVVDVSHEAPEVQFNWYVDGVEVHNAKTKPREEQFNSTFRVVSVLTVVHQDWLNGKEYKCKVSNKGLPAPIEKTISKTK | 100 |
| DG2DCH2 | PCPAPPVAGPSVFLFPPKPKDTLMISRTPEVTCVVVAVSHEAPEVQFNWYVDGVEVHNAKTKPREEQFNSTFRVVSVLTVVHQDWLNGKEYKCKVSNKGLPAPIEKTISKTK | 101 |
| PG2-GA | PPPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKALPAPIEKTISKTK | 122 |
| PG2-TA | PPPAPPVAGPSVFLFPPKPKDTLMISRTPEVTCVVVDVSHEDPEVQFNWYVDGVEVHNAKTKPREEQFNSTFRVVSVLTV | 123 |

TABLE 24-continued

CH2 amino acid sequence of Fc with reduced FcγR binding ability

| Combination No. | Amino acid sequence of CH2 | SEQ ID NO |
|---|---|---|
| | VHQDWLNGKEYKCKVSNKGL PAPIEKTISKAK | |
| G2D-GA | PCPAPPVAGPSVFLFPPKPK DTLMISRTPEVTCVVVDVSH EAPEVQFNWYVDGVEVHNAK TKPREEQFNSTFRVVSVLTV VHQDWLNGKEYKCKVSNKAL PAPIEKTISKTK | 124 |
| G2D-TA | PCPAPPVAGPSVFLFPPKPK DTLMISRTPEVTCVVVDVSH EAPEVQFNWYVDGVEVHNAK TKPREEQFNSTFRVVSVLTV VHQDWLNGKEYKCKVSNKGL PAPIEKTISKAK | 125 |
| G2D-GATA | PCPAPPVAGPSVFLFPPKPK DTLMISRTPEVTCVVVDVSH EAPEVQFNWYVDGVEVHNAK TKPREEQFNSTFRVVSVLTV VHQDWLNGKEYKCKVSNKAL PAPIEKTISKAK | 126 |
| PDG2D | PPPAPPVAGPSVFLFPPKPK DTLMISRTPEVTCVVVAVSH EAPEVQFNWYVDGVEVHNAK TKPREEQFNSTFRVVSVLTV VHQDWLNGKEYKCKVSNKGL PAPIEKTISKTK | 127 |
| C229LG2CH2 | PLPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 128 |
| C229FG2CH2 | PFPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 129 |
| C229RG2CH2 | PRPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 130 |
| C229VG2CH2 | PVPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 131 |
| C229QG2CH2 | PQPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 132 |
| C229KG2CH2 | PKPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 133 |
| C229DG2CH2 | PDPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 134 |
| C229IG2CH2 | PIPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 135 |
| C229YG2CH2 | PYPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 136 |
| C229NG2CH2 | PNPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 137 |
| C229MG2CH2 | PMPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 138 |
| C229TG2CH2 | PTPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 139 |
| C229HG2CH2 | PHPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 140 |
| C229EG2CH2 | PEPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 141 |
| C229WG2CH2 | PWPAPPVAGPSVFLFPPKPK DTLMISRTPEVTCVVVDVSH EDPEVQFNWYVDGVEVHNAK TKPREEQFNSTFRVVSVLTV VHQDWLNGKEYKCKVSNKGL PAPIEKTISKTK | 142 |
| D265PG2CH2 | PCPAPPVAGPSVFLFPPKPK DTLMISRTPEVTCVVVPVSH EDPEVQFNWYVDGVEVHNAK TKPREEQFNSTFRVVSVLTV VHQDWLNGKEYKCKVSNKGL PAPIEKTISKTK | 143 |
| D265KG2CH2 | PCPAPPVAGPSVFLFPPKPK DTLMISRTPEVTCVVVKVSH EDPEVQFNWYVDGVEVHNAK | 144 |

TABLE 24-continued

CH2 amino acid sequence of Fc with reduced FcγR binding ability

| Combination No. | Amino acid sequence of CH2 | SEQ ID NO |
|---|---|---|
| | TKPREEQFNSTFRVVSVLTV VHQDWLNGKEYKCKVSNKGL PAPIEKTISKTK | |
| D265SG2CH2 | PCPAPPVAGPSVFLFPPKPK DTLMISRTPEVTCVVVSVSH EDPEVQFNWYVDGVEVHNAK TKPREEQFNSTFRVVSVLTV VHQDWLNGKEYKCKVSNKGL PAPIEKTISKTK | 145 |
| D265FG2CH2 | PCPAPPVAGPSVFLFPPKPK DTLMISRTPEVTCVVVFVSH EDPEVQFNWYVDGVEVHNAK TKPREEQFNSTFRVVSVLTV VHQDWLNGKEYKCKVSNKGL PAPIEKTISKTK | 146 |
| D265RG2CH2 | PCPAPPVAGPSVFLFPPKPK DTLMISRTPEVTCVVVRVSH EDPEVQFNWYVDGVEVHNAK TKPREEQFNSTFRVVSVLTV VHQDWLNGKEYKCKVSNKGL PAPIEKTISKTK | 147 |
| D265LG2CH2 | PCPAPPVAGPSVFLFPPKPK DTLMISRTPEVTCVVVLVSH EDPEVQFNWYVDGVEVHNAK TKPREEQFNSTFRVVSVLTV VHQDWLNGKEYKCKVSNKGL PAPIEKTISKTK | 148 |
| D265GG2CH2 | PCPAPPVAGPSVFLFPPKPK DTLMISRTPEVTCVVVGVSH EDPEVQFNWYVDGVEVHNAK TKPREEQFNSTFRVVSVLTV VHQDWLNGKEYKCKVSNKGL PAPIEKTISKTK | 149 |
| D265TG2CH2 | PCPAPPVAGPSVFLFPPKPK DTLMISRTPEVTCVVVTVSH EDPEVQFNWYVDGVEVHNAK TKPREEQFNSTFRVVSVLTV VHQDWLNGKEYKCKVSNKGL PAPIEKTISKTK | 150 |
| D265YG2CH2 | PCPAPPVAGPSVFLFPPKPK DTLMISRTPEVTCVVVYVSH EDPEVQFNWYVDGVEVHNAK TKPREEQFNSTFRVVSVLTV VHQDWLNGKEYKCKVSNKGL PAPIEKTISKTK | 151 |
| D265WG2CH2 | PCPAPPVAGPSVFLFPPKPK DTLMISRTPEVTCVVVWVSH EDPEVQFNWYVDGVEVHNAK TKPREEQFNSTFRVVSVLTV VHQDWLNGKEYKCKVSNKGL PAPIEKTISKTK | 152 |
| D265HG2CH2 | PCPAPPVAGPSVFLFPPKPK DTLMISRTPEVTCVVVHVSH EDPEVQFNWYVDGVEVHNAK TKPREEQFNSTFRVVSVLTV VHQDWLNGKEYKCKVSNKGL PAPIEKTISKTK | 153 |
| D265VG2CH2 | PCPAPPVAGPSVFLFPPKPK DTLMISRTPEVTCVVVVVSH EDPEVQFNWYVDGVEVHNAK TKPREEQFNSTFRVVSVLTV VHQDWLNGKEYKCKVSNKGL PAPIEKTISKTK | 154 |
| D265QG2CH2 | PCPAPPVAGPSVFLFPPKPK DTLMISRTPEVTCVVVQVSH EDPEVQFNWYVDGVEVHNAK TKPREEQFNSTFRVVSVLTV VHQDWLNGKEYKCKVSNKGL PAPIEKTISKTK | 155 |
| D265EG2CH2 | PCPAPPVAGPSVFLFPPKPK DTLMISRTPEVTCVVVEVSH EDPEVQFNWYVDGVEVHNAK TKPREEQFNSTFRVVSVLTV VHQDWLNGKEYKCKVSNKGL PAPIEKTISKTK | 156 |
| D265MG2CH2 | PCPAPPVAGPSVFLFPPKPK DTLMISRTPEVTCVVVMVSH EDPEVQFNWYVDGVEVHNAK TKPREEQFNSTFRVVSVLTV VHQDWLNGKEYKCKVSNKGL PAPIEKTISKTK | 157 |
| D265NG2CH2 | PCPAPPVAGPSVFLFPPKPK DTLMISRTPEVTCVVVNVSH EDPEVQFNWYVDGVEVHNAK TKPREEQFNSTFRVVSVLTV VHQDWLNGKEYKCKVSNKGL PAPIEKTISKTK | 158 |
| D265IG2CH2 | PCPAPPVAGPSVFLFPPKPK DTLMISRTPEVTCVVVIVSH EDPEVQFNWYVDGVEVHNAK TKPREEQFNSTFRVVSVLTV VHQDWLNGKEYKCKVSNKGL PAPIEKTISKTK | 159 |
| D270LG2CH2 | PCPAPPVAGPSVFLFPPKPK DTLMISRTPEVTCVVVDVSH ELPEVQFNWYVDGVEVHNAK TKPREEQFNSTFRVVSVLTV VHQDWLNGKEYKCKVSNKGL PAPIEKTISKTK | 160 |
| D270RG2CH2 | PCPAPPVAGPSVFLFPPKPK DTLMISRTPEVTCVVVDVSH ERPEVQFNWYVDGVEVHNAK TKPREEQFNSTFRVVSVLTV VHQDWLNGKEYKCKVSNKGL PAPIEKTISKTK | 161 |
| D270PG2CH2 | PCPAPPVAGPSVFLFPPKPK DTLMISRTPEVTCVVVDVSH EPPEVQFNWYVDGVEVHNAK TKPREEQFNSTFRVVSVLTV VHQDWLNGKEYKCKVSNKGL PAPIEKTISKTK | 162 |
| D270GG2CH2 | PCPAPPVAGPSVFLFPPKPK DTLMISRTPEVTCVVVDVSH EGPEVQFNWYVDGVEVHNAK TKPREEQFNSTFRVVSVLTV VHQDWLNGKEYKCKVSNKGL PAPIEKTISKTK | 163 |
| D270VG2CH2 | PCPAPPVAGPSVFLFPPKPK DTLMISRTPEVTCVVVDVSH EVPEVQFNWYVDGVEVHNAK TKPREEQFNSTFRVVSVLTV VHQDWLNGKEYKCKVSNKGL PAPIEKTISKTK | 164 |
| D270HG2CH2 | PCPAPPVAGPSVFLFPPKPK DTLMISRTPEVTCVVVDVSH | 165 |

TABLE 24-continued

CH2 amino acid sequence of Fc with reduced FcγR binding ability

| Combination No. | Amino acid sequence of CH2 | SEQ ID NO |
|---|---|---|
| | EHPEVQFNWYVDGVEVHNAKTKPREEQFNSTFRVVSVLTVVHQDWLNGKEYKCKVSNKGLPAPIEKTISKTK | |
| D270YG2CH2 | PCPAPPVAGPSVFLFPPKPKDTLMISRTPEVTCVVVDVSHEYPEVQFNWYVDGVEVHNAKTKPREEQFNSTFRVVSVLTVVHQDWLNGKEYKCKVSNKGLPAPIEKTISKTK | 166 |
| D270IG2CH2 | PCPAPPVAGPSVFLFPPKPKDTLMISRTPEVTCVVVDVSHEIPEVQFNWYVDGVEVHNAKTKPREEQFNSTFRVVSVLTVVHQDWLNGKEYKCKVSNKGLPAPIEKTISKTK | 167 |
| D270EG2CH2 | PCPAPPVAGPSVFLFPPKPKDTLMISRTPEVTCVVVDVSHEEPEVQFNWYVDGVEVHNAKTKPREEQFNSTFRVVSVLTVVHQDWLNGKEYKCKVSNKGLPAPIEKTISKTK | 168 |
| D270FG2CH2 | PCPAPPVAGPSVFLFPPKPKDTLMISRTPEVTCVVVDVSHEFPEVQFNWYVDGVEVHNAKTKPREEQFNSTFRVVSVLTVVHQDWLNGKEYKCKVSNKGLPAPIEKTISKTK | 169 |
| D270KG2CH2 | PCPAPPVAGPSVFLFPPKPKDTLMISRTPEVTCVVVDVSHEKPEVQFNWYVDGVEVHNAKTKPREEQFNSTFRVVSVLTVVHQDWLNGKEYKCKVSNKGLPAPIEKTISKTK | 170 |
| D270WG2CH2 | PCPAPPVAGPSVFLFPPKPKDTLMISRTPEVTCVVVDVSHEWPEVQFNWYVDGVEVHNAKTKPREEQFNSTFRVVSVLTVVHQDWLNGKEYKCKVSNKGLPAPIEKTISKTK | 171 |
| D270SG2CH2 | PCPAPPVAGPSVFLFPPKPKDTLMISRTPEVTCVVVDVSHESPEVQFNWYVDGVEVHNAKTKPREEQFNSTFRVVSVLTVVHQDWLNGKEYKCKVSNKGLPAPIEKTISKTK | 172 |
| D270TG2CH2 | PCPAPPVAGPSVFLFPPKPKDTLMISRTPEVTCVVVDVSHETPEVQFNWYVDGVEVHNAKTKPREEQFNSTFRVVSVLTVVHQDWLNGKEYKCKVSNKGLPAPIEKTISKTK | 173 |
| D270QG2CH2 | PCPAPPVAGPSVFLFPPKPKDTLMISRTPEVTCVVVDVSHEQPEVQFNWYVDGVEVHNAKTKPREEQFNSTFRVVSVLTVVHQDWLNGKEYKCKVSNKGLPAPIEKTISKTK | 174 |
| D270MG2CH2 | PCPAPPVAGPSVFLFPPKPKDTLMISRTPEVTCVVVDVSHEMPEVQFNWYVDGVEVHNAKTKPREEQFNSTFRVVSVLTVVHQDWLNGKEYKCKVSNKGLPAPIEKTISKTK | 175 |
| D270NG2CH2 | PCPAPPVAGPSVFLFPPKPKDTLMISRTPEVTCVVVDVSHENPEVQFNWYVDGVEVHNAKTKPREEQFNSTFRVVSVLTVVHQDWLNGKEYKCKVSNKGLPAPIEKTISKTK | 176 |

TABLE 25

CH3 amino acid sequence of Fc that forms a heterodimer

| Combination No. | Amino acid Sequence of CH3-A | SEQ ID NO | Amino acid Sequence of CH3-B | SEQ ID NO |
|---|---|---|---|---|
| WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 103 |
| W:SAV | GQPREPQVYTLPPSRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 104 | GQPREPQVYTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 105 |
| CSAVRF:CW | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPGK | 106 | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 107 |
| CW:CSAV | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 108 | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 109 |

TABLE 25-continued

CH3 amino acid sequence of Fc that forms a heterodimer

| Combination No. | Amino acid Sequence of CH3-A | SEQ ID NO | Amino acid Sequence of CH3-B | SEQ ID NO |
|---|---|---|---|---|
| WDD:RKA | GQPREPQVYTLPPSRDELTKNQVSLWCLVKGFYPSDIAVEWESNGQPENNYDTTPPVLDSDGSFFLYSDLTVDKSRWQQGNVFSCSVMHEALHNHYTQKSLSLSPGK | 110 | GQPREPQVYTLPPSRDELTKNQVSLTCRVKGFYPSDIAVEWESNGQPENNYKTTPPVLKSDGSFFLASKLTVDKSRWQQGNVFSCSVMHEALHNHYTQKSLSLSPGK | 111 |
| DD:KK | GQPREPQVYTLPPSRDELTKNQVSLTCLVKGFYPSDIAVEWESNGQPENNYDTTPPVLDSDGSFFLYSDLTVDKSRWQQGNVFSCSVMHEALHNHYTQKSLSLSPGK | 112 | GQPREPQVYTLPPSRKELTKNQVSLTCLVKGFYPSDIAVEWESNGQPENNYKTTPPVLKSDGSFFLYSKLTVDKSRWQQGNVFSCSVMHEALHNHYTQKSLSLSPGK | 113 |
| CSAV:CWRF | GQPREPQVCTLPPSRDELTKNQVSLSCAVKGFYPSDIAVEWESNGQPENNYKITPPVLDSDGSFFLVSKLTVDKSRWQQGNVFSCSVMHEALHNHYTQKSLSLSPGK | 114 | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNRFTQKSLSLSPGK | 115 |

Specific Sequences of Antigens

TABLE 26

Amino acid sequence of tumor antigen

| Name of tumor Antigen (Source) | Amino acid sequence | SEQ ID NO |
|---|---|---|
| Human CD38 (Source: UniProtKB-P28907) | VPRWRQQWSGPGTTKRFPETVLARCVKYTEIHPEMRHVDCQSVWDAFKGAFISKHPCNITEEDYQPLMKLGTQTVPCNKILLWSRIKDLAHQFTQVQRDMFTLEDTLLGYLADDLTWCGEFNTSKINYQSCPDWRKDCSNNPVSVFWKTVSRRFAEAACDVVHVMLNGSRSKIFDKNSTFGSVEVHNLQPEKVQTLEAWVIHGGREDSRDLCQDPTIKELESIISKRNIQFSCKNIYRPDKFLQCVKNPEDSSCTSEI | 116 |
| Human BCMA (Source: UniProtKB-Q02223) | MLQMAGQCSQNEYFDSLLHACIPCQLRCSSNTPPLTCQRYCNASVTNSVKGTNA | 117 |
| Human PD-L1 (Source: UniProtKB-Q9NZQ7) | FTVTVPKDLYVVEYGSNMTIECKFPVEKQLDLAALIVYWEMEDKNIIQFVHGEEDLKVQHSSYRQRARLLKDQLSLGNAA | 118 |
| Human SLAMF7 (Source: UniProtKB-Q9NQ25) | LQITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNERSGPVKELVGSVGGAVTFPLKSKVKQVDSIVWTFNTTPLVTIQPEGGTIIVTQNRNRERVDFPDGGYSLKLSKLKKNDSGIYYVGIYSSSLQQPSTQEYVLHVYEHLSKPKVTMGLQSNKNGTCVTNLTCCMEHGEEDVIYTWKALGQAANESHNGSILPISWRWGESDMTFICVARNPVSRNFSSPILARKLCEGAADDPDSSM | 119 |
| human CEA (Source: UniProtKB-P06731) | KLTIESTPFNVAEGKEVLLLVHNLPQHLFGYSWYKGERVDGNRQIIGYVIGTQQATPGPAYSGREIIYPNASLLIQNIIQNDTGFYTLHVIKSDLVNEEATGQFRVYPELPKPSISSNNSKPVEDKDAVAFTCEPETQDATYLWWVNNQSLPVSPRLQLSNGNRTLTLFNVTRNDTASYKCETQNPVSARRSDSVILNVLYGPDAPTISPLNTSYRSGENLNLSCHAASNPPAQYSWFVNGTFQQSTQELFIPNITVNNSGSYTCQAHNSDTGLNRTTVTTITVYAEPPKPFITSNNSNPVEDEDAVALTCEPEIQNTTYLWWVNNQSLPVSPRLQLSNDNRTLTLLSVTRNDVGPYECGIQNKLSVDHSDPVILNVLYGPDDPTISPSYTYYRPGVNLSLSCHAASNPPAQYSWLIDGNIQQHTQELFISNITEKNSGLYTCQANNSASGHSRTTVKTITVSAELPKPSISSNNSKPVEDKDAVAFTCEPEAQNTTYLWWVNGQSLPVSPRLQLSNGNRTLTLFNVTRNDARAYVCGIQNSVSANRSDPVTLDVLYGPDTPIISPPDSSYLSGANLNLSCHSASNPSPQYSWRINGIPQQHTQVLFIAKITPNNNGTYACFVSXLATGRNNSIVKSITVSASGTSPGLSA | 120 |

TABLE 27

Amino acid sequence of immune cell antigen

| Name of immune cell antigen (Source) | Amino acid sequence | SEQ ID NO |
|---|---|---|
| Human CD3ε (Source: UniProtKB-P07766) | DGNEEMGGITQTPYKVSISGTTVILTCPQYPGSEILWQHNDKNIGGDEDDKNIGSDEDHLSLKEFSELEQSGYYVCYPRGSKPEDANFYLYLRARVCENCMEMD | 121 |

BRIEF DESCRIPTION OF THE DRAWINGS

FIG. 1 is a structural schematic diagram of multifunctional antibody 1, wherein

FIG. 2 is a structural schematic diagram of multifunctional antibody 2, wherein

FIG. 3 is a structural schematic diagram of multifunctional antibody 3, wherein

DETAILED DESCRIPTION OF THE INVENTION

The specific embodiments of the present disclosure will be described in detail below with reference to the accompanying drawings. The present disclosure can be implemented in many other ways which are different from those described herein, and those skilled in the art can make similar improvements without departing from the spirit of

EXAMPLE 1

Preparation Of An Antibody

A. Construction Of Antibody Expression Plasmid

According to the sequences in Tables 28 to 30, the coding sequence DNA was synthesized by Wuhan Genecreate and cloned into the vector pcDNA3.1 (purchased from Invitrogen). Then the vector was transformed into Trans10 competent cells (purchased from Beijing TransGen Biotech). After sequencing, the expression plasmid was obtained.

Figure 1A:
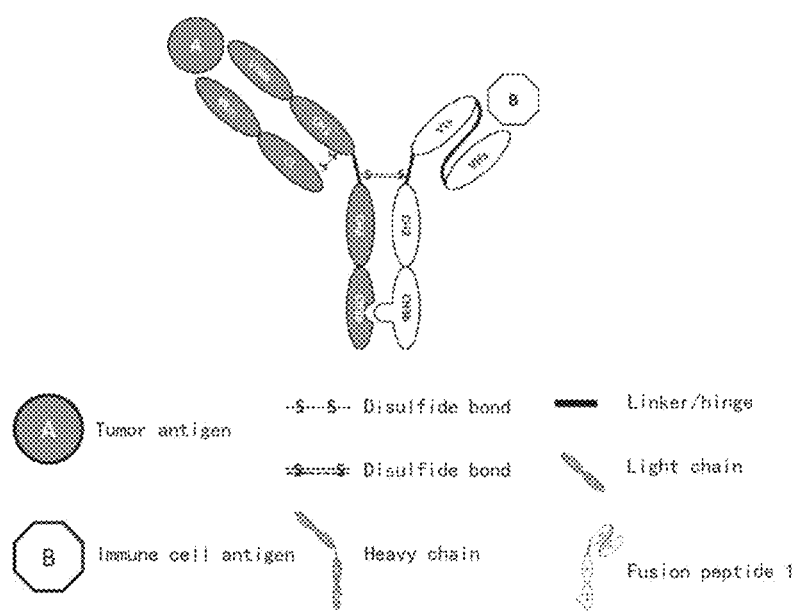
FIG. 1A is a structural schematic diagram of multifunctional antibody 1.
Figure 1B:
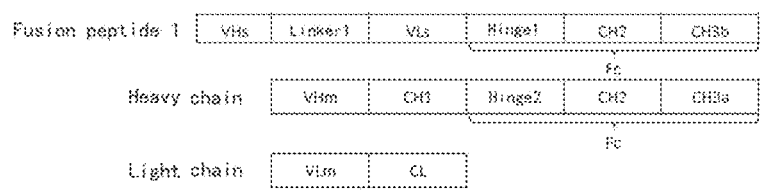
FIG. 1B is a schematic diagram of the primary protein structure of each component of the multifunctional antibody 1.

The construction of the specific expression plasmids involved is as follows:

1) The multifunctional antibody structure 1 in FIG. 1 involves construction of three plasmids. The three plasmids are a light chain expression plasmid (pL), a heavy chain expression plasmid (pH), and a fusion peptide 1 expression plasmid (pF1) respectively.
2) The multifunctional antibody structure 2 in FIG. 2 involves construction of three plasmids. The three plasmids are a light chain expression plasmid (pL), a heavy chain expression plasmid (pH), and a fusion peptide 2 expression plasmid (pF2) respectively.
3) The multifunctional antibody structure 3 in FIG. 3 involves construction of four plasmids. The four plasmids are a light chain expression plasmid (pL), a heavy chain expression plasmid (pH), a cross light chain expression plasmid (pcL) and a fusion heavy chain expression plasmid (pFH) respectively.

B. Method Of Expressing Multifunctional Antibody

Two transient transfection expression systems, CHO-S (purchased from Gibco) or 293E (purchased from ATCC), were used for transfection.

Figure 2A:
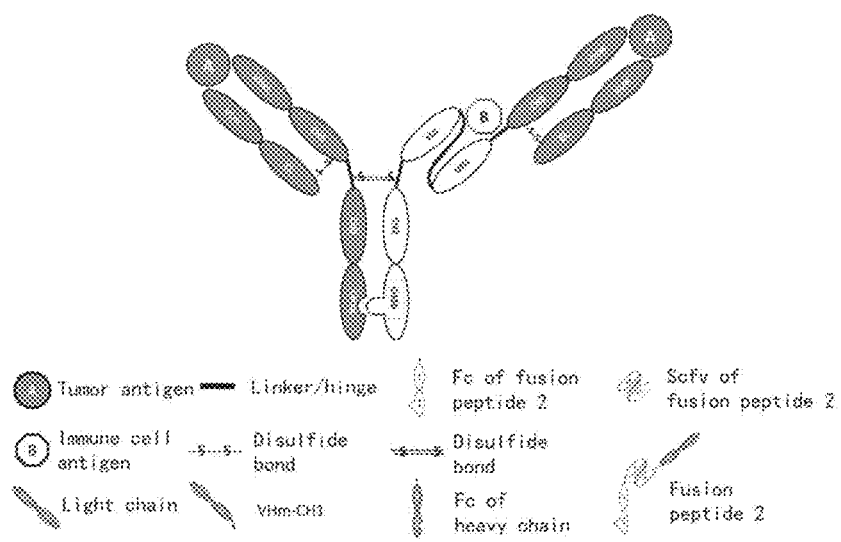
FIG. 2A is a structural schematic diagram of multifunctional antibody 2.
Figure 2B:
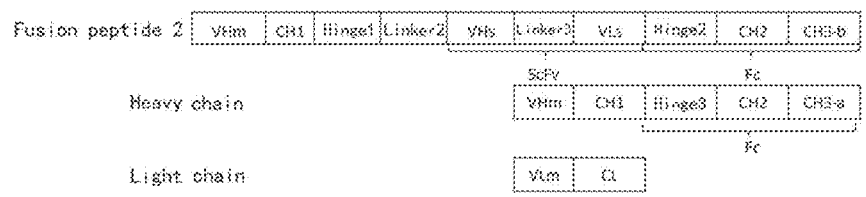
FIG. 2B is a schematic diagram of the primary protein structure of each component of the multifunctional antibody 2.
Figure 3A:
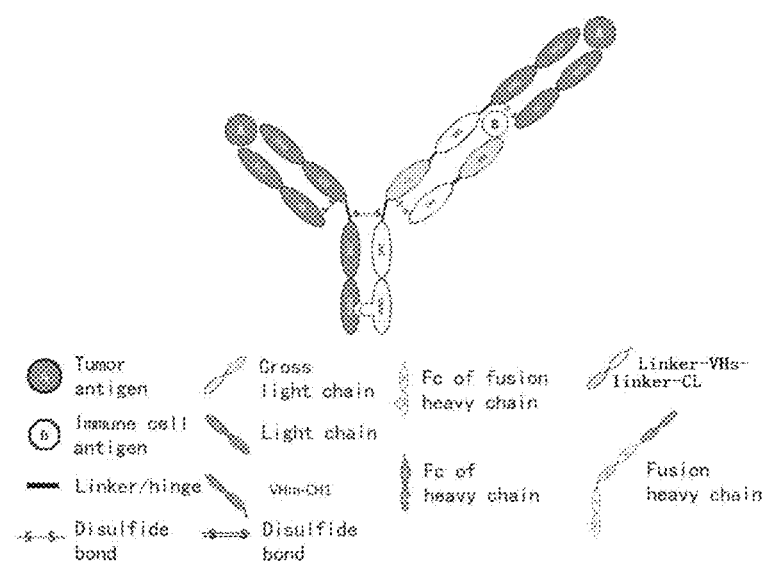
FIG. 3A is a structural schematic diagram of multifunctional antibody 3.
Figure 3B:
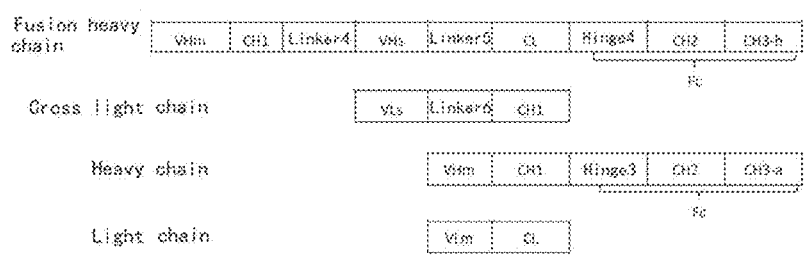
FIG. 3B is a schematic diagram of the primary protein structure of each component of the multifunctional antibody 3.

The co-transfected plasmid DNA was as follows:

1) To express the multifunctional antibody 1 shown in FIG. 1, the plasmids pL, pH and pF1 were required to be co-transfected into CHO-S or 293E cells for expression;
2) To express the multifunctional antibody 2 shown in FIG. 2, the plasmids pL, pH and pF2 were required to be co-transfected into CHO-S or 293E cells for expression;
3) To express the multifunctional antibody 3 shown in FIG. 3, the plasmids pL, pH, pcL and pFH were required to be co-transfected into CHO-S or 293E cells for expression.

In general, if two plasmids were co-transfected for expression, the mole ratio of the two plasmids may be 1:1, or any other ratio; if three plasmids were co-transfected for expression, the mole ratio of the three plasmids may be 1:1:1, or any other ratio; if four plasmids were used, the mole ratio of the four plasmids may be 1:1:1:1, or any other ratio.

C. Method Of Purifying Multifunctional Antibody:

Antibody purification method mainly includes affinity chromatography, ion exchange chromatography, hydrophobic chromatography and molecular sieves, which are routine operations in the art. For details, please refer to the Molecular Cloning Experiment Guide. The first step of the purification method in the Example was protein A affinity chromatography, and then ion exchange chromatography was used to remove aggregates, so that the final protein purity reached to more than 95%.

The codes of some specifically expressed antibodies and the amino acid sequences of corresponding variable regions of antibody are shown in the following table:

TABLE 28

Code and amino acid sequence of some antibodies with multifunctional antibody structure 1
(CDR is underlined in bold)

| Antibody Code | Poly-Peptide | Domain | Code | Amino acid sequence | SEQ ID NO |
|---|---|---|---|---|---|
| PDL1-M1-NQ | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWQQKPGQAPRGLTGGTKFLAPGTPARFSGSLLGGKAALTLSGVQPEDEAEYYCVLWYSNRWVFGGGTKLITVL | 10 |
| | | Hinge1 | Hin3 | GGGGSDKTHTCP | 68 |
| | Heavy Chain | CH2 | N297Q | PCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAK | 89 |
| | | CH3-b | CW: CSAV | GQPREPQVCTLPPSRDELTKNQVSLSCAVKGFYPSDIAVEWESNGQPENNYKLTPVLDSDGSFFLVSKLTVDKSRWQQGNVFSCSVMHEALHNHYTQKSLSLSPGK | 109 |
| | | VHm | S70 | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGGFDYWGQGTLVTVSS | 31 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Light Chain | Hinge2 | Hin1 | DKTHTCP | 66 |
| | | CH2 | N297Q | PCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAK | 89 |
| | | CH3-a | CW: CSAV | GQPREPQVTLPPCRDELTKNQVSLWCLVKGFYPSDENNYKTTPVLDSDGSFFLYSKLTVDKSRWQQGNVFSCSVMHEALHNHYTQKSLSLSPGK | 108 |
| | | VLm | S70 | DIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGTKVEIK | 32 |
| | | CL | CH1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| PDL1-M1-NQ-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRPPSKNTLYLQMNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | Hinge1 | Hin4 | RGRGSDKTHTCP | 69 |
| | Heavy Chain | CH2 | N297Q | PCPAPELLGGPSVFLFPPKPKDTLMISRTPEVTCVVVDVSHEDPEVKFNWYVDGVEVHNAKTKPREEQYQSTYRVVSVLTVLHQDWLNGKEYKCKVSNKALPAPIEKTISKAK | 89 |
| | | CH3-b | CW: CSAV | GQPREPQVCTLPPSRDELTKNQVSLSCAVKGFYPSDIAVEWESNGQPENNYKLTPVLDSDGSFFLVSKLTVDKSRWQQGNVFSCSVMHEALHNHYTQKSLSLSPGK | 109 |
| | | VHm | S70 | EVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARRHWPGGGFDYWGQGTLVTVSS | 31 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Heavy Chain | Hinge2 | Hin1 | DKTHTCP | 66 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | N297Q | PCPAPELLCGPSVFLFPPKPKDTLMISRTPEVTCVVVDVSHEDPEVKFNWYVDGVEVHNAKTKPREEQYQSTYRVVSVLTVLHQD WLNGKEYKCKVSNKALPAPIEKTISKAK | 89 |
| | | CH3-a | CW: CSAV | GQPREPQVYTLPPCRDELTKNQVSLWCLVKGFYPSDIAVEWESNGQPENNYKTTPPVLDSGSFFLYSKLTVDKSRWQQGNVFSC SVMHEALHNHYTQKSLSLSPGK | 108 |
| | Light Chain | VLm | S70 | DIQMTQSPSSLSASVGDRVTITCRASQDVSTAVAWYQQKPGKAPKLLIYSASFLYSGVPSRFSGSGSGTDFTLTISSLQPEDFATYYC QQYLYHPATFGQGTKVEIK | 32 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| PDL1-M1-G2 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | Hinge1 | CH2 | Hin4 G2CH2 | RGRGSDKTHTCP PCPAPPVAGPSVFLFPPKPKDTLMISRIPEVTCVVVDVSHEDPEVQFNWYVDGVEVHNAKTKPREEQFNSTFRVVSVLTVVHQDW LNGKEYCKVSNKGLPAPIEKTISKTK | 69 94 |
| | | CH3-b | CW: CSAV | GQPREPQVCTLPPSRDELTKNQVSLSCAVKGFYPSDIAVEWESNGQPENNYKTTPPVLDSGSFFLVSKLTVDKSRWQQGNVFSC SVMHEALHNHYTQKSLSLSPGK | 109 |
| | Heavy Chain | VHm | S70 | EVQLVESGGGLVQPGGSLRLSCAASGFTFSDSWIHWVRQAPGKGLEMWAWISPYGGSTYYADSVKGRFTISADTSKNTAYLQM NSLRAEDTAVYYCARRHWPGGFRDYWGQGTKVTSS | 31 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | Hinge2 | CH2 | Hin1 G2CH2 | DKTHTCP PCPAPPVAGPSVFLFPPKPKDTLMISRTPEVTCVVVDVSHEDPEVQFNWYVDGVEVHNAKTKPREEQFNSTFRVVSVLTVVHQDW LNGKEYCKVSNKGLPAPIEKTISKTK | 66 94 |
| | | CH3-a | CW:CS AV | GQPREPQVTLPPSRDELTKNQVSLWCLVKGFYPSDIAVEWESNGQPENNYKTTPPVLDSGSFFLYSKLTVDKSRWQQGNVFSC SVMHEALHNHYTQKSLSLSPGK | 108 |
| | Light Chain | VLm | S70 | DIQMTQSPSSLSASVGDRVTITCRASQDVSTAVAWYQQKPGKAPKLLIYSASFLYSGVPSRFSGSGSGTDFTLTISSLQPEDFATYYC QQYLYHPATFGQGTKVEIK | 32 |
| | | CL | Lc1 | RTVAAPSVFIFPPSDEQLKSGTASVVCLLNNFYPREAKVQWKVDNALQSGNSQESVTEQDSKDSTYSLSSITITSKADYEKHKVY ACEVTHQGLSSPVTKSFNRGEC | 75 |
| PDL1-M1-SG2 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | Hinge1 | CH2 | Hin4 SG2CH 2 | RGRGSDKTHTCP PSPAPPVAGPSVFLFPPKPKDTLMISRTPEVTCVVVDVSHEDPEVQFNWYVDGVEVHNAKTKPREEQFNSTFRVVSVLTVVHQDW LNGKEYCKVSNKGLPAPIEKTISKTK | 69 95 |
| | | CH3-b | CW: CSAV | GQPREPQVCTLPPSRDELTKNQVSLSCAVKGFYPSDIAVEWESNGQPENNYKTTPPVLDSGSFFLVSKLTVDKSRWQQGNVFSC SVMHEALHNHYTQKSLSLSPGK | 109 |

TABLE 28-continued

Code and amino acid sequence of some antibodies with multifunctional antibody structure 1

| Antibody Code | Polypeptide | Domain | Code | Amino acid sequence (CDR is underlined in bold) | SEQ ID NO |
|---|---|---|---|---|---|
| | Heavy Chain | VHm | S70 | EVQLVESGGGLVQPGGSLRLSCAASGFTFSSDSWIHWVRQAPGKGLEWVAWISPYGGSTYYADSVKGRFTISADTSKNTAYLQM NSLRAEDTAVYYCARRHWPGGFDYWGQGTLVTVSS | 31 |
| | | CH1 | Hin1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | SG2CH2 | DKTHTCP PSPAPPVAGPSVFLFPPKPKDTLMISRTPEVTCVVVDVSHEDPEVQFNWYVDGVEVHNAKTKPREQFNSTFRVVSVLTVHQDW LNGKEYKCKVSNKGLPAPIEKTISKTK | 66 95 |
| | | CH3-a | CW:CSAV | GQPREPQVYTLPPSRDELTKNQVSLMCLVKGFYPSDIAVEWESNGQPENNYKTTPVLDSDGSFFLYSKLTVDKSRWQQGNVFSC SVMHEALHNHYTQKSLSLSPGK | 108 |
| | Light Chain | VLm | S70 | DIQMTQSPSSLSASVGDRVTITCRASQDVSTAVAWYQQKPGKAPKLLIYSASFLYSGVPSRFSGSGSGTDFTLTISSLQPEDFATYYC QQYLYHPATFGQGTKVEIK | 32 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| PDL1-M1-FES | Fusion Peptide 1 | VHs | 2a5 | QVQLVESGGGVVQPGRSLRLSCAASGFTFSTYAMNWVRQAPGKGLEWVARIRSKYNNYATTYADVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 CH2 | Hin4 FES | RGRGSDKTHTCP PCPAPEFEGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPASIEKTISKAK | 69 85 |
| | | CH3-b | CW:CSAV | GQPREPQVCTLPPSRDELTKNQVSLSCAVKGFYPSDIAVEWESNGQPENNYKTTPVLDSDGSFFLVSKLTVDKSRWQQGNVFSC SVMHEALHNHYTQKSLSLSPGK | 109 |
| | Heavy Chain | VHm | S70 | EVQLVESGGGLVQPGGSLRLSCAASGFTFSSDSWIHWVRQAPGKGLEWVAWISPYGGSTYYADSVKGRFTISADTSKNTAYLQM NSLRAEDTAVYYCARRHWPGGQFDYWGQGTLVTVSS | 31 |
| | | CH1 | Hin1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 FES | DKTHTCP PCPAPEFEGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPASIEKTISKAK | 66 85 |
| | | CH3-a | CW:CSAV | GQPREPQVYTLPPSRDELTKNQVSLMCLVKGFYPSDIAVEWESNGQPENNYKTTPVLDSDGSFFLYSKLTVDKSRWQQGNVFSC SVMHEALHNHYTQKSLSLSPGK | 108 |
| | Light Chain | VLm | S70 | DIQMTQSPSSUSASVGDRVTITCRASQDVSTAVAWYQQKPGKAPKLLIYSASFLYSGVPSRFSGSGSGTDFTLTISSLQPEDFATYYC QQYLYHPATFGQGTKVEIK | 32 |
| | | CL | Lc1 | RTVAAPSVFIFPPSDEQLKSGTASVVCLLNNFYPREAKVQWKVDNALQSGNSQESVTEQDSKDSTYSLSSTLITLSKADYEKHKVY ACEVTHQGLSSPVTKSFNRGEC | 75 |
| Pdl1-M1-Lala | Fusion Peptide 1 | VHs | 2a5 | QVQLVESGGGVVQPGRSLRLSCAASGFTFSTYAMNWVRQAPGKGLEWVARIRSKYNNYATTYADVKDRFTISRDDSKNTLYLQ MNSLRAEDTAVYYCARHGNFGNSYVSWFAYQGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin4 | RGRGSDKTHTCP | 69 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | LALA | PCPAPEAAGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALPAPIEKTISKAK | 90 |
| | | CH3-b | CW:CSAV | GQPREPQVCTLPPSRDELTKNQVSLSCAVKGFYPSDIAVEWESNGQPENNYKITPPVLDSDGSFFLVSKLTVDKSRWQQGNVFSC SVMHEALHNHYTQKSLSLSPGK | 109 |
| | Heavy Chain | VHm | S70 | EVQLVESGGGLVQPGGSLRLSCAASGFTFSDSWIHWVRQAPGKGLEWVAWISPYGGSTYYADSVKGRFTISADTSKNTAYLQM NSLRAEDTAVYYCARRHWPGGFDYWGQGTLVTSS | 31 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 LALA | DKTHTCP PCPAPEAAGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALPAPIEKTISKAK | 66 90 |
| | | CH3-a | CW:CSAV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | S70 | DIQMTQSPSSLSASVGDRVTITCRASQDVSTAVAWYQQKPGKAPKLLIYSASFLYSGVPSRFSGSGSGTDFTLTISSLQPEDFATYYC QQYLYHPATFGQGTKVEIK | 32 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| Fusion Peptide 1 | | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYYSWFAYWGQGTLVTSS | 1 |
| | | Linker1 VLs | Lin10 2a5 | GGGGSGGGGSGGGGS QTVVTQKPSLTVSPGGTVTLTCRSSTGAVTTSNYANWVQQKPGQAPRGLIGGTNKRAPGVPARFSGSLLGGKAALTLSGVPEDK AEYYCALWYSNLWVFGGGIKVEIK | 54 2 |
| | | Hinge1 CH2 | Hin4 WT | RGRGSDKTHTCP PCPAPELLGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPAPIEKTISKAK | 69 83 |
| | | CH3-b | CW:CSAV | GQPREPQVCTLPPSRDELTKNQVSLSCAVKGFYPSDIAVEWESNGQPENNYKITPPVLDSDGSFFLVSKLTVDKSRWQQGNVFSC SVMHEALHNHYTQKSLSLSPGK | 109 |
| PDL1-M1-WT | Heavy Chain | VHm | S70 | EVQLVESGGGLVQPGGSLRLSCAASGFTFSDSWIHWVRQAPGKGLEWVAWISPYGGSTYYADSVKGRFTISADTSKNTAYLQM NSLRAEDTAVYYCARRHWPGGFDYWGQGTLVTSS | 31 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 WT | DKTHTCP PCPAPELLGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPAPIEKTISKAK | 66 83 |
| | | CH3-a | CW:CSAV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | S70 | DIQMTQSPSSLSASVGDRVTITCRASQDVSTAVAWYQQKPGKAPKLLIYSASFLYSGVPSRFSGSGSGTDFrLTISSLQPEDFATYYC QQYLYHPATFGQGTKVEIK | 32 |
| | | CL | Lc1 | RTVAAPSVFIFPPSDEQLKSGTASVVCLLNNFYPREAKVQWKVDNALQSGNSQESVTEQDSKDSTYSLSSTLTLSKADYBKHKVY ACEVTHQGLSSPVTKSFNRGEC | 75 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| CD38-M1-FES | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDSKNTLYLQMNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPEDEAFYYCALWYSNLWVFGGGTKVFIK | 2 |
| | | Hinge1 | Hin3 | GGGSDKTHTCP | 68 |
| | | CH2 | FES | PCPAPEFEGGPSVFLFPPKPKDTLMISRTPEVTCVVVDVSHEDPEVKFNWYVDGVEVHNAKTLPREEQYNSTYRVVSVLTVLHQDWLNGKEYKCKVSNKALPASIEKTISKAK | 85 |
| | | CH3-b | CW:CSAV | GQPREPQVCTLPPSRDELTKNQVSLSCAVKGFYPSDIAVEWESNGQPEXNYKTTPPVLDSGSFFLVSKLTVDKSRWQQGNVFSCSVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge2 | Hin1 | DKTHTCP | 66 |
| | | CH2 | FES | PCPAPEFEGGPSVFLFPPKPKDTLMISRTPEVTCVVVDVSHEDPEVKFNWYVDGVEVHNAKTLPREEQYNSTYRVVSVLTVLHQDWLNGKEYKCKVSNKALPASIEKTISKAK | 85 |
| | | CH3-a | CW:CSAV | GQPREPQVYTLPPCRDELTKNQVSLMCVLVKGFYPSDIAVEWESNGQPENNYKITPPVLDSDGSFFLYSKLTVDKSRWQQGNVFSCSVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQQRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| CD38-M1-G2 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDSKNTLYLQMNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPEDEAEYYCALWYSNLWVFGGGTKVEIK | 2 |
| | | Hinge1 | Hin6 | GRGRGSDKTHTCP | 71 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 94 |
| | | CH3-b | CW:CSAV | GQPREPQVCTLPPSRDELTKNQVSLSCAVKGFYPSDIAVEWESNGQPENNYKTTPPVLDSGSFFLVSKLTVDKSRWQQGNVFSCSVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge2 | Hin1 | DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 94 |
| | | CH3-a | CW:CSAV | GQPREPQVYTLPPCRDELTKNQVSLMCVLVKGFYPSDIAVEWESNGQPENNYKTTPPVLDSDGSFFLYSKLTVDKSRWQQGNVFSCSVMHEALHNHYTQKSLSLSPGK | 108 |

TABLE 28-continued

Code and amino acid sequence of some antibodies with multifunctional antibody structure 1

| Antibody Code | Polypeptide | Domain | Code | Amino acid sequence (CDR is underlined in bold) | SEQ ID NO |
|---|---|---|---|---|---|
| CD38-M1-SG2 | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| | Fusion Peptide 1 | VHs | 2a5 | QVQLVESGGGVVQPGRSLRLSCAASGFTFSTYAMNWVRQAPGKGLKMVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin6 | GRGRGSDKTHTCP | 71 |
| | | CH2 | SG2CH2 | PSPAPPVAGPSVFLFPPKPKDTLMISRTPEVTCVVVDSHEDPEVQFNWYVDGVEVHNAKTKPREEQFNSTFRVVSVLTVVHQDW LNGKEYKCKVSNKGLPAPIEKTISKTK | 95 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | SG2CH2 | PSPAPPVAGPSVFLFPPKPKDTLMISRTPEVTCVVVDSHEDPEVQFNWYVDGVEVHNAKTKPREEQFNSTFRVVSVLTVVHQDW LNGKEYKCKVSNKGLPAPIEKTISKTK | 95 |
| | | CH3-a | CW:CSAV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| CD38-M1-SG2-1 | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTWTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin6 | GRGRGSDKTHTCP | 71 |
| | | CH2 | SG2CH2 | PSPAPPVAGPSVFLFPPKPKDTLMISRTPEVTCVVVDSHEDPEVQFNWYVDGVEVHNAKTKPREEQFNSTFRVVSVLTVVHQDW LNGKEYKCKVSNKGLPAPIEKTISKTK | 95 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 2F5 | QVQLVQSGAEVKKPGSSVKVSCKASGGTFSSYAFSWVRQAPGQGLEMMGRVIPFLGIANSAQKFQGRVHTADKSTSTAYMDL SSLRSEDTAVYYCARDDIAALGPFDYWGQCTLVTVSS | 19 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |

TABLE 28-continued

Code and amino acid sequence of some antibodies with multifunctional antibody structure 1

| Antibody Code | Poly- Peptide | Domain | Code | Amino acid sequence (CDR is underlined in bold) | SEQ ID NO |
|---|---|---|---|---|---|
| | | CH2 | SG2CH2 | PSPAPPVAGPSVFLFPPKPKDTLMISRTPEVTCVVVDVSHEDPQFNWYDGVEVHNAKTPREKQFNSTFRVVSVLTVVHQDW LNGKEYKCCKVSNKGLPAPIEKTISKTK | 95 |
| | | CH3-a | CW:CSAV | GQPREPQVYTLPPCRDELTKNQVSLMCLVKGFYPSDIAVEWESNGQPENNYKITPPVLDSDGSFFLYSKLTVDKSRWQQGNVFSC SVMHEALHNHYTQKSLSLSPGK | 108 |
| | Light Chain | VLm | 2F5 | DIQMTQSPSSLSASVGDRVTITCRASQGISSWLAWYQQKPEKAPKSLIYAASSLQSGVPSRFSGSGSGTDFTLTISSLQPEDFATYY CQQYNSYPRTFGQGTKVEIK | 20 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| CD38- M1-G2- 3 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 54 |
| | | Linker1 | Lin10 | GGGGSGGGGSGGGGS | 2 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 71 94 |
| | | Hinge1 | Hin6 | GRGRGSDKTHTCP | 109 |
| | | CH2 | G2CH2 | PCPAPPVAGPSVFLFPPKPKDTLMISRTPEVTCVVVDVSHEDPEVQFNWYDGVEVHNAKTPREEQFNSTFRVVSVLTVVHQDW LNGKEYKCCKVSNKGLPAPIEKTISKTK | 19 82 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 108 |
| | Heavy Chain | VHm | 2F5 | QVQLVQSGAEVKKPGSSVKVSCKASGGTFSSYAFSWVRQAPGQGLEMMGRVIPFLGIANSAQKFQGRVnTADKSTSTAYMDL SSLRSEDTAVYYCARDDIAALGPFDYWGQCTLVTVSS | 19 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | G2CH2 | PCPAPPVAGPSVFLFPPKPKDTLMISRTPEVTCVVVDVSHEDPEVQFNWYDGVEVHNAKTPREEQFNSTFRVVSVLTVVHQDW LNGKEYKCCKVSNKGLPAPIEKTISKTK | 94 |
| | | CH3-a | CW:CSAV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 2F5 | DIQMTQSPSSLSASVGDRVTITCRASQGISSWLAWYQQKPEKAPKSLIYAASSLQSGVPSRFSGSGSGTDFTLTISSLQPEDFATYY CQQYNSYPRTFGQGTKVEIK | 20 |
| | | CL | Lc1 | RTVAAPSVFIFPPSDEQLKSGTASVVCLLNNFYPREAKVQWKVDNALQSGNSQESVTEQDSKDSTYSUSSSTLTLSKADYEKHKVY ACEVTHQGLSSPVTKSFNRGEC | 75 |
| CD38- M1- SG2-2 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 54 |
| | | Linker1 | Lin10 | GGGGSGGGGSGGGGS | 2 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 71 |
| | | Hinge1 | Hin6 | GRGRGSDKTHTCP | 95 |
| | | CH2 | SG2CH2 | PSPAPPVAGPSVFLFPPKPKDTLMISRTPEVTCVVVDVSHEDPQFNWYDGVEVHNAKTPREKQFNSTFRVVSVLTVVHQDW LNGKEYKCCKVSNKGLPAPIEKTISKTK | |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | Heavy Chain | VHm | MOR | QVQLVESGGGLVQPGGSLRLSCAASGFTFSSYYMNWVRQAPGKGLEWVSGISGDPSNTYYADSVKGRFTISRDNSKNTLYLQM | 17 |
| | | CH1 | CH1 | NSLRAEDTAVYYCARDLPLVTTGFAYWGQGTLVTVSSASTKGPS | 82 |
| | | Hinge1 | Hin1 | VFPLAPSSKSTSGGTAALGCLVKDYFPEPVTVSWNSGALTSGVHTFPAVLQSSGLYSLSSVVTVPSSSLGTQTYICNVNH | 66 |
| | | Hinge2 CH2 | SG2CH2 | KPSNTKVDKKVEPKSC | 95 |
| | | | | DKTHTCP | |
| | | | | PSPAPPVAGPSVFLFPPKPKDTLMISRTPEVTCVVVDVSHEDPEVQFNWYVDGVEVHNAKTKPREEQFNSTFRVVSVLTVVHQDW | |
| | | | | LNGKEYKCKVSNKGLPAPIEKTISKTK | |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | MOR | DIELTQPPSVSVAPGQTARISCSCSGDNLRHYVYWYQQKPGQAPVLVIYGDSKRPSGIPERFSGSGNSGNTATLTISGTQAEDEADYYC QTYTGGASLVFGGGTKLTVLGQ | 18 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| CD38-M1-G2-2 | Fusion Peptide 1 | VHs | 2a5 | QVQLVESGGGVVQPGRSLRLSCAASGFTFSTYAMNWVRQAPGKGLFWVARIRSKYNNYATYYADSVKDRFTISRDDSKNTLYLQ MNSLRAEDTAVYYCARHGNFGNSYVSWFA1WGQGTLVTVSS | 1 |
| | | Linker1 VLs | Lin10 2a5 | GGGGSGGGGSGGGGS QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKLTVLQ | 54 2 |
| | | Hinge1 CH2 | Hin6 G2CH2 | GRGRGSDKTHTCP PCPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 71 94 |
| | | CH3-b | CW: CSAV | GQPREPQVCTLPPSRDELTKNQVSLSCAVKGFYPSDIAVEWESNGQPENNYKTTPPVLDSDGSFFLYSKLTVDKSRWQQGNVFSC SVMHEALHNHYTQKSLSLSPGK | 109 |
| | Heavy Chain | VHm | MOR | QVQLVESGGGLVQPGGSLRLSCAASGFTFSSYYMNWVRQAPGKGLEWVSGISGDPSNTYYADSVKGRFTISRDNSKNTLYLQM | 17 |
| | | CH1 | CH1 | NSLRAEDTAVYYCARDLPLVTTQFAYWGQGTLVTVSS ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 G2CH2 | DKTHTCP PCPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 66 94 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | |
| | Light Chain | VLm | MOR | DIELTQPPSVSVAPGQTARISCSCSGDNLRHYVYWYQQKPGQAPVLVIYGDSKRPSGIPERFSGSGNSGNTATLTISGTQAEDEADYYC QTYTGGASLVFGGGTKLTVLGQ | 18 |
| | | CL | Lc1 | RTVAAPSVFIFPPSDEQLKSGTASVVCLLNNFYPREAKVQWKVDNALQSGNSQESVTEQDSKDSTYSLSSTLITLSKADYEKHKVY ACEVTHQGLSSPVTKSFNRGEC | 75 |
| | | VHs Linker1 | 2a5 Lin10 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFA1WGQGTLVTVSS GGGGSGGGGSGGGGS | 1 54 |
| CD38 M1-WT | Fusion Peptide 1 | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin6 | GRGRGSDKTHTCP | 71 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPAPIEKTISKAK | 83 |
| | | CH3-b | CW:CS AV | GQPREPQVCTLPPSRDELTKNQVSLTCLVKGFYPSDIAVEWESNGQPENNYKTTPPVLDSGSFFLVSKLTVDKSRWQQGNVFSC SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 WT | DKTHTCP PCPAPELLGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPAPIEKTISKAK | 66 83 |
| | | CH3-a | CW:CS AV | GQPREPQVYTLPPCRDELTKNQVSLWCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| CD38-M1-FES-1 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 1 |
| | | Linker1 VLs | Lin10 I2C | GGGSGGGGSGGGGS QTVVTQEPSLTVSPGGTVTLTCGSSTGAVTSGNYPNWVQQKPGQAPRGLIGQTKFLAPGTPARFSGSLLGGKAALTLSGVQPED EAEYYCVLWYSNRWVFGGGTKLTVL | 54 10 |
| | | Hinge1 CH2 | Hin3 FES | GGGSDKTHTCP PCPAPEFEGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPASIEKTISKAK | 68 85 |
| | | CH3-b | CW:CS AV | GQPREPQVCTLPPSRDELTKNQVSLTCLVKGFYPSDIAVEWESNGQPENNYKTTPPVLDSGSFFLVSKLTVDKSRWQQGNVFSC SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 FES | DKTHTCP PCPAPEFEGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPASIEKTISKAK | 66 85 |
| | | CH3-a | CW:CS AV | GQPREPQVYTLPPCRDELTKNQVSLWCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| CD38 | Fusion | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ | 1 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| M1-WT | Peptide 1 | Linker1 VLs | Lin10 2a5 | MNSLRAEDTAVYYCAHGNFGNSYVSWFAYWGQGTLVTVSS<br>GGGSGGGGSGGGGS | 54<br>2 |
| | | Hinge1 CH2 | Hin6 WT | QTVTQEPSLTVSPGGTVTLTCRSSTGAVTTSNYANWVQQKPGQAPRGLIGQTNKRAPGVPARFSGSLLGGKAALTLSGVQPEDE<br>AEYYCALWYSNLWVFGGGTKVEIK<br>GRGRGSDKTHTCP | 71<br>83 |
| | | CH3-b | CW:CS AV | PCPAPELLGGPSVFLFPPKPKDTLMISRTPEVTCVVVDVSHEDPEVKFNWYVDGVEHNAKTKPREEQYNSTYRVVSVLTVLHQD<br>WLNGKEYKCKVSNKALPAPIEKTISKAK<br>GQPREPQVCTLPPSRDELTKNQVSLSCAVKGFYPSDIAVEWESNGQPENNYKTTPPVLDSDGSFFLVSKLTVDKSRWQQGNVFSC<br>SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN<br>SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH<br>KPSNTKVDKKVEPKSC | 82 |
| | | Hinge2 CH2 | Hin1 WT | DKTHTCP | 66<br>83 |
| | | CH3-a | CW:CS AV | PCPAPELLGGPSVFLFPPKPKDTLMISRTPEVTCVVVDVSHEDPEVKFNWYVDGVEHNAKTKPREEQYNSTYRVVSVLTVLHQD<br>WLNGKEYKCKVSNKALPAPIEKTISKAK<br>GQPREPQVYTLPPCRDELTKNQVSLMCLVKGFYPSDIAVEWESNGQPENNYKTTPPVLDSDGSFFLYSKLTVDKSRWQQGNVFSC<br>SVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ<br>QRSNWPPTFGQGTKVEIK | 16<br>75 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY<br>ACEVTHQGLSSPVTKSFNRGEC | |
| CD38-M1-FES-1 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY<br>LQMNNLKTEDTAVYYCVRHGNFGNSYISYWA**YWGQGTLVTVSS | Q<br>54 |
| | | Linker1 VLs | Lin10 I2C | GGGSGGGGSGGGGS<br>QTVVTQEPSLTVSPGGTVTLTCGSSTGAVTTSGNYPNWVQQKPGQAPRGLIGQTKFLAPGTPARFSGSLLGGKAALTLSGVQPED<br>EAEYYCVLWYSNRWVFGGGTKLTVL | 10 |
| | | Hinge1 CH2 | Hin3 FES | GGGGSDKTHTCP<br>PCPAPEFEGGPSVFLFPPKPKDTLMISRTPEVTCVVVDVSHEDPEVKFNWYVDGVEHNAKTKPREEQYNSTYRVVSVLTVLHQD<br>WLNGKEYKCKVSNKALPASIEKTISKAK | 68<br>85 |
| | | CH3-b | CW:CS AV | GQPREPQVCTLPPSRDELTKNQVSLSCAVKGFYPSDIAVEWESNGQPENNYKTTPPVLDSDGSFFLVSKLTVDKSRWQQGNVFSC<br>SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN<br>SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNNSGALTSGVHTFPAVLQSSGLYSLSSVVTVPSSSLGTQTYICNVNH<br>KPSNTKVDKKVEPKSC | 82 |
| | | Hinge2 CH2 | Hin1 FES | DKTHTCP<br>PCPAPEFEGGPSVFLFPPKPKDTLMISRTPEVTCVVVDVSHEDPEVKFNWYVDGVEHNAKTKPREEQYNSTYRVVSVLTVLHQD<br>WLNGKEYKCKVSNKALPASIEKTISKAK | 66<br>85 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC<br>SVMHEALHNHYTQKSLSLSPGK | 108 |
| | Light | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ | 16 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | Chain | CL | Lc1 | QRSNWPPTTFGQGTKVEIK<br>RTVAAPSVFIFPPSDEQLKSGTASVVCLLNNFYPREAKVQWKVDNALQSGNSQESVTEQDSKDSTYSLSSTLTLSKADYEKHKVY<br>ACEVTHQGLSSPVTKSFNRGEC | 75 |
| CD38-M1-G2-1 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY<br>LQMNNLKTEDTAVYYCVRHGNFGNSYISYWAYWGQGTLVTVSS | 9<br>54 |
| | | Linker1<br>VLs | Lin10<br>I2C | GGGGSGGGGSGGGGS<br>QTVVTQEPSLTVSPGGTVTLTCGSSTGAVTSGNYPNWVQQKPGQAPRGLIGGTKFLAPGTPARFSGSLLGGKAALTLSGVQPED<br>EAEYYCVLWYSNRWVFGGGTKLTVL | 10<br>68<br>94 |
| | | Hinge1<br>CH2 | Hin3<br>G2CH2 | GGGSDKTHTCP<br>PCPAPPVAGPSVFLFPPKPKDTLMISRTPEVTCVVVDVSHEDPEVQFNWYVDGVEVHNAKTKPREEQFNSTFRVVSLTVVHQDW<br>LNGKEYKCKVSNKGLPAPIEKTISKTK | 109 |
| | | CH3-b | CW:CS<br>AV | GQPREPQVCTLPPSRDELTKNQVSLSCAVKGFYPSDIAVEWESNGQPENNYKTTPVLDSDGSFFLVSKLTVDKSRWQQGNVFSC<br>SVMHEALHNHYTQKSLSLSPGK | |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN<br>SLRAEDTAVYFCAKDKILWFGEPVFDYWGQGTLVTVSS | 15<br>82 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH<br>KPSNTKVDKKVEPKSC | 66<br>94 |
| | | Hinge2<br>CH2 | Hin1<br>G2CH2 | DKTHTCP<br>PCPAPPVAGPSVFLFPPKPKDTLMISRTPEVTCVVVDVSHEDPEVQFNWYVDGVEVHNAKTKPREEQFNSTFRVVSLTVVHQDW<br>LNGKEYKCKVSNKGLPAPIEKTISKTK | |
| | | CH3-a | CW:CS<br>AV | GQPREPQVYTLPPCRDELTKNQVSLMCLVKGFYPSDIAVEWESNGQPENNYKTTPVLDSDGSFFLYSKLTVDKSRWQQGNVFSC<br>SVMHEALHNHYTQKSLSLSPGK | 108 |
| | Light Chain | VLm | Dara | EIVLTQSPATLSLSPGERATLSCRASQSVSSYLAWYQQKPGQAPRLLLIYDASNRATGIPARFSGSGSGTDPTLTISSLEPEDFAVYYCQ<br>QRSNWPPTTFGQGTKVEIK | 16<br>75 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY<br>ACEVTHQGLSSPVTKSFNRGEC | |
| CD38-M1-SG2-3 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY<br>LQMNNLKTEDTAVYYCVRHGNFGNSYISYWAYWGQGTLVTVSS | 9<br>54 |
| | | Linker1<br>VLs | Lin10<br>I2C | GGGGSGGGGSGGGGS<br>QTVVTQEPSLTVSPGGTVTLTCGSSTGAVTSGNYPNWVQQKPGQAPRGLIGGTKFLAPGTPARFSGSLLGGKAALTLSGVQPED<br>EAEYYCVLWYSNRWVFGGGTKLTVL | 10<br>68<br>95 |
| | | Hinge1<br>CH2 | Hin3<br>SG2CH2 | GGGSDKTHTCP<br>PSPAPPVAGPSVFLFPPKPKDTLMISRTPEVTCVVVDVSHEDPEVQFNWYVDGVEVHNAKTKPREEQFNSTFRVVSLTVVHQDW<br>LNGKEYKCKVSNKGLPAPIEKTISKTK | |
| | | CH3-b | CW:CS<br>AV | GQPREPQVCTLPPSRDELTKNQVSLSCAVKGFYPSDIAVEWESNGQPENNYKLTPVLDSDGSFFLVSKLTVDKSRWQQGNVFSC<br>SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN<br>SLRAEDTAVYFCAKDKILWFGEPVFDYWGQGTLVTVSS | 15<br>82 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH<br>KPSNTKVDKKVEPKSC | |
| | | Hinge2 | Hin1 | DKTHTCP | 66 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | SG2CH2 | PSPAPPVAGPSVFLFPPKPKDTLMISRTPEVTCVVVDVSHEDPEVQFNWYVDGVEVHNAKTPREEQFNSTFRVVSVLTVVHQDW LNGKEYKCCKVSNKGLPAPIEKTISKTK | 95 |
| | | CH3-a | CW:CSAV | GQPREPQVYTLPPCRDELTKNQVSLWCLVKGFYPSDIAVEWESNGQPENNYKTTPPVLDSGSFFLYSKLTVDKSRWQQGNVFSC SVMHEALHNHYTQKSLSLSPGK | 108 |
| Light Chain | | VLm | Dara | EIVLTQSPATLSLSPGERATLSCRASQSVSSYLAWYQQKPGQAPRLLIYDASNRATGIPARFSGSGSCiTDFTLTISSLEPEDFAVYYCQ QRSNWPPTFGQGTKVEIK | 16<br>75 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | |
| CD38-M1-AG2 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDNSKNTAY LQMNNLKTEDTAVYYCVRHGNFGNSYISYWAYWGQGTLVTVSS | 9<br>54 |
| | | Linker1 | | GGGGSGGGGSGGGGS | |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLTVL | 10<br>68 |
| | | Hinge1 | Hin3 | GGGGSDKTHTCP | 96 |
| | | CH2 | AG2CH2 | PAPAPPVAGPSVFLFPPKPKDTLMISRTPEVTCVVVDVSHEDPEVQFNWYVDGVEVHNAKTPREEQFNSTFRVVSVLTVVHQD WLNGKEYKCCKVSNKGLPAPIEKTISKTK | |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| Heavy Chain | | VHm | Dara | EVQLLESGGGLVQPGRSLRLSCAVSGFTFNSFAMSWVRQAPGKGLEMVSAISGSGGGTYYADSVKGRFTISRDNSKNTLYLQMN SLRAEDTAVYYCAKDKILWFGEPVFDYWGQGTLVTVSS | 15<br>82 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | |
| | | Hinge2 | Hin1 | DKTHTCP | 66 |
| | | CH2 | AG2CH2 | PAPAPPVAGPSVFLFPPKPKDTLMISRTPEVTCVVVDVSHEDPEVQFNWYVDGVEVHNAKTPREEQFNSTFRVVSVLTVVHQD WLNGKEYKCCKVSNKGLPAPIEKTISKTK | 96 |
| | | CH3-a | CW:CSAV | GQPREPQVYTLPPCRDELTKNQVSLWCLVKGFYPSDIAVEWESNGQPENNYKTTPPVLDSGSFFLYSKLTVDKSRWQQGNVFSC SVMHEALHNHYTQKSLSLSPGK | 108 |
| Light Chain | | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16<br>75 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | |
| | | VHs | I2C | EVQLVESGGGLVQPGGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9<br>54 |
| | | Linker1 | Lin10 | GGGGSGGGGSGGGGS | |
| CD38-M1-GG2 | Fusion Peptide 1 | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLTVL | 10<br>68 |
| | | Hinge1 | Hin3 | GGGGSDKTHTCP | 97 |
| | | CH2 | GG2CH2 | PGPAPPVAGPSVFLFPPKPKDTLMISRTPEVTCVVVDVSHEDPEVQFNWYVDGVEVHNAKTPREEQFNSTFRVVSVLTVVHQD WLNGKEYKCCKVSNKGLPAPIEKTISKTK | |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| CD38-M1-PG2 | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge2 | Hin1 | DKTHTCP | 66 |
| | | CH2 | GG2CH2 | PGPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 97 |
| | | CH3-a | CW:CSAV | GQPREPQVYTLPPCRDELTKNQVSLWCLVKGFYPSDIAVEWESNGQPENNYKTTPVLDSGSFFLYSKLTVDKSRWQQGNVFSCSVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQQRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS | 9 |
| | | Linker1 | | GGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGKAALTLSGVQPEDEAEYYCVLWYSNRWVFGGGTKLTVL | 10 |
| | | Hinge1 | Hin3 | GGGSDKTHTCP | 68 |
| CD38-M1-DG2 | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMNSLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge2 | Hin1 | DKTHTCP | 66 |
| | | CH2 | PG2CH2 | PPPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 98 |
| | | CH3-b | CW:CSAV | GQPREPQVCTLPPSRDELTKNQVSLSCAVKGFYPSDIAVEWESNGQPENNYKTTPVLDSGSFFLVSKLTVDKSRWQQGNVFSCSVMHEALHNHYTQKSLSLSPGK | 109 |
| | Light Chain | VLm | Dara | EIVLTQSPATLSLSPGERATLSCRASQSVSSYLAWYQQKPGQAPRLLIYDASNRATGIPARFSGSGSGTDFTLNSLEPEDFAVYYCQQRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS | 9 |
| | | Linker1 | | GGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGKAALTLSGVQPEDEAEYYCVLWYSNRWVFGGGTKLTVL | 10 |
| | | Hinge1 | Hin3 | GGGSDKTHTCP | 68 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSVLTVVHQDW LNGKEYKCCKVSNKGLPAPIEKTISKTK | 99 |
| | | CH3-b | CW:CSAV | GQPREPQVCTLPPSRDELTKNQVSLTCAVKGFYPSDIAVEWESNGQPENNYKTTPVLDSGSFFLYSKLTVDKSRWQQGNVFSC SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge1 | Hin1 | DKTHTCP | 66 |
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSVLTVVHQDW LNGKEYKCCKVSNKGLPAPIEKTISKTK | 99 |
| | | CH3-a | CW:CSAV | GQPREPQVYTLPPCRDLTKNQVSLWCLVKGFYPSDIAVEWESNGQPENNYKTTPVLDSDGSFFLYSKLTVDKSRWQQGNVFSC SVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| CD38-M1-G2D | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAY**WGQGTLVTVSS | 9 |
| | | Linker1 | | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLTVL | 10 |
| | | Hinge1 | Hin3 | GGGGSDKTHTCP | 68 |
| | | CH2 | G2DCH2 | PCPAPPVAGPSVFLFPPKPKDTLMISRTPEVTCVVVDVSHEAPEVQFNWYVDGVEVHNAKTKPREEQFNSTFRVVSVLTVVHQDW LNGKEYKCCKVSNKGLPAPIEKTISKTK | 100 |
| | | CH3-b | CW:CSAV | GQPREPQVCTLPPSRDELTKNQVSLTCAVKGFYPSDIAVEWESNGQPENNYKTTPVLDSGSFFLYSKLTVDKSRWQQGNVFSC SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN SLRAEDTAVYFCAKDKILWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | G2DCH2 | PCPAPPVAGPSVFLFPPKPKDTLMISRTPEVTCVVVDVSHEAPEVQFNWYVDGVEVHNAKTKPREEQFNSTFRVVSVLTVVHQDW LNGKEYKCCKVSNKGLPAPIEKTISKTK | 100 |
| | | CH3-a | CW:CSAV | GQPREPQVYTLPPCRDLTKNQVSLWCLVKGFYPSDIAVEWESNGQPENNYKTTPVLDSDGSFFLYSKLTVDKSRWQQGNVFSC SVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDFTLTISSLEPEDFAVYYCQ QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLILSKADYEKHKVY ACEVTHQGLSSPVTKSFNRGEC | 75 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| CD38-M1-DG2D | Fusion Peptide 1 | VHs | I2C | EVQLVESGGGLVQPGGSLRLSCAASGFTFNKYAMNWVRQAPGKGLEWVARIRSKYNNYATYYADSVKDRFTISRDDSKNTAY<br>LQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED<br>EAEYYCVLWYSNRWVFGGGTKLTVL | 10 |
| | | Hinge1 | Hin3 | GGGGSDKTHTCP | 68 |
| | | CH2 | DG2DC H2 | PCPAPPVAGPSVFLFPPKPKDTLMISRTPEVTCVVVAVSHEAPEVQFNWYVDGVEVHNAKTKPREEQFNSTFRVVSLTVVHQDW<br>LNGKEYKCKVSNKGLPAPIEKTISKTK | 101 |
| | | CH3-a | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC<br>SVMHEALHNHYTQKSLSLSPGK | 109 |
| | Heavy Chain | VHm | Dara | EVQLLESGGGLVQPGGSLRLSCAVSGFTFNSFAMSWVRQAPGKGLEWVSAISGSGGGTYYADSVKGRFTISRDNSKNTLYLQMN<br>SLRAEDTAVYFCAKDKILLWFGEPVFDYWGQGTLVTVSS | 15 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH<br>KPSNTKVDKKVEPKSC | 82 |
| | | Hinge2 | Hin1 | DKTHTCP | 66 |
| | | CH2 | DG2DC H2 | PCPAPPVAGPSVFLFPPKPKDTLMISRTPEVTCVVVAVSHEAPEVQFNWYVDGVEVHNAKTKPREEQFNSTFRVVSLTVVHQDW<br>LNGKEYKCKVSNKGLPAPIEKTISKTK | 101 |
| | | CH3-b | CW:CSAV | GQPREPQVYTLPPCRDELTKNQVSLMCLVKGFYPSDIAVEWESNGQPENNYKTTPPVLDSDGSFFLYSKLTVDKSRWQQGNVFSC<br>SVMHEALHNHYTQKSLSLSPGK | 108 |
| | Light Chain | VLm | Dara | EIVLTQSPATLSLSPGERATLSCRASQSVSSYLAWYQQKPGQAPRLLIYDASNRATGIPARFSGSGSGTDPTLTISSLEPHDFAVYYCQ<br>QRSNWPPTFGQGTKVEIK | 16 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY<br>ACEVTHQGLSSPVTKSFNRGEC | 75 |
| CD38-M1-FES-3 | Fusion Peptide 1 | VHs | I2C | EVQLVESGGGLVQPGGSLRLSCAASGFTFNKYAVINWVRQAPGKGLEWVARIRSKYNNYATYYADSVKDRFTISRDDSKNTAY<br>LQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED<br>EAEYYCVLWYSNRWVFGGGTKLTVL | 10 |
| | | Hinge1 | Hin3 | GGGGSDKTHTCP | 68 |
| | | CH2 | FES | PCPAPEFEGGPSVFLFPPKPKDTLMISRTPEVTCVVVDSHEDPEVKFNWYVDGVEVHNAKTKPREEQYNSTYRVVSLTVLHQD<br>WLNGKEYKCKVSNKALPASIEKTISKAK | 85 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC<br>SVMHEALHNHYTQKSLSLSPGK | 109 |
| | Heavy Chain | VHm | MOR | QVQLVESGGGLVQPGGSLRLSCAASGFTFSSYYMNWVRQAPGKGLEWVSGISGDPSNTYYADSVKGRFTISRDNSKNTLYLQM<br>NSLRAEDTAVYYCARDLPLVTTGFAXWGQGTLVTVSS | 17 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH<br>KPSNTKVDKKVEPKSC | 82 |
| | | Hinge2 | Hin1 | DKTHTCP | 66 |
| | | CH2 | FES | PCPAPEFEGGPSVFLFPPKPKDTLMISRTPEVTCVVVDSHEDPEVKFNWYVDGVEVHNAKTKPREEQYNSTYRVVSLTVLHQD<br>WLNGKEYKCKVSNKALPASIEKTISKAK | 85 |
| | | CH3-a | CW:CSAV | GQPREPQVYTLPPCRDELTKNQVSLMCLVKGFYPSDIAVEWESNGQPENNYKTTPPVLDSDGSFFLYSKLTVDKSRWQQGNVFSC<br>SVMHEALHNHYTQKSLSLSPGK | 108 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| CD38-M1-G2D-1 | Light Chain | VLm | M0R | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ | 18 |
| | | CL | Lc3 | GQPKAAPSVTLFPPSSEELQANKATLVCLISDFYPGAVTVAWKADSSPVKAGVEITTPSKQSNNKYAASSYLSLTPEQWKSHRSYSCQVTHEGSTVEKTVAPTECS | 77 |
| | Fusion Peptide 1 | VHs | 2a5 | QVQLVESGGGVVQPGRSLRLSCAASGFTFNKYAMNWVRQAPGKGLEWVARIRSKYNNYATYYADSVKDRFTISRDDSKNTLYLQMNSLRAEDTAVYYCARHGNFGNSYISWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPEDE | 2 |
| | | Hinge1 | Hin6 | AEYYCALWYSNLWVFGGGTKVEIK GRGRGSDKTHTCP | 71 |
| | | CH2 | G2DCH | PCPAPPVAGPSVFLFPPKPKDTLMISRTPEVTCVVVDVSHEAPEVQFNWYVDGVEVHNAKTKPREEQFNSTFRVVSVLTVVHQDWLNGKEYKCKVSNKGLPAPIEKTISKTK | 100 |
| | | CH3-a | CW:CSAV | GQPREPQVCRLPPSRDELTKNQVSLSCAVKGFYPSDIAVEWESNGQPENNYKTTPVLDSDGSFFLVSKLTVDKSRWQQGNVFSCSVMHEALHNHYTQKSLSLSPGK | 109 |
| | Heavy Chain | VHm | M0R | QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVTTQFAWGQGTLVTVSS | 17 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCP | 82 |
| | | Hinge2 | Hin1 | PCPAPPVAGPSVFLFPPKPKDTLMISRTPEVTCVVVDVSHEAPEVQFNWYVDGVEVHNAKTKPREEQFNSTFRVVSVLTVVHQDW | 66 |
| | | CH2 | G2DCH2 | LNGKEYKCKVSNKGLPAPIEKTISKTK | 100 |
| | | CH3-b | CW:CSAV | GQPREPQVTLPPCRDELTKNQVSLMCLVKGFYPSDIAVEWESNGQPENNYKTTPVLDSDGSFFLYSKLTVDKSRWQQGNVFSCSVMHEALHNHYTQKSLSLSPGK | 108 |
| M1IC-SG2 | Light Chain | VLm | M0R | DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ | 18 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVPEDEAEYYCVLWYSNRWVFGGGTKLITVL | 10 |
| | | Hinge1 | Hin3 | GGGGSDKTHTCP | 68 |
| | | CH2 | SG2CH2 | PSPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTK | 95 |
| | | CH3-b | CW:CSAV | GQPREPQVCTLPPSRDELTKNQVSLSCAVKGFYPSDIAVEWESNGQPENNYKTTPVLDSDGSFFLVSKLTVDKSRWQQGNVFSCSVMHEALHNHYTQKSLSLSPGK | 109 |
| | Heavy Chain | VHm | 4420 | EVKLDETGGGLVQPGRPMKLSCVASGFTFSDYWMNWVRQSPEKGLEWVAQIRNKPYNYETYYSDVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGAITSGVHTFPAVLQSSGLYSLSSVVTVPSSSLGTQTYICNVNHKPSNTKVDKKVEPKSC | 82 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | Hinge2 CH2 | Hin1 SG2CH 2 | DKTHTCP PSPAPPVAGPSVFLFPPKPKDTLMISRTPEVTCVVVDVSHEDPKVQFNWYVDGVEVHNAKTPREEQFNSTFRVVSVLTVVHQDW | 66 95 |
| | | CH3-a | CW:CS AV | LNGKEYKCCKVSNKGLPAPIEKTISKTK GQPREPQVYTLPPCRDELTKNQVSLMCLVKGFYPSDIAVEWESNGQPENNYKTTPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVHAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-G2 | Fusion Peptide 1 | VHs Linker1 | I2C Lin10 | EVQLVESGGGLVQPGGSLKLSCAASGFTFNKYAMNWVRQAPGKGLEWVARIRSKINNYATYYADSVKDRFTISRDDSKNTAY LQMNNLKTEDTAVYYCVRHGNFGNSYISYWAYWGQGTLVTVSS GGGGSGGGGSGGGGS | 9 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLITVL | 10 |
| | | Hinge1 CH2 | Hin3 G2CH2 | GGGGSDKTHTCP PCPAPPVAGPSVFLFPPKPKDTLMISRTPEVTCVVVDVSHEDPEVQFNWYVDGVEVHNAKTPREEQFNSTFRVVSVLTVVHQDW LNGKEYKCCKVSNKGLPAPIEKTISKTK | 68 94 |
| | | CH3-a | CW:CS AV | GQPREPQVCTLPPSRDELTKNQVSLSCAVKGFYPSDIAVEWESNGQPENNYKITPVLDSDGSFFLYSKLTVDKSRWQQGNVFSC SVMHEALHNHYTQKSLSLSPGK | 109 |
| | Heavy Chain | VHm | 4420 | EVKLDTEGGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSMNSGALTSGVHTFPAVLQSSGLYSLSSVVTVPSSSLGTQTYICNVNH KPSNTKVDKKVEPKSC | 82 |
| | | Hinge2 CH2 | Hin1 G2CH2 | DKTHTCP PCPAPPVAGPSVFLFPPKPKDTLMISRTPEVTCVVVDVSHEDPEVQFNWYVDGVEVHNAKTPREEQFNSTFRVVSVLTVVHQDW LNGKEYKCCKVSNKGLPAPIEKTISKTK | 66 94 |
| | | CH3-a | CW:CS AV | GQPREPQVCTLPPSRDELTKNQVSLSCAVKGFYPSDIAVEWESNGQPENNYKITPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-FES | Fusion Peptide 1 | VHs Linker1 | I2C Lin10 | EVQLVESGGGLVQPGGSLKLSCAASGFTFNKYAMNWVRQAPGKGLEWVARIRSKINNYATYYADSVKDRFTISRDDSKNTAY LQMNNLKTEDTAVYYCVRHGNFQNSYISYWAYWGQGTLVTVSS GGGGSGGGGSGGGGS | 9 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLITVL | 10 |
| | | Hinge1 CH2 | Hin3 FES | GGGGSDKTHTCP PCPAPEFEGGPSVFLFPPKPKDTLMISRTPEVTCVVVDVSHEDPEVKFNWYVDGVEVHNAKTPREEQYNSTYRVVSVLTVLHQD WLNGKEYKCCVSNKALPASIEKTISKAK | 68 85 |
| | | CH3-b | CW:CS AV | GQPREPQVCTLPPSRDELTKNQVSLSCAVKGFYPSDIAVEWESNGQPENNYKTTPVLDSDGSFFLVSKLTVDKSRWQQGNVFSC SVMHEALHNHYTQKSLSLSPGK | 109 |

TABLE 28-continued

Code and amino acid sequence of some antibodies with multifunctional antibody structure 1

| Antibody Code | Polypeptide | Domain | Code | Amino acid sequence (CDR is underlined in bold) | SEQ ID NO |
|---|---|---|---|---|---|
| M1IC-NA | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge2 CH2 | Hin1 FES | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 66 85 |
| | | CH3-a | CW:CS AV | GQPREPQVYTLPPCRDELTKNQVSLWCLVKGFYPSDIAVEWESNGQPENNYKTTPVLDSDGSFFLYSKLTVDKSRWQQGNVFSCSVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHQNpQNSYISYWAYWGQGTLVTVSS | 9 |
| | | Linker1 VLs | Lin10 I2C | GGGGSGGGGSGGGGS QTVVTQEPSLTVSPGGTVTLTCGSSTGAVTSGNYPNWVQQKPGQAPRGLIGGTKFLAPGTPARFSGSLLGKAALTLSGVQPEDEAEYYCVLWYSNRWVFGGGTKLTVL | 54 10 |
| | Hinge1 CH2 | Hin3 N297A | GGGGSDKTHTCP PCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAK | 68 87 |
| | | CH3-b | CW:CS AV | GQPREPQVCTLPPSRDELTKNQVSLCAVKGFYPSDIAVEWESNGQPENNYKITPVLDSDGSFFLVSKLTVDKSRWQQGNVFSCSVMHEALHNHYTQKSLSLSPGK | 109 |
| M1IC-NQ | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge2 CH2 | Hin1 N297A | PCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAK | 66 87 |
| | | CH3-a | CW:CS AV | GQPREPQVYTLPPCRDELTKNQVSLWCLVKGFYPSDIAVEWESNGQPENNYKTTPVLDSDGSFFLYSKLTVDKSRWQQGNVFSCSVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Fusion Peptide 1 | VHs | 2a5 | QVQLVESGGGVVQPGRSLRLSCAASGFTFSTYAMNWVRQAPGKGLEWVARIRSKYNNYATYVADSVKDRFTISRDDSKNTLYLQMNSLRAEDTAVYYCARHGNFGNSYYSWFAYWGQGTLVTVSS | 1 |
| | | Linker1 VLs | Lin10 2a5 | GGGGSGGGGSGGGGS QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 54 2 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | Hinge1 CH2 | Hin3 N297Q | GGGGSDKTHTCP PCPAPELLGGPSVFLFPPKPKDTLMISRTPEVTCVVVDVSHEDPEVKFNWYVDGVEVHNAKTKPREEQYQSTYRVVSVLTVLHQD WLNGKEYKCKVSNKALPAPIEKTISKAK | 68 89 |
| | | CH3-b | CW:CS AV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| Heavy Chain | | VHm | 4420 | EVKLDETGGGLVQPGGLVQPGRPMKLSCVASGFTFSDYWMNWVRQSPEKGLEWVAQIRNKPYNYETYYSDSVKGRFTISRDDSKSSVYL QMNNLRVEDMGIYYCRGSSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 66 |
| | | Hinge2 CH2 | Hin1 N297Q | DKTHTCP PCPAPELLGGPSVFLFPPKPKDTLMISRTPEVTCVVVDVSHEDPEVKFNWYVDGVEVHNAKTKPREEQYQSTYRVVSVLTVLHQD WLNGKEYKCKVSNKALPAPIEKTISKAK | 89 |
| | | CH3-a | CW:CS AV | GQPREPQVYTLPPCRDELTKNQVSLMCLVKGFYPSDIAVEWESNGQPENNYKITPPVLDSDGSFFLYSKLTVDKSRWQQGNVFSC SVMHEALHNHYTQKSLSLSPGK | 108 |
| Light Chain | | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-AAG | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 54 |
| | | Linker1 VLs | Lin10 I2C | GGGGSGGGGSGGGGS QTVVTQEPSLTVSPGGTVTLTCGSSTGAVTTSGNYPNWVQQKPGQAPRGLIGGTKFLAPGTPARFSGSLLGGKAALTLSGVQPED EAEYYCVLWYSNRWVFGGGTKLTVL | 10 |
| | | Hinge1 CH2 | Hin3 AAG | GGGGSDKTHTCP PCPAPEAAGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALGAPIEKTISKAK | 68 84 |
| | | CH3-b | CW:CS AV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| Heavy Chain | | VHm | 4420 | EVKLDETGGGLVQPGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 CH2 | Hin1 AAG | DKTHTCP PCPAPEAAGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALGAPIEKTISKAK | 66 84 |
| | | CH3-a | CW:CS AV | GQPREPQVYTLPPCRDELTKNQVSLMCLVKGFYPSDIAVEWESNGQPENNYKITPPVLDSDGSFFLYSKLTVDKSRWQQGNVFSC SVMHEALHNHYTQKSLSLSPGK | 108 |
| Light Chain | | VLm | 4420 | DVVMTQLTLSLPVSLGDQASISCRSSQSLVHSNGNTYLRWYLQKPGQSPKVLIYKVSNRFSGVPDRFSGSGSGTDFRLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| M1IC-AG2 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY LQMNNLKTEDTAVYYCVRHgNFgNSYISYWAYWGQGTLVTVSS | 9 |
| | | Linker1 | | GGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTTSGVPED EAEYYCVLWYSNRWVFGGGTKLTVL | 10 |
| | | Hinge1 | Hin3 | GGGSDKTHTCP | 68 |
| | | CH2 | AG2CH2 | PAPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 96 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | AG2CH2 | PAPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 96 |
| | | CH3-a | CW:CSAV | GQPREPQVTLPPCRDELTKNQVSLWCLVKGFYPSDIAVEWESNGQPENNYKITPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRWLQKPGQSPKVLIYKVSNRFSGVPDRFSGSGSGTDFTLKISRVEAE DLGVFYCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-GG2 | Fusion Peptide 1 | VHs | I2C | EVQLVESGGGLVQPGGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 |
| | | Linker1 | | GGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALrLSGVPED EAEYYCVLWYSNRWVFGGGTKLTVL | 10 |
| | | Hinge1 | Hin3 | GGGSDKTHTCP | 68 |
| | | CH2 | GG2CH2 | PGPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 97 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | GG2CH2 | PGPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 97 |
| | | CH3-a | CW:CSAV | GQPREPQVTLPPCRDELTKNQVSLWCLVKGFYPSDIAVEWESNGQPENNYKTTPPVLDSDGSFFLYSKLTVDKSRWQQGNVFSC SVMHEALHNHYTQKSLSLSPGK | 108 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| M1IC-PG2 | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| | Fusion Peptide 1 | VHs | I2C | EVQLVESGGGLVQPGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLTVL | 10 |
| | | Hinge1 | Hin3 | GGGGSDKTHTCP | 68 |
| | | CH2 | PG2CH2 | PPPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 98 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTTSRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | PG2CH2 | PPPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 98 |
| | | CH3-a | CW:CSAV | GQPREPQVYTLPPCRDELTKNQVSLMCLVKGFYPSDIAVEWESNGQPENNYKTTPPVLDSGSFFLYSKLTVDKSRWQQGNVFSC SVMHEALHNHYTQKSLSLSPGK | 108 |
| M1IC-DG2 | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| | Fusion Peptide 1 | VHs | I2C | EVQLVESGGGLVQPGSLKLSCAASGFTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGTKLTVL | 10 |
| | | Hinge1 | Hin3 | GGGGSDKTHTCP | 68 |
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSVLTVVHQDW LNGKEYKCKVSNKGLPAPIEKTISKTK | 99 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | DG2CH2 | PCPAPPVAGPSVFLFPPKPKDTLMISRTPEVTCVVVASVSHEDPEVQFNWYVDGVEVHNAKTKPREEQFNSTFRVVSVLTVVHQDW LNGKEYKCKVSNKGLPAPIEKTISKTK | 99 |
| | | CH3-a | CW:CSAV | GQPREPQVYTLPPCRDELTKNQVSLWCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-G2D | Fusion Peptide 1 | VHs | I2C | EVQLVESGGGLVQPGGSLKLSCAASGFTFSDYWMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 |
| | Linker1 | | | GGGGSGGGGSGGGGS | 54 |
| | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGGTKLTVL | 10 |
| | Hinge1 | CH2 | Hin3 | GGGGSDKTHTCP | 68 |
| | | | DG2CH2 | PCPAPPVAGPSVFLFPPKPKDTLMISRTPEVTCVVVASVSHEDPEVQFNWYVDGVEVHNAKTKPREEQFNSTFRVVSVLTVVHQDW LNGKEYKCKVSNKGLPAPIEKTISKTK | 100 |
| | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | I2C | EVKLDETGGGLVQPGRPMKLSCVASGFTFSDYWMNWVRQSPEKGLEMVAQIRNKPYNYETYYSDSVKGRFTISRDDSKSSVYL QMNNLRVEDMGIYYCTGSYTGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | Hinge2 | | Hin1 | DKTHTCP | 66 |
| | | CH2 | DG2CH2 | PCPAPPVAGPSVFLFPPKPKDTLMISRTPEVTCVVVASVSHEDPEVQFNWYVDGVEVHNAKTKPREEQFNSTFRVVSVLTVVHQDW LNGKEYKCKVSNKGLPAPIEKTISKTK | 100 |
| | CH3-a | CW:CSAV | GQPREPQVYTLPPCRDELTKNQVSLWCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-DG2D | Fusion Peptide 1 | VHs | I2C | EVQLVESGGGLVQPGGSLKLSCAASGFTFSDYWMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 |
| | Linker1 | | | GGGGSGGGGSGGGGS | 54 |
| | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRWVFGGGGTKLTVL | 10 |
| | Hinge1 | CH2 | Hin3 | GGGGSDKTHTCP | 68 |
| | | | DG2DCH2 | PCPAPPVAGPSVFLFPPKPKDTLMISRTPEVTCVVVASVSHEDPEVQFNWYVDGVEVHNAKTKPREEQFNSTFRVVSVLTVVHQDW LNGKEYKCKVSNKGLPAPIEKTISKTK | 101 |
| | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| M1IC-WT | Heavy Chain | VHm | 4420 | EVKLDETGGGLVQPGRPMKLSCVASGFTFSDYWMNWVRQSPEKGLEWVAQIRNKPYNYETYYSDSVYKGRFTISRDDSKSSVYL QMNNLKTEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | DG2DC H2 | PCPAPPVAGPSVFLFPPKPKDTLMISRTPEVTCVVVAVSHEAPEVQFNWYVDGVEVHNAKTKPREQFNSTFRVVSVLTVHQDW LNGKEYKCKVSNKGLPAPIEKTISKTK | 101 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| Fusion Peptide 1 | | VHs | I2C | EVQLVESGGGLVQPGGSLKLSCAASGFTFSTFNKYAMNWVRQAPGKGLEWVARIRSKYNNYATYYADSVKDRFTISRDDSKNTAY LQMNNLKTEDTAVYYCVRHGNFGNSYISYWAYWGQGTLVTVSS | 9 |
| | | Linker1 | Lin10 | GGGGSGGGGSGGGGS | 54 |
| | | VLs | I2C | QTVVTQEPSLTVSPGGTVTLTCGSSTGAVTSGNYPNWVQQKPGQAPRGLIGGTKFLAPGTPARFSGSLLGGKAALTLSGVQPED EAEYYCVLWYSNRFVFGGGTKLTVL | 10 |
| | Hinge1 | | | GGGGSDKTHTCP | 68 |
| | Heavy Chain | CH2 | Hin3 WT | PCPAPELLGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPAPIEKTISKAK | 83 |
| | | CH3-b | CW:CS AV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGRPMKLSCVASGFTFSDYWMNWVRQSPEKGLEWVAQIRNKPYNYETYYSDSVYKGRFTISRDDSKSSVYL QMNNLKTEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQIYICNVNH KPSNTKVDKKVEPKSC | 82 |
| | | Hinge2 | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPAPIEKTISKAK | 83 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-FES-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | Hinge1 | | | GGGGSDKTHTCP | 68 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | FES | PCPAPEFECGPSVFLFPPKDTLMISRTPEVTCVVVDVSHEDPEVKFNWYVDGVEVHNAKTKPREEQYNSTYRVVSVLTVLHQD WLNGKEYKCKVSNKALPASIEKTISKAK | 85 |
| | | CH3-b | CW:CSAV | GQPREPQVCTLPPSRDELTKNQVSLCAVKGFYPSDIAVEWESNGQPENNYKITPPVLDSGSFFLVSKLTVDKSRWQQGNVFSC SVMHEALHNHYTQKSLSLSPGK | 109 |
| Heavy Chain | | VHm | 4420 | EVKLDETGGGLVQPGRPMKLSCVASGFITSDYWMNWVRQSPEKGLEWVAQIRNKPYNYETYYSDYKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | Hinge2 | Hin1 | FES | DKTHTCP | 66 |
| | CH2 | | | PCPAPEFEGGPSVFLFPPKPKDTLMISRTPEVTCVVVDVSHEDPEVKFNWYVDGVEVHNAKTKPREEQYNSTYRVVSVLTVLHQD WLNGKEYKCKVSNKALPASIEKTISKAK | 85 |
| | CH3-a | CW:CSAV | GQPREPQVYTLPPCRDLTKNQVSLWCLVKGFYPSDIAVEWESNGQPENNYKTTPVLDSGSFFLYSKLTVDKSRWQQGNVFSC SVMHEALHNHYTQKSLSLSPGK | 108 |
| Light Chain | | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-AAG-1 | Fusion Peptide 1 | VHs | 2a5 | QVQLVESGGGVVQPGRSLRLSCAASGFTFSTYAMNWVRQAPGKGLEWVARIRSKYNNYATTYADSVKGRFTISRDDSKNTLYLQ MNSLRAEDTAVYYCARHGNFGNSYVSWFA**YWGQGTLVTVSS | 1 |
| | Linker1 | Lin10 | | GGGSGGGSGGGS | 54 |
| | VLs | 2a5 | | QTVVTQEPSLTVSPGGTVTLTCRSSTGAVTTSNYANWVQQKPGQAPRGLIGGTNKRAPGVPARFSGSLLGKAALTLSGVQPEDE AEYYCALWYSNLWVFGGGSDKTHTCP | 2 |
| | Hinge1 | Hin3 | AAG | GGGSDKTHTCP | 68 |
| | CH2 | | | PCPAPEAAGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALGAPIEKTISKAK | 84 |
| | CH3-b | CW:CSAV | GQPREPQVCTLPPSRDELTKNQVSLCAVKGFYPSDIAVEWESNGQPENNYKTTPPVLDSGSFFLVSKLTVDKSRWQQGNVFSC SVMHEALHNHYTQKSLSLSPGK | 109 |
| Heavy Chain | | VHm | 4420 | EVKLDETGGGLVQPGRPMKLSCVASGFITSDYWMNWVRQSPEKGLEWVAQIRNKPYNYETYYSDYKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | Hinge2 | Hin1 | AAG | DKTHTCP | 66 |
| | CH2 | | | PCPAPEAAGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALGAPIEKTISKAK | 84 |
| | CH3-a | CW:CSAV | GQPREPQVYTLPPCRDLTKNQVSLWCLVKGFYPSDIAVEWESNGQPENNYKTTPVLDSGSFFLYSKLTVDKSRWQQGNVFSC SVMHEALHNHYTQKSLSLSPGK | 108 |
| Light Chain | | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC- | Fusion | VHs | 2a5 | QVQLVESGGGVVQPGRSLRLSCAASGFTFSTYAMNWVRQAPGKGLEWVARIRSKYNNYATTYADSVKGRFTISRDDSKNTLYLQ | 1 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| G2-1 | Peptide 1 | Linker1 VLs | Lin10 2a5 | MNSLRAEDTAVYYCARHGNFGNSYVSWFAYWGQGTLVTVSS GGGGSGGGGSGGGGS<br>QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 54<br>2 |
| | | Hinge1 CH2 | Hin3 G2CH2 | GGGGSDKTHTCP<br>PCPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 68<br>94 |
| | | CH3-b | CW:CS AV | GQPREPQVCTLPPSRDELTKNQVSLSCAVKGFYPSDIAVEWESNGQPENNYKTTPPVLDSDGSFFLIVSKLTVDKSRWQQGNVFSC SVMHEALHNHYTQKSLSLSPGK | 109 |
| | Heavy Chain | VHm CH1 | 4420 CH1 | EVKLDETGGGLVQPGRPMKLSCVASGFTFSDYYMNWVRQSPEKGLEWVAQIRNKPYNYETYYSDSVKGRFTISRDDSKSSVYL QMNNLRVEDMGIYYCTGSYYGMDYWGQGTSVTVSS ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 43<br>82 |
| | | Hinge2 CH2 | Hin1 G2CH2 | DKTHTCP<br>PCPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 66<br>94 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm CL | 4420 Lc1 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK<br>RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 44<br>75 |
| M1IC-SG2-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 VLs | Lin10 2a5 | GGGGSGGGGSGGGGS<br>QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 54<br>2 |
| | | Hinge1 CH2 | Hin3 SG2CH2 | GGGGSDKTHTCP<br>PSPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 68<br>95 |
| | | CH3-b | CW:CS AV | GQPREPQVCTLPPSRDELTKNQVSLSCAVKGFYPSDIAVEWESNGQPENNYKTTPPVLDSDGSFFLIVSKLTVDKSRWQQGNVFSC SVMHEALHNHYTQKSLSLSPGK | 109 |
| | Heavy Chain | VHm CH1 | 4420 CH1 | EVKLDETGGGLVQPGRPMKLSCVASGFTFSDYYMNWVRQSPEKGLEWVAQIRNKPYNYETYYSDSVKGRFTISRDDSKSSVYL QMNNLRVEDMGIYYCTGSYYGVIDYWGQGTSVTVSS ASTKGPSVFPLAPSSKSTSGGTAALGCLVKDYFPEPVTVSWNNSGALTSGVHTFPAVLQSSGLYSLSSVVTVPSSSLGTQTYICNVNH KPSNTKVDKKVEPKSC | 43<br>82 |
| | | Hinge2 CH2 | Hin1 SG2CH2 | DKTHTCP<br>PSPAPPVAGPSVFLFPPKPKDTLMISRTPEVTCVVVDVSHEDPEVQFNWYVDGVEVHNAKTKPREEQFNSTFRVVSVLTVVHQDW LNGKEYKCKVSNKGLPAPIEKTISKTK | 66<br>95 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE | 44 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | Chain | CL | Lc1 | DLGVYFCSQSTHVPWTFGGGTKLEIK RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-AG2-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin3 | GGGSDKTHTCP | 68 |
| | | CH2 | AG2CH2 | PAPAPPVAGPSVFLFPPKPKDTLMISRTPEVTCVVVDSHEDPEVQFNWYVDGVEVHNAKTKPREEQFNSTFRVVSLTVVHQD WLNGKEYKCCKVSNKGLPAPIEKTISKTK | 96 |
| | | CH3-b | Cw:CSAV | GQPREPQVCTLPPSRDELTKNQVSLSCAVKGFYPSDIAVEWESNGQPENNYKTTPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGGSLKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | AG2CH2 | PAPAPPVAGPSVFLFPPKPKDTLMISRTPEVTCVVVDSHEDPEVQFNWYVDGVEVHNAKTKPREEQFNSTFRVVSLTVVHQD WLNGKEYKCCKVSNKGLPAPIEKTISKTK | 96 |
| | | | AV | GQPREPQVTLPPSRCDELTKNQVSLMCLVKGFYPSDIAVEWESNGQPENNYKTTPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-GG1-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin3 | GGGGSDKTHTCP | 68 |
| | | CH2 | GG2CH2 | PGPAPPVAGPSVFLFPPKPKDTLMISRTPEVTCVVVDSHEDPEVQFNWYVDGVEVHNAKTKPREEQFNSTFRVVSLTVVHQD WLNGKEYKCCKVSNKGLPAPIEKTISKTK | 97 |
| | | CH3-b | Cw:CSAV | GQPREPQVCTLPPSRDELTKNQVSLSCAVKGFYPSDIAVEWESNGQPENNYKTTPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGGSLKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | GG2CH2 | PGPAPPVAGPSVFLFPPKPKDTLMISRTPEVTCVVVDVSHEDPEVQFNWYVDGVEVHNAKTPREEQFNSTFRVVSVLTVVHQD | 97 |
| | | CH3-a | CW:CSAV | WLNGKEYKCKVSNKGLPAPIEKTISKTK<br>GQPREPQVYTLPPCRDELTKNQVSLWCLVKGFYPSDIAVEWESNGQPENNYKTTPPVLDSGSFFLYSKLTVDKSRWQQGNVFSC<br>SVMHEALHNHYTQKSLSLSPGK | 108 |
| | Light Chain | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEAE<br>DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY<br>ACEVTHQGLSSPVTKSFNRGEC | 75 |
| M1IC-PG2-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ<br>MNSLRAEDTAVYYCARHGNFGNSYVSWFAYWGQGTLVTVSS | 1 54 |
| | | Linker1 | | GGGGSGGGGSGGGGS | 2 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE<br>AEYYCALWYSNLWVFGGGTKVEIK | |
| | | Hinge1 | Hin3 | GGGGSDKTHTCP | 68 98 |
| | | CH2 | PG2CH2 | PPAPPVAGPSVFLFPPKPKDTLMISRTPEVTCVVVDVSHEDPEVQFNWYVDGVEVHNAKTPREEQFNSTFRVVSVLTVVHQDW<br>LNGKEYKCKVSNKGLPAPIEKTISKTK | |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC<br>SVMHEALHNHYTQKSLSLSPGK | 109 |
| | Heavy Chain | VHm | 4420 | EVKLDETGGLVQPGRPMKLSCVASGFTESDYVVMNWVRQSPEKGLEWVAQIRNKPYNYETYYSDSVKGRETISRDDSKSSVYL<br>QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH<br>KPSNTKVDKKVEPKSC | 82 |
| | | Hinge2 | Hin1 | DKTHTCP | 66 |
| | | CH2 | PG2CH2 | PPAPPVAGPSVFLFPPKPKDTLMISRTPEVTCVVVDVSHEDPEVQFNWYVDGVEVHNAKTPREEQFNSTFRVVSVLTVVHQDW<br>LNGKEYKCKVSNKGLPAPIEKTISKTK | 98 |
| | | CH3-a | CW:CSAV | GQPREPQVYTLPPCRDELTKNQVSLWCLVKGFYPSDIAVEWESNGQPENNYKTTPPVLDSGSFFLYSKLTVDKSRWQQGNVFSC<br>SVMHEALHNHYTQKSLSLSPGK | 108 |
| | Light Chain | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEAE<br>DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY<br>ACEVTHQGLSSPVTKSFNRGEC | 75 |
| M1IC-DG2-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ<br>MNSLRAEDTAVYYCARHGNFGNSYVSWFAYWGQGTLVTVSS | 1 |
| | | Linker1 | | GGGGSGGGGSGGGGS | 54 2 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE<br>AEYYCALWYSNLWVFGGGTKVEIK | |
| | | Hinge1 | Hin3 | GGGGSDKTHTCP | 68 |
| | | CH2 | DG2CH2 | PCPAPPVAGPSVFLFPPKPKDTLMISRTPEVTCVVVAVSHEDPEVQFNWYVDGVEVHNAKTPREEQFNSTFRVVSVLTVVHQDW<br>LNGKEYKCKVSNKGLPAPIEKTISKTK | 99 |
| | | CH3-b | CW:CSAV | GQPREPQVCTLPPSRDELTKNQVSLSCAVKGFYPSDIAVEWESNGQPENNYKTTPPVLDSDGSFFLVSKLTVDKSRWQQGNVFSC<br>SVMHEALHNHYTQKSLSLSPGK | 109 |

TABLE 28-continued

Code and amino acid sequence of some antibodies with multifunctional antibody structure 1

| Antibody Code | Polypeptide | Domain | Code | Amino acid sequence (CDR is underlined in bold) | SEQ ID NO |
|---|---|---|---|---|---|
| M1IC-G2D-1 | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | G2DCH | PCPAPPVAGPSVFLFPPKPKDILMISRIPEVTCVVVAVSHEDPEVQFNWYVDGVEVHNAKIPREEQFNSIFRVVSVLTVVHQDW LNGKEYKCCKVSNKGLPAPIEKTISKTK | 99 |
| | | CH3-a | CW:CSAV | GQPREPQVYTLPPCRDELTKNQVSLMCLVKGFYPSDIAVEWESNGQPENNYKITPPVLDSDGSFFLYSKLTVDKSRWQQGNVFSC SVMHEALHNHYTQKSLSLSPGK | 108 |
| | Light Chain | VLm | 4420 | DVVMIQIPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-G2D-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin3 | GGGGSDKTHTCP | 68 |
| | | CH2 | G2DCH | PCPAPPVAGPSVFLFPPKPKDTLMISRTPEVTCVVVDVSHEAPEVQFNWYVDGVEVHNAKTPREEQFNSTFRVVSVLTVVHQDW LNGKEYKCCKVSNKGLPAPIEKTISKTK | 100 |
| | | CH3-b | CW:CSAV | GQPREPQVCTLPPSRDELTKNQVSLSCAVKGFYPSDIAVEWESNGQPENNYKTTPPVLDSDGSFFLYSKLTVDKSRWQQGNVFSC SVMHEALHNHYTQKSLSLSPGK | 109 |
| M1IC-DG2D-1 | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | G2DCH | PCPAPPVAGPSVFLFPPKPKDTLMISRTPEVTCVVVDVSHEAPEVQFNWYVDGVEVHNAKTPREEQFNSTFRVVSVLTVVHQDW LNGKEYKCCKVSNKGLPAPIEKTISKTK | 100 |
| | | CH3-a | CW:CSAV | GQPREPQVCTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-DG2D-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | | Hinge1 | Hin3 | GGGGSDKTHTCP | 68 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | DG2DC H2 | PCPAPPVAGPSVFLFPPKPKDTLMISRTPEVTCVVVDVSHEDPEVQFNWYVDGVEVHNAKTPREEQFNSTFRVVSVLTVVHQDW LNGKEYKCCKVSNKGLPAPIEKTISKTK | 101 |
| | | CH3-b | CW:CS AV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLSPGK | 109 |
| | Heavy Chain | VHm | 4420 | EVKLDETGGGLVQPGGSVFLFPPKPKDTLMISRTPEVTCVVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | DG2DC H2 | PCPAPPVAGPSVFLFPPKPKDTLMISRTPEVTCVVVAVSHEAPEVQFNWYVDGVEVHNAKTPREEQFNSTFRVVSVLTVVHQDW LNGKEYCKVSNKGLPAPIEKTISKTK | 101 |
| | | CH3-a | CW:CS AV | GQPREPQVYTLPPCRDELTKNQVSLMCLVKGFYPSDIAVEWESNGQPENNYKTTPPVLDSDGSFFLYSKLTVDKSRWQQGNVFSC SVMHEALHNHYTQKSLSLSPGK | 108 |
| | Light Chain | VLm | 4420 | DVVMTQTPLSLPVSLGDQASISCRSSQSLVHSNGNTYLRVVYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC-DG2D-1A | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | Linker1 | Linker10 | | GGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDE AEYYCALWYSNLWVFGGGTKVEIK | 2 |
| | Hinge1 | Hin3 | | GGGGSDKTHTCP | 68 |
| | CH2 | DG2DC H2 | | PCPAPPVAGPSVFLFPPKPKDTLMISRTPEVTCVVVDVSHEDPEVQFNWYVDGVEVHNAKTPREEQFNSTFRVVSVLTVVHQDW LNGKEYKCCKVSNKGLPAPIEKTISKTK | 101 |
| | CH3-b | CSAVR F:CW | | GQPREPQVYTLPPSRDELTKNQVSLMCLVKGFYPSDIAVEWESNGQPENNYKTTPPVLDSDGSFFLVSKLTVDKSRWQQGNVFSC SVMHEALHNHYTQKSLSLSPGK | 107 |
| | Heavy Chain | VHm | 4420 | EVKLDETGGGLVQPGGSVFLFPPKPKDTLMISRTPEVTCVVASGFTFSDYWMNWVRQSPEKGLHWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | DG2DC H2 | PCPAPPVAGPSVFLFPPKPKDTLMISRTPEVTCVVVDVSHEDPEVQFNWYVDGVEVHNAKTPREEQFNSTFRVVSVLTVVHQDW LNGKEYCKVSNKGLPAPIEKTISKTK | 101 |
| | | CH3-a | CSAVR F:CW | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| M1IC- | Fusion | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ | 1 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| DG2D-1B | Peptide 1 | Linker1 | Lin10 | MNSLRAEDTAVYYCARHGNFGNSYVSWFAYWGQGTLVTVSS GGGGSGGGGSGGGGS | 54 |
| | | VLs | 2a5 | QTVVTQEPSLTVSPGGTVTLTCRSSTGAVTTSNYAN WVQQKPGQAPRGLIGGTNKRAPGVPARFSGSLLGGKAALTLSGVQPEDE AEYYCALWYSNLWVFGGGTKVEIK | 2 |
| | | Hinge1 | Hin3 | GGGGSDKTHTCP | 68 |
| | | CH2 | DG2DC H2 | PCPAPPVAGPSVFLFPPKPKDTLMISRTPEVTCVVVASHEAPEVQFNWYVDGVEVHNAKTKPREEQFNSTFRVVSVLTVVHQDW LNGKEYKCKVSNKGLPAPIEKTISKTK | 101 |
| | | CH3-b | CSAV:C WRF | GQPREPQVYTLPPCRDELTKNQVSLMCVLVKGFYPSDIAVEWESNGQPENNYKTTPPVLDSDGSFFLYSKLTVDKSRWQQGNVFSCS VMHEALHNRFTQKSLSLPGK | 115 |
| | Heavy Chain | VHm | 4420 | EVKLDETGGGLVQPGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSVNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |
| | | CH2 | DG2DC H2 | PCPAPPVAGPSVFLFPPKPKDTLMISRTPEVTCVVVASHEAPEVQFNWYVDGVEVHNAKTKPREEQFNSTFRVVSVLTVVHQDW LNGKEYKCKVSNKGLPAPIEKTISKTK | 101 |
| | | CH3-a | CSAV:C WRF | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLPGK | 114 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAE DLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC | 75 |
| MIC-WT-1 | Fusion Peptide 1 | VHs | 2a5 | QVQLVESGGGVVQPGRSLRLSCAASGFTFSTYAMNWVRQAPGKGLEWVARIRSKYNNYATYYADSVKDRFTISRDDSKNTLYLQ MNSLRAEDTAVYYCARHGNFGNSYVSWFAYWGQGTLVTVSS | 1 |
| | | Linker1 | Lin10 | GGGGSGGGGSGGGGS | 54 |
| | | VLs | 2a5 | QTVVTQEPSLTVSPGGTVTLTCRSSTGAVTTSNYAN WVQQKPGQAPRGLIGGTNKRAPGVPARFSGSLLGGKAALTLSGVQPEDE AEYYCALWYSNLWVFGGGTKVEIK | 2 |
| | | Hinge1 | Hin3 WT | GGGGSDKTHTCP | 68 |
| | | CH2 | | PCPAPELLGGPSVFLFPPKPKDTLMISRTPEVTCWDVSHED PEVKFNWYVDGVEVHNAKTKPREEQYNSTYRVVSVLTVLHQD WLNGKEYKCKVSNKALPAPIEKTISKAK | 83 |
| | | CH3-b | CW:CS AV | GQPREPQVCTLPPSRDELTKNQVSLSCAVKGFYPSDIAVEWESNGQPENNYKTTPPVLDSDGSFFLVSKLTVDKSRWQQGNVFSC SVMHEALHNHYTQKSLSLPGK | 109 |
| | Heavy Chain | VHm | 4420 | EVKLDETGGGLVQPGGLVQPGRPMKLSCVASGFTFSDYWMNWVRQSPEKGLEWVAQIRNKPYNYETYYSDSVKGRFTISRDDSKSSVYL QMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSVNSGALTSGVHTFPAVLQSSGLYSLSSVVTVPSSSLGTQTYICNVNH KPSNTKVDKKVEPKSC | 82 |
| | | Hinge2 | Hin1 | DKTHTCP | 66 |

TABLE 28-continued

Code and amino acid sequence of some antibodies with multifunctional antibody structure 1

| Antibody Code | Poly-Peptide | Domain | Code | Amino acid sequence (CDR is underlined in bold) | SEQ ID NO |
|---|---|---|---|---|---|
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 83 |
| | | CH3-a | CW:CSAV | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 108 |
| Light Chain | VLm | | 4420 | DVVMTQTPLSLPVSLGDQASISCRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | CL | | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |

TABLE 29

Code and amino acid sequence of some antibodies with multifunctional antibody structure 2 (CDR is underlined in bold)

| Antibody Code | Polypeptide | Domain | Code | Amino acid sequence | 序列号 |
|---|---|---|---|---|---|
| BCMA-M2-WT | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSVTAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSTVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPEDEAEYYCALWYSNLWVFGGGTKVEIK | 2 |
| | | Hinge2 | Hin3 | GGGGSDKTHTCP | 68 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 83 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSVTAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge3 | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 83 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGNNNIGSKSVHWYQQPPGQAPVVVVYDDSDRPSGIPERPSGNSNGNTATLTISRVEAGDEAVYYCQVWDSSSDHVVFGGGTKLTVL | 30 |
| | | CL | Lc1 | RTVAAPSVFIFPPSDEQLKSGTASVVCLLNNFYPREAKVQNKVDNALQSGNSQESVTEQDSKDSTYSLSSTLTLSKADYEKHKVYACEVTHQGLSSPVTKSFNRGEC | 75 |
| BCMA-M2-FES | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSVTAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSTVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPEDEAEYYCALWYSNLWVFGGGTKVEIK | 2 |
| | | Hinge2 | Hin3 | GGGGSDKTHTCP | 68 |
| | | CH2 | FES | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 85 |

TABLE 29-continued

Code and amino acid sequence of some antibodies with multifunctional antibody structure 2

| Antibody Code | Polypeptide | Domain | Code | Amino acid sequence (CDR is underlined in bold) | 片列号 |
|---|---|---|---|---|---|
| | Heavy Chain | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | FES | PCPAPEFEGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALPASIEKTISKAK | 85 |
| | | CH3-a | CSAVRF: CW | GQPREPQVCTLPPSRDELTKNQVSLCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGGNNIGSKSVHWYQQKPGQAPVLVVYDDSDRPSGIPERFSGSNSGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| BCMA-M2-G2 | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
| | | Linker3 | Lin10 | GGGSGGGGSGGGGS | 54 |
| | | VLs | 2a5 | QTVVTQEPSLTVSPGGTVTLTCRSSTGAVTTSNYANWVQQKPGQAPRGLIIGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 94 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 94 |
| | | CH3-a | CSAVRF: CW | GQPREPQVCTLPPSRDELTKNQVSLCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGGNNIGSKSVHWYQQKPGQAPVLVVYDDSDRPSGIPERFSGSNSGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| BCMA-M2-SG2 | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | SG2CH2 | PSPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 95 |
| | | CH3-b | CSAVRF:CW | GQPREPQVYTLPPSRDELTKNQVSLTCAVKGFYPSDIAVEWESNGQPENNYKTTPVLDSDGSFFLYSKLTVDKSRWQQGNVFS CSVMHEALHNRFTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | SG2CH2 | PSPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 95 |
| | | CH3-a | CSAVRF:CW | GQPREPQVCTLPPSRDELTKNQVSLSCAVKGFYPSDIAVEWESNGQPENNYKTTPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGNNIGSKSVHWYQQPPGQAPVVVVYDDSDRPSGIPERFSGSNSNGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| BCMA-M2-AG2 | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | AG2CH2 | PAPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 96 |
| | | CH3-b | CSAVRF:CW | GQPREPQVYTLPPSRDELTKNQVSLMCLVKGFYPSDIAVEWESNGQPENNYKTTPVLDSDGSFFLYSKLTVDKSRWQQGNVFS CSVMHEALHNHYTQKSLSLSPGK | 107 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | Hin1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | AG2CH2 | PAPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 96 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGGNNIGSKSVHWYQQPPGQAPVVVVYDDSDRPSGIPERFSGNSGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| BCMA-M2-GG2 | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | Hin1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSIYSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | GG2CH2 | PGPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 97 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | Hin1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | GG2CH2 | PGPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 97 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGGNNIGSKSVHWYQQPPGQAPVVVVYDDSDRPSGIPERFSGNSGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| BCMA-M2-PG2 | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | PG2CH2 | PPPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 98 |
| | | CH3-b | CSAVRF:CW | GQPREPQVYTLPPSRDELTKNQVSLTCLVKGFYPSDIAVEWESNGQPENNYKTTPVLDSDGSFFLYSKLTVDKSRMQQGNVFS CSVMHEALHNRFTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | PG2CH2 | PPPAPPVAGPSVFLFPPKPKDTLMISRTPEVTCVVVDSHEDPEVQFNWYVDGVEVHNAKTKPREEQFNSTFRVVSVLTVVHQD WLNGKEYKCKVSNKGLPAPIEKTISKTK | 98 |
| | | CH3-a | CSAVRF:CW | GQPREPQVCTLPPSRDELTKNQVSLSCAVKGFYPSDIAVEWESNGQPENNYKTTPVLDSDGSFFLVSKLTVDKSRMQQGNVFS CSVMHEALHNRFTQKSLSLSPGK | 106 |
| | Light Chain | VLm | B69 | SYVLTQPPSVSVAPGQTARITCGNNIGSKSVHWYQQPGQAPVVVVYDDSDRPSGIPERFSGNSNGNTATLTISRVEAGDEAVY YCQVWDSSSDHVVFGGGTLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| BCMA-M2-DG2 | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSVLTVVHQD WLNGKEYKCKVSNKGLPAPIEKTISKTK | 99 |
| | | CH3-b | CSAVRF:CW | GQPREPQVYTLPPSRDELTKNQVSLTCLVKGFYPSDIAVEWESNGQPENNYKTTPVLDSDGSFFLYSKLTVDKSRMQQGNVFS CSVMHEALHNRFTQKSLSLSPGK | 107 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | G2CH2 | PCPAPPVAGPSVFLFPPKPKDTLMISRTPEVTCVVVAVSHEDPEVQFNWYVDGVEVHNAKTKPREEQFNSTFRVVSVLTVVHQD WLNGKEYKCKVSNKGLPAPIEKTISKTK | 99 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGGNNIGSKSVHWYQQPPGGQAPVVVVYDDSDRPSGIPERFSGNSGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| BCMA-M2-G2D | Fusion Peptide 2 | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATTYADSVKDRFTISRDDSKNTLYL QMNSLRAEDTAVYYCARHGNNFGNSIYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPED EAEYYCALWYSNLWVFGGGTKVEIK | 2 |
| | | Hinge2 | Hin3 | GGGGSDKTHTCP | 68 |
| | | CH2 | G2DCH2 | PCPAPPVAGPSVFLFPPKPKDTLMISRTPEVTCVVVSHEAPEVQFNWYVDGVEVHNAKTKPREEQFNSTFRVVSVLTVVHQD WLNGKEYKCKVSNKGLPAPIEKTISKTK | 100 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | G2DCH2 | PCPAPPVAGPSVFLFPPKPKDTLMISRTPEVTCVVVSHEAPEVQFNWYVDGVEVHNAKTKPREEQFNSTFRVVSVLTVVHQD WLNGKEYKCKVSNKGLPAPIEKTISKTK | 100 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | B69 | SYVLTQPPSVSVAPGQTARITCGGNNIGSKSVHWYQQPPGGQAPVVVVYDDSDRPSGIPERFSGNSGNTATLTISRVEAGDEAVY YCQVWDSSSDHVVFGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| BCMA-M2- | Fusion Peptide | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTVSS | 29 |

TABLE 29-continued

Code and amino acid sequence of some antibodies with multifunctional antibody structure 2

| Antibody Code | Polypeptide | Domain | Code | Amino acid sequence (CDR is underlined in bold) | 片列号 |
|---|---|---|---|---|---|
| DG2D | 2 | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYYSWFAYWGQGTLVTVSS | 1 |
| | | Linker3 | Lin10 | GGGGSGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGSDKTHTCP | 68 |
| | | CH2 | DG2DCH2 | PCPAPPVAGPSVFLFPPKPKDTLMISRTPEVTCVVVAVSHEAPEVQFNWYVDGVEVHNAKTKPREEQFNSTFRVVSVLTVVHQD WLNGKEYKCKVSNKGLPAPIEKTISKTK | 101 |
| | | CH3-b | CSAVRF:CW | GQPREPQVYTLPPCRDELTKNQVSLWCLVKGFYPSDIAVEWESNGQPENNYKTTPVLDSDGSFFLYSKLTVDKSRWQQGNVFS CSVMHEALHNHYTQKSLSLSPGK | 107 |
| | Heavy Chain | VHm | B69 | QLQLQESGPGLVKPSETLSLTCTVSGGSISSGSYFWGWIRQPPGKGLEWIGSIYYSGITYYNPSLKSRVTISVDTSKNQFSLKLSSV TAADTAVYYCARHDGAVAGLFDYWGQGTLVTSS | 29 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN | 82 |
| | | Hinge2 | Hin1 | DKTHTCP | 66 |
| | | CH2 | DG2DCH2 | PCPAPPVAGPSVFLFPPKPKDTLMISRTPEVTCVVVAVSHEAPEVQFNWYVDGVEVHNAKTKPREEQFNSTFRVVSVLTVVHQD WLNGKEYKCKVSNKGLPAPIEKTISKTK | 101 |
| | | CH3-a | CSAVRF:CW | GQPREPQVCTLPPSRDELTKNQVSLSCAVKGFYPSDIAVEWESNGQPENNYKTTPVLDSDGSFFLVSKLTVDKSRMQQGNVFS CSVMHEALHNRFTQKSLSLSPGK | 106 |
| | Light Chain | VLm | B69 | SYVLTQPPSVSVAPGQTARITCGGNNIGSKSVHWYQQPPGQAPVVVVYDDSDRPSGIPERFSGNSNGNTATLTISRVEAGDEAVY YCQVWDSSSDHVV**FGGGTKLTVL | 30 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| M2IC-WT | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYYSWFAYWGQGTLVTVSS | 1 |
| | | Linker3 | Lin10 | GGGGSGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGSDKTHTCP | 68 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALPAPIEKTISKAK | 83 |
| | | CH3-b | CSAVRF:CW | GQPREPQVYTLPPCRDELTKNQVSLWCLVKGFYPSDIAVEWESNGQPENNYKTTPVLDSDGSFFLYSKLTVDKSRWQQGNVFS CSVMHEALHNHYTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVY | 43 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| M2IC-AAG | | | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge3 | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 83 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATTYADSVKDRFTISRDDSKNTLYLQMNSLRAEDTAVYYCARHGNFGNSYVSWFAYWGQGTLVTVSS | 1 |
| | | | | GGGSGGGGSGGGGS | |
| | | Linker3 | Lin10 | QTVTVTQEPSLTVSPGGTVTLTCRSSTGAVTTSNYANWVQQKPGQAPRGLIGGTNKRAPGVPARFSGSLLGKAALTLSGVQPED | 54 |
| | | VLs | 2a5 | EAEYYCALWYSNLWVFGGGTKVEIK | 2 |
| | | Hinge2 | Hin3 | GGGSDKTHTCP | 68 |
| | | CH2 | AAG | PCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAK | 84 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNRFTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge3 | Hin1 | DKTHTCP | 66 |
| | | CH2 | AAG | PCPAPEAAGGPSVFLFPPKPKDTLMISRTPEVTCVVVDVSHEDPEVKFNWYVDGVEVHNAKTKPREEQYNSTYRVVSVLTVLH | 84 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| M2IC-NA | Fusion Peptide | VHm | 4420 | EVKLDETGGGLVQPGRPMKLSCVASGFTFSDYWMNWVRQSPEKGLEWVAQIRNKPYNYETYYSDSVKGRFTISRDDSKSSVY | 43 |

TABLE 29-continued

Code and amino acid sequence of some antibodies with multifunctional antibody structure 2

| Antibody Code | Polypeptide | Domain | Code | Amino acid sequence (CDR is underlined in bold) | 片<br>列<br>号 |
|---|---|---|---|---|---|
| | 2 | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN<br>HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATVADSVKDRFTISRDDSKNTLYL<br>QMNSLRAEDTAVYYCARHGNFGNSYYSWFAYWGQGTLVTVSS | 1 |
| | | Linker3 | Lin10 | GGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED<br>EAEYYCALWYSNLWVFGGGTKVEIK | 2 |
| | | Hinge2 | Hin3 | GGGSDKTHTCP | 68 |
| | | CH2 | N297A | PCPAPELLGGPSVFLFPPKPKDTLMISRTPEVTCVVVDVSHEDPEVKFNWYVDGVEVHNAKTKPREEQYASTYRVVSVLTVLHQ<br>DWLNGKEYKCKVSNKALPAPIEKTISKAK | 87 |
| | | CH3-b | CSAVRF:<br>CW | GQPREPQVYTLPPCRDELTKNQVSLWCLVKGFYPSDIAVEWESNGQPENNYKTTPPVLDSDGSFFLYSKLTVDKSRWQQGNVFS<br>CSVMHEALHNHYTQKSLSLSPGK | 107 |
| | Heavy<br>Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY<br>LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN<br>HKPSNTKVDKKVEPKSC | 82 |
| | | Hinge3 | Hin1 | DKTHTCP | 66 |
| | | CH2 | N297A | PCPAPELLGGPSVFLFPPKPKDTLMISRTPEVTCVVVDVSHEDPEVKFNWYVDGVEVHNGQPENNYKTTPPVLDSDGSFFLVSKLTVDKSRMQQGNVFS | 87 |
| | | CH3-a | CSAVRF:<br>CW | GQPREPQVCTLPPSRDELTKNQVSLSCAVKGFYPSDIAVKEWESNGQPENNYKTTPPVLDSDGSFFLVSKLTVDKSRMQQGNVFS | 106 |
| | Light<br>Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA<br>EDLGVFFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV<br>YACEVTHQGLSSPVTKSFNRGEC | 75 |
| M2IC-<br>FES | Fusion<br>Peptide<br>2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY<br>LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN<br>HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL<br>QMNSLRAEDTAVYYCARHGNFGNSYYSWFAYWGQGTLVTVSS | 1 |
| | | Linker3 | Lin10 | GGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED<br>EAEYYCALWYSNLWVFGGGTKVEIK | 2 |
| | | Hinge2 | Hin3 | GGGSDKTHTCP | 68 |
| | | CH2 | FES | PCPAPEFEGGPSVFLFPPKPKDTLMISRTPEVTCVVVDVSHEDPEVKFNWYVDGVEVHNAKTKPREEQYNSTYRVVSVLTVLHQ<br>DWLNGKEYKCKVSNKALPASIEKTISKAK | 85 |
| | | CH3-b | CSAVRF:<br>CW | GQPREPQVYTLPPCRDELTKNQVSLWCLVKGFYPSDIAVEWESNGQPENNYKTTPPVLDSDGSFFLYSKLTVDKSRWQQGNVFS<br>CSVMHEALHNHYTQKSLSLSPGK | 107 |
| | Heavy<br>Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY<br>LQMNNLRVEDMGIYYCTGSYYGMDYWGQGTSVTVSS | 43 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| M2IC-G2 | | | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | FES | PCPAPEFEGGPSVFLFPPKPKDTLMISRTPEVTCVVVDVSHEDPEVKFNWYVDGVEVHNAKTKPREEQYNSTYRVVSVLTVLHQ DWLNGKEYKCKVSNKALPASIEKTISKAK | 85 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | 4420 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATTYADSVKDRFTISRDDSKNTLYL QMNSLRAEDTAVYYCARHGNFGNSYVSWFAYWGQGTLVTVSS | 1 |
| | | Linker3 | Lin10 | GGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGKAALTLSGVQPED EAEYYCALWYSNLWVFGGGTKVEIK | 2 |
| | | Hinge2 | Hin3 | GGGSDKTHTCP | 68 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQD WLNGKEYKCCKVSNKGLPAPIEKTISKTK | 94 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNRFTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | 4420 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQD WLNGKEYKCCKVSNKGLPAPIEKTISKTK | 94 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| M2IC-SG2 | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | 4420 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYVADSVKDRFTISRDDSKNTLYL QMNSLRAEDTAVYYCARHGNFGNSYVSWFAYWGQGTLVTVSS | 1 |
| | | Linker3 | Lin10 | GGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | SG2CH2 | PSPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 95 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | SG2CH2 | PSPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 95 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| M2IC-AG2 | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYVADSVKDRFTISRDDSKNTLYL QMNSLRAEDTAVYYCARHGNFGNSYVSWFAYWGQGTLVTVSS | 1 |
| | | Linker3 | Lin10 | GGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | | CH2 | AG2CH2 | PAPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 96 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |

TABLE 29-continued

Code and amino acid sequence of some antibodies with multifunctional antibody structure 2

| Antibody Code | Polypeptide | Domain | Code | Amino acid sequence (CDR is underlined in bold) | 片列号 |
|---|---|---|---|---|---|
| M2IC-GG2 | Light Chain | CH2 | AG2CH2 | PAPAPPVAGPSVFLFPPKPKDTLMISRTPEVTCVVVDVSHEDPEVQFNWYVDGVEVHNAKTPREEQFNSTFRVVSVLTVVHQD WLNGKEYKCKVSNKGLPAPIEKTISKTK | 96 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNTANWVQQKPGQAPRGLIGGTNKRAPGVPARFSGSLLGGKAALTLSGVQPED EAEYYCALWYSNLWVFGGGTKVEIK | 2 |
| | | Hinge2 | Hin3 | GGGGSDKTHTCP | 68 |
| | Heavy Chain | CH2 | GG2CH2 | PGPAPPVAGPSVFLFPPKPKDTLMISRTPEVTCVVVDVSHEDPEVQFNWYVDGVEVHNAKTPREEQFNSTFRVVSVLTVVHQD WLNGKEYKCKVSNKGLPAPIEKTISKTK | 97 |
| | | CH3-b | CSAVRF: CW | GQPREPQVTLPPCRDELTKNQVSLWCLVKGFYPSDIAVEWESNGQPENNYKTTPPVLDDGSFFLYSKLTVDKSRWQQGNVFS CSVMHEALHNRFTQKSLSLSPGK | 107 |
| | | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | GG2CH2 | PGPAPPVAGPSVFLFPPKPKDTLMISRTPEVTCVVVDVSHEDPEVQFNWYVDGVEVHNAKTPREEQFNSTFRVVSVLTVVHQD WLNGKEYKCKVSNKGLPAPIEKTISKTK | 97 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| M2IC-PG2 | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |

TABLE 29-continued

Code and amino acid sequence of some antibodies with multifunctional antibody structure 2

| Antibody Code | Polypeptide | Domain | Code | Amino acid sequence (CDR is underlined in bold) | 序列号 |
|---|---|---|---|---|---|
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPED EAEYYCALWYSNLWVFGGGTKVEIK | 2 |
| | | Hinge2 | Hin3 | GGGGSDKTHTCP | 68 |
| | | CH2 | PG2CH2 | PPPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 98 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | PG2CH2 | PPPAPPVAGPSVFLFPPKPKDTLMISRTPEVTCVVVDVSHEDPEVQFNWYVDGVEVHNAKTKPREEQFNSTFRVVSVLTVVHQD WLNGKEYKCKVSNKGLPAPIEKTISKTK | 98 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRMQQGNVFS | 106 |
| | Light Chain | VLm | 4420 | DVVMTQTPLSLPVSLGDQASISCRSSQSLVHSNGNTYLHWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| M2IC-DG2 | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge1 | Hin9 | DKTHT | 74 |
| | | Linker2 | Lin4 | GGGSAAA | 48 |
| | | VHs | 2a5 | QVQLVESGGGVVQPGRSLRLSCAASGFTFSTYAMNWVRQAPGKGLEWVARIRSKYNNYATYVADSVKDRFTISRDDSKNTLYL QMNSLRAEDTAVYYCARHGNFPGNSYVSWFAYWGQGTLVTVSS | 1 |
| | | Linker3 | Lin10 | GGGGSGGGGSGGGGS | 54 |
| | | VLs | 2a5 | QTVVTQEPSLTVSPGGTVTLTCRSSTGAVTTSNYANWVQQKPGQAPRGLIGGTNKRAPGVPARFSGSLLGGKAALTLSGVPED EAEYYCALWYSNLWVFGGGTKVEIK | 2 |
| | | Hinge2 | Hin3 | GGGGSDKTHTCP | 68 |
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSVLTVVHQD WLNGKEYKCKVSNKGLPAPIEKTISKTK | 99 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSVLTVVHQD WLNGKEYKCKVSNKGLPAPIEKTISKTK | 99 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRMQQGNVFS | 106 |

TABLE 29-continued

Code and amino acid sequence of some antibodies with multifunctional antibody structure 2

| Antibody Code | Polypeptide | Domain | Code | Amino acid sequence (CDR is underlined in bold) | 片列号 |
|---|---|---|---|---|---|
| M2IC-G2D | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA EDLGVYFCSQSTHVPWTFGGGTKLEIK | 44 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
|  | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
|  |  | CH1 | CH1 | ASTKGPSVFPLAPSSKSTSGGTAALGCLVKDYFPEPVTVSNSGALTSGVHTFPAVLQSSGLYSLSSVVTVPSSSLGTQTYICNVN HKPSNTKVDKKVEPKSC | 82 |
|  |  | Hinge1 | Hin9 | DKTHT | 74 |
|  |  | Linker2 | Lin4 | GGGSAAA | 48 |
|  |  | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
|  |  | Linker3 | Lin10 | GGGSGGGGSGGGGS | 54 |
|  |  | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
|  |  | Hinge2 | Hin3 | GGGSDKTHTCP | 68 |
|  |  | CH2 | G2DCH2 | PCPAPPVAGPSVFLFPPKPKDTLMISRTPEVTCVVVDVSHEAPEVQFNWYVDGVEVHNAKTKPREEQFNSTFRVVSVLTVVHQD WLNGKEYKCKVSNKGLPAPIEKTISKTK | 100 |
|  |  | CH3-b | CSAVRF:CW | GQPREPQVCTLPPSRDELTKNQVSLSCAVKGFYPSDIAVEWESNGQPENNYKTTPPVLDDGSFFLYSKLTVDKSRWQQGNVFS CSVMHEALHNHYTQKSLSLSPGK | 107 |
|  | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
|  |  | CH1 | CH1 | ASTKGPSVFPLAPSSKSTSGGTAALGCLVKDYFPEPVTVSNSGALTSGVHTFPAVLQSSGLYSLSSVVTVPSSSLGTQTYICNVN HKPSNTKVDKKVEPKSC | 82 |
|  |  | Hinge3 | Hin1 | DKTHTCP | 66 |
|  |  | CH2 | G2DCH2 | PCPAPPVAGPSVFLFPPKPKDTLMISRTPEVTCVVVDVSHEAPEVQFNWYVDGVEVHNAKTKPREEQFNSTFRVVSVLTVVHQD WLNGKEYKCKVSNKGLPAPIEKTISKTK | 100 |
|  |  | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| M2ic-Dg2d | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA EDLGVYFCSQSTHVPWTFGGGTKLEIK | 44 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
|  | Fusion Peptide 2 | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
|  |  | CH1 | CH1 | ASTKGPSVFPLAPSSKSTSGGTAALGCLVKDYFPEPVTVSNSGALTSGVHTFPAVLQSSGLYSLSSVVTVPSSSLGTQTYICNVN HKPSNTKVDKKVEPKSC | 82 |
|  |  | Hinge1 | Hin9 | DKTHT | 74 |
|  |  | Linker2 | Lin4 | GGGSAAA | 48 |
|  |  | VHs | 2a5 | QVQLVESGGGVVQPGRSLRLSCAASGFTFSTYAMNWVRQAPGKGLEWVARIRSKYNNYATYYADSVKDRFTISRDDSKNTLYL QMNSLRAEDTAVYYCARHGNFGNSYVSWFAYWGQGTLVTVSS | 1 |
|  |  | Linker3 | Lin10 | GGGSGGGGSGGGGS | 54 |
|  |  | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPED EAEYYCALWYSNLWVFGGGTKVEIK | 2 |
|  |  | Hinge2 | Hin3 | GGGSDKTHTCP | 68 |

TABLE 29-continued

Code and amino acid sequence of some antibodies with multifunctional antibody structure 2

| Antibody Code | Polypeptide | Domain | Code | Amino acid sequence (CDR is underlined in bold) | 片列号 |
|---|---|---|---|---|---|
| | | CH2 | DG2DCH2 | PCPAPPVAGPSVFLFPPKPKDTLMISRTPEVTCVVVAVSHEAPEVQFNWYDGVEVHNAKTKPREQFNSTFRVVSVLTVVHQD WLNGKEYKCKVSNKGLPAPIEKTISKTK | 101 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNVFS CSVMHEALHNHYTQKSLSLSPGK | 107 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVY LQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge3 | Hin1 | DKTHTCP | 66 |
| | | CH2 | DG2DCH2 | PCPAPPVAGPSVFLFPPKPKDTLMISRTPEVTCVVVAVSHEAPEVQFNWYDGVEVHNAKTKPREQFNSTFRVVSVLTVVHQD WLNGKEYKCKVSNKGLPAPIEKTISKTK | 101 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNVFS CSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEA EDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |

TABLE 30

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| CEA-M3-WT | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTSS | 41 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTSTYAMNWVRQAPGKGLEWVARIRSKYNNYATYYADSVKDRFTISRDDSKNT LYLQMNSLRAEDTAVYYCARHGNFPGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVL HQDWLNGKEYKCKVSNKALPAPIEKTISKAK | 83 |
| | | CH3-b | CSAVRF: CW | GQPREPQVYTLPPCRDELTKNQVSLWCLVKGFYPSDIAVEWESNGQPENNYKTTPPVLDSDGSFFLYSKLITVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWQQKPGQAPRGLIGGTNKRAPGVPARFSGSLLGGKAALTLSGVQ PEDEAEYYCALWYSNLMVFGGGTKVEIK SS | 2 |
| | | Linker6 | Lin1 | | 45 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTSS | 41 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | WT | DKTHTCP | 66 |
| | | CH2 | | PCPAPELLGGPSVFLFPPKPKDTLMISRTPEVTCVVVDVSHEDPEVKFNWYVDGVEVHNAKTKPREEQYNSTYRVVSVLTVL HQDWLNGKEYKCKVSNKALPAPIEKTISKAK | 83 |
| | | CH3-a | CSAVRF: CW | GQPREPQVCTLPPSRDELITKNQVSLSCAVKGFYPSDIAVEWESNGQPENNYKTTPPVLDSDGSFFLVSKLITVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TTYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-AAG | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTSS | 41 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTSTYAMNWVRQAPGKGLEWVARIRSKYNNYATYYADSVKDRFTISRDDSKNT LYLQMNSLRAEDTAVYYCARHGNFPGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | CH2 | AAG | PCPAPEAAGGPSVFLFPPKPKDTLMISRTPEVTCVVVDVSHEDPEVKFNWYVDGVEVHNAKTKPREEQYNSTYRVVSVLTV LHQDWLNGKEYKCKVSNKALGAPIEKTISKAK | 84 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEMGWINTKTGEATYVEEFKGRFVFSLDTSVSTA YLQISSLKADDTAVYYCARWDFYDYVEAMDYWGQGTTVTSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | AAG | PCPAPEAAGGPSVFLFPPKPKDTLMISRTPEVTCVVVDVSHEDPEVKFNWYVDGVEVHNAKTKPREEQYNSTYRVVSVLTV LHQDWLNGKEYKCKVSNKALGAPIEKTISKAK | 84 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTIITCKASQNVGTNVAWYQQKPGKAPKLLIYSASYRYSGVPSRFSGSGSGTDFTFTISSLQPEDIA TYYCHQYYTYPLPFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-NA | Fusion Heavy Chain | VHm | hPR1A3 | QVQLVQSGSELKKPGASVKVSCKASGYTFTVFGMNWVRQAPGQGLEMGWINTKTGEATYVEEFKGRFVFSLDTSVSTA YLQISSLKADDTAVYYCARWDFYDYVEAMDYWGQGTTVTSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYSVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | N297A | PCPAPELLGGPSVFLFPPKPKDTLMISRTPEVTCVVVDVSHEDPEVKFNWYVDGVEVHNAKTKPREEQYASTYRVVSVLTVL HQDWLNGKEYKCKVSNKALPAPIEKTISKAK | 87 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEMGWINTKTGEATYVEEFKGRFVFSLDTSVSTA YLQISSLKADDTAVYYCARWDFYDYVEAMDYWGQGTTVTSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | Hinge3 CH2 | Hin1 N297A | DKTHTCP PCPAPELLGGPSVFLFPPKPKDTLMISRTPEVTCVVVDVSHEDPEVKFNWYVDGVEVHNAKTKPREEQYASTYRVVSVLTVL HQDWLNGKEYKCKVSNKALPAPIEKTISKAK | 66 87 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-FES | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 VHs | Lin7 2a5 | GGGGSGGGGS QVQLVESGGGVVQPGRSLRLSCAASGFTFSTSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 51 1 |
| | | Linker5 CL | Lin2 Lc7 | AS VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 46 81 |
| | | Hinge4 CH2 | Hin1 FES | DKTHTCP PCPAPEFEGGPSVFLFPPKPKDTLMISRTPEVTCVVVDVSHEDPEVKFNWYVDGVEVHNAKTKPREEQYNSTYRVVSVLTVL HQDWLNGKEYKCKVSNKALPASIEKTISKAK | 66 85 |
| | | CH3-b | CSAVRF: CW | GQPREPQVVTLPPCRDELTKNQVSLWCLVKGFYPSDIAVEWESNGQPENNYKTTPPVLDSDGSFFLYSKLTVDKSRWQQGNV FSCSVMHEALHNRFTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 CH1 | Lin1 CH1 | SS ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 45 82 |
| | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 CH2 | Hin1 FES | DKTHTCP PCPAPEFEGGPSVFLFPPKPKDTLMISRTPEVTCVVVDVSHEDPEVKFNWYVDGVEVHNAKTKPREEQYASTYRVVSVLTVL HQDWLNGKEYKCKVSNKALPAPIEKTISKAK | 66 85 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3- | Fusion Heavy | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| G2 | Chain | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTERVVSVLTVVH QDWLNGKEYKCKVSNKGLPAPIEKTISKTK | 94 |
| | | CH3-b | CSAVRF: CW | GQPREPQVYTLPPSRDELTKNQVSLMCLVKGFYPSDIAVEWESNGQPENNYKTTPPVLDSDGSFFLYSKLITVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLMVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFFDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | DKTHTCP | DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTERVVSVLTVVH QDWLNGKEYKCKVSNKGLPAPIEKTISKTK | 94 |
| | | CH3-a | CSAVRF: CW | GQPREPQVCTLPPSRDELTKNQVSLTCAVKGFYPSDIAVEWESNGQPENNYKTTPPVLDSDGSFFLVSKLITVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRPSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-SG2 | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFFDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | SG2CH2 | PSPAPPVAGPSVFLFPPKPKDTLMISRTPEVTCVVVKGFYPSDIAVEWESNGQPENNYKTTPPVLDSDGSFFLYSKLITVDKSRWQQGNV QDWLNGKEYKCKVSNKGLPAPIEKTISKTK | 95 |
| | | CH3-b | CSAVRF: CW | GQPREPQVYTLPPSRDELTKNQVSLMCLVKGFYPSDIAVEWESNGQPENNYKTTPPVLDSDGSFFLYSKLITVDKSRWQQGNV FSCSVMHEALHNHYTQKSLSLSPGK | 107 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | SG2CH2 | PSPAPPVAGPSVFLFPPKPKDTLMISRTPEVTCVVVDVSHEDPEVQFNWYVDGVEVHNAKTPREEQFNSTERVVSVLTVVH QDWLNGKEYKCKVSNKGLPAPIEKTISKTK | 95 |
| | | CH3-a | CSAVRFCW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-AG2 | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGSGGGS | 51 |
| | | VHs | 2a5 | QVQLVESGGGVVQPGRSLRLSCAASGFTFSTTAMNWRQAPGKLEWVARIRSKYNNYATYYADSVKDRFTISRDDSKNT LYLQMNSLRAEDTAVYYCARHGNFGNSYSVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | AG2CH2 | PAPAPPVAGPSVFLFPPKPKDTLMISRTPEVTCVVVDVSHEDPEVQFNWYVDGVEVHNAKTPREEQFNSTFRVVSVLTVVH QDWLNGKEYKCKVSNKGLPAPIEKTISKTK | 96 |
| | | CH3-b | CSAVRFCW | GQPREPQVTTLPPCRDELITKNQVSLWCLVKGFYPSDIAVEWESNGQPENNYKTTPPVLDSDGSFFLYSKLITVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | AG2CH2 | PAPAPPVAGPSVFLFPPKPKDTLMISRTPEVTCVVVDVSHEDPEVQFNWYVDGVEVHNAKTPREEQFNSTFRVVSVLTVVH QDWLNGKEYKCKVSNKGLPAPIEKTISKTK | 96 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| CEA-M3-GG2 | | CH3-a | CSAVRFCW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGGGGS | 51 |
| | | VHs | 2a5 | QVQLVESGGSVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | GG2CH2 | PGPAPPVAGPSVFLFPPKPKDTLMISRTPEVTCVVVDVSHEDPEVQFNWYVDGVEVHNAKTKPREEQFNSTERVVSVLTVVH QDWLNGKEYKCKVSNKGLPAPIEKTISKTK | 97 |
| | | CH3-b | CSAVRFCW | GQPREPQVCTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| CEA-M3-PG2 | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | GG2CH2 | PGPAPPVAGPSVFLFPPKPKDTLMISRTPEVTCVVVDVSHEDPEVQFNWYVDGVEVHNAKTKPREEQFNSTERVVSVLTVVH QDWLNGKEYKCKVSNKGLPAPIEKTISKTK | 97 |
| | | CH3-a | CSAVRFCW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| | Fusion Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLQISSLKADDTAVYYCARWDFYDYVEAMDYWGQGTTVTSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGGGGS | 51 |

TABLE 30-continued

Code and amino acid sequence of some antibodies with multifunctional antibody structure 3
(CDR is underlined in bold)

| Antibody Code | Polypeptide | Domain | Code | Amino acid sequence | 序列号 |
|---|---|---|---|---|---|
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYVSWFAYWGQGTTVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | PG2CH2 | PPPAPPVAGPSVFLFPPKPKDTLMISRTPEVTCVVVDVSHEDPEVQFNWYVDGVEVHNAKTKPREEQFNSTERVVSLTVVH QDWLNGKEYKCKVSNKGLPAPIEKTISKTK | 98 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| Heavy Chain | | VHm | hPR1A3 | QVQLVQSGSELKKPGASVKVSCKASGYTFTFVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | PG2CH2 | DKTHTCP | 66 |
| | | CH2 | | PPPAPPVAGPSVFLFPPKPKDTLMISRTPEVTCVVVDVSHEDPEVQFNWYVDGVEVHNAKTKPREEQFNSTERVVSLTVVH QDWLNGKEYKCKVSNKGLPAPIEKTISKTK | 98 |
| | | CH3-a | CSAVRF: CW | GQPREPQVCTLPPSRDELTKNQVSLSCAVKGFYPSDIAVEWESNGQPENNYKTTPPVLDSDGSFFLYVSKLITVDKSRWQQGNV FSCSVMHEALHNRFTQKSLSLSPGK | 106 |
| Light Chain | | VLm | hPR1A3 | DIQMTQSPSSLSASVGDRVTIITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-DG2 | Fusion Heavy Chain | VHm | hPR1A3 | QVQLVQSGSELKKPGASVKVSCKASGYTFTFVFGMNWVRQAPGQGLEWMGWINTKTGEATYVEEFKGRFVFSLDTSVSTA YLQISSLKADDTAVYYCARWDFYDYVEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYVSWFAYWGQGTTVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | DG2CH2 | PCPAPPVAGPSVFLFPPKPKDTLMISRTPEVTCVVVAVSHEDPEVQWKVDNALQSGNSQESVTEQDSKDSTYSLSSTLTLSKADYEKHKV QDWLNGKEYKCKVSNKGLPAPIEKTISKTK | 99 |
| | | CH3-b | CSAVRF: CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | Heavy Chain | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | VHm | hPR1A3 | QVQLVQSGSELKKPGASVKVSCKASGYTFTVFGMNWVRQAPGQGLEMGWINTKTGEATYVEEFKGRFVFSLDTSVSTA YLQISSLKADDTAVYYCARWDFYDYEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | DG2CH2 | PCPAPPVAGPSVFLFPPKPKDTLMISRTPEVTCVVVDVSHEDPEVQFNWYVDGVEVHNAKTPREEQFNSTFRVVSLTVVH QDWLNGKEYKCKVSNKGLPAPIEKTISKTK | 99 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| CEA-M3-G2D | Fusion Heavy Chain | VHm | hPR1A3 | QVQLVQSGSELKKPGASVKVSCKASGYTFTVFGMNWVRQAPGQGLEMGWINTKTGEATYVEEFKGRFVFSLDTSVSTA YLQISSLKADDTAVYYCARWDFYDYEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | G2DCH2 | PCPAPPVAGPSVFLFPPKPKDTLMISRTPEVTCVVVDVSHEDPEVQFNWYVDGVEVHNAKTPREEQFNSTFRVVSLTVVH QDWLNGKEYKCKVSNKGLPAPIEKTISKTK | 100 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANVQQKPGQAPRGLIGGTNKRAPGVPARFSGSLLGGKAALTLSGVQ PEDEAEYYCALWYSNLWVFGGGTKVEIK | 2 |
| | | CL | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEMGWINTKTGEATYVEEFKGRFVFSLDTSVSTA YLQISSLKADDTAVYYCARWDFYDYEAMDYWGQGTTVTVSS | 41 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | G2DCH2 | PCPAPPVAGPSVFLFPPKPKDTLMISRTPEVTCVVVDVSHEDPEVQFNWYVDGVEVHNAKTPREEQFNSTFRVVSLTVVH QDWLNGKEYKCKVSNKGLPAPIEKTISKTK | 100 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | hPR1A3 | DIQMTQSPSSLSASVGDRVTITCKASQNVGTNVAWYQQKPGKAPKLLIYSASYRYSGVPSRFSGSGSGTDFTFTISSLQPEDIA TYYCHQYYTYPLFTFGQGTKVEIK | 42 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| CEA-M3-DG2D | Fusion Heavy Chain | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| | | VHm | hPR1A3 | QVQLVQSGSELKKPGASVKVSCKASGYTFTVFGMNWVRQAPGQGLEWMGWINTKTGEATYVEEFKGRFVFSLDTSVSTA YLIQISSLKADDTAVYYCARWDFYDYVEAMDYWGQGTTVTVSS | 41 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | DG2DCH2 | PCPAPPVAGPSVFLFPPKPKDTLMISRTPEVTCVVVAVSHEAPEVQFNWYDGVEVHNAKTKPREEQFNSTERVVSLTVVH QDWLNGKEYKCKVSNKGLPAPIEKTISKTK | 101 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVLTCRSSTGAVTTSNYANWVQQKPGQAPRGLIGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | hPR1A3 | QVQLVQSGSELKKPGASVKVSCKASGYTFTVFGMNWVRQAPGQGLEWMGWINTKTGEATYVEEFKGRFVFSLDTSVSTA YLIQISSLKADDTAVYYCARWDFYDYVEAMDYWGQGTTVTVSS | 41 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | DG2DCH2 | PCPAPPVAGPSVFLFPPKPKDTLMISRTPEVTCVVVAVSHEAPEVQFNWYDGVEVHNAKTKPREEQFNSTERVVSLTVVH QDWLNGKEYKCKVSNKGLPAPIEKTISKTK | 101 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | 4420 | DIQMTQSPSSLSASVGDRVTITCKASQNVGTNVAWYQQKPGKAPKLLIYSASYRYSGVPSRFSGSGSGTDFTFTISSLQPEDIA TYYCHQYTYTYPLFTFGQGTKVEIK | 42 |
| | | CL | hPR1A3 Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-WT | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYIQMNNLRVEDMGIYYCTGSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | Hinge4 | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVL | 83 |
| | | CH3-b | CSAVRF:CW | HQDWLNGKEYKCKVSNKALPAPIEKTISKAK<br>GQPREPQVYTLPPCRDELTKNQVSLWCLVKGFYPSDIAVEWESNGQPENNYKTTPPVLDSDGSFFLYSKLTVDKSRWQQGNV<br>FSCSVMHEALHNHYTQKSLSLSPGK | 107 |
| Crosslight Chain | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ<br>PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN<br>VNHKPSNTKVDKKVEPKSC | 82 |
| Heavy Chain | | VHm | 4420 | EVKLDETGGGLVQPGRPMKLSCVASGFTFSDYWMNWVRQSPEKGLEWVAQIRNKPYNYETYYSDSVKGRFTISRDDSKSS<br>VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN<br>VNHKPSNTKVDKKVEPKSC | 82 |
| | | Hinge3 | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAK | 83 |
| | | CH3-a | CSAVRF:CW | GQPREPQVCTLPPSRDELTKNQVSLCAVKGFYPSDIAVEWESNGQPENNYKTTPPVLDSDGSFFLVSKLTVDKSRWQQGNV<br>FSCSVMHEALHNRFTQKSLSLSPGK | 106 |
| Light Chain | | VLm | 4420 | DVVMTQTPLSLPVSLGDQASICRSSGISLVHSNGNTYLRWYLQKPGQSPKVLIYKVSNRFSGVPDRFSGSGSGTDFTLKISR<br>VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH<br>KVYACEVTHQGLSSPVTKSFNRGEC | 75 |
| Fusion Heavy Chain | | VHm | 4420 | EVKLDETGGGLVQPGRPMKLSCVASGFTFSDYWMNWVRQSPEKGLEWVAQIRNKPYNYETYYSDSVKGRFTISRDDSKSS<br>VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN<br>VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT<br>LYLQMNSLRAEDTAVYYCARHGNFGNSYVSWFAYWGQGTLVTVSS | 1 |
| | | Linker2 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV<br>YACEVTHQGLSSPVTKSFNRGEC | 81 |
| | | Hinge4 | Hin1 | DKTHTCP | 66 |
| | | CH2 | AAG | PCPAPEAAGGPSVFLFPPKPKDTLKNQVSLWCLVKGFYPSDIAVEWESNGQPENNYKTTPPVLDSDGSFFLYSDGVEVHNAKTKPREEQYNSTYRVVSVLTVL<br>LHQDWLNGKEYKCKVSNKALGAPIEKTISKAK | 84 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNV<br>FSCSVMHEALHNHYTQKSLSLSPGK | 107 |
| Crosslight Chain | | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ<br>PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN<br>VNHKPSNTKVDKKVEPKSC | 82 |
| Heavy Chain | M3IC-AAG | VHm | 4420 | EVKLDETGGGLVQPGRPMKLSCVASGFTFSDYWMNWVRQSPEKGLEWVAQIRNKPYNYETYYSDSVKGRFTISRDDSKSS<br>VYLQMNNLRVEDMGIYYCTGSYYGMDYWGQGTSVTVSS | 43 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 CH2 | Hin1 AAG | DKTHTCP PCPAPEAAGGPSVFLFPPKDTLMISRTPEVTCVVVDVSHEDPEVKFNWYVDGVEVHNAKTKPREEQYNSTYRVVSVLTV LHQDWLNGKEYKCKVSNKALGAPIEKTISKAK | 66 84 |
| | | CH3-a | CSAVRF CW | GQPREPQVCTLPPSRDELTKNQVSLSCAVKGFYPSDIAVEWESNGQPENNYKTTPPVLDSDGSFFLYSKLTVDKSRWQQGNV FSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISR VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-NA | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 VHs | Lin7 2a5 | GGGGSGGGGS QVQLVESGGGVVQPGRSLRLSCAASGFTFSSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 51 1 |
| | | Linker5 CL | Lin2 Lc7 | AS VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 46 81 |
| | | Hinge4 CH2 | Hin1 N297A | DKTHTCP PCPAPELLGGPSVFLFPPKPKDTLMISRTPEVTCVVVDVSHEDPEVKFNWYVDGVEVHNAKTKPREEQYASTYRVVSVLTVL HQDWLNGKEYKCKVSNKALPAPIEKTISKAK | 66 87 |
| | | CH3-b | CSAVRF CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGKAALTLSGVQ PEDEAEYYCALWYSNLNVFGGGTKVEIK | 2 |
| | | Linker6 CH1 | Lin1 CH1 | SS ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 45 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 CH2 | Hin1 N297A | DKTHTCP PCPAPELLGGPSVFLFPPKPKDTLMISRTPEVTCVVVDVSHEDPEVKFNWYVDGVEVHNAKTKPREEQYASTYRVVSVLTVL HQDWLNGKEYKCKVSNKALPAPIEKTISKAK | 66 87 |
| | | CH3-a | CSAVRF CW | GQPREPQVCTLPPSRDELTKNQVSLSCAVKGFYPSDIAVEWESNGQPENNYKTTPPVLDSDGSFFLYSKLTVDKSRWQQGNV FSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISR VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| M3IC-FES | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Linker7 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
| | | Linker2 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 81 |
| | | Hinge4 | Hin1 | DKTHTCP | 66 |
| | | CH2 | FES | PCPAPEFRGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 85 |
| | | CH3-b | CSAVRFCW | GQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 107 |
| M3IC-FES | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge3 | FES | DKTHTCP | 66 |
| | | CH2 | | PCPAPEFRGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 85 |
| | | CH3-a | CSAVRFCW | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| M3IC-G2 | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSSVYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Linker7 | Lin7 | GGGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
| | | Linker2 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 81 |
| | | Hinge4 | Hin1 | DKTHTCP | 66 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | CH2 | G2CH2 | PCPAPPVAGPSVFLFPPKPKDTLMISRTPEVTCVVVDVSHEDPEVQFNWYDGVEVHNAKTPREEQFNSTERVVSVLTVVH QDWLNGKEYKCKVSNKGLPAPIEKTISKTK | 94 |
| | | CH3-b | CSAVRF:CW | GQPREPQVYTLPPCRDELTKNQVSLWCLVKGFYPSDIAVEWESNGQPENNYKTTPPVLDSGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | G2CH2 | PCPAPPVAGPSVFLFPPKPKDTLMISRTPEVTCVVVDVSHEDPEVQFNWYDGVEVHNAKTPREEQFNSTERVVSVLTVVH QDWLNGKEYKCKVSNKGLPAPIEKTISKTK | 94 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | 4420 | DVVMTQTPLSLPVSLGDQASISCRSSGISLVHSNGNTYLRWYLQKPGQSPKVLIYKVSNRFSGVPDRFSGSGSGTDFTLKISR VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-SG2 | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDTWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | SG2CH2 | PSPAPPVAGPSVFLFPPKPKDTLMISRTPEVTCVVVDVSHEDPEVQFNWYDGVEVHNAKTPREEQFNSTERVVSVLTVVH QDWLNGKEYKCKVSNKGLPAPIEKTISKTK | 95 |
| | | CH3-b | CSAVRF:CW | GQPREPQVYTLPPCRDELTKNQVSLWCLVKGFYPSDIAVEWESNGQPENNYKTTPPVLDSGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |

TABLE 30-continued

Code and amino acid sequence of some antibodies with multifunctional antibody structure 3
(CDR is underlined in bold)

| Antibody Code | Polypeptide | Domain | Code | Amino acid sequence | 序列号 |
|---|---|---|---|---|---|
| | | Hinge3 | Hin1 | DKTHTCP | 66 |
| | | CH2 | SG2CH2 | PSPAPPVAGPSVFLFPPKPKDTLMISRTPEVTCVVVDVSHEDPEVQFNWYVDGVEVHNAKTKPREEQFNSTFRVVSVLTVVH QDWLNGKEYKCKVSNKGLPAPIEKTISKTK | 95 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISR VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-AG2 | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | AG2CH2 | PAPAPPVAGPSVFLFPPKPKDTLMISRTPEVTCVVVDVSHEDPEVQFNWYVDGVEVHNAKTKPREEQFNSTFRVVSVLTVVH QDWLNGKEYKCKVSNKGLPAPIEKTISKTK | 96 |
| | | CH3-b | CSAVRF:CW | GQPREPQVTLPPCRDELTKNQVSLWCLVKGFYPSDIAVEWESNGQPENNYKTTPPVLDSDGSFFLYSKLTVDKSRWQQGNV FSCSVMHEALHNRFTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | AG2CH2 | PAPAPPVAGPSVFLFPPKPKDTLMISRTPEVTCVVVDVSHEDPEVQFNWYVDGVEVHNAKTKPREEQFNSTFRVVSVLTVVH QDWLNGKEYKCKVSNKGLPAPIEKTISKTK | 96 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISR VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-GG2 | Fusion Heavy | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | Chain | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYIQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | GG2CH2 | PGPAPPVAGPSVFLFPPKPKDTLMISRTPEVTCVVVDVSHEDPEVQFNWYVDGVEVHNAKTPREEQFNSTFRVVSVLTVVH QDWLNGKEYKCKVSNKGLPAPIEKTISKTK | 97 |
| | | CH3-b | CSAVRF:CW | GQPREPQVYTLPPSRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | GG2CH2 | DKTHTCP PGPAPPVAGPSVFLFPPKPKDTLMISRTPEVTCVVVDVSHEDPEVQFNWYVDGVEVHNAKTPREEQFNSTFRVVSVLTVVH QDWLNGKEYKCKVSNKGLPAPIEKTISKTK | 106 |
| | | CH3-a | CSAVRF:CW | GQPREPQVCTLPPSRDELTKNQVSLSCAVKGFYPSDIAVEWESNGQPENNYKTTPPVLDSDGSFFLYSKLTVDKSRWQQGNV FSCSVMHEALHNRFTQKSLSLPGK | 44 |
| | Light Chain | VLm | 4420 | DVVMTQTPLSLPVSLGDQASISCRSSQSLVHSNGNTTLRWYLQKPGQSPKVLIYKVSNRFSGVPDRPSGSGSGTDFTLKISR VEAEDLGVYFCSQSTHVPWTFGGGTKLEIK | 75 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-PG2 | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGSGGGGS | 51 |
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYIQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | PG2CH2 | PPPAPPVAGPSVFLFPPKPKDTLMISRTPEVTCVVVDVSHEDPEVQFNWYVDGVEVHNAKTPREEQFNSTFRVVSVLTVVH QDWLNGKEYKCKVSNKGLPAPIEKTISKTK | 98 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNVETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | PG2CH2 | PPPAPPVAGPSVFLFPPKPKDTLMISRTPEVTCVVVDVSHEDPEVQFNWYVDGVEVHNAKTKPREEQFNSTFRVVSVLTVVH QDWLNGKEYKCKVSNKGLPAPIEKTISKTK | 98 |
| | | CH3-a | CSAVRF: CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| | Light Chain | VLm | 4420 | DVVMTQTPLSLPVSLGDQASISCRSSQSLVHSNGNTYLRWYLQKPGQSPKVLIYKVSNRFSGVPDRFSGSGSGTDFTLKISR VEAEDLGVYFCSQQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |
| M3IC-DG2 | Fusion Heavy Chain | VHm | 4420 | EVKLDETGGGLVQPGRSLRLSCAASGFTFSTYAMNWVRQAPGKGLEWVARIRSKYNNYATYYADSVKDRFTISRDDSKNT VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Linker4 | Lin7 | GGGGSGGGGS | 51 |
| | | VHs | 2a5 | QVQLVESGGGVVQPGRSLRLSCAASGFTFSTTAMNWVRQAPGKGLEWVARIRSKYNNYATYYADSVKDRFTISRDDSKNT LYLQMNSLRAEDTAVYYCARHGNFGNSVSWFAYWGQGTLVTVSS | 1 |
| | Linker5 | CL | Lc7 | AS | 46 |
| | | CL | | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | DG2CH2 | DKTHTCP | 66 |
| | | CH2 | | PCPAPPVAGPSVFLFPPKPKDTLMISRTPEVTCVVVVAVSHEDPEVQFNWYVDGVEVHNAKTKPREEQFNSTFRVVSVLTVVH QDWLNGKEYKCKVSNKGLPAPIEKTISKTK | 99 |
| | | CH3-b | CSAVRF: CW | GQPREPQVTLPPCRDELITKNQVSLWCLVKGFYPSDIAVEWESNGQPENNYKTTPPVLDSDGSFFLYSKLITVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNVETYYSDSVKGRFTISRDDSKSS VYLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | DG2CH2 | PCPAPPVAGPSVFLFPPKPKDTLMISRTPEVTCVVVVAVSHEDPEVQFNWYVDGVEVHNAKTKPREEQFNSTFRVVSVLTVVH QDWLNGKEYKCKVSNKGLPAPIEKTISKTK | 99 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | CH3-a | CSAVRFCW | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPGK | 106 |
| | Light Chain | VLm | 4420 | DVVMTQTPLSLPVSLGDQASICRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| M3IC-G2D | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDDSKSSVYLQMNNLRVEDMGIYYCTGSSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Linker4 | VHs | Lin7 2a5 | GGGSGGGGS | 51 |
| | | | | QVQLVESGGSVVQPGRSLRLSCAASGFTFSTYAMNWVRQAPGKGLEWVARIRSKYNNYATYADSVKDRFTISRDDSKNTLYLQMNSLRAEDTAVYYCARHGNFGNSVSWFAYWGQGTLVTVSS | 1 |
| | Linker5 | CL | Lin2 Lc7 | AS | 46 |
| | | | | VAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 81 |
| | Hinge4 | CH2 | Hin1 G2DCH2 | DKTHTCP | 66 |
| | | | | PCPAPPVAGPSVFLFPPKPKDTLMISRTPEVTCVVVDVSHEAPEVQFNWYVDGVEVHNAKTKPREEQFNSTERVVSVLTVVHQDWLNGKEYKCKVSNKGLPAPIEKTISKTK | 100 |
| | | CH3-b | CSAVRFCW | GQPREPQVTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 107 |
| | Crosslight Chain | VLs | 2a5 | QTVVTQPESLITVSPGGTVLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | | | SS | 45 |
| | Linker6 | CH1 | Lin1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Heavy Chain | VHm | 4420 | EVKLDETGGGLVQPGRPMKLSCVASGFTFSDYWMNWVRQSPEKGLEWVAQIRNKPYNYETYYSDSVKGRFTISRDDDSKSSVYLQMNNLRVEDMGIYYCTGSSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Hinge3 | CH2 | Hin1 G2DCH2 | DKTHTCP | 66 |
| | | | | PCPAPPVAGPSVFLFPPKPKDTLMISRTPEVTCVVVDVSHEAPEVQFNWYVDGVEVHNAKTKPREEQFNSTERVVSVLTVVHQDWLNGKEYKCKVSNKGLPAPIEKTISKTK | 100 |
| | | CH3-a | CSAVRFCW | GQPREPQVCTLPPSRDELTKNQVSLSCAVKGFYPSDIAVEWESNGQPENNYKTTPPVLDSDGSFFLVSKLTVDKSRWQQGNVFSCSVMHEALHNRFTQKSLSLSPGK | 106 |
| | Light Chain | VLm | 4420 | DVVMTQTPLSLPVSLGDQASICRSSQSLVHSNGNTYLRWYLQKPGQSPKVLIYKVSNRFSGVPDRFSGSGSGTDFTLKISRVEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| M3IC-DG2D | Fusion Heavy Chain | VHm | 4420 | EVKLDETGGGLVQPGRPMKLSCVASGFTFSDYWMNWVRQSPEKGLEWVAQIRNKPYNYETYYSDSVKGRFTISRDDDSKSSVYLQMNNLRVEDMGIYYCTGSSYYGMDYWGQGTSVTVSS | 43 |
| | | CH1 | | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Linker4 | | Lin7 | GGGSGGGGS | 51 |

TABLE 30-continued

Code and amino acid sequence of some antibodies with multifunctional antibody structure 3

| Antibody Code | Polypeptide | Domain | Code | Amino acid sequence (CDR is underlined in bold) | 序列号 |
|---|---|---|---|---|---|
| | | VHs | 2a5 | QVQLVESGGGVVQPGRSLRLSCAASGFTFSTYAMNWVRQAPGKGLEWVARIRSKYNNYATYYADSVKDRFTISRDDSKNT LYLQMNSLRAEDTAVYYCARHGNFGNSYVSWFAYWGQGTLVTVSS | 1 |
| | | Linker5 | Lin2 | AS | 46 |
| | | CL | Lc7 | VAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 81 |
| | | Hinge4 | Hin1 | DKTHTCP | 66 |
| | | CH2 | DG2DCH2 | PCPAPPVAGPSVFLFPPKPKDTLMISRTPEVTCVVVDVSHEDPEVQFNWYVDGVEVHNAKTKPREEQFNSTFRVVSVLTVVH QDWLNGKEYKCKVSNKGLPAPIEKTISKTK | 101 |
| | | CH3-b | CSAVRF:CW | GQPREPQVYTLPPCRDELTKNQVSLWCLVKGFYPSDIAVEWESNGQPENNYKTTPPVLDSDGSFFLYSKLTVDKSRWQQGNV FSCSVMHEALHNHYTQKSLSLSPGK | 107 |
| | Crosslight Chain | VLs | 2a5 | QTVVTQEPSLTVSPGGTVTLTCRSSTGAVTTSNYANWVQQKPGQAPRGLIGGTNKRAPGVPARFSGSLLGGKAALTLSGVQ PEDEAEYYCALWYSNLWVFGGGTKVEIK | 2 |
| | | Linker6 | Lin1 | SS | 45 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| Heavy Chain | | VHm | 4420 | EVKLDETGGGLVQPGRPMKLSCVASGFTFSDYWMNWVRQSPEKGLEWVAQIRNKPYNVETYYSDSVKGRFTISRDDSKSS VYLQMNNLRVEDMGIYYCTGSYYGMDIWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICN VNHKPSNTKVDKKVEPKSC | 82 |
| | | Hinge3 | Hin1 | DKTHTCP | 66 |
| | | CH2 | DG2DCH2 | PCPAPPVAGPSVFLFPPKPKDTLMISRTPEVTCVVVDVSHEDPEVQFNWYVDGVEVHNAKTKPREEQFNSTFRVVSVLTVVH QDWLNGKEYKCKVSNKGLPAPIEKTISKTK | 101 |
| | | CH3-a | CSAVRF:CW | GQPREPQVCTLPPSRDELTKNQVSLSCAVKGFYPSDIAVEWESNGQPENNYKTTPPVLDSDGSFFLVSKLTVDKSRWQQGNV FSCSVMHEALHNRFTQKSLSLSPGK | 106 |
| Light Chain | | VLm | 4420 | DVVMTQTPLSLPVSLGDQASISCRSSQSLVHSNGNTYLRWYLQKPGQSPKVLIYKVSNRFSGVPDRFSGSGSGTDFTLKISR VEAEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKH KVYACEVTHQGLSSPVTKSFNRGEC | 75 |

EXAMPLE 2

Detection of Antibody Biological Activity

1. Cell Affinity

1) Cell preparation: T cells isolated from CD3-positive human whole blood were used for a CD3 end affinity detection of multifunctional antibody molecule; positive tumor cells of corresponding antigen were used for detecting affinity of tumor antigen; for example, CD38-positive MM. 1S cells (purchased from the Cell Resource Center of Shanghai Institutes for Biological Sciences, Chinese Academy of Sciences) or RPMI 8226 cells (purchased from the Cell Resource Center of Shanghai Institutes for Biological Sciences, Chinese Academy of Sciences) were used for CD38 antigen detection, and PD-L1 positive H358 cells (purchased from the Cell Resource Center of Shanghai Institutes for Biological Sciences, Chinese Academy of Sciences) were used for PD-L1 antigen detection, and so on. The cells were resuspended with 1% FBS-PBS, adjusted to a density of $4 \times 10^6$/ml, and 50 μl of cells were taken from each well, and then plated at $2 \times 10^5$ per well. Cell plating was operated on ice 2) Addition of the antibody: according to the experimental design, the antibody was diluted gradually, and dilution of antibody was operated on ice. For example, the initial concentration of antibody for dilution was 3000 nM, and the antibody was diluted by 3 times with 11 concentration gradients. The diluted antibody was added to a cell well at 50 μl per well, mixed well, and shaked and incubated at 4° C. 1100 rpm/min for 2 h; after washing, the cells were resuspend in 1% FBS-PBS, and a diluted secondary antibody PE anti-human IgG FC (Biolegend, 409304) was added with a final concentration of 8 ug/ml and a volume of 50 μl/well. At the same time, a well only added with cells and secondary antibody was set as a control, the components were mixed well, and incubated under shaking at 1100 rpm/min at 4° C. for 1 h;

3) Washing and fixation: after the washed cells were resuspended in 1% FBS-PBS, 2% paraformaldehyde was added into each well to fix the cells at room temperature;

4) Flow cytometry detection: the cells were resuspended with 1% FBS-PBS, and detected on a flow cytometer;

5) Data analysis: the data was analyzed by a flow analysis software FlowJo 7.6 thereby obtaining an average fluorescence intensity of the specific antibody concentration, plotted by a Graphpad Prism 5 with the antibody concentration (nM) as an abscissa and the average fluorescence intensity as an ordinate; the EC50 value was calculated by the method of One site—Specific binding, and the EC50 value indicated the cell affinity of the antibody to the corresponding target antigen.

TABLE 31

Cell affinity and transient transfection expression level of some antibodies with the multifunctional antibody structure 1

| Antibody Code | Affinity to Tumor Cell (Nm) | Affinity to Human CD3 Positive T Cell (Nm) | Affinity to Monkey CD3 Positive T Cell (Nm) | Transient Transfection Expression Level in 293E (Mg/L) |
|---|---|---|---|---|
| PDL1-M1-NQ | 1.48 | 3.61 | 6.89 | 67.9 |
| PDL1-M1-NQ-1 | 0.95 | 145 | 168 | 33.4 |
| PDL1-M1-G2 | 1.29 | 191 | 239 | 87.7 |
| PDL1-M1-SG2 | 1.06 | 177 | 194 | 76.8 |
| PDL1-M1-FES | 1.01 | 200 | 207 | 41.4 |
| PDL1-M1-LALA | 1.38 | 153 | 196 | 62.6 |
| PDL1-M1-WT | 1.41 | 135 | 161 | 88.3 |
| CD38-M1-FES | 1.53 | 192 | 291 | 67.4 |
| CD38-M1-G2 | 2.69 | 91.9 | 142 | 60.2 |
| CD38-M1-SG2 | 1.76 | 107 | 159 | 62.8 |
| CD38-M1-WT | 2.33 | 129 | 150 | 28.4 |
| CD38-M1-SG2-1 | 11.9 | 88.1 | 94.13 | 89.9 |
| CD38-M1-SG2-2 | 106 | 437 | 461 | 67.1 |
| CD38-M1-G2-2 | 104 | 478 | 491 | 70.5 |
| CD38-M1-G2-3 | 10.2 | 91.7 | 103 | 96.5 |
| CD38-M1-FES-1 | 3.20 | 8.50 | 9.18 | 29.6 |
| CD38-M1-G2-1 | 2.10 | 9.21 | 12.61 | 78.2 |
| CD38-M1-SG2-3 | 1.54 | 6.48 | 7.59 | 55.2 |
| CD38-M1-AG2 | 1.79 | 6.19 | 10.19 | 63.0 |
| CD38-M1-GG2 | 1.87 | 7.31 | 10.42 | 69.8 |
| CD38-M1-PG2 | 2.33 | 8.16 | 11.47 | 59.9 |
| CD38-M1-DG2 | 2.40 | 8.22 | 11.04 | 50.4 |
| CD38-M1-G2D | 2.16 | 8.67 | 10.08 | 69.2 |
| CD38-M1-DG2D | 1.62 | 6.48 | 7.05 | 53.6 |
| CD38-M1-FES-3 | 11.1 | 20 | 34.05 | 39.2 |
| CD38-M1-G2D-1 | 100 | 405 | 420 | 77.2 |
| M1IC-FES | No binding | 7.61 | 11.39 | 62.5 |
| M1IC-NA | No binding | 7.68 | 9.63 | 52.3 |
| M1IC-NQ | No binding | 194 | 378 | 50.9 |
| M1IC-AAG | No binding | 5.94 | 8.79 | 55.2 |
| M1IC-G2 | No binding | 6.65 | 10.39 | 58.7 |
| M1IC-SG2 | No binding | 9.38 | 13.24 | 63.3 |
| M1IC-AG2 | No binding | 11.0 | 14.2 | 50.0 |
| M1IC-GG2 | No binding | 9.93 | 13.0 | 64.5 |
| M1IC-PG2 | No binding | 11.27 | 17.8 | 52.6 |
| M1IC-DG2 | No binding | 7.52 | 14.5 | 59.9 |
| M1IC-G2D | No binding | 5.77 | 10.6 | 64.9 |
| M1IC-DG2D | No binding | 9.37 | 16.0 | 58.9 |
| MlIC-WT | No binding | 7.15 | 19.8 | 55.5 |
| M1IC-FES-1 | No binding | 170 | 295 | 54.2 |
| M1IC-AAG-1 | No binding | 152 | 205 | 47.4 |
| M1IC-SG2-1 | No binding | 122 | 222 | 87.5 |
| M1IC-G2-1 | No binding | 127 | 165 | 44.6 |
| M1IC-AG2-1 | No binding | 163 | 197 | 69.9 |
| M1IC-GG2-1 | No binding | 168 | 166 | 55.6 |
| M1IC-PG2-1 | No binding | 116 | 146 | 52.6 |
| M1IC-DG2-1 | No binding | 120 | 130 | 71.3 |
| M1IC-G2D-1 | No binding | 101 | 143 | 69.8 |
| M1IC-DG2D-1 | No binding | 128 | 181 | 70.3 |
| M1IC-WT-1 | No binding | 153 | 174 | 78.8 |

Note: PDL1-M1 series of molecules were antibodies targeting both PD-L1 and CD3 with multifunctional antibody structure 1; CD38-M1 series of molecules were antibodies targeting both CD38 and CD3 with multifunctional antibody structure 1; M1IC series of molecules were all isotype control antibodies with multifunctional antibody structure 1 and targeting CD3 and luciferase (without tumor targeting ability).

TABLE 32

Cell affinity and transient transfection expression level of some antibodies with the multifunctional antibody structure 2

| Antibody Code | Affinity to Human Tumor Cell (Nm) | Affinity to Human CD3 Positive T Cell (Nm) | Affinity to Monkey CD3 Positive T Cell (Nm) | Transient Transfection Expression Level in293E (Mg/L) |
|---|---|---|---|---|
| BCMA-M2-WT | 20.3 | 588 | 676 | 62.5 |
| BCMA-M2-FES | 15.3 | 532 | 630 | 37.2 |
| BCMA-M2-G2 | 19.1 | 515 | 591 | 53.8 |
| BCMA-M2-SG2 | 17.0 | 400 | 461 | 48.4 |
| BCMA-M2-AG2 | 23.8 | 613 | 668 | 50.0 |
| BCMA-M2-GG2 | 23.6 | 448 | 636 | 44.6 |
| BCMA-M2-PG2 | 24.0 | 599 | 716 | 48.3 |
| BCMA-M2-DG2 | 17.4 | 550 | 501 | 53.0 |
| BCMA-M2-G2D | 19.2 | 351 | 510 | 59.7 |
| BCMA-M2-DG2D | 18.8 | 534 | 641 | 41.7 |
| M2IC-WT | No binding | 499 | 540 | 81.0 |
| M2IC-AAG | No binding | 515 | 528 | 59.8 |
| M2IC-NA | No binding | 547 | 561 | 35.9 |
| M2IC-FES | No binding | 411 | 506 | 40.2 |
| M2IC-G2 | No binding | 408 | 488 | 75.5 |
| M2IC-SG2 | No binding | 481 | 525 | 70.7 |
| M2IC-AG2 | No binding | 535 | 607 | 51.6 |
| M2IC-GG2 | No binding | 556 | 538 | 43.3 |
| M2IC-PG2 | No binding | 467 | 656 | 70.8 |
| M2IC-DG2 | No binding | 357 | 570 | 44.7 |
| M2IC-G2D | No binding | 367 | 538 | 72.1 |
| M2IC-DG2D | No binding | 452 | 519 | 67.6 |

Note: BCMA-M2 series were antibodies targeting both BCMA and CD3 with multifunctional antibody structure 2; M2IC series were all isotype control antibodies with multifunctional antibody structure 2 and targeting CD3 and luciferase (without tumor targeting ability).

TABLE 33

Cell affinity and transient transfection expression level of some antibodies with the multifunctional antibody structure 3

| Antibody Code | Affinity to Human Tumor Cell (Nm) | Affinity to Human CD3 Positive T Cell (Nm) | Affinity to Monkey CD3 Positive T Cell (Nm) | Transient Transfection Expression Level in 293E |
|---|---|---|---|---|
| CEA-M3-SG2 | 30.48 | 631 | 669 | 76.3 |
| CEA-M3-G2 | 36.30 | 638 | 755 | 70.9 |
| CEA-M3-WT | 35.82 | 624 | 757 | 91.1 |
| CEA-M3-AAG | 30.12 | 646 | 662 | 67.1 |
| CEA-M3-NA | 32.13 | 688 | 798 | 58.1 |
| CEA-M3-FES | 42.90 | 639 | 732 | 63.2 |
| CEA-M3-AG2 | 38.07 | 602 | 757 | 56.0 |
| CEA-M3-GG2 | 39.15 | 695 | 762 | 59.5 |
| CEA-M3-PG2 | 41.94 | 654 | 838 | 79.7 |
| CEA-M3-DG2 | 31.89 | 609 | 634 | 58.6 |
| CEA-M3-G2D | 38.35 | 670 | 699 | 73.0 |
| CEA-M3-DG2D | 34.18 | 611 | 775 | 49.8 |
| M3IC-SG2 | No binding | 677 | 681 | 67.4 |
| M3IC-G2 | No binding | 701 | 771 | 70.4 |
| M3IC-WT | No binding | 637 | 709 | 67.0 |
| M3IC-AAG | No binding | 606 | 659 | 42.3 |
| M3IC-NA | No binding | 739 | 935 | 43.2 |
| M3IC-FES | No binding | 662 | 671 | 51.9 |
| M3IC-AG2 | No binding | 674 | 747 | 52.4 |
| M3IC-GG2 | No binding | 609 | 866 | 54.7 |
| M3IC-PG2 | No binding | 696 | 712 | 72.1 |
| M3IC-DG2 | No binding | 710 | 704 | 52.4 |
| M3IC-G2D | No binding | 607 | 848 | 69.9 |
| M3IC-DG2D | No binding | 638 | 747 | 63.9 |

Note: CEA-M3 series were antibodies targeting both CEA and CD3 with multifunctional antibody structure 3; M3IC series were all isotype control antibodies with multifunctional antibody structure 3 and targeting CD3 and luciferase (without tumor targeting ability).

Based on the above data, it can be seen that for the same antibody structure and antibody variable region sequence, there is no significant difference in the binding activity of the antibody to the target with different modifications to the Fc, and there is no significant difference in the expression amount of each antibody.

2. In Vitro Killing
1) Sufficient amount of tumor cells were taken to prepare a single cell suspension;
2) CFSE staining of tumor cells: a certain amount of cell suspension was taken for centrifuge (300×g, 5 min) to remove the supernatant; 2 ml of CFSE solution prepared with PBS was added with a final concentration of 5 μM; the cells were incubated in a 5% $CO_2$, 37° C. incubator for 15 minutes; the cells were taken out, washed with PBS, centrifuged at 300×g for 5 min to remove the supernatant, and then washed repeatly for three times, resuspended in a complete medium, and then the suspension was taken to count the cells;
3) Tumor cell plating: the cells were resuspended with a complete medium to a density of $2 \times 10^5$/ml, and then added into a 96-well plate at $2 \times 10^4$ cells/well (i.e., 100 μl/well);
4) Addition of effector cell PBMC (peripheral blood mononuclear cells, isolated from human whole blood): the effector cells were resuspended in a complete medium which was used by the tumor cells, and a corresponding number of effector cells was added according to the E:T in the experimental design with a volume of 50 μl/well;
5) Addition of diluted antibody: according to the experimental design, the highest concentration of antibody was 10 μg/ml, since the antibody was supplemented with a volume of 50 μl which accounted for ¼ of the total volume of 200 μl, the antibody was required to be prepared at 4 times of the final concentration before supplement, so the antibody should be diluted to 40 μg/ml, and then subjected to 10-fold dilution from 40 μg/ml with 9 gradients, and the antibody was added with a volume of 50 μl/well;
6) the 96-well plate was observed under a microscope to ensure that the cells were evenly dispersed in the culture wells, and then the cells were cultured in a 5% CO2, 37° C. incubator for detection;
7) treatment of adherent cells after reaching the detection time: the cell supernatant was aspirated and washed with 30 μl/well PBS, and the washing liquid was aspirated and added into the previously aspirated supernatant; 30 μl/well of trypsin was added into the cell well, and the cells were digested in a 5% CO2, 37° C. incubator for 3 to 5 min; the supernatant collected previously was added, the cells in each well were pipetted to a single cell suspension; the suspension cells were treated by pipetting and mixing for several times;
8) PI (final concentration of 10 μg/ml) was added at 10 μl/well for each sample 10 to 15 min before flow cytometry;
9) the samples were detected by flow cytometer; the result of flow cytometer was analyzed by a FlowJo software, the data was output in a Microsoft Excel, and analyzed by GraphPad; the ratio of CFSE and PI double-positive cells to CFSE-positive cells was the target cell-killing rate which was calculated as follows:

target cell-killing rate (%)=the number of PI and CFSE double-positive cells/the number of CFES positive cells×100%

10) Calculation of the killing ability of antibodies against tumor cells: the target cell killing rate at each antibody concentration was calculated according to the calculation formula of target cell killing rate, and plotted with the antibody concentration as an abscissa and the target cell killing rate as an ordinate, the data were analyzed by Graphpad Prism 5, and the EC50 value was calculated by log(agonist) vs. response—Variable slope, indicating the cell killing ability of the antibody.

3. T cell activation (antibody+PBMC co-culture system)
1) PBMC were separated from the whole blood of healthy volunteers by density gradient centrifugation, and then added into a tumor cell plate according to the E:T in the experimental design;
2) the antibody was subjected to a series of 3-fold concentration gradient dilution according to the experimental design, and each concentration of antibody was added;
3) the 96-well plate was incubated in a 37° C., 5% $CO_2$ incubator until the detection time; the suspended PBMC cells were collected, added with corresponding CD3, CD69, CD25 detection antibodies (all purchased from BD), incubated for 1 hour, washed to remove excess antibodies, and then resuspended, subjected to flow cytometric detection to obtain the ratio of CD3 and CD69 double-positive cells or the ratio of CD3 and CD25 double-positive cells, that is, the activation ratio of T cells in PBMC induced by the antibody, which was calculated as follows:

ratio of CD3 and CD69 double-positive cells (%)=the number of CD3 and CD69 double-positive cells/the total number of CD3 positive-cells×100% ratio of CD3 and CD25 double-positive cells (%)=the number of CD3 and CD25 double-positive cells/the total number of CD3 positive-cells×100%

Nonlinear fitting (log(agonist) vs. response—Variable slope) was performed by a "GraphPad Prism 5" software with diabody concentration as an abscissa and CD3&CD69 (CD3&CD25)% value as an ordinate, to calculate the T cell activation curve and EC50 value.

4. T cell activation (antibody+tumor cell+PBMC co-culture system)
1) Tumor cells in good culture condition were collected and prepared as a single cell suspension, and then plated into a 96-well plate at $2*10^4$/well;
2) PBMC were separated from the whole blood of healthy volunteers by density gradient centrifugation, and then added into a tumor cell plate according to the E:T in the experiment design;
3) the antibody was subjected to a series of concentration gradient dilution according to the experimental design, and each concentration of antibody was added;
4) the 96-well plate was incubated in a 37° C., 5% $CO_2$ incubator until the detection time, the suspended PBMC cells were collected, added with corresponding CD3, CD69, CD25 detection antibodies, incubated for 1 hour, washed to remove excess antibodies, and then resuspended, subjected to flow cytometric detection to obtain the ratio of CD3 and CD69 double-positive cells or the ratio of CD3 and CD25 double-positive cells, that is, the activation ratio of T cells in PBMC induced by the antibody, which was calculated as follows:

ratio of CD3 and CD69 double-positive cells (%)=the number of CD3 and CD69 double-positive cells/the total number of CD3 positive-cells×100% ratio of CD3 and CD25 double-positive cells (%)=the number of CD3 and CD25 double-positive cells/the total number of CD3 positive-cells×100%

Nonlinear fitting (log(agonist) vs. response—Variable slope) was performed by a "GraphPad Prism 5" software with diabody concentration as an abscissa and CD3&CD69 (CD3&CD25)% value as an ordinate, to calculate the T cell activation curve and EC50 value.

5. Jurkat-luciferase cell activation
  1) Different FcγRs (FcγR1, FcγR2, FcγR3A (all purchased from ACRO Biosystems)) were coated onto a microplate reader with a protein concentration of 1 ug/ml and a volume of 100 μl/well, and incubated overnight at 4° C.; the coating solution was discarded and the plate was washed with PBS;
  2) 40 ul of antibodies with different concentrations (1~10000 ng/ml) and a certain amount of Jurkat-luciferase cells (2×10$^6$/ml, 40 ul/well) were added into each well of the microplate reader, and incubated for 6 h at 37° C.;
  3) fluorescence was displayed according to the instruction of the kit Bio-Glo Luciferase Assay System (Cat. No. G7940, Promega), and the fluorescence signal value was detected by a fluorescence microplate reader (LUX 3020, Thermo).

Results

1. The killing ability of the PD-L1×CD3 antibody with multifunctional antibody structure 1 to non-small cell lung cancer cells H358 (PD-L1 positive expression, Cell Resource Center of Shanghai Institutes for Biological Sciences, Chinese Academy of Sciences) was shown in FIG. 4 (wherein the ratio of the number of effector cells, human PBMC, to the number of target cells, H358, was 10:1, the treatment time was 48 h, and PD-L1 mAb was purchased from Roche). hIgG was a IgG antibody isolated from human serum as a negative control, and E+T was a negative control without adding any antibodies, which were also applied below.

TABLE 34

EC50 value of the PD-L1 × CD3 antibody with multifunctional antibody structure 1 in killing tumor cells H358

| Type | Antibody Code | Maximum Killing (%) | EC50 (pM) |
|---|---|---|---|
| PD-L1 × CD3 Antibody With Multifunctional Antibody Structure 1 | PDL1-M1-NQ | 69.48 | 8.779 |
| | PDL1-M1-NQ-1 | 57.08 | 14.67 |
| | PDL1-M1-G2 | 69.09 | 7.264 |
| | PDL1-M1-SG2 | 70.77 | 10.52 |
| | PDL1-M1-FES | 71.97 | 9.646 |
| | PDL1-M1-LALA | 73.18 | 10.36 |
| | PDL1-M1-WT | 73.82 | 11.84 |
| | PD-L1 mAb | 7.06 | Not calculated |
| None | hIgG | 7.14 | Not calculated |
| None | E + T | 7.84 | None |

Figure 4:
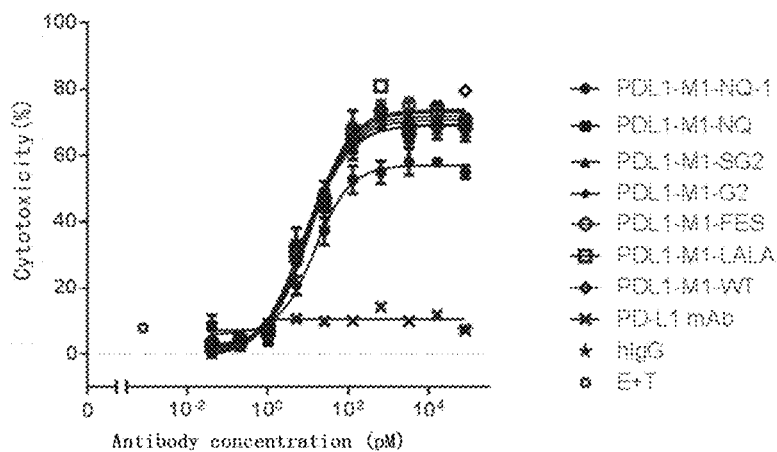
FIG. 4 shows the in vitro killing ability of different multifunctional antibodies with the multifunctional antibody structure 1 on non-small cell lung cancer cell H358.

As can be seen from FIG. 4 and Table 34, if the antibody sequence with multifunctional antibody structure 1 is the same, different modification of Fc has no significant difference in the killing ability to tumor cell H358, which indicates that the modification of Fc does not affect the cytotoxicity of the antibody with double-targeting function, that is, does not affect the efficacy of the antibody.

2. The killing ability of the isotype control antibody (4420×CD3) with multifunctional antibody structure 1 to non-small cell lung cancer cells H358 was shown in FIG. 5 (wherein the ratio of the number of effector cells, human PBMC, to the number of target cells, H358, was 10:1, and the treatment time was 48 h).

TABLE 35

EC50 Value Of The Isotype Control Antibody With Multifunctional Antibody Structure 1 In Killing Tumor Cells H358

| Type | Antibody Code | Maximum Killing (%) | EC50 (pM) |
|---|---|---|---|
| Isotype Control Antibody 4420 × CD3 With Multifunctional Antibody Structure 1 | M1IC-FES-1 | No Significant Killing | None |
| | M1IC-SG2-1 | No Significant Killing | None |
| | M1IC-G2-1 | No Significant Killing | None |
| | M1IC-NQ | 16.17 | Not calculated |
| | M1IC-WT | 52.07 | 1153 |
| | M1IC-AG2 | No Significant Killing | None |
| | M1IC-GG2 | No Significant Killing | None |
| | M1IC-PG2 | No Significant Killing | None |
| | M1IC-DG2 | No Significant Killing | None |
| | M1IC-G2D | No Significant Killing | None |
| | M1IC-DG2D | No Significant Killing | None |
| PD-L1 Monoclonal Antibody | PD-L1 mAb | No Significant Killing | None |
| None | hIgG | No Significant Killing | None |
| None | E + T | No Significant Killing | None |

Figure 5:
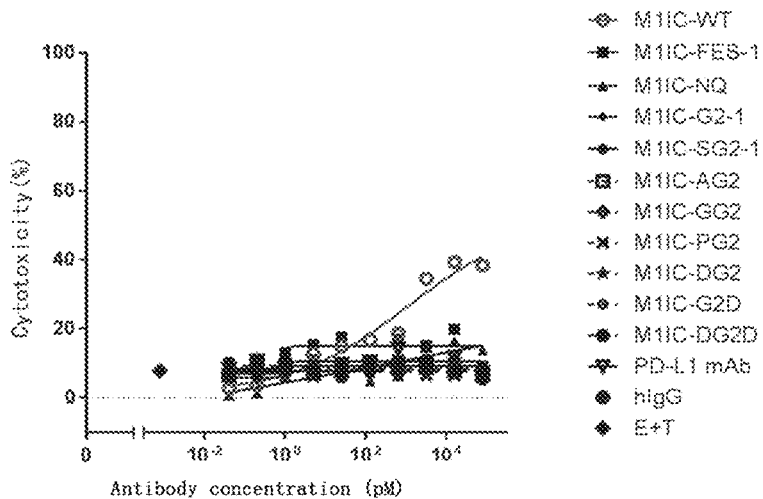
FIG. 5 shows the in vitro killing ability of different isotype control antibodies with the multifunctional antibody structure 1 on non-small cell lung cancer cell H358.

As can be seen from FIG. 5 and Table 35, the isotype control antibodies subjected to different Fc modifications have different killing abilities on tumor cells H358. The isotype control antibody itself is only CD3-targeted, not tumor antigen-targeted, therefore the killing of the isotype control antibody is caused by non-specific activation of CD3-positive T cells, wherein, M1IC-WT has significant killing ability, indicating that the Fc of antibody (with corresponding CH2 of WT, SEQ ID NO: 83) can lead to significant non-specific activation of T cells; M1IC-NQ has a significantly higher maximum killing, indicating that it can lead to specific activation of T cells when the CH2 corresponding to Fc is N297Q (SEQ ID NO: 89); other antibodies do not activate T cells, indicating that the modification of Fc significantly reduces the non-specific activation of T cells.

3. The killing ability of CD38×CD3 antibody with multifunctional antibody structure 1 to multiple myeloma cells MC/CAR (CD38 positive, purchased from ATCC) (wherein the ratio of the number of effector cells human PBMC to the number of target cells MC/CAR was 5:1; the treatment time was 48 h; the CD38 mAb was CD38 monoclonal antibody control, and the sequence of CD38 mAb was: VL was SEQ ID NO: 16, CL was SEQ ID NO: 75, and VH was SEQ ID NO: 15, CH1 was SEQ ID NO: 82, hinge was SEQ ID NO: 66, CH2 was SEQ ID NO: 83, CH3 was SEQ ID NO: 102)was shown in FIG. 6.

TABLE 36

EC50 Value Of CD38 × CD3 Antibody With Multifunctional Antibody Structure 1 In Killing Tumor Cells MC/CAR

| Type | Antibody Code | Maximum Killing (%) | EC50 (pM) |
|---|---|---|---|
| CD38 × CD3 Antibody With Multifunctional Antibody Structure 1 | CD38-M1-FES | 64.02 | 1.092 |
| | CD38-M1-G2 | 64.04 | 0.9789 |
| | CD38-M1-SG2 | 65.34 | 1.213 |
| | CD38-M1-WT | 61.45 | 1.002 |
| | CD38-M1-SG2-1 | 63.4 | 1.116 |
| | CD38-M1-SG2-2 | 55.32 | 30.27 |
| | CD38-M1-G2-2 | 63.57 | 47.65 |
| | CD38-M1-G2-3 | 64.38 | 1.006 |
| | CD38-M1-FES-1 | 62.69 | 1.01 |
| | CD38-M1-G2-1 | 76.99 | 1.654 |
| | CD38-M1-SG2-3 | 66.9 | 1.466 |
| | CD38-M1-FES-2 | 61.47 | 1.825 |
| | CD38-M1-NA | 61.49 | 1.452 |
| | CD38-M1-FES-3 | 58.14 | 0.7104 |
| | CD38-M1-AG2 | 65.29 | 1.403 |
| | CD38-M1-GG2 | 66.34 | 1.664 |
| | CD38-M1-PG2 | 65.67 | 1.419 |
| | CD38-M1-DG2 | 67.22 | 1.369 |
| | CD38-M1-G2D | 67.3 | 1.365 |
| | CD38-M1-DG2D | 67.32 | 1.918 |
| CD38 Monoclonal Antibody | CD38 mAb | 10.66 | ~6.023 |
| None | hIgG | 0.75 | None |
| None | E + T | 0.87 | None |

Figure 6:
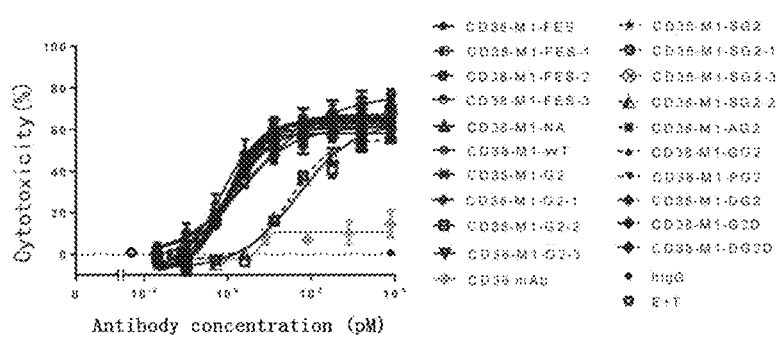
FIG. 6 shows the in vitro killing ability of CD38xCD3 antibody with the multifunctional antibody structure 1 on multiple myeloma cells MC/CAR.

As can be seen from FIG. 6 and Table 36, for a multifunctional antibody with the same variable region sequence, different modification of Fc has no significant difference in the killing ability to MC/CAR tumor cells, which indicates that the modification of Fc does not affect the cytotoxicity of the antibody with double-targeting function, that is, does not affect the efficacy of the antibody.

4. The killing ability of the isotype control antibody (4420×CD3) with multifunctional antibody structure 1 to multiple myeloma cells MC/CAR (CD38 positive) (wherein the ratio of the number of effector cells, human PBMC, to the number of target cells, MC/CAR, was 5:1, and the treatment time was 48 h) was shown in FIG. 7.

TABLE 37

EC50 value of the isotype control antibody with multifunctional antibody structure 1 in non-specific killing of tumor cells MC/CAR

| Type | Antibody Code | Maximum Killing (%) | EC50 (pM) |
|---|---|---|---|
| | M1IC-G2 | 24.4 | Not calculated |
| | M1IC-SG2 | 19.5 | Not calculated |
| | M1IC-AG2 | No Significant Killing | Not calculated |
| | M1IC-GG2 | No Significant Killing | Not calculated |
| | M1IC-PG2 | No Significant Killing | Not calculated |
| | M1IC-DG2 | No Significant Killing | Not calculated |
| | M1IC-G2D | No Significant Killing | Not calculated |
| | M1IC-DG2D | No Significant Killing | Not calculated |
| | M1IC-WT | 36.1 | Not calculated |
| | M1IC-SG2-1 | 15.73 | Not calculated |
| | M1IC-G2-1 | No Significant Killing | Not calculated |
| | M1IC-AG2-1 | No Significant Killing | Not calculated |
| | M1IC-GG2-1 | No Significant Killing | Not calculated |
| | M1IC-PG2-1 | No Significant Killing | Not calculated |
| | M1IC-DG2-1 | No Significant Killing | Not calculated |
| | M1IC-G2D-1 | No Significant Killing | Not calculated |
| | M1IC-DG2D-1 | No Significant Killing | Not calculated |
| | M1IC-WT-1 | 37.5 | Not calculated |
| CD38 Monoclonal Antibody | CD38 mAb | 10.66 | Not calculated |
| None | hIgG | No Significant Killing | Not calculated |
| None | E + T | No Significant Killing | none |

Figure 7:
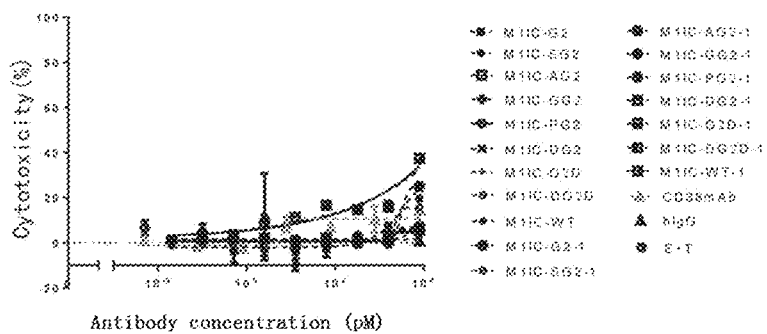
FIG. 7 shows the in vitro non-specific killing ability of the isotype control antibody with the multifunctional antibody structure 1 on multiple myeloma cells MC/CAR.

As can be seen from FIG. 7 and Table 37, the isotype control antibodies subjected to different Fc modifications have different killing abilities to tumor cells MC/CAR. The isotype control antibody itself is only CD3-targeted, not tumor antigen-targeted, therefore the killing of the isotype control antibody is caused by non-specific activation of CD3-positive T cells, wherein, M1IC-WT has a significant killing ability, indicating that the Fc of antibody (with corresponding CH2 of WT) can lead to significant non-specific activation of T cells. In contrast, the isotype control antibody containing the modified Fc of the present disclosure only leads to weak non-specific activation of T cells or can completely avoid non-specific activation of T cells.

5. Activation experiment of T cells in peripheral blood mononuclear cells by isotype control antibody (4420 ×CD3) with multifunctional antibody structure 1. The results were shown in FIG. 8 and FIG. 9.

TABLE 38

EC50 value of the isotype control antibody with multifunctional antibody structure 1 in activation of Tcells in PBMC

| | | CD3+ CD69+ T Cells | | CD3+ CD25+ T Cells | |
|---|---|---|---|---|---|
| | Antibody Code | Maximum Activation (%) | EC50 (pM) | Maximum Activation (%) | Maximum Activation (%) |
| Type | M1IC-G2 | 83.4 | 3030 | No significant activation | Not calculated |
| | M1IC-SG2 | 44.00 | 4132 | No significant activation | Not calculated |
| | M1IC-AG2 | No significant activation | Not calculated | No significant activation | Not calculated |

TABLE 38-continued

EC50 value of the isotype control antibody with multifunctional antibody structure 1 in activation of Tcells in PBMC

| | CD3+ CD69+ T Cells | | CD3+ CD25+ T Cells | |
|---|---|---|---|---|
| Antibody Code | Maximum Activation (%) | EC50 (pM) | Maximum Activation (%) | Maximum Activation (%) |
| M1IC-GG2 | No significant activation | 8459 | No significant activation | Not calculated |
| M1IC-PG2 | No significant activation | Not calculated | No significant activation | Not calculated |
| M1IC-DG2 | No significant activation | Not calculated | No significant activation | Not calculated |
| M1IC-G2D | No significant activation | Not calculated | No significant activation | Not calculated |
| M1IC-DG2D | No significant activation | Not calculated | No significant activation | Not calculated |
| M1IC-WT | 82.33 | 1.252 | 50.97 | 0.2317 |
| M1IC-G2-1 | 38.5 | ~7960 | No significant activation | Not calculated |
| M1IC-SG2-1 | 32.33 | 2799 | No significant activation | Not calculated |
| M1IC-AG2-1 | No significant activation | Not calculated | No significant activation | Not calculated |
| M1IC-GG2-1 | No significant activation | Not calculated | No significant activation | Not calculated |
| M1IC-PG2-1 | No significant activation | Not calculated | No significant activation | Not calculated |
| M1IC-DG2-1 | No significant activation | Not calculated | No significant activation | Not calculated |
| M1IC-G2D-1 | No significant activation | Not calculated | No significant activation | Not calculated |
| M1IC-DG2D-1 | No significant activation | Not calculated | No significant activation | Not calculated |
| M1IC-WT-1 | 78.53 | ~0.8307 | 52.59 | 0.04556 |
| None h-IgG | No significant activation | Not calculated | No significant activation | Not calculated |

Figure 8:
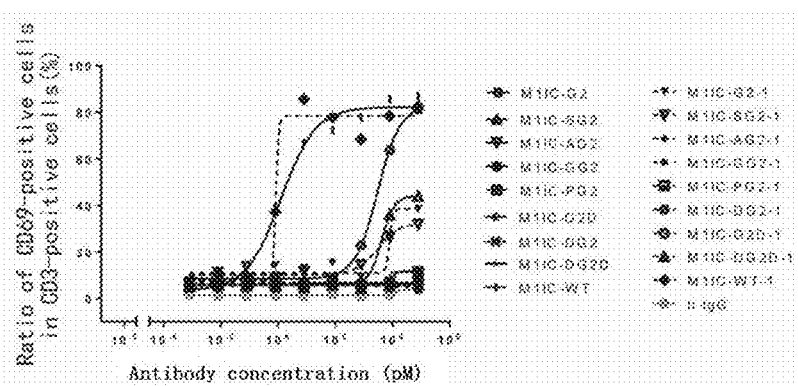
FIG. 8 shows the activation of T cells in PBMC by the isotype control antibody with the multifunctional antibody structure 1 and the ratio of CD3+CD69+ T cells.
Figure 9:
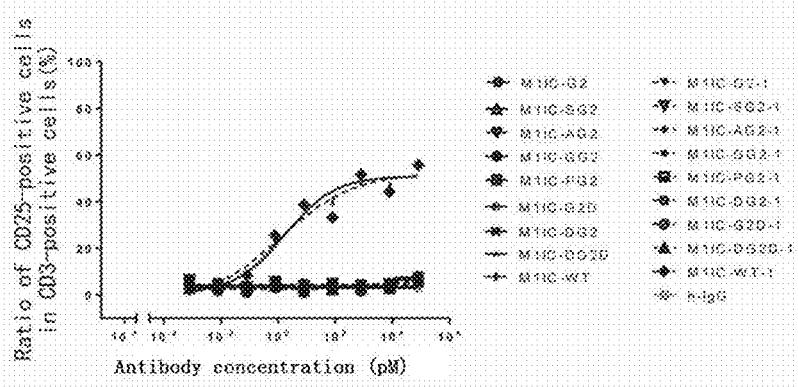
FIG. 9 shows the activation of T cells in PBMC by the isotype control antibody with the multifunctional antibody structure 1 and the ratio of CD3+CD25+ T cells.

As can be seen from FIG. 8, FIG. 9 and Table 38, among the above isotype control antibodies in PBMCs, M1IC-WT had the strongest non-specific activation of T cells, M1IC-SG2, M1IC-G2, M1IC-SG2-1 and M1IC-G2-1 had weaker non-specific activation of T cells, and M1IC-AG2/GG2/DG2/G2D/DG2D had no activation of T cells. It showed that when the antibody with multifunctional antibody structure 1 were CD3-targeted and CH2 was SG2CH2 (SEQ ID NO: 95) or G2CH2 (SEQ ID NO: 94), the antibody had a weakened non-specific activation of T cells; when the isotype control antibodies with multifunctional antibody structure 1 were AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), it was more effective to avoid non-specific activation of T cells.

Figure 10:
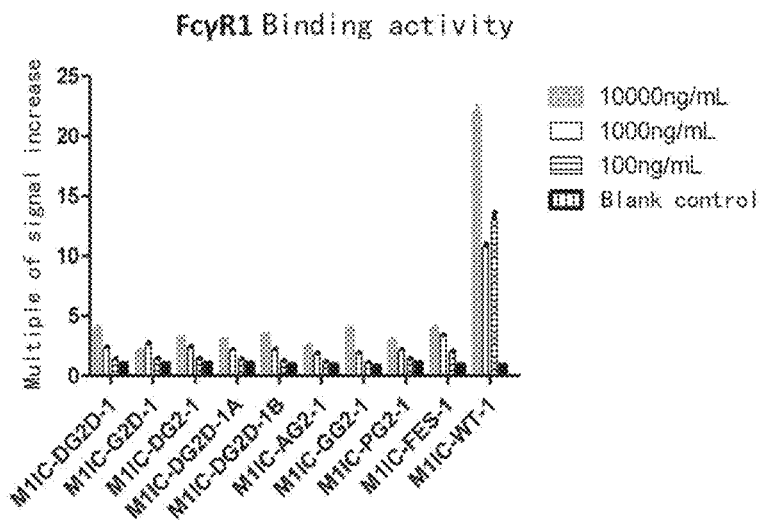
FIG. 10 shows the binding ability of the isotype control antibody with the multifunctional antibody structure 1 to FcγR1 and the detection of activated fluorescent signal of Jurkat-luciferase cells.
Figure 11:
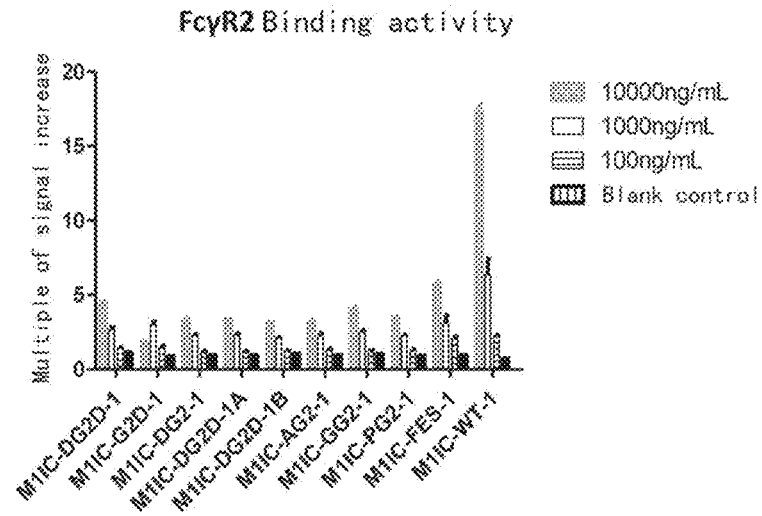
FIG. 11 shows the binding ability of the isotype control antibody with the multifunctional antibody structure 1 to FcγR2 and the detection of activated fluorescent signal of Jurkat-luciferase cells.
Figure 12:
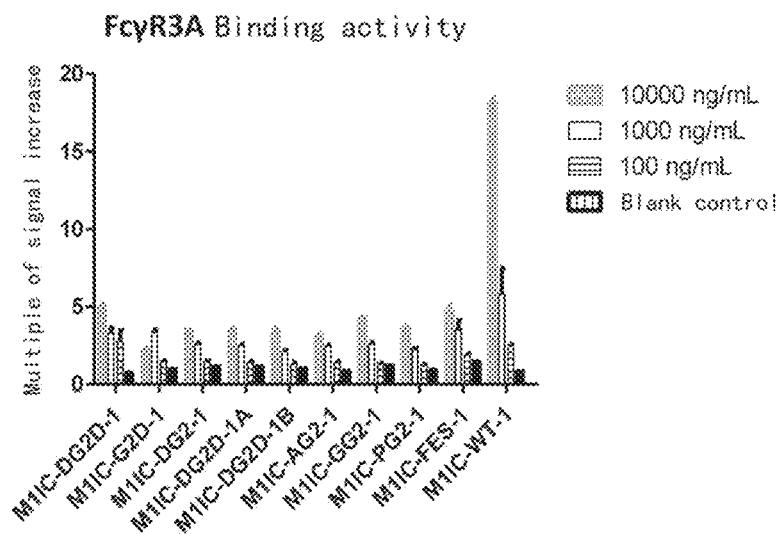
FIG. 12 shows the binding ability of the isotype control antibody with the multifunctional antibody structure 1 to FcγR3A and the detection of activated fluorescent signal of Jurkat-luciferase cells.

6. Activation experiment of Jurkat-luciferase cells by isotype control antibody (4420×CD3) with multifunctional antibody structure 1. The results were shown in FIG. 10, FIG. 11 and FIG. 12.

If the anti-CD3 antibody bound to the immobilized Fc receptor and then bound to Jurkat-luciferase cells with CD3 surface antigen, the cells can be activated and fluorescent signals can be detected. Stronger fluorescence signals indicated higher activation of cells, and further indicated that the binding of the antibody to Fc receptor was stronger. As can be seen from FIGS. 10 to 12, among the above isotype control antibodies, M1IC-WT-1 has the strongest activation to Jurkat-luciferase cells; when the immobilized antigen was FcγR2, M1IC-FES-1 had a relatively significant activation to Jurkat-luciferase cells; the activation of Jurkat-luficerase cells by M1IC-AG2-1, M1IC-GG2-1, M1IC-PG2-1, M1IC-DG2-1, M1IC-G2D-1, M1IC-DG2D-1, M1IC-DG2D-1A and M1IC-DG2D-1B was very weak and there was no significant difference between the activation by the above antibodies. It was shown that when the CH2 of isotype control antibody with multifunctional antibody structure 1 were AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2D (SEQ ID NO: 101), it was more effective to avoid non-specific activation of T cells than FES (SEQ ID NO: 85).

7. The killing ability of the BCMAxCD3 antibody with multifunctional antibody structure 2 to myeloma cell U266B1 (BCMA positive expression, China Center for Type Culture Collection) (wherein the ratio of the number of effector cells, human PBMC, to the number of target cells, U266B1, was 5:1, and the treatment time was 48 h) were shown in FIG. 13 and FIG. 14.

TABLE 39

Killing effect and EC50 value of BCMA × CD3 antibody with multifunctional antibody structure 2 and isotype control antibody in killing tumor cells U266B1

| Type | Antibody Code | Maximum Killing (%) | EC50 (pM) |
|---|---|---|---|
| BCMA × CD3 Antibody With Multifunctional Antibody Structure 2 | BCMA-M2-SG2 | 66.94 | 1.83 |
| | BCMA-M2-G2 | 66.99 | 3.092 |
| | BCMA-M2-FES | 68.29 | 2.004 |
| | BCMA-M2-WT | 69.21 | 1.678 |
| | BCMA-M2-AG2 | 71.26 | 1.724 |
| | BCMA-M2-GG2 | 71.51 | 1.552 |
| | BCMA-M2-PG2 | 71.92 | 1.768 |
| | BCMA-M2-DG2 | 73.79 | 1.612 |
| | BCMA-M2-G2D | 73.08 | 1.587 |
| | BCMA-M2-DG2D | 71.82 | 1.672 |
| None | E + T | None | None |

Figure 13:
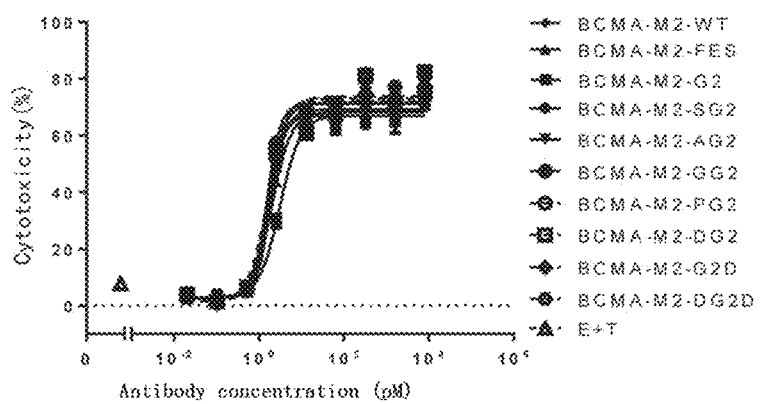
FIG. 13 shows the in vitro killing ability of different multifunctional antibodies with the multifunctional antibody structure 2 on myeloma cells U266B1.

As can be seen from FIG. 13 and Table 39, for the BCMA×CD3 antibody with multifunctional antibody structure 2, different modification of Fc can significantly kill the tumor cell U266B1, and there was no significant difference in killing effect, which indicated that the modification of Fc did not affect the cytotoxicity of the antibody with double-targeting function, that is, did not affect the efficacy of the antibody.

TABLE 40

Killing effect and EC50 value of isotype control antibody (4420 × CD3) with multifunctional antibody structure 2 in killing tumor cells U266B1

| Type | Antibody Code | Maximum Killing (%) | EC50 (pM) |
|---|---|---|---|
| | M2IC-WT | 50.15 | 1240 |
| | M2IC-G2 | 27.93 | ~1604 |
| | M2IC-SG2 | No Significant Killing | None |
| | M2IC-AG2 | No Significant Killing | None |
| | M2IC-GG2 | No Significant Killing | None |
| | M2IC-PG2 | No Significant Killing | None |
| | M2IC-DG2 | No Significant Killing | None |
| | M2IC-G2D | No Significant Killing | None |
| | M2IC-DG2D | No Significant Killing | None |
| None | E + T | None | None |

Figure 14:
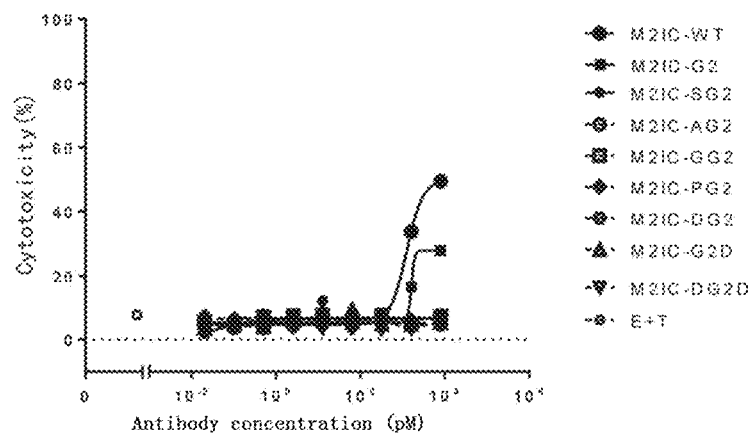
FIG. 14 shows the in vitro killing ability of different isotype control antibodies with the multifunctional antibody structure 2 on myeloma cells U266B1.

As can be seen from FIG. 14 and Table 40, for the antibodies with multifunctional antibody structure 2 in which the sequence of variable region was the same and the Fc was subjected to different modifications, the isotype control antibody M2IC-WT can significantly kill U266B1, indicating that the Fc can lead to non-specific activation of T cells; when the CH2 of Fc was G2CH2 (SEQ ID NO: 94), a weaker killing effect was observed, indicating that it may lead to a weaker non-specific activation of T cells; when the CH2 of Fc was SG2CH2 (SEQ ID NO: 95), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), there was no cell killing, indicating that these five Fcs did not lead to non-specific activation of T cells.

8. Activation experiment of T cells in peripheral blood mononuclear cells (PBMC) by isotype control antibody with multifunctional antibody structure 2 (treatment time was 48 h). The results were shown in FIG. 15 and FIG. 16.

TABLE 41

Activation ratio and EC50 value of the isotype control antibody with multifunctional antibody structure 2 in activation of T cells in PBMC

| | | CD3+ CD69+ T cells | | CD3+ CD25+ T cells | |
|---|---|---|---|---|---|
| Type | Antibody Code | Maximum Activation (%) | EC50 (pM) | Maximum Activation (%) | EC50 (pM) |
| 4420 × CD3 isotype control antibody with | M2IC-WT | 32.61 | 13211 | 25.44 | 8008 |
| | M2IC-G2 | 13.15 | Not calculated | 21.65 | Not calculated |

TABLE 41-continued

Activation ratio and EC50 value of the isotype control antibody with multifunctional antibody structure 2 in activation of T cells in PBMC

| | | CD3+ CD69+ T cells | | CD3+ CD25+ T cells | |
|---|---|---|---|---|---|
| Type | Antibody Code | Maximum Activation (%) | EC50 (pM) | Maximum Activation (%) | EC50 (pM) |
| multifunctional antibody structure 2 | M2IC-SG2 | 12.49 | Not calculated | No significant activation | Not calculated |
| | M2IC-AG2 | No significant activation | Not calculated | No significant activation | Not calculated |
| | M2IC-GG2 | No significant activation | Not calculated | No significant activation | Not calculated |
| | M2IC-PG2 | No significant activation | Not calculated | No significant activation | Not calculated |
| | M2IC-DG2 | No significant activation | Not calculated | No significant activation | Not calculated |
| | M2IC-G2D | No significant activation | Not calculated | No significant activation | Not calculated |
| | M2IC-DG2D | No significant activation | Not calculated | No significant activation | Not calculated |
| None | hIgG | 3.75 | Not calculated | 3.114 | Not calculated |

Figure 15:
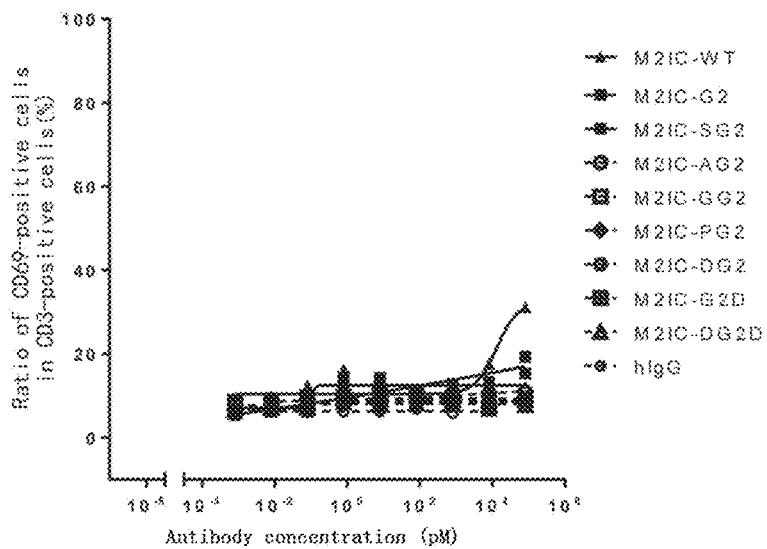
FIG. 15 shows the activation of T cells in PBMC by the isotype control antibody with the multifunctional antibody structure 2 and the ratio of CD3+CD69+ T cells.
Figure 16:
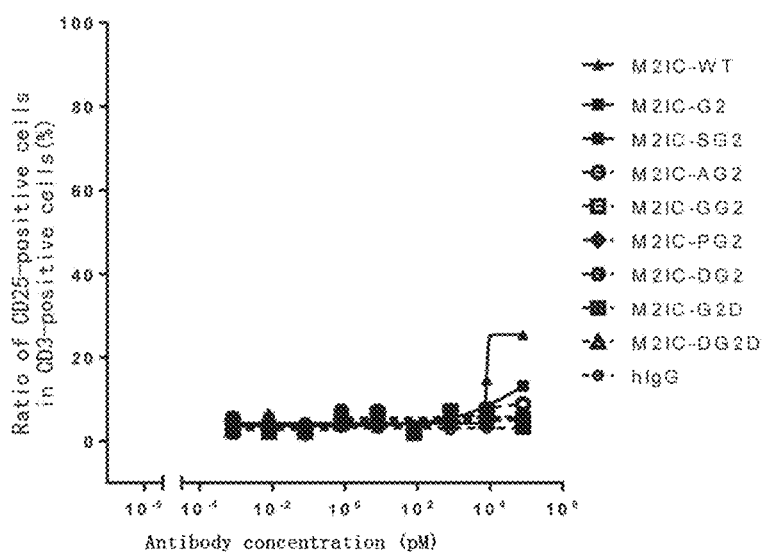
FIG. 16 shows the activation of T cells in PBMC by the isotype control antibody with the multifunctional antibody structure 2 and the ratio of CD3+CD25+ T cells.

As can be seen from FIG. 15, FIG. 16 and Table 41, in the absence of relevant tumor cells, the analysis of the maximum activation showed that M2IC-WT had a significant non-specific activation to T cells, and M2IC-G2 and M2IC-SG2 had a weakened non-specific activation to T cells, and the remaining antibodies did not have a significant activation to T cells. When the CH2 of Fc was AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), there was no cell killing, indicating that these five Fc did not lead to non-specific activation of T cells.

9. The killing ability of the CEA×CD3 antibody with multifunctional antibody structure 3 to gastric cancer cell MKN-45 (CEA positive expression, Basic Medical Cell Center, Institute of Basic Medicine, Chinese Academy of Medical Sciences) (wherein the ratio of the number of effector cells, human PBMC, to the number of target cells, MKN-45, was 5:1, and the treatment time was 48 h) were shown in FIG. 17 and FIG. 18.

TABLE 42

Killing effect and EC50 value of CEA × CD3 antibody with multifunctional antibody structure 3 in killing tumor cells MKN-45

| Type | Antibody Code | Maximum Killing (%) | EC50 (pM) |
|---|---|---|---|
| CEA × CD3 Antibody With Multifunctional Antibody Structure 3 | CEA-M3-WT | 46.33 | 259.0 |
| | CEA-M3-AAG | 46.55 | 249.0 |
| | CEA-M3-NA | 50.28 | 260.0 |
| | CEA-M3-FES | 48.95 | 368.8 |
| | CEA-M3-G2 | 49.6 | 409.3 |
| | CEA-M3-SG2 | 47.76 | 255.8 |
| | CEA-M3-AG2 | 48.84 | 256.0 |
| | CEA-M3-GG2 | 45.62 | 253.0 |
| | CEA-M3-PG2 | 47.9 | 263.9 |
| | CEA-M3-DG2 | 47.53 | 358.5 |
| | CEA-M3-G2D | 46.87 | 250.4 |

TABLE 42-continued

Killing effect and EC50 value of CEA × CD3 antibody with multifunctional antibody structure 3 in killing tumor cells MKN-45

| Type | Antibody Code | Maximum Killing (%) | EC50 (pM) |
|---|---|---|---|
| | CEA-M3-DG2D | 45.39 | 287.8 |
| None | E + T | 4.68 | None |

Figure 17:
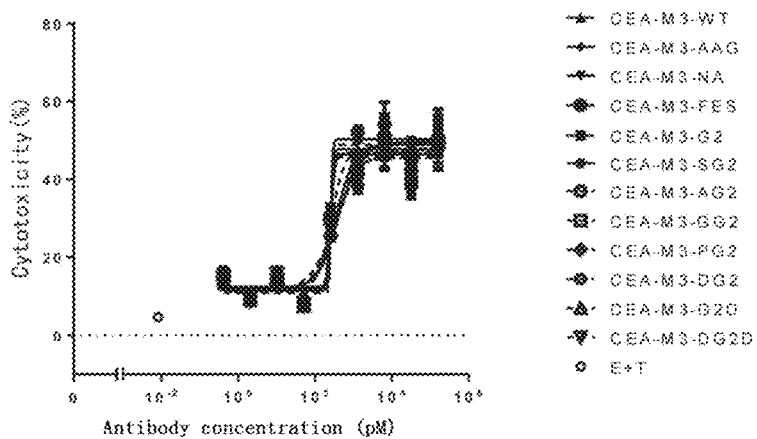
FIG. 17 shows the in vitro killing ability of CEAxCD3 antibody with the multifunctional antibody structure 3 on gastric cancer cell MKN-45.

As can be seen from FIG. 17 and Table 42, when the sequence of CEAxCD3 antibody with multifunctional antibody structure 3 was identical, different modification of Fc had no significant difference in the killing ability to tumor cell MKN-45, which indicated that the modification of Fc did not affect the cytotoxicity of the antibody with double-targeting function, that is, did not affect the efficacy of the antibody.

TABLE 43

Killing effect and EC50 value of isotype control antibody (4420 × CD3) with multifunctional antibody structure 3 in killing tumor cells MKN-45

| Type | Antibody Code | Maximum Killing (%) | EC50 (pM) |
|---|---|---|---|
| Isotype Control Antibody With Multifunctional Antibody Structure 3 | M3IC-WT | 29.09 | Not calculated |
| | M3IC-G2 | 17.60 | Not calculated |
| | M3IC-SG2 | 12.43 | Not calculated |
| | M3IC-AG2 | No Significant Killing | Not calculated |
| | M3IC-GG2 | No Significant Killing | Not calculated |
| | M3IC-PG2 | No Significant Killing | Not calculated |
| | M3IC-DG2 | No Significant Killing | Not calculated |
| | M3IC-G2D | No Significant Killing | Not calculated |

TABLE 43-continued

Killing effect and EC50 value of isotype control antibody (4420 × CD3) with multifunctional antibody structure 3 in killing tumor cells MKN-45

| Type | Antibody Code | Maximum Killing (%) | EC50 (pM) |
|---|---|---|---|
|  | M3IC-DG2D | No Significant Killing | Not calculated |
| None | E + T | No Significant Killing | None |

Figure 18:
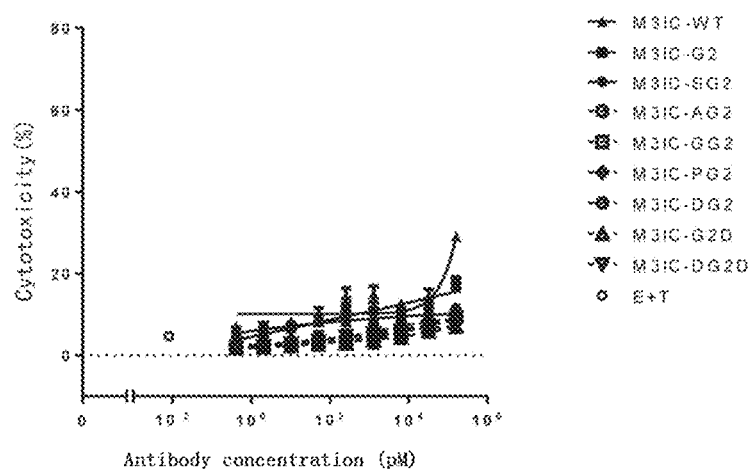
FIG. 18 shows the in vitro killing ability of isotype control antibodies with the multifunctional antibody structure 3 on gastric cancer cell MKN-45.

As can be seen from FIG. 18 and Table 43, the maximum killing showed that the antibody M3IC-WT had a significant killing; M3IC-G2 and M3IC-SG2 had a weaker killing, while the other antibodies had no significant killing, indicating that the modification of CH2 of Fc of the multifunctional antibody structure 3 to G2CH2 (SEQ ID NO: 94) and SG2CH2 (SEQ ID NO: 95) had the effect of weakening the non-specific activation of T cells compared with the control M3IC-WT, while the following five Fc, AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), did not lead to non-specific activation of T cells.

10. Activation experiment of T cells in peripheral blood mononuclear cells(PBMC) by isotype control antibody (4420×CD3) with multifunctional antibody structure 3 (treatment time was 48 h). The results were shown in FIG. 19 and FIG. 20.

TABLE 44

Activation ratio and EC50 value of the isotype control antibody with multifunctional antibody structure 3 in activation of T cells in PBMC

| | | CD3+ CD69+ T cells | | CD3+ CD25+ T cells | |
|---|---|---|---|---|---|
| Type | Antibody Code | Maximum Activation (%) | EC50 (pM) | Maximum Activation (%) | EC50 (pM) |
| 4420 × CD3 Isotype Control Antibody With Multifunctional Antibody Structure 3 | M3IC-WT | 41.2 | Not calculated | 26.75 | Not calculated |
| | M3IC-G2 | 26.97 | Not calculated | 14.21 | Not calculated |
| | M3IC-SG2 | 14.90 | Not calculated | No significant activation | Not calculated |
| | M3IC-AG2 | 12.59 | Not calculated | No significant activation | Not calculated |
| | M3IC-GG2 | 9.026 | Not calculated | No significant activation | Not calculated |
| | M3IC-PG2 | 9.869 | Not calculated | No significant activation | Not calculated |
| | M3IC-DG2 | 10.39 | Not calculated | No significant activation | Not calculated |
| | M3IC-G2D | 6.614 | Not calculated | No significant activation | Not calculated |
| | M3IC-DG2D | 10.26 | Not calculated | No significant activation | Not calculated |
| None | hIgG | 3.75 | Not calculated | 3.114 | Not calculated |

Figure 19:
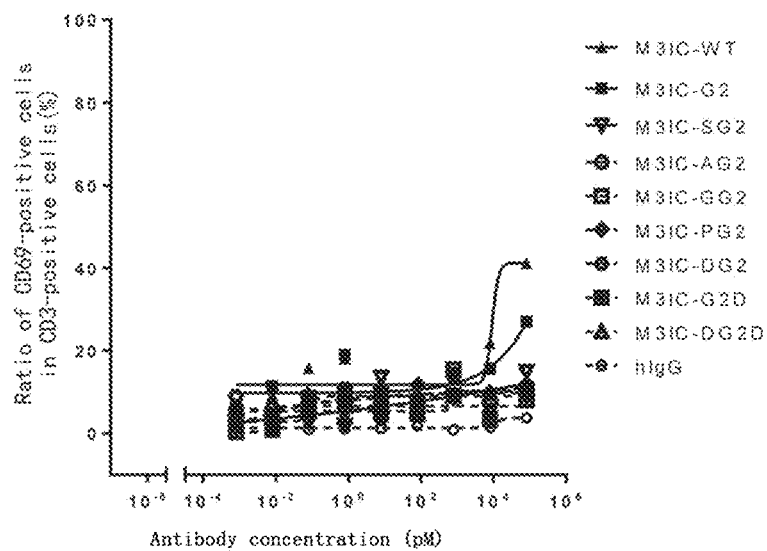
FIG. 19 shows the activation of T cells in PBMC by the isotype control antibody with the multifunctional antibody structure 3 and the ratio of CD3+CD69+ T cells.
Figure 20:
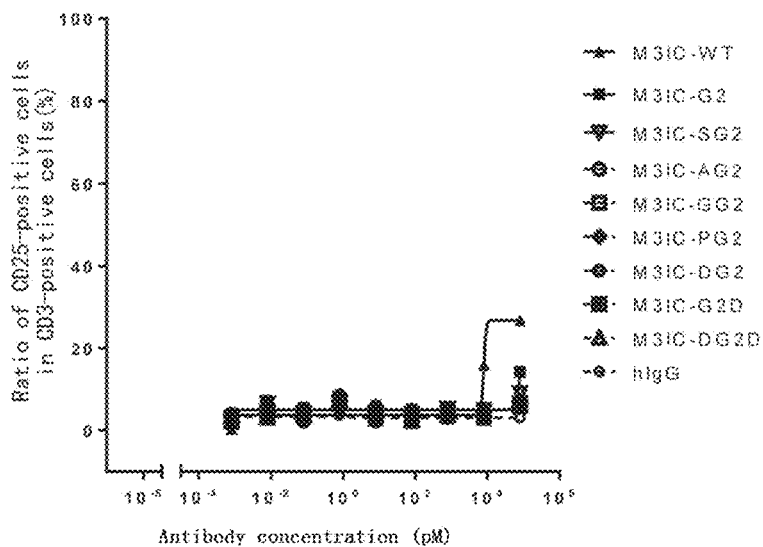
FIG. 20 shows the activation of T cells in PBMC by the isotype control antibody with the multifunctional antibody structure 3 and the ratio of CD3+CD25+ T cells.

As can be seen from FIG. 19, FIG. 20 and Table 44, among the isotype control antibodies with multifunctional antibody structure 3, M3IC-WT had the strongest significant activation to T cells, and M3IC-G2 had a weaker activation to T cells. When CH2 was G2CH2 (SEQ ID NO: 94), the antibody showed a weakened non-specific activation to T cell as compared with M2IC-WT, and the remaining antibodies showed a even weaker activation to T cells as compared with M2IC-WT, wherein, the CH2 was most preferably G2DCH2 (SEQ ID NO: 100).

EXAMPLE 3

Detection of Antibody Stability

Experimental Steps:
A. The specific steps of accelerated thermal stability test at 40° C. were:
1) the sample was substituted into a buffer, and the constituents of the buffer was 20 mM citric acid, pH 5.5, and the sample concentration was adjusted to 1 mg/mL;

2) each sample was divided into 500 μL per tube (6 tubes in total) and placed in a 40° C. water bath after being sealed. On day 0, day 3, day 5, day 7, day 10, and day 14, samples were taken for HPLC-SEC. The water bath time was 14 days in total.

B. Acid resistance test, also known as low-pH stability, was a test to detect whether the antibody molecule can maintain its original state after being treated in an acidic environment for a period of time and then being neutralized to physiological conditions. The specific steps were:

When antibody molecules were subjected to protein A affinity chromatography, the eluted antibody solution was not neutralized in the acid elution step (citrate buffer at pH 3.5 was used). After being kept in the buffer for a period of time, samples were taken at 30 min and 60 mM, and 1/10 volume of 1M Tris-HCl (pH 8.0) was added for neutralization, and the sample was tested by HPLC-SEC.

Results

1. The test results of 40° C. accelerated thermal stability test of the multifunctional antibody structure 1 were shown in FIG. 21.

Figure 21:
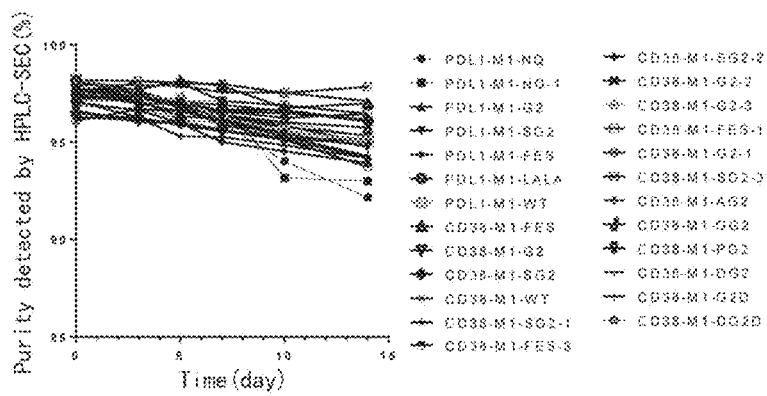
FIG. 21 shows the accelerated thermal stability detection of different antibodies with the multifunctional antibody structure 1 treated at 40° C. for 14 days.

As can be seen from FIG. 21, the purity of the different antibodies with multifunctional antibody structure 1 remained above 90% after being treated at 40° C. for 14 days, without a large amount of aggregation or degradation. Among them, the purity of the antibody with N297Q as the CH2 of Fc was significantly reduced as compared to the purity of other antibodies, and there was no significant difference among other CH2 modified antibodies, which indicated that the multifunctional antibody structure 1 had a good thermal stability when CH2 was G2CH2 (SEQ ID NO: 94), SG2CH2 (SEQ ID NO: 95), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101).

2. The results of acid resistance test of the multifunctional antibody structure 1 were shown in FIG. 22.

Figure 22:
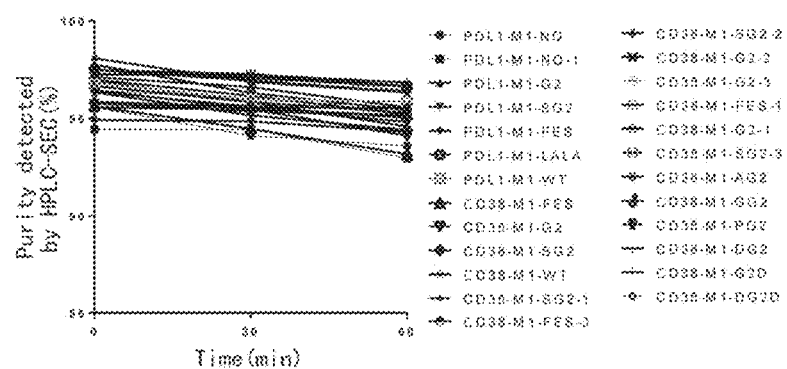
FIG. 22 shows the acid resistance detection of different antibodies with multifunctional antibody structure 1.

As can be seen from FIG. 22, for the different Fc-modified antibodies with multifunctional antibody structure 1, the antibody purity did not change significantly after being treated under low pH conditions for 60 minutes, and there was no significant difference between different antibodies, indicating the above-mentioned Fc-modified multifunctional antibody structure 1 had a good acid resistance.

As can be seen from FIG. 21 and FIG. 22, the antibody with multifunctional antibody structure 1 (wherein the CH2 of the antibody was G2CH2 (SEQ ID NO: 94), SG2CH2 (SEQ ID NO: 95), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101)) had a good thermal stability and acid resistance.

3. The results of 40° C. accelerated thermal stability test of the multifunctional antibody structure 2 were shown in FIG. 23.

Figure 23:
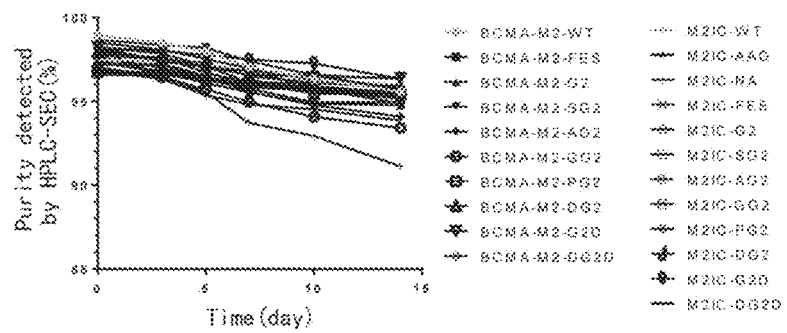
FIG. 23 shows the accelerated thermal stability detection of different antibodies with the multifunctional antibody structure 2 treated at 40° C. for 14 days.

As can be seen from FIG. 23, if the CH2 of the multifunctional antibody structure 2 was N297A (SEQ ID NO: 87), the purity of antibody after being treated at 40° C. for 14 days was decreased significantly; the purity of other antibodies did not change significantly, and there was no significant difference between antibodies, which proved that these antibodies with multifunctional antibody structure 2 other than M2IC-NA had a good accelerated thermal stability.

4. The results of acid resistance test of the multifunctional antibody structure 2 were shown in FIG. 24.

Figure 24:
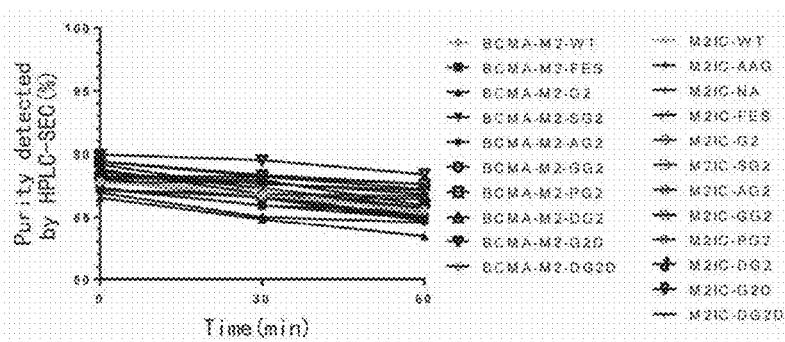
FIG. 24 shows the acid resistance detection of different antibodies with multifunctional antibody structure 2.

As can be seen from FIG. 24, for the different Fc-modified antibodies with multifunctional antibody structure 1, the antibody purity did not change significantly after being treated under low pH conditions for 60 minutes, and there was no significant difference between different antibodies, indicating that the above-mentioned Fc-modified multifunctional antibody structure 2 had a good acid resistance.

As can be seen from FIG. 23 and FIG. 24, the antibody with multifunctional antibody structure 2 (wherein the CH2 of the antibody was G2CH2 (SEQ ID NO: 94), SG2CH2 (SEQ ID NO: 95), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101)) had a good thermal stability and acid resistance.

5. The results of 40° C. accelerated thermal stability test of the multifunctional antibody structure 3 were shown in FIG. 25.

Figure 25:
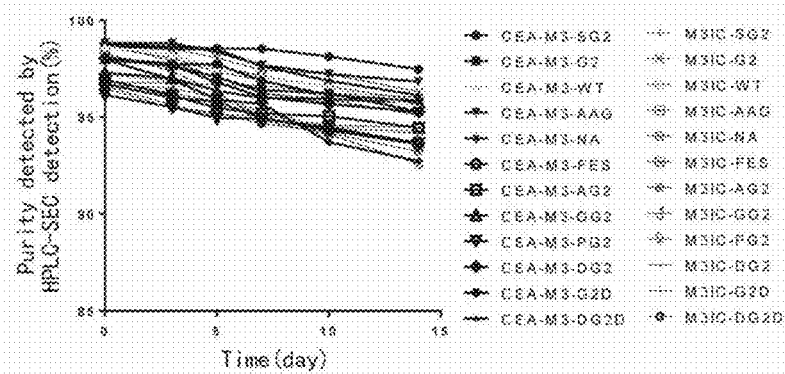
FIG. 25 shows the accelerated thermal stability detection of different antibodies with the multifunctional antibody structure 3 treated at 40° C. for 14 days.

As can be seen from FIG. 25, the purity of different antibodies with multifunctional antibody structure 3 did not change significantly after being treated at 40° C. for 14 days, and there was no significant difference between the antibodies, which proved that the above-mentioned antibodies with multifunctional antibody structure 3 had a good accelerated thermal stability.

6. The results of acid resistance test of the multifunctional antibody structure 3 were shown in FIG. 26.

Figure 26:
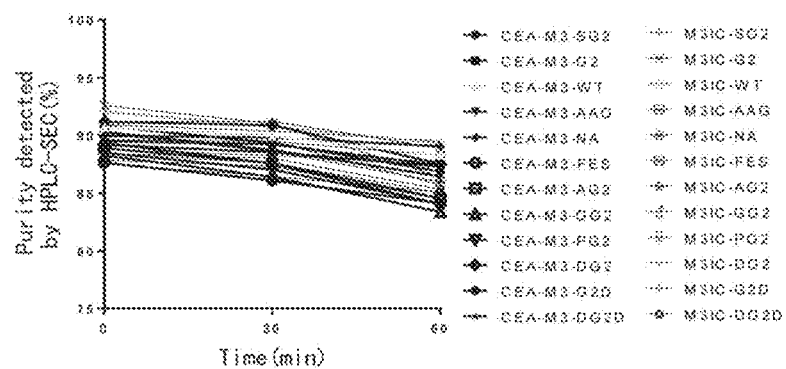
FIG. 26 shows the acid resistance detection of different antibodies with multifunctional antibody structure 3.

As can be seen from FIG. 26, for the different Fc-modified antibodies with multifunctional antibody structure 3, the antibody purity did not change significantly after being treated under low pH conditions for 60 minutes, and there was no significant difference between different antibodies, indicating that the above-mentioned Fc-modified multifunctional antibody structure 3 had a good acid resistance.

As can be seen from FIG. 25 and FIG. 26, the antibody with multifunctional antibody structure 3 (wherein the CH2 of the antibody was G2CH2 (SEQ ID NO: 94), SG2CH2 (SEQ ID NO: 95), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101)) had a good thermal stability and acid resistance.

EXAMPLE 4

Binding Experiment Of Fc-modified Monoclonal Antibodies And FcγR-Expressing Cells 1. Preparation of Monoclonal Antibodies
   (1) In the present disclosure, the prepared monoclonal antibody had the same or similar structure as the natural antibody such as human IgG1, IgG2, IgG3 or IgG4 subtype, and the structure was in a form of symmetrical "Y", with a bivalent Fc domain binding to the same target antigen and the corresponding subtype.

Figure 27:
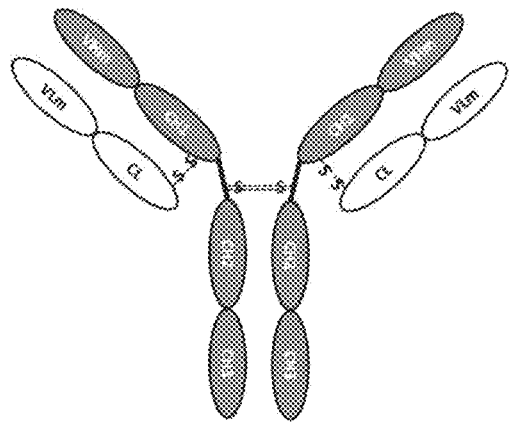
FIG. 27 is a structural schematic diagram of monoclonal antibodies.

FIG. 27 showed a schematic diagram of the specific structure.
   (2) The construction of expression plasmid, the transfection expression and the purification method of the monoclonal antibody were consistent with the methods of multifunctional antibody involved in Example 1 of the present disclosure, and the used sequences were shown in Table 45.

TABLE 45

Codes and the amino acid sequences of variable region of some monoclonal antibodies (CDR is underlined in bold)

| Antibody code | Polypeptide | Domain | Code | Amino acid sequence | 序列号 |
|---|---|---|---|---|---|
| 4420 mAb-WT | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge | Hin1 | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLH QDWLNGKEYKCKVSNKALPAPIEKTISKAK | 83 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVES CSVMHEALHNHYTQKSLSLSPGK | 102 |
| 4420 mAb-G2 | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge | Hin1 | DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSVLTVVHQ DWLNGKEYKCKVSNKGLPAPIEKTISKTK | 94 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-SG2 | Light Chain | VL | 4420 | DVVMTQTPLSLPVSLGDQASISCRSSQSLVHSNGNTYLRWYLQKPGQSPKVLIYKVSNRFSGVPDRESGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge | Hin1 | DKTHTCP | 66 |
| | | CH2 | SG2CH2 | PSPAPPVAGPSVFLFPPKPKDTLMISRTPEVTCVVVDVSHEDPEVQFNWYVDGVEVHNAKTKPREEQFNSTFRVVSVLTVVHQ DWLNGKEYKCKVSNKGLPAPIEKTISKTK | 95 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-AG2 | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |

TABLE 45-continued

Codes and the amino acid sequences of variable region of some monoclonal antibodies
(CDR is underlined in bold)

| Antibody code | Polypeptide | Domain | Code | Amino acid sequence | 序列号 |
|---|---|---|---|---|---|
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge CH2 | Hin1 AG2CH2 | DKTHTCP PAPAPVAGPSVFLFPPKPKDTLMISRTPEVTCVVVDVSHEDPEVQFNWYVDGVEVHNAKTKPREEQFNSTFRVVSLTVVHQ DWLNGKEYKCKVSNKGLPAPIEKTISKTK | 66 96 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-GG2 | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge CH2 | Hin1 GG2CH2 | DKTHTCP PGPAPPVAGPSVFLFPPKPKDTLMISRTPEVTCVVVDVSHEDPEVQFNWYVDGVEVHNAKTKPREEQFNSTFRVVSLTVVHQ DWLNGKEYKCKVSNKGLPAPIEKTISKTK | 66 97 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-PG2 | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge CH2 | Hin1 PG2CH2 | DKTHTCP PPPAPPVAGPSVFLFPPKPKDTLMISRTPEVTCVVVDVSHEDPEVQFNWYVDGVEVHNAKTKPREEQFNSTFRVVSLTVVHQ DWLNGKEYKCKVSNKGLPAPIEKTISKTK | 66 98 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-DG2 | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge | Hin1 | DKTHTCP | 66 |

TABLE 45-continued

Codes and the amino acid sequences of variable region of some monoclonal antibodies
(CDR is underlined in bold)

| Antibody code | Polypeptide | Domain | Code | Amino acid sequence | 序列号 |
|---|---|---|---|---|---|
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSLTVVHQ DWLNGKEYKCKVSNKGLPAPIEKTISKTK | 99 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-G2D | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge | | DKTHTCP | 66 |
| | | CH2 | G2DCH2 | PCPAPPVAGPSVFLFPPKPKDTLMISRTPEVTCVVVDVSHEAPEVQFNWYVDGVEVHNAKTKPREEQFNSTFRVVSLTVVHQ DWLNGKEYKCKVSNKGLPAPIEKTISKTK | 100 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFS CSVMHEALHNHYTQKSLSLSPGK | 102 |
| 4420 mAb-DG2D | Light Chain | VL | 4420 | DVVMTQTPLSLPVSLGDQASISCRSSQSLVHSNGNTYLRWYLQKPGQSPKVLIYKVSNRFSGVPDRFSGSGSGTDFTLKISRVE AEDLGVYFCSQSTHVPWTFGGGTKLEIK | 44 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKV YACEVTHQGLSSPVTKSFNRGEC | 75 |
| | Heavy Chain | VH | 4420 | EVKLDETGGGLVQPGRPMKLSCVASGFTFSDYWMNWVRQSPEKGLEWVAQIRNKPYNYETYYSDSVKGRFTISRDDSKSSV YLQMNNLRVEDMGIYYCTGSYYGMDYWGQGTSVTVSS | 43 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSC | 82 |
| | | Hinge | | DKTHTCP | 66 |
| | | CH2 | DG2CH2 | PCPAPPVAGPSVFLFPPKPKDTLMISRTPEVTCVVVAVSHEDPEVQFNWYVDGVEVHNAKTKPREEQFNSTFRVVSLTVVHQ DWLNGKEYKCKVSNKGLPAPIEKTISKTK | 101 |
| | | CH3 | WT | GQPREPQVYTLPPSRDELTKNQVSLTCLVKGFYPSDIAVEWESNGQPENNYKTTPPVLDSDGSFELYSKLTVDKSRWQQGNVFS CSVMHEALHNHYTQKSLSLSPGK | 102 |

2. Binding Experiment of Monoclonal Antibody To FcγR-Expressing Cells (1) There are three types of FcγR that bind to human IgG antibody Fc: FcγRI, FcγRII and FcγRIII. Among them, FcγRI (also known as CD64) and FcγRIIA are expressed on macrophages and neutrophils; FcγRIIB is expressed on B cells, and FcγRIIIA (also known as CD16A) is expressed on natural killer (NK) cells. The surface marker of dendritic cells is CD83, the surface marker of macrophages is CD14, the surface marker of B cells is CD20, and the surface marker of NK cells is CD56.

Nine monoclonal antibodies in Table 45 were prepared and then were labeled with biotin. The negative control was 4420 antibody with Fab structure (wherein, VL was SEQ ID NO: 44, CL was SEQ ID NO: 75, VH was SEQ ID NO: 43, CH1 was SEQ ID NO: 82) and without Fc, and was also biotin-labeled.

PBMCs were isolated from the blood of healthy donors and divided into three groups:

a) the binding ability of 4420 mAb Fc to macrophages was detected in group 1; PBMC and PE-labeled anti-CD14 antibody (purchased from Thermofisher) and the aforementioned 9 biotin-labeled 4420 mAbs (three concentrations of 500 µg/ml, 50 µg/ml and 5 µg/ml for each antibody) were incubated for 2 h (at room temperature), washed for 3 times, then incubated for 30 minutes (at room temperature) after being added with FITC-labeled avidin, washed for 5 times and then subjected to flow cytometry; PE fluorescent cell population was circled, and then the average fluorescence intensity of FITC was analyzed;

b) the binding ability of 4420 mAb Fc to B cells was detected in group 2, the steps were the same as in a), except that PE-labeled anti-CD20 antibody (purchased from Thermofisher) was used instead of PE-labeled anti-CD14 antibody;

c) the binding ability of 4420 mAb Fc to NK cells was detected in group 3, the steps were the same as in a), except that anti-CD56 antibody (purchased from Thermofisher) was used instead of PE-labeled anti-CD14 antibody.

Figure 28:
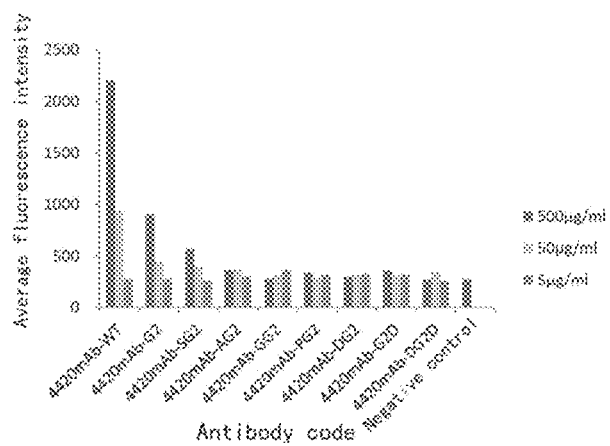
FIG. 28 shows the binding of different Fc-modified 4420 mAbs to macrophages by flow cytometry detection and analysis.
Figure 29:
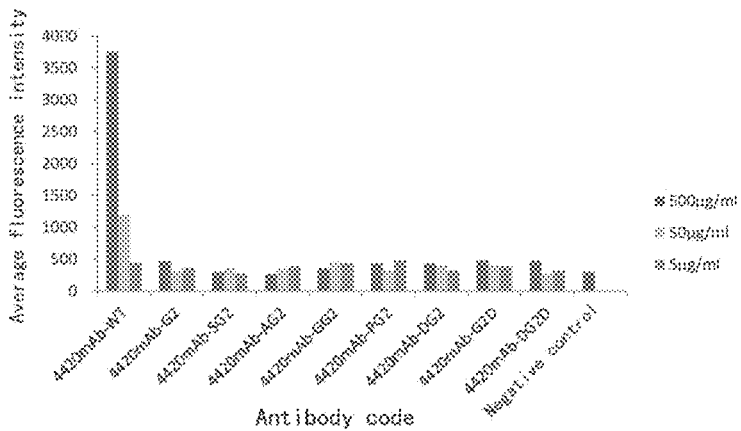
FIG. 29 shows the binding of different Fc-modified 4420 mAbs to B cells by flow cytometry detection and analysis.
Figure 30:
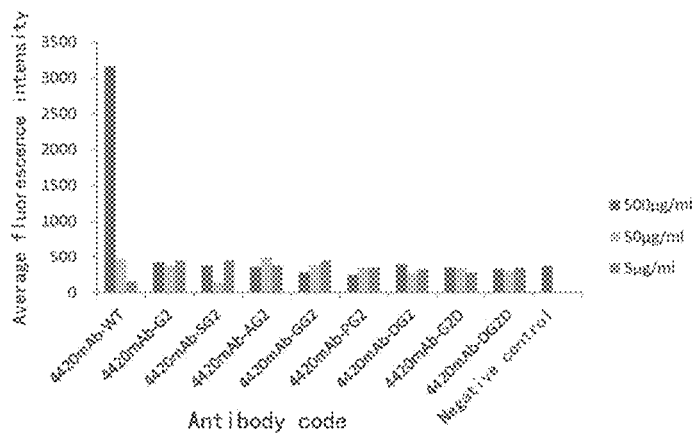
FIG. 30 shows the binding of different Fc-modified 4420 mAbs to NK cells by flow cytometry detection and analysis.

The results of flow cytometry were shown in FIGS. 28 to 30. As can be seen from FIG. 28, 4420mAb-WT significantly bound to to macrophages; and if CH2 was G2CH2 (SEQ ID NO:94), SG2CH2 (SEQ ID NO:95), AG2CH2 (SEQ ID NO:96), GG2CH2 (SEQ ID NO:97), PG2CH2 (SEQ ID NO:98), DG2CH2 (SEQ ID NO:99), G2DCH2 (SEQ ID NO:100) and DG2DCH2 (SEQ ID NO: 101), the binding to FcγRI or FcγRIIA was significantly reduced or lost.

As can be seen from FIG. 29, 4420mAb-WT significantly bound to to B cells; compared with 4420mAb-WT, if the CH2 of the Fc of antibody was SG2CH2 (SEQ ID NO: 95), G2CH2 (SEQ ID NO: 94), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), the binding to FcγRIIB was significantly reduced or lost.

As can be seen from FIG. 30, only 4420mAb-WT had a significant binding to NK, indicating that if the CH2 of the Fc was SG2CH2 (SEQ ID NO: 95), G2CH2 (SEQ ID NO: 94), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), the binding to FcγRIIIA was significantly reduced or lost.

Based on FIGS. 28 to 30, it can be seen that if the CH2 of Fc was modified to G2CH2 (SEQ ID NO: 94), SG2CH2 (SEQ ID NO: 95), AG2CH2 (SEQ ID NO: 96), GG2CH2 (SEQ ID NO: 97), PG2CH2 (SEQ ID NO: 98), DG2CH2 (SEQ ID NO: 99), G2DCH2 (SEQ ID NO: 100) and DG2DCH2 (SEQ ID NO: 101), the binding function of antibody Fc to its receptor FcγRI, FcγRIIA, FcγRIIB and FcγRIIIA was greatly reduced or lost. It is known that the activation of T cells by CD3 antibody is largely caused by the binding of antibody Fc to FcγR on the surface of other cells. In the present disclosure, the Fc was innovatively modified, wherein the CH2 domain in the Fc of human IgG1 was substituted with a CH2 domain of human IgG2, preferably subjected to substitution of several amino acid residues; and antibodies or fusion proteins with significantly reduced or even lost binding ability to FcγR were obtained; and these Fc modification methods did not affect the stability and biological activity of the antibody itself.

EXAMPLE 5

Activation Experiment of T Cells by Anti-CD3 Monoclonal Antibody

1. Preparation of Monoclonal Antibodies

See Part 1 "Preparation of monoclonal antibodies" in Example 4, and the used sequences were shown in Table 46.

TABLE 46

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-WT | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Hinge | Hin1 | DKTHTCP | DKTHTCP | 66 |
| | | CH2 | WT | PCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK | 83 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-FES | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Hinge | Hin1 | FES | DKTHTCP | 66 |
| | | CH2 | CH2 | PCPAPEFEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAK | 85 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-AAG | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | Hinge | Hin1 | AAG | DKTHTCP | 66 |
| | | CH2 | CH2 | PCPAPEAAGGPSVFLEPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAK | 84 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2 | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |

TABLE 46-continued

Codes and amino acid sequences of variable region of some monoclonal antibodies (CDR is underlined in bold)

| Antibody Code | Polypeptide | Domain | Code | Amino acid sequence | SEQ ID NO |
|---|---|---|---|---|---|
| CD3 mAb-SG2 | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK | 82 |
| | | Hinge | Hin1 | VDKKVEPKSC DKTHTCP | 66 |
| | | CH2 | G2CH2 | PCPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 94 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | | ASTKGPSVFPLAPSSKSTSGGTAALGCLVKDYFPEPVTVSWNSGALTSGVHTPAVLQSSGLYSLSSVVTVPSSSLGTYICNVNHKPSNTK | 82 |
| | | Hinge | Hin1 | VDKKVEPKSC DKTHTCP | 66 |
| | | CH2 | SG2CH2 | PSPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 95 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-AG2 | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK | 82 |
| | | Hinge | Hin1 | VDKKVEPKSC DKTHTCP | 66 |
| | | CH2 | AG2CH2 | PAPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 96 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-GG2 | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK | 82 |
| | | Hinge | Hin1 | VDKKVEPKSC DKTHTCP | 66 |

TABLE 46-continued

Codes and amino acid sequences of variable region of some monoclonal antibodies (CDR is underlined in bold)

| Antibody Code | Poplypeptide | Domain | Code | Amino acid sequence | SEQ ID NO |
|---|---|---|---|---|---|
| | | CH2 | GG2CH2 | PGPAPPVAGPSVFLFPPKPKDTLMISRTPEVTCVVVDVSHEDPEVQFNWYVDGVEVHNAKTPREEQFNSTFRVVSLTVVHQDWLNGKE YKCKVSNKGLPAPIEKTISKTK | 97 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-PG2 | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | PG2CH2 | PLPAPPVAGPSVFLFPPKPKDTLMISRTPEVTCVVVDVSHEDPEVQFNWYVDGVEVHNAKTPREEQFNSTFRVVSLTVVHQDWLNGKE YKCKVSNKGLPAPIEKTISKTK | 98 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-C229L | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | C229LG2CH2 | PLPAPPVAGPSVFLFPPKPKDTLMISRTPEVTCVVVDVSHEDPEVQFNWYVDGVEVHNAKTPREEQFNSTFRVVSLTVVHQDWLNGKE YKCKVSNKGLPAPIEKTISKTK | 128 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-C229F | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | C229FG2CH2 | PFPAPPVAGPSVFLFPPKPKDTLMISRTPEVTCVVVDVSHEDPEVQFNWYVDGVEVHNAKTPREEQFNSTFRVVSLTVVHQDWLNGKE YKCKVSNKGLPAPIEKTISKTK | 129 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-C229R | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | C229RG2CH2 | PRPAPPVAGPSVFLFPPKPKDTLMISRTPEVTCVVVDVSHEDPEVQFNWYVDGVEVHNAKTKPREEQFNSTFRVVSLTVVHQDWLNGKEYKCKVSNKGLPAPIEKTISKTK | 130 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-C229V | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | C229VG2CH2 | PVPAPPVAGPSVFLFPPKPKDTLMISRTPEVTCVVVDVSHEDPEVQFNWYVDGVEVHNAKTKPREEQFNSTFRVVSLTVVHQDWLNGKEYKCKVSNKGLPAPIEKTISKTK | 131 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-C229Q | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | C229QG2CH2 | PQPAPPVAGPSVFLFPPKPKDTLMISRTPEVTCVVVDVSHEDPEVQFNWYVDGVEVHNAKTKPREEQFNSTFRVVSLTVVHQDWLNGKEYKCKVSNKGLPAPIEKTISKTK | 132 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-C229K | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-C229D | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNEGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | C229KG2CH2 | PKPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 133 |
| | | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| CD3 mAb-G2-C229I | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | C229DG2CH2 | PDPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 134 |
| | | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| CD3 mAb-G2-C229Y | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | C229IG2CH2 | PIPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 135 |
| | | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |

TABLE 46-continued

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-G2-C229N | Light Chain | CH2 | C229YG2CH2 | PYPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 136 |
|  |  | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
|  |  | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
|  | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
|  |  | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
|  |  | Hinge | Hin1 | DKTHTCP | 66 |
|  |  | CH2 | C229NG2CH2 | PNPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 137 |
|  |  | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-C229M | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
|  | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
|  |  | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
|  |  | Hinge | Hin1 | DKTHTCP | 66 |
|  |  | CH2 | C229MG2CH2 | PMPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 138 |
|  |  | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-C229T | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
|  | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
|  |  | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
|  |  | Hinge | Hin1 | DKTHTCP | 66 |
|  |  | CH2 | C229TG2CH2 | PTPAPPVAGPSVFLFPPKPKDTLMISRTPEVTCVVVDVSHEDPEVQFNWYVDGVEVHNAKTKPREEQFNSTFRVVSLTVVHQDWLNGKE YKCKVSNKGLPAPIEKTISKTK | 139 |
|  |  | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |

TABLE 46-continued

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-G2-C229H | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAY**WGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | C229HG2CH2 | PHPAPPVAGPSVFLFPPKPKDTLMISRTPEVTCVVVDVSHEDPEVQFNWYVDGVEVHNAKTKPREEQFNSTFRVVSLTVVHQDWLNGKEYKCKVSNKGLPAPIEKTISKTK | 140 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-C229E | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAY**WGQGTLVTVSS | 1 |
| | | CH1 | CH1 VDKKVEPKSC | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKDKTHTCP | 82 |
| | | Hinge | Hin1 | DKTHTCP | 66 |
| | | CH2 | C229EG2CH2 | PEPAPPVAGPSVFLFPPKPKDTLMISRTPEVTCVVVDVSHEDPEVQFNWYVDGVEVHNAKTKPREEQFNSTFRVVSLTVVHQDWLNGKEYKCKVSNKGLPAPIEKTISKTK | 141 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-C229W | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAY**WGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | C229WG2CH2 | PWPAPPVAGPSVFLFPPKPKDTLMISRTPEVTCVVVDVSHEDPEVQFNWYVDGVEVHNAKTKPREEQFNSTFRVVSLTVVHQDWLNGKEYKCKVSNKGLPAPIEKTISKTK | 142 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-DG2 | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D265P | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | DG2CH2 | PCPAPPVAGPSVFLFPPKPKDTLMISRTPEVTCVVVDVSHEDPEVQFNWYVDGVEHNAKTKPREEQFNSTFRVVSLTVVHQDWLNGKE YKCKVSNKGLPAPIEKTISKTK | 99 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| CD3 mAb-G2-D265K | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265KG2CH2 | PCPAPPVAGPSVFLFPPKPKDTLMISRTPEVTCVVVDVSHEDPEVQFNWYVDGVEHNAKTKPREEQFNSTFRVVSLTVVHQDWLNGKE YKCKVSNKGLPAPIEKTISKTK | 143 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| CD3 mAb-G2-D265S | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |

TABLE 46-continued

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-G2-D265F | Light Chain | CH2 | D265SG2CH2 | PCPAPPVAGPSVFLFPPKPKDTLMISRTPEVTCVVVSHEDPEVQFNWYVDGVEVHNAKTPREEQFNSTFRVVSLTVVHQDWLNGKE YKCKVSNKGLPAPIEKTISKTK | 145 |
| | | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265FG2CH2 | PCPAPPVAGPSVFLFPPKPKDTLMISRTPEVTCVVVSHEDPEVQFNWYVDGVEVHNAKTPREEQFNSTFRVVSLTVVHQDWLNGKE YKCKVSNKGLPAPIEKTISKTK | 146 |
| | | CH3 | WT | GQPREPQVVTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D265R | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265RG2CH2 | PCPAPPVAGPSVFLFPPKPKDTLMISRTPEVTCVVVSHEDPEVQFNWYVDGVEVHNAKTPREEQFNSTFRVVSLTVVHQDWLNGKE YKCKVSNKGLPAPIEKTISKTK | 147 |
| | | CH3 | WT | GQPREPQVVTLPPSRDELTKNQVSLTCLVKGFYPSDIAVEWESNGQPENNYKTTPPVLDSDGSFELYSKLTVDKSRWQQGNVFSCSVMHEA LHNHYTQKSLSLSPGK | 102 |
| CD3 mAb-G2-D265L | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIEPPSDEQLKSGTASVVCLLNNEYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265LG2CH2 | PCPAPPVAGPSVFLFPPKPKDTLMISRTPEVTCVVVSHEDPEVQFNWYVDGVEVHNAKTPREEQFNSTFRVVSLTVVHQDWLNGKE YKCKVSNKGLPAPIEKTISKTK | 148 |
| | | CH3 | WT | GQPREPQVVTLPPSRDELTKNQVSLTCLVKGFYPSDIAVEWESNGQPENNYKTTPPVLDSDGSFELYSKLTVDKSRWQQGNVFSCSVMHEA LHNHYTQKSLSLSPGK | 102 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D265G | Light Chain | VL | 2a5 | QTVVTQEPSLTVSPGGTVTLTCRSSTGAVTTSNYANWVQQKPGQAPRGLIGGTNKRAPGVPARESGSLLGKAALTLSGVQPEDEAEYYC ALWYSNLWVFGGGTKVEIK | 2 |
| | | CL | Lc1 | RTVAAPSVFIEPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265GG2CH2 | PCPAPPVAGPSVFLFPPKPKDTLMISRTPEVTCVVVGSHEDPEVQFNWYVDGVEVHNAKTKPREEQENSTERVVSVLTVVHQDWLNGKE YKCKVSNKGLPAPIEKTISKTK | 149 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D265T | Light Chain | VL | 2a5 | QTVVTQEPSLTVSPGGTVTLTCRSSTGAVTTSNYANWVQQKPGQAPRGLIGGTNKRAPGVPARESGSLLGKAALTLSGVQPEDEAEYYC ALWYSNLWVFGGGTKVEIK | 2 |
| | | CL | Lc1 | RTVAAPSVFIEPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265TG2CH2 | PCPAPPVAGPSVFLFPPKPKDTLMISRTPEVTCVVVTSHEDPEVQFNWYVDGVEVHNAKTKPREEQENSTERVVSVLTVVHQDWLNGKE YKCKVSNKGLPAPIEKTISKTK | 150 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D265Y | Light Chain | VL | 2a5 | QTVVTQEPSLTVSPGGTVTLTCRSSTGAVTTSNYANWVQQKPGQAPRGLIGGTNKRAPGVPARESGSLLGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265YG2CH2 | PCPAPPVAGPSVFLFPPKPKDTLMISRTPEVTCVVVYSHEDPEVQFNWYVDGVEVHNAKTKPREEQFNSTFRVVSVLTVVHQDWLNGKE YKCKVSNKGLPAPIEKTISKTK | 151 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D265W | Light Chain | VL | 2a5 | QTVVTQEPSLTVSPGGTVTLTCRSSTGAVTTSNYANWVQQKPGQAPRGLIGGTNKRAPGVPARESGSLLGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D265H | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D265HG2CH2 | PCPAPPVAGPSVFLFPPKPKDTLMISRTPEVTCVVVHVSHEDPEVQFNWYVDGVEVHNAKTKPREEQFNSTFRVVSLTVVHQDWLNGKEYKCKVSNKGLPAPIEKTISKTK | 153 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCCSVMHEALHNHYTQKSLSLSPGK | 102 |
| CD3 mAb-G2-D265V | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D265VG2CH2 | PCPAPPVAGPSVFLFPPKPKDTLMISRTPEVTCVVVVSHEDPEVQFNWYVDGVEVHNAKTKPREEQFNSTFRVVSLTVVHQDWLNGKEYKCKVSNKGLPAPIEKTISKTK | 154 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCCSVMHEALHNHYTQKSLSLSPGK | 102 |
| CD3 mAb-G2-D265Q | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D265QG2CH2 | PCPAPPVAGPSVFLFPPKPKDTLMISRTPEVTCVVVQSHEDPEVQFNWYVDGVEVHNAKTKPREEQFNSTFRVVSLTVVHQDWLNGKEYKCKVSNKGLPAPIEKTISKTK | 155 |

TABLE 46-continued

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-G2-D265E | Light Chain | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | | VL | 2a5 | QTVVTQEPSLTVSPGGTVTLTCRSSTGAVTTSNYAN WVQQKPGQAPRGLIGGTNKRAP GVPARFSGSLLGGKAALTLSGVQPEDEAEYYC ALWYSNLWV FGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFS TYAMN WVRQAPGKGLEWVAR IRSKYNNYATYYADSVK DRFTISRDDSKNTLYLQMNSLR AEDTAVYYCAR HGNFGNSYVSWFAY WGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265EG2CH2 | PCPAPPVAGPSVFLFPPKPKDTLMISRTPEVTCVVVESHEDPEVQFNWYVDGVEVHNAKTKPREEQFNSTFRVVSLTVVHQDWLNGKE YKCKVSNKGLPAPIEKTISKTK | 156 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D265M | Light Chain | VL | 2a5 | QTVVTQEPSLTVSPGGTVTLTCRSSTGAVTTSNYAN WVQQKPGQAPRGLIGGTNKRAP GVPARFSGSLLGGKAALTLSGVQPEDEAEYYC ALWYSNLWV FGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFS TYAMN WVRQAPGKGLEWVAR IRSKYNNYATYYADSVK DRFTISRDDSKNTLYLQMNSLR AEDTAVYYCAR HGNFGNSYVSWFAY WGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265MG2CH2 | PCPAPPVAGPSVFLFPPKPKDTLMISRTPEVTCVVVMSHEDPEVQFNWYVDGVEVHNAKTKPREEQFNSTFRVVSLTVVHQDWLNGKE YKCKVSNKGLPAPIEKTISKTK | 157 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D265N | Light Chain | VL | 2a5 | QTVVTQEPSLTVSPGGTVTLTCRSSTGAVTTSNYAN WVQQKPGQAPRGLIGGTNKRAP GVPARFSGSLLGGKAALTLSGVQPEDEAEYYC ALWYSNLWV FGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFS TYAMN WVRQAPGKGLEWVAR IRSKYNNYATYYADSVK DRFTISRDDSKNTLYLQMNSLR AEDTAVYYCAR HGNFGNSYVSWFAY WGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265NG2CH2 | | 158 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb- | Light Chain | VL | 2a5 | QTVVTQEPSLTVSPGGTVTLTCRSSTGAVTTSNYAN WVQQKPGQAPRGLIGGTNKRAP GVPARFSGSLLGGKAALTLSGVQPEDEAEYYC ALWYSNLWV FGGGTKVEIK | 2 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D265I | Heavy Chain | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D265IG2CH2 | PCPAPPVAGPSVFLFPPKPKDTLMISRTPEVTCVVVIVSHEDPEVQFNWYVDGVEVHNAKTKPREEQFNSTFRVVSLTVVHQDWLNGKE YKCKVSNKGLPAPIEKTISKTK | 159 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D270L | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D270LG2CH2 | PCPAPPVAGPSVFLFPPKPKDTLMISRTPEVTCVVVDVSHELPEVQFNWYVDGVEVHNAKTKPREEQFNSTFRVVSLTVVHQDWLNGKE YKCKVSNKGLPAPIEKTISKTK | 160 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D270R | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D270P | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D270PG2CH2 | PCPAPPVAGPSVFLFPPKPKDTLMISRTPEVTCVVVDVSHERPEVQFNWYVDGVEVHNAKTKPREEQFNSTFRVVSLTVVHQDWLNGKEYKCKVSNKGLPAPIEKTISKTK | 161 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270G | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D270GG2CH2 | PCPAPPVAGPSVFLFPPKPKDTLMISRTPEVTCVVVDVSHEGPEVQFNWYVDGVEVHNAKTKPREEQFNSTFRVVSLTVVHQDWLNGKEYKCKVSNKGLPAPIEKTISKTK | 162 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270V | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D270VG2CH2 | PCPAPPVAGPSVFLFPPKPKDTLMISRTPEVTCVVVDVSHEVPEVQFNWYVDGVEVHNAKTKPREEQFNSTFRVVSLTVVHQDWLNGKEYKCKVSNKGLPAPIEKTISKTK | 164 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D270H | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D270HG2CH2 | PCPAPPVAGPSVFLFPPKPKDTLMISRTPEVTCVVVDVSHEHPEVQFNWYVDGVEVHNAKTKPREEQFNSTFRVVSVLTVVHQDWLNGKEYKCKVSNKGLPAPIEKTISKTK | 165 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270Y | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D270YG2CH2 | PCPAPPVAGPSVFLFPPKPKDTLMISRTPEVTCVVVDVSHEYPEVQFNWYVDGVEVHNAKTKPREEQFNSTFRVVSVLTVVHQDWLNGKEYKCKVSNKGLPAPIEKTISKTK | 166 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270I | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | D270IG2CH2 | PCPAPPVAGPSVFLFPPKPKDTLMISRTPEVTCVVVDVSHEIPEVQFNWYVDGVEVHNAKTKPREEQFNSTFRVVSVLTVVHQDWLNGKEYKCKVSNKGLPAPIEKTISKTK | 167 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270E | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D270F | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
|  | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
|  |  | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
|  |  | Hinge CH2 | Hin1 D270FG2CH2 | DKTHTCP PCPAPPVAGPSVFLFPPKPKDTLMISRTPEVTCVVVDVSHEEPVQFNWYVDGVEVHNAKTKPREEQFNSTFRVVSLTVVHQDWLNGKEYKCKVSNKGLPAPIEKTISKTK | 66 168 |
|  |  | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270K | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
|  | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
|  |  | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
|  |  | Hinge CH2 | Hin1 D270KG2CH2 | DKTHTCP PCPAPPVAGPSVFLFPPKPKDTLMISRTPEVTCVVVDVSHEKPEVQFNWYVDGVEVHNAKTKPREEQFNSTFRVVSLTVVHQDWLNGKEYKCKVSNKGLPAPIEKTISKTK | 66 170 |
|  |  | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |
| CD3 mAb-G2-D270W | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
|  |  | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
|  | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
|  |  | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
|  |  | Hinge CH2 | Hin1 D270WG2CH2 | DKTHTCP PCPAPPVAGPSVFLFPPKPKDTLMISRTPEVTCVVVDVSHEWPEVQFNWYVDGVEVHNAKTKPREEQFNSTFRVVSLTVVHQDWLNGKEYKCKVSNKGLPAPIEKTISKTK | 66 171 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| CD3 mAb-G2-D270S | Light Chain | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D270SG2CH2 | PCPAPPVAGPSVFLFPPKPKDTLMISRTPEVTCVVVDVSHESPEVQFNWYVDGVEVHNAKTKPREEQFNSTFRVVSLTVVHQDWLNGKE YKCKVSNKGLPAPIEKTISKTK | 172 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D270T | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D270TG2CH2 | PCPAPPVAGPSVFLFPPKPKDTLMISRTPEVTCVVVDVSHETPEVQFNWYVDGVEVHNAKTKPREEQFNSTFRVVSLTVVHQDWLNGKE YKCKVSNKGLPAPIEKTISKTK | 173 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D270Q | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSIVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D270QG2CH2 | PCPAPPVAGPSVFLFPPKPKDTLMISRTPEVTCVVVDVSHEQPEVQFNWYVDGVEVHNAKTKPREEQFNSTFRVVSLTVVHQDWLNGKE YKCKVSNKGLPAPIEKTISKTK | 174 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb- | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |

TABLE 46-continued

Codes and amino acid sequences of variable region of some monoclonal antibodies

| Antibody Code | Polypeptide | Domain | Code | Amino acid sequence (CDR is underlined in bold) | SEQ ID NO |
|---|---|---|---|---|---|
| G2-D270M | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D270MG2CH2 | PCPAPPVAGPSVFLFPPKPKDTLMISRTPEVTCVVVDVSHEMPEVQFNWYVDGVEVHNAKTPREEQFNSTFRVVSLTVVHQDWLNGKE YKCKVSNKGLPAPIEKTISKTK | 175 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2-D270N | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | D270NG2CH2 | PCPAPPVAGPSVFLFPPKPKDTLMISRTPEVTCVVVDVSHENPEVQFNWYVDGVEVHNAKTPREEQFNSTFRVVSLTVVHQDWLNGKE YKCKVSNKGLPAPIEKTISKTK | 176 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-PG2-GA | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK VDKKVEPKSC | 82 |
| | | Hinge | Hin1 | DKTHTCP | 66 |
| | | CH2 | PG2-GA | PPPAPPVAGPSVFLFPPKPKDTLMISRTPEVTCVVVDVSHEDPEVQFNWYVDGVEVHNAKTPREEQFNSTFRVVSLTVVH QDWLNGKEYKCKVSNKALPAPIEKTISKTK | 122 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-PG2-TA | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTPAVLQSSGLYSLSSVVTVPSSSLGTQTYICNVNHKPSNTK VDKKVEPKSC | 82 |

TABLE 46-continued

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-G2D-GA | | Hinge CH2 | Hin1 PG2-TA | DKTHTCP PPPAPPVAGPSVFLFPPKPKDTLMISRTPEVTCVVVSHEDPEVQFNWYVDGVEVHNAKTPREEQFNSTFRVVSLTVVH QDWLNGKEYKCKVSNKGLPAPIEKTISKAK | 66 123 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge CH2 | Hin1 G2D-GA | DKTHTCP PCPAPPVAGPSVFLFPPKPKDTLMISRTPEVTCVVVDVSHEAPEVQFNWYVDGVEVHNAKTPREEQFNSTFRVVSLTVVHQDWLNGKE YKCKVSNKGLPAPIEKTISKAK | 66 124 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2D-TA | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge CH2 | Hin1 G2D-TA | DKTHTCP PCPAPPVAGPSVFLFPPKPKDTLMISRTPEVTCVVVDVSHEAPEVQFNWYVDGVEVHNAKTPREEQFNSTFRVVSLTVVHQDWLNGKE YKCKVSNKGLPAPIEKTISKAK | 66 125 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |
| CD3 mAb-G2D-GATA | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYC ALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTH QGLSSPVTKSFNRGEC | 75 |
| | Heavy Chain | VH | 2a5 | QVQLVESGGGVVQPGRSLRLSCAASGFTFSTYAMNWVRQAPGKGLEWVARIRSKYNNYATYYADSVKDRFTISRDDSKNTLYLQMNSLR AEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTK VDKKVEPKSC | 82 |
| | | Hinge CH2 | Hin1 G2D- | DKTHTCP PCPAPPVAGPSVFLFPPKPKDTLMISRTPEVTCVVVDVSHEAPEVQFNWYVDGVEVHNAKTPREEQFNSTFRVVSLTVVHQDWLNGKE GATAYKCKVSNKALPAPIEKTISKAK | 66 126 |
| | | CH3 | WT | GQPREPQVYTLPPSRDELTKNQVSLTCLVKGFYPSDIAVEWESNGQPENNYKTTPPVLDSDGSFFLYSKLTVDKSRWQQGNVFSCSVMHEA LHNHYTQKSLSLSPGK | 102 |

TABLE 46-continued

Codes and amino acid sequences of variable region of some monoclonal antibodies

| Antibody Code | Poplypeptide | Domain | Code | Amino acid sequence (CDR is underlined in bold) | SEQ ID NO |
|---|---|---|---|---|---|
| CD3 mAb-PDG2D | Light Chain | VL | 2a5 | QTVVTQEPSLTVSPGGTVTLTCRSSTGAVTTSNYANWVQQKPGQAPRGLIGGTNKRAPGVPARFSGSLLGGKAALTLSGVQPEDEAEYYCALWYSNLWVFGGGTKVEIK | 2 |
| | | CL | Lc1 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 75 |
| | Heavy Chain | VH | 2a5 | QVQLVESGGGVQPGRSLRLSCAASGFTFSTYAMNWVRQAPGKGLEWVARIRSKYNNYATYYADSVKDRFTISRDDSKNTLYLQMNSLRAEDTAVYYCARHGNFGNSYVSWFAYWGQGTLVTVSS | 1 |
| | | CH1 | CH1 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 82 |
| | | Hinge | Hin1 | DKTHTCP | 66 |
| | | CH2 | PDG2D | PPPAPPVAGPSVFLEPPKPKDTLMISRTPEVTCVVVAVSHEAPEVQFNWYVDGVEVHNAKTKPREEQFNSTFRVVSVLTVVHQDWLNGKEYKCKVSNKGLPAPIEKTISKTK | 127 |
| | | CH3 | WT | GQPREPQVTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 102 |

2. Activation of T Cells in PBMC by CD3 Monoclonal Antibody

The method in the Example is the same as that of "3. T cell activation (antibody+PBMC co-culture system)" in "Example 2: Detection of antibody biological activity". The results were shown in Tables 47 to 48 and FIGS. 31 to 34.

TABLE 47

Activation of T cells in PBMC by anti-CD3 monoclonal antibodies with single point mutated Fc

| Antibody Code | Maximum Activation Ratio (%) Of CD3+ CD69+ T Cells | Maximum Activation Ratio (%) Of CD3+ CD25+ T Cells |
|---|---|---|
| CD3mAb-WT | 72.28 | 50.78 |
| CD3mAb-G2 | 23.17 | 11.14 |
| CD3mAb-SG2 | 25.39 | 12.41 |
| CD3mAb-AG2 | 21.46 | 12.03 |
| CD3mAb-GG2 | 19.22 | 9.845 |
| CD3mAb-PG2 | 20.77 | 9.591 |
| CD3mAb-G2-C229L | 52.2 | 14.803 |
| CD3mAb-G2-C229F | 14.68 | 5.25 |
| CD3mAb-G2-C229R | 34.41 | 14.78 |
| CD3mAb-G2-C229V | 46.1 | 22.94 |
| CD3mAb-G2-C229Q | 35.77 | 16.04 |
| CD3mAb-G2-C229K | 31.73 | 11.73 |
| CD3mAb-G2-C229D | 45.73 | 24.27 |
| CD3mAb-G2-C229I | 48.74 | 26.35 |
| CD3mAb-G2-C229Y | 48.21 | 25.53 |
| CD3mAb-G2-C229N | 45.81 | 19.53 |
| CD3mAb-G2-C229M | 37.2 | 16.05 |
| CD3mAb-G2-C229T | 30.77 | 11.31 |
| CD3mAb-G2-C229H | 35.49 | 15.38 |
| CD3mAb-G2-C229E | 38.9 | 16.88 |
| CD3mAb-G2-C229W | 42.06 | 22.29 |
| CD3mAb-DG2 | 24.84 | 9.6 |
| CD3mAb-G2-D265P | 36.91 | 11.15 |
| CD3mAb-G2-D265K | 34.12 | 9.819 |
| CD3mAb-G2-D265S | 35.15 | 13.19 |
| CD3mAb-G2-D265F | 46.8 | 20.15 |
| CD3mAb-G2-D265R | 41.17 | 13.471 |
| CD3mAb-G2-D265L | 35.58 | 10.36 |
| CD3mAb-G2-D265G | 39 | 12.22 |
| CD3mAb-G2-D265T | 34.99 | 9.867 |
| CD3mAb-G2-D265Y | 37.11 | 12.8 |
| CD3mAb-G2-D265W | 30.84 | 8.829 |
| CD3mAb-G2-D265H | 30.4 | 8.31 |
| CD3mAb-G2-D265V | 32.87 | 11.7 |
| CD3mAb-G2-D265Q | 34.17 | 10.54 |
| CD3mAb-G2-D265E | 25.59 | 5.316 |
| CD3mAb-G2-D265M | 32.27 | 10.24 |
| CD3mAb-G2-D265N | 27.28 | 9.442 |
| CD3mAb-G2-D265I | 27.46 | 11.51 |
| CD3mAb-G2D | 22.78 | 11.41 |
| CD3mAb-G2-D270L | 30.97 | 10.6 |
| CD3mAb-G2-D270R | 33.92 | 13.39 |
| CD3mAb-G2-D270P | 39.38 | 18.98 |
| CD3mAb-G2-D270G | 32.78 | 11.41 |
| CD3mAb-G2-D270V | 20.44 | 5.258 |
| CD3mAb-G2-D270H | 24.41 | 7.125 |
| CD3mAb-G2-D270Y | 27.48 | 6.706 |
| CD3mAb-G2-D270I | 26.51 | 5.853 |
| CD3mAb-G2-D270E | 57.36 | 41.08 |
| CD3mAb-G2-D270F | 27.18 | 5.516 |
| CD3mAb-G2-D270K | 26.95 | 6.55 |
| CD3mAb-G2-D270W | 25.45 | 6.546 |
| CD3mAb-G2-D270S | 26.01 | 6.332 |

TABLE 47-continued

Activation of T cells in PBMC by anti-CD3 monoclonal antibodies with single point mutated Fc

| Antibody Code | Maximum Activation Ratio (%) Of CD3+ CD69+ T Cells | Maximum Activation Ratio (%) Of CD3+ CD25+ T Cells |
|---|---|---|
| CD3mAb-G2-D270T | 22.55 | 6.742 |
| CD3mAb-G2-D270Q | 29.21 | 9.175 |
| CD3mAb-G2-D270M | 22.28 | 6.278 |
| CD3mAb-G2-D270N | 22.4 | 5.406 |
| PBMC | none | none |

Figure 31A:
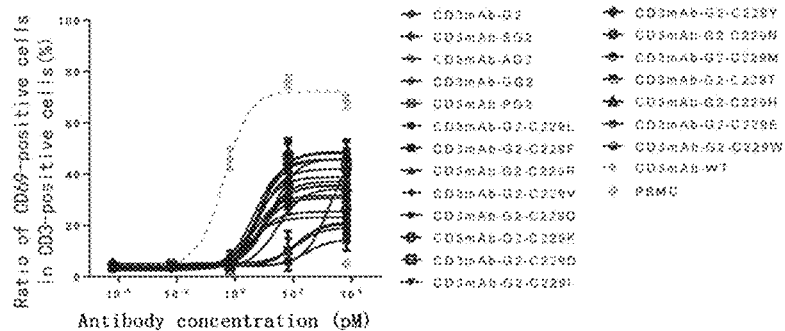
FIG. 31 shows the degree of activation of T cells in PBMC by CD3 monoclonal antibody with the residue at position 229 of Fc substituted by different amino acid residues via flow cytometry after the CH2 domain of the Fc of IGG1 CD3 monoclonal antibody is substituted with CH2 of IGG2, wherein (A) shows the ratio of CD69+ in T cells, (B) shows the ratio of CD25+ in T cells.
Figure 31B:
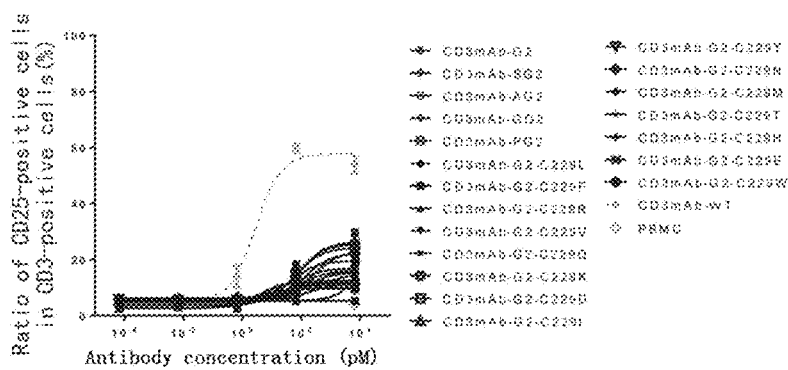
Figure 32A:
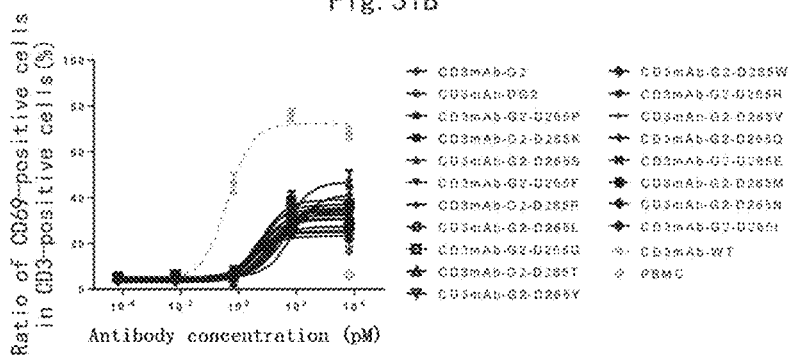
FIG. 32 shows the degree of activation of T cells in PBMC by CD3 monoclonal antibody with the residue at position 265 of Fc substituted by different amino acid residues via flow cytometry after the CH2 domain of the Fc of IGG1 CD3 monoclonal antibody is substituted with CH2 of IGG2, wherein (A) shows the ratio of CD69+ in T cells, (B) shows the ratio of CD25+ in T cells.
Figure 32B:
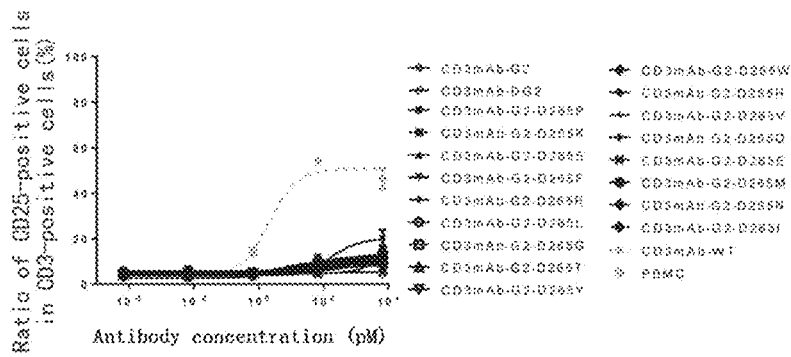
Figure 33A:
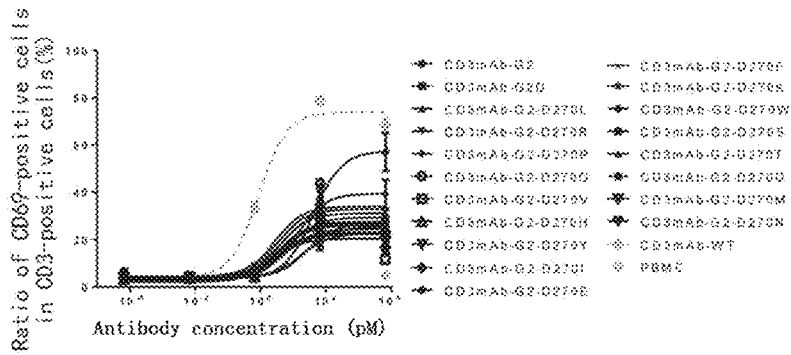
FIG. 33 shows the degree of activation of T cells in PBMC by CD3 monoclonal antibody with the residue at position 270 of Fc substituted by different amino acid residues via flow cytometry after the CH2 domain of the Fc of IGG1 CD3 monoclonal antibody is substituted with CH2 of IGG2, wherein (A) shows the ratio of CD69+ in T cells, (B) shows the ratio of CD25+ in T cells.
Figure 33B:
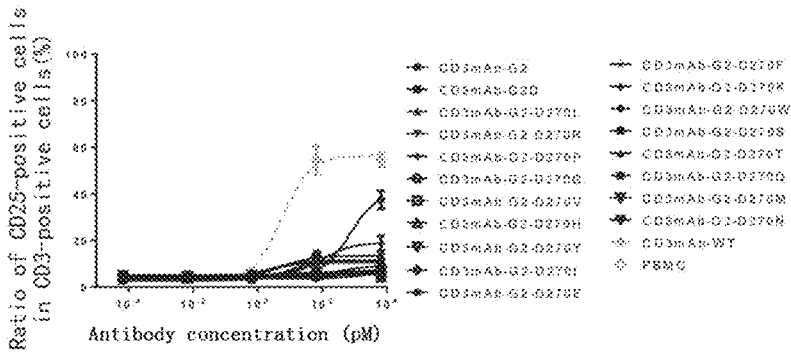

As can be seen from Table 47 and FIGS. 31 to 33, for a IgG1 type CD3 monoclonal antibody in which the CH2 domain of Fc was substituted with a CH2 of IgG2 and then the cysteine(C) at position 229, the aspartic acid (D) at position 265 or the the aspartic acid (D) at position 270 was substituted with other essential amino acids, T cell activation can be significantly reduced as compared with the antibody with CH1 domain of Fc.

TABLE 48

Activation of T cells in PBMC by anti-CD3 monoclonal antibodies with multiple point mutated Fc

| Antibody Code | CD3+ CD69+ T Cells Maximum Activation (%) | CD3+ CD25+ T Cells Maximum Activation (%) |
|---|---|---|
| CD3mAb-WT | 70.45 | 37.29 |
| CD3mAb-FES | 41.75 | 12.62 |
| CD3mAb-AAG | 33.05 | 11.75 |
| CD3mAb-G2 | 29.17 | 11.14 |
| CD3mAb-SG2 | 31.39 | 12.41 |
| CD3mAb-AG2 | 31.9 | 12.03 |
| CD3mAb-GG2 | 30.61 | 9.845 |
| CD3mAb-PG2 | 31.56 | 9.591 |
| CD3mAb-DG2 | 30.84 | 9.6 |
| CD3mAb-G2D | 28.78 | 11.41 |
| CD3mAb-PG2-GA | 37.36 | 12.1 |
| CD3mAb-PG2-TA | 28.75 | 9.479 |
| CD3mAb-G2D-GA | 27.57 | 8.237 |
| CD3mAb-G2D-TA | 27.75 | 9.435 |
| CD3mAb-G2D-GATA | 31.6 | 8.595 |
| CD3mAb-PDG2D | 31.89 | 11.85 |
| PBMC | none | none |

Figure 34A:
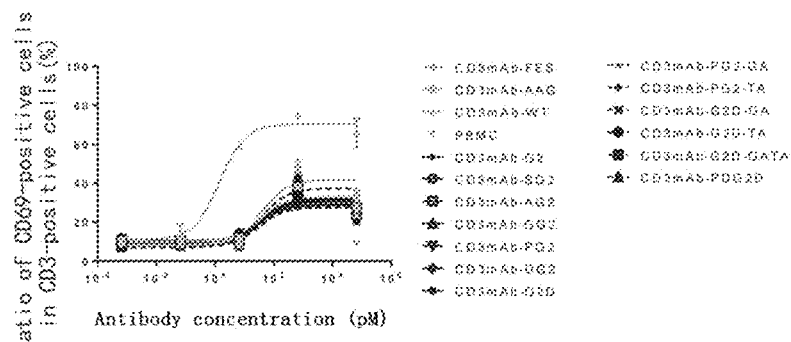
FIG. 34 shows the degree of activation of T cells in PBMC by CD3 monoclonal antibody with multiple site mutations of Fc via flow cytometry after the CH2 domain of the Fc of IGG1 CD3 monoclonal antibody is substituted with CH2 of IGG2, wherein (A) shows the ratio of CD69+ in T cells, (B) shows the ratio of CD25+ in T cells.
Figure 34B:
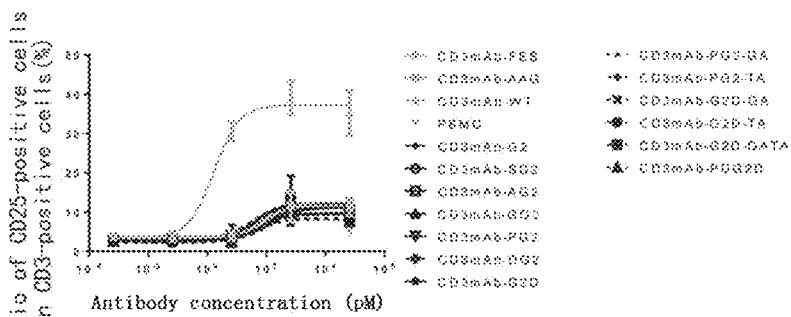

As can be seen from Table 48 and FIG. 34, after the CH2 domain of Fc of the IgG1-type CD3 monoclonal antibody was substituted with the CH2 of IgG2, some amino acids were substituted as follows: (1) no substitution; (2) single-site substitution, C229S, C229A, C229G, C229P, D265A, D270A; (3) two-sites substitution, C229P/G327A, C229P/T339A, D270A/G327A, D270A/T339A; (4) three-sites substitution, D270A/G327A/T339A, C229P/D265A/D270A, etc.; it can be seen that activation of T cells was significantly weakened by the above-mentioned four types of substituted monoclonal antibodies as compared with wild-type IgG1, and the weakening was even more significant than that of FES.

We claim:

1. A polypeptide comprising a modified Fc fragment comprising a human IgG1 CH3 and a human IgG2 CH2 which further comprises a D270A mutation, according to EU numbering, wherein the human IgG2 CH2 comprises an amino acid sequence selected from the group consisting of SEQ ID NO:100, 101, 124, 125, 126 and 127.

2. The polypeptide of claim 1, wherein the human IgG2 CH2 comprises the amino acid sequence of SEQ ID NO: 100.

3. The polypeptide of claim 1, which is an antibody or antigen-binding fragment thereof.

4. The polypeptide of claim 3, wherein the antibody specifically binds to an antigen selected from the group consisting of a tumor antigen, a viral or bacterial antigen, an endotoxin, and an immune antigen.

5. The polypeptide of claim 4, wherein the antibody is an asymmetric bispecific antibody comprising a first antigen-binding unit comprising a light chain and a heavy chain, and a second antigen-binding unit comprising a single chain fragment (scFv) and one of the chains of the modified Fc fragment.

6. The polypeptide of claim 5, wherein the light chain variable region and the heavy chain variable region, respectively, are selected from the group consisting of:

(1) SEQ ID NO: 12 and SEQ ID NO: 11 which target a tumor antigen B7-H3;
(2) SEQ ID NO: 14 and SEQ ID NO: 13 which target a tumor antigen B7-H3;
(3) SEQ ID NO: 16 and SEQ ID NO: 15 which target a tumor antigen CD38;
(4) SEQ ID NO: 18 and SEQ ID NO: 17 which target a tumor antigen CD38;
(5) SEQ ID NO: 20 and SEQ ID NO: 19 which target a tumor antigen CD38;
(6) SEQ ID NO: 22 and SEQ ID NO: 21 which target a tumor antigen EpCAM;
(7) SEQ ID NO: 24 and SEQ ID NO: 23 which target a tumor antigen EpCAM;
(8) SEQ ID NO: 26 and SEQ ID NO: 25 which target a tumor antigen BCMA;
(9) SEQ ID NO: 28 and SEQ ID NO: 27 which target a tumor antigen BCMA;

(10) SEQ ID NO: 30 and SEQ ID NO: 29 which target a tumor antigen BCMA;
(11) SEQ ID NO: 32 and SEQ ID NO: 31 which target a tumor antigen PD-L1;
(12) SEQ ID NO: 34 and SEQ ID NO: 33 which target a tumor antigen PD-L1;
(13) SEQ ID NO: 36 and SEQ ID NO: 35 which target a tumor antigen PD-L1;
(14) SEQ ID NO: 38 and SEQ ID NO: 37 which target a tumor antigen CD19;
(15) SEQ ID NO: 40 and SEQ ID NO: 39 which target a tumor antigen SLAMF7;
(16) SEQ ID NO: 42 and SEQ ID NO: 41 which target a tumor antigen CEA;
(17) SEQ ID NO: 2 and SEQ ID NO: 1 which target an immune antigen CD3;
(18) SEQ ID NO: 4 and SEQ ID NO: 3 which target an immune antigen CD3;
(19) SEQ ID NO: 6 and SEQ ID NO: 5 which target an immune antigen CD3;
(20) SEQ ID NO: 8 and SEQ ID NO: 7 which target an immune antigen CD3; and
(21) SEQ ID NO: 10 and SEQ ID NO: 9 which target an immune antigen CD3.

7. The polypeptide of claim 5, wherein:
(1) the second antigen-binding unit comprises SEQ ID NO: 9, SEQ ID NO: 54, SEQ ID NO: 10, SEQ ID NO: 68, SEQ ID NO: 100 and SEQ ID NO: 109; the heavy chain comprises SEQ ID NO: 15, SEQ ID NO: 82, SEQ ID NO: 66, SEQ ID NO: 100 and SEQ ID NO: 108; and the light chain comprises SEQ ID NO: 16 and SEQ ID NO: 75;
(2) the second antigen-binding unit comprises SEQ ID NO: 1, SEQ ID NO: 54, SEQ ID NO: 2, SEQ ID NO: 71, SEQ ID NO: 100 and SEQ ID NO: 109; the heavy chain comprises SEQ ID NO: 17, SEQ ID NO: 82, SEQ ID NO: 66, SEQ ID NO: 100 and SEQ ID NO: 108; and the light chain comprises SEQ ID NO: 18 and SEQ ID NO: 75;
(3) the second antigen-binding unit comprises SEQ ID NO: 9, SEQ ID NO: 54, SEQ ID NO: 10, SEQ ID NO: 68, SEQ ID NO: 100 and SEQ ID NO: 109; the heavy chain comprises SEQ ID NO: 43, SEQ ID NO: 82, SEQ ID NO: 66, SEQ ID NO: 100 and SEQ ID NO: 108; and the light chain comprises SEQ ID NO: 44 and SEQ ID NO: 75;
(4) the second antigen-binding unit comprises SEQ ID NO: 1, SEQ ID NO: 54, SEQ ID NO: 2, SEQ ID NO: 68, SEQ ID NO: 100 and SEQ ID NO: 109; the heavy chain comprises SEQ ID NO: 43, SEQ ID NO: 82, SEQ ID NO: 66, SEQ ID NO: 100 and SEQ ID NO: 108; and the light chain comprises SEQ ID NO: 44 and SEQ ID NO: 75;
(5) the second antigen-binding unit comprises SEQ ID NO: 29, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 100 and SEQ ID NO: 107; the heavy chain comprises SEQ ID NO: 29, SEQ ID NO: 82, SEQ ID NO: 66, SEQ ID NO: 100 and SEQ ID NO: 106; and the light chain comprises SEQ ID NO: 30 and SEQ ID NO: 75;
(6) the second antigen-binding unit comprises SEQ ID NO: 43, SEQ ID NO: 82, SEQ ID NO: 74, SEQ ID NO: 48, SEQ ID NO: 1, SEQ ID NO: 54, SEQ ID NO: 2, SEQ ID NO: 68, SEQ ID NO: 100 and SEQ ID NO: 107; the heavy chain comprises SEQ ID NO: 43, SEQ ID NO: 82, SEQ ID NO: 66, SEQ ID NO: 100 and SEQ ID NO: 106; and the light chain comprises SEQ ID NO: 44 and SEQ ID NO: 75;
(7) the second antigen-binding unit comprises SEQ ID NO: 41, SEQ ID NO: 82, SEQ ID NO: 51, SEQ ID NO: 1, SEQ ID NO: 46, SEQ ID NO: 81, SEQ ID NO: 66, SEQ ID NO: 100 and SEQ ID NO: 107; the cross light chain comprises SEQ ID NO: 2, SEQ ID NO: 45 and SEQ ID NO: 82; the heavy chain comprises SEQ ID NO: 41, SEQ ID NO: 82, SEQ ID NO: 66, SEQ ID NO: 100 and SEQ ID NO: 106; and the light chain comprises SEQ ID NO: 42 and SEQ ID NO: 75; or
(8) the second antigen-binding unit comprises SEQ ID NO: 43, SEQ ID NO: 82, SEQ ID NO: 51, SEQ ID NO: 1, SEQ ID NO: 46, SEQ ID NO: 81, SEQ ID NO: 66, SEQ ID NO: 100 and SEQ ID NO: 107; the cross light chain comprises SEQ ID NO: 2, SEQ ID NO: 45 and SEQ ID NO: 82; the heavy chain comprises SEQ ID NO: 43, SEQ ID NO: 82, SEQ ID NO: 66, SEQ ID NO: 100 and SEQ ID NO: 106; and the light chain comprises SEQ ID NO: 44 and SEQ ID NO: 75.

8. A polynucleotide encoding the polypeptide of claim 1.

* * * * *

SEQUENCE LISTING

<160> NUMBER OF SEQ ID NOS: 176

<210> SEQ ID NO 1
<211> LENGTH: 125
<212> TYPE: PRT

<213> ORGANISM: Artificial Sequence
<220> FEATURE:
<223> OTHER INFORMATION: Synthetic

<400> SEQUENCE: 1

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 2
<211> LENGTH: 109
<212> TYPE: PRT
<213> ORGANISM: Artificial Sequence
<220> FEATURE:
<223> OTHER INFORMATION: Synthetic

<400> SEQUENCE: 2

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Val Glu Ile Lys
            100                 105
```

<210> SEQ ID NO 3
<211> LENGTH: 125
<212> TYPE: PRT
<213> ORGANISM: Artificial Sequence
<220> FEATURE:
<223> OTHER INFORMATION: Synthetic

<400> SEQUENCE: 3

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45
```

```
Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Ala
            100                 105                 110

Ala Tyr Trp Gly Gln Gly Thr Leu Val Thr Val Ser Ser
        115                 120                 125

<210> SEQ ID NO 4
<211> LENGTH: 109
<212> TYPE: PRT
<213> ORGANISM: Artificial Sequence
<220> FEATURE:
<223> OTHER INFORMATION: Synthetic

<400> SEQUENCE: 4

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Phe Gln Gln Lys Pro Gly Gln Ala Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Val Glu Ile Lys
            100                 105

<210> SEQ ID NO 5
<211> LENGTH: 119
<212> TYPE: PRT
<213> ORGANISM: Artificial Sequence
<220> FEATURE:
<223> OTHER INFORMATION: Synthetic

<400> SEQUENCE: 5

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
```

<210> SEQ ID NO 6
<211> LENGTH: 106
<212> TYPE: PRT
<213> ORGANISM: Artificial Sequence
<220> FEATURE:
<223> OTHER INFORMATION: Synthetic

<400> SEQUENCE: 6

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105
```

<210> SEQ ID NO 7
<211> LENGTH: 119
<212> TYPE: PRT
<213> ORGANISM: Artificial Sequence
<220> FEATURE:
<223> OTHER INFORMATION: Synthetic

<400> SEQUENCE: 7

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115
```

<210> SEQ ID NO 8
<211> LENGTH: 106
<212> TYPE: PRT
<213> ORGANISM: Artificial Sequence
<220> FEATURE:
<223> OTHER INFORMATION: Synthetic

<400> SEQUENCE: 8

```
Asp Ile Gln Leu Thr Gln Ser Pro Ala Ile Met Ser Ala Ser Pro Gly
1               5                   10                  15
```

```
Glu Lys Val Thr Met Thr Cys Arg Ala Ser Ser Val Ser Tyr Met
             20                  25                  30

Asn Trp Tyr Gln Gln Lys Ser Gly Thr Ser Pro Lys Arg Trp Ile Tyr
         35                  40                  45

Asp Thr Ser Lys Val Ala Ser Gly Val Pro Tyr Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys
                100                 105
```

<210> SEQ ID NO 9
<211> LENGTH: 125
<212> TYPE: PRT
<213> ORGANISM: Artificial Sequence
<220> FEATURE:
<223> OTHER INFORMATION: Synthetic

<400> SEQUENCE: 9

```
Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Asn Lys Tyr
             20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Asn Leu Lys Thr Glu Asp Thr Ala Val Tyr
                 85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125
```

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

```
Gln Thr Val Val Thr Gln Glu Pro Ser Leu Thr Val Ser Pro Gly Gly
 1               5                  10                  15

Thr Val Thr Leu Thr Cys Gly Ser Thr Gly Ala Val Thr Ser Gly
             20                  25                  30

Asn Tyr Pro Asn Trp Val Gln Gln Lys Pro Gly Gln Ala Pro Arg Gly
         35                  40                  45

Leu Ile Gly Gly Thr Lys Phe Leu Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Val Leu Trp Tyr Ser Asn
```

```
                    85                  90                  95

Arg Trp Val Phe Gly Gly Gly Thr Lys Leu Thr Val Leu
                100                 105
```

<210> SEQ ID NO 11
<211> LENGTH: 118
<212> TYPE: PRT
<213> ORGANISM: Artificial Sequence
<220> FEATURE:
<223> OTHER INFORMATION: Synthetic

<400> SEQUENCE: 11

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asn Tyr
                20                  25                  30

Asp Ile Asn Trp Val Arg Gln Arg Pro Glu Gln Gly Leu Glu Trp Ile
            35                  40                  45

Gly Trp Ile Phe Pro Gly Asp Gly Ser Thr Gln Tyr Asn Glu Lys Phe
        50                  55                  60

Lys Gly Lys Ala Thr Leu Thr Thr Asp Thr Ser Ser Ser Thr Ala Tyr
65                  70                  75                  80

Met Gln Leu Ser Arg Leu Thr Ser Glu Asp Ser Ala Val Tyr Phe Cys
                85                  90                  95

Ala Arg Gln Thr Thr Ala Thr Trp Phe Ala Tyr Trp Gly Gln Gly Thr
                100                 105                 110

Leu Val Thr Val Ser Ser
            115
```

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Leu
                85                  90                  95

Thr Phe Gly Ala Gly Thr Lys Leu Glu Leu Lys
                100                 105
```

<210> SEQ ID NO 13
<211> LENGTH: 120
<212> TYPE: PRT
<213> ORGANISM: Artificial Sequence
<220> FEATURE:
<223> OTHER INFORMATION: Synthetic

<400> SEQUENCE: 13

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
            35                  40                  45

Gly Thr Ile Tyr Pro Gly Asp Gly Asp Thr Arg Tyr Thr Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
            85                  90                  95

Ala Arg Arg Gly Ile Pro Arg Leu Trp Tyr Phe Asp Val Trp Gly Ala
            100                 105                 110

Gly Thr Thr Val Thr Val Ser Ser
            115                 120

<210> SEQ ID NO 14
<211> LENGTH: 107
<212> TYPE: PRT
<213> ORGANISM: Artificial Sequence
<220> FEATURE:
<223> OTHER INFORMATION: Synthetic

<400> SEQUENCE: 14

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
            85                  90                  95

Thr Phe Gly Gly Gly Thr Lys Leu Glu Ile Lys
            100                 105

<210> SEQ ID NO 15
<211> LENGTH: 122
<212> TYPE: PRT
<213> ORGANISM: Artificial Sequence
<220> FEATURE:
<223> OTHER INFORMATION: Synthetic

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr

-continued

```
                65                  70                  75                  80
Leu Gln Met Asn Ser Leu Arg Ala Glu Asp Thr Ala Val Tyr Phe Cys
                    85                  90                  95

Ala Lys Asp Lys Ile Leu Trp Phe Gly Glu Pro Val Phe Asp Tyr Trp
                100                 105                 110

Gly Gln Gly Thr Leu Val Thr Val Ser Ser
            115                 120

<210> SEQ ID NO 16
<211> LENGTH: 107
<212> TYPE: PRT
<213> ORGANISM: Artificial Sequence
<220> FEATURE:
<223> OTHER INFORMATION: Synthetic

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 17
<211> LENGTH: 120
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Tyr Met Asn Trp Val Arg Gln Ala Pro Gly Lys Gly Leu Glu Trp Val
            35                  40                  45

Ser Gly Ile Ser Gly Asp Pro Ser Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
                100                 105                 110

Gly Thr Leu Val Thr Val Ser Ser
            115                 120

<210> SEQ ID NO 18
<211> LENGTH: 109
```

```
<212> TYPE: PRT
<213> ORGANISM: Artificial Sequence
<220> FEATURE:
<223> OTHER INFORMATION: Synthetic

<400> SEQUENCE: 18

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105

<210> SEQ ID NO 19
<211> LENGTH: 120
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser
        115                 120

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
```

```
                    35                  40                  45
Tyr Ala Ala Ser Ser Leu Gln Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                     85                  90                  95

Thr Phe Gly Gln Gly Thr Lys Val Glu Ile Lys
                100                 105

<210> SEQ ID NO 21
<211> LENGTH: 115
<212> TYPE: PRT
<213> ORGANISM: Artificial Sequence
<220> FEATURE:
<223> OTHER INFORMATION: Synthetic

<400> SEQUENCE: 21

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Leu Trp Asn Tyr Trp Gly Gln Gly Thr Leu Val Thr
                100                 105                 110

Val Ser Ser
        115

<210> SEQ ID NO 22
<211> LENGTH: 109
<212> TYPE: PRT
<213> ORGANISM: Artificial Sequence
<220> FEATURE:
<223> OTHER INFORMATION: Synthetic

<400> SEQUENCE: 22

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Ile Ile
             35                  40                  45

Tyr Gly Ala Ser Thr Thr Ala Ser Gly Ile Pro Ala Arg Phe Ser Ala
         50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Ala Tyr Thr Phe Gly Gln Gly Thr Lys Leu Glu Ile Lys
                100                 105
```

<210> SEQ ID NO 23
<211> LENGTH: 113
<212> TYPE: PRT
<213> ORGANISM: Artificial Sequence
<220> FEATURE:
<223> OTHER INFORMATION: Synthetic

<400> SEQUENCE: 23

```
Glu Val Gln Leu Val Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Thr Ala Val Tyr Trp Gly Gln Gly Thr Thr Val Thr Val Ser
            100                 105                 110

Ser
```

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Val Ser
            20                  25                  30

Leu Ser Trp Leu Gln Gln Glu Pro Asp Gly Thr Ile Lys Arg Leu Ile
        35                  40                  45

Tyr Ala Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Trp
                85                  90                  95

Thr Phe Gly Gly Gly Thr Lys Leu Glu Ile Lys
            100                 105
```

<210> SEQ ID NO 25
<211> LENGTH: 119
<212> TYPE: PRT
<213> ORGANISM: Artificial Sequence
<220> FEATURE:
<223> OTHER INFORMATION: Synthetic

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30
```

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
        50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Ser
            115

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95

Ser Ile Tyr Pro Trp Thr Phe Gly Gln Gly Thr Lys Leu Glu Ile Lys
                100                 105                 110

<210> SEQ ID NO 27
<211> LENGTH: 121
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Ser His Asp Met Trp Ser Glu Asp Trp Gly

```
                  100                 105                 110

Gln Gly Thr Leu Val Thr Val Ser Ser
            115                 120

<210> SEQ ID NO 28
<211> LENGTH: 112
<212> TYPE: PRT
<213> ORGANISM: Artificial Sequence
<220> FEATURE:
<223> OTHER INFORMATION: Synthetic

<400> SEQUENCE: 28

Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
        35                  40                  45

Ile Tyr Ser Asn Asn Gln Arg Pro Pro Gly Val Pro Val Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110

<210> SEQ ID NO 29
<211> LENGTH: 121
<212> TYPE: PRT
<213> ORGANISM: Artificial Sequence
<220> FEATURE:
<223> OTHER INFORMATION: Synthetic

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser
            115                 120

<210> SEQ ID NO 30
<211> LENGTH: 108
<212> TYPE: PRT
<213> ORGANISM: Artificial Sequence
<220> FEATURE:
<223> OTHER INFORMATION: Synthetic

<400> SEQUENCE: 30
```

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Tyr
        35                  40                  45

Asp Asp Ser Asp Arg Pro Ser Gly Ile Pro Glu Arg Phe Ser Gly Asn
    50                  55                  60

Ser Asn Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 31
<211> LENGTH: 118
<212> TYPE: PRT
<213> ORGANISM: Artificial Sequence
<220> FEATURE:
<223> OTHER INFORMATION: Synthetic

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115
```

<210> SEQ ID NO 32
<211> LENGTH: 107
<212> TYPE: PRT
<213> ORGANISM: Artificial Sequence
<220> FEATURE:
<223> OTHER INFORMATION: Synthetic

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Leu Tyr His Pro Ala
                    85                  90                  95
Thr Phe Gly Gln Gly Thr Lys Val Glu Ile Lys
            100                 105

<210> SEQ ID NO 33
<211> LENGTH: 120
<212> TYPE: PRT
<213> ORGANISM: Artificial Sequence
<220> FEATURE:
<223> OTHER INFORMATION: Synthetic

<400> SEQUENCE: 33

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ile Met Met Trp Val Arg Gln Ala Pro Gly Lys Gly Leu Glu Trp Val
            35                  40                  45
Ser Ser Ile Tyr Pro Ser Gly Gly Ile Thr Phe Tyr Ala Asp Thr Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile Lys Leu Gly Thr Val Thr Val Asp Tyr Trp Gly Gln
            100                 105                 110
Gly Thr Leu Val Thr Val Ser Ser
        115                 120

<210> SEQ ID NO 34
<211> LENGTH: 110
<212> TYPE: PRT
<213> ORGANISM: Artificial Sequence
<220> FEATURE:
<223> OTHER INFORMATION: Synthetic

<400> SEQUENCE: 34

Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
                20                  25                  30
Asn Tyr Val Ser Trp Tyr Gln Gln His Pro Gly Lys Ala Pro Lys Leu
            35                  40                  45
Met Ile Tyr Asp Val Ser Asn Arg Pro Ser Gly Val Ser Asn Arg Phe
50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Ser Ser
                85                  90                  95
Ser Thr Arg Val Phe Gly Thr Gly Thr Lys Val Thr Val Leu
            100                 105                 110

<210> SEQ ID NO 35
<211> LENGTH: 123
<212> TYPE: PRT
<213> ORGANISM: Artificial Sequence
<220> FEATURE:
```

<223> OTHER INFORMATION: Synthetic

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
            115                 120

<210> SEQ ID NO 36
<211> LENGTH: 106
<212> TYPE: PRT
<213> ORGANISM: Artificial Sequence
<220> FEATURE:
<223> OTHER INFORMATION: Synthetic

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 37
<211> LENGTH: 121
<212> TYPE: PRT
<213> ORGANISM: Artificial Sequence
<220> FEATURE:
<223> OTHER INFORMATION: Synthetic

<400> SEQUENCE: 37

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe

```
                    50                  55                  60
Gln Gly Arg Val Thr Ile Ser Ser Asp Lys Ser Ile Ser Thr Ala Tyr
 65                  70                  75                  80

Met Glu Leu Ser Ser Leu Arg Ser Glu Asp Thr Ala Met Tyr Tyr Cys
                    85                  90                  95

Ala Arg Gly Thr Tyr Tyr Tyr Gly Thr Arg Val Phe Asp Tyr Trp Gly
                100                 105                 110

Gln Gly Thr Leu Val Thr Val Ser Ser
                115                 120

<210> SEQ ID NO 38
<211> LENGTH: 112
<212> TYPE: PRT
<213> ORGANISM: Artificial Sequence
<220> FEATURE:
<223> OTHER INFORMATION: Synthetic

<400> SEQUENCE: 38

Asp Ile Val Met Thr Gln Ser Pro Ala Thr Leu Ser Leu Ser Pro Gly
  1               5                  10                  15

Glu Arg Ala Thr Leu Ser Cys Arg Ser Ser Lys Ser Leu Gln Asn Val
                 20                  25                  30

Asn Gly Asn Thr Tyr Leu Tyr Trp Phe Gln Gln Lys Pro Gly Gln Ser
             35                  40                  45

Pro Gln Leu Leu Ile Tyr Arg Met Ser Asn Leu Asn Ser Gly Val Pro
 50                  55                  60

Asp Arg Phe Ser Gly Ser Gly Ser Gly Thr Glu Phe Thr Leu Thr Ile
 65                  70                  75                  80

Ser Ser Leu Glu Pro Glu Asp Phe Ala Val Tyr Tyr Cys Met Gln His
                 85                  90                  95

Leu Glu Tyr Pro Ile Thr Phe Gly Ala Gly Thr Lys Leu Glu Ile Lys
                100                 105                 110

<210> SEQ ID NO 39
<211> LENGTH: 119
<212> TYPE: PRT
<213> ORGANISM: Artificial Sequence
<220> FEATURE:
<223> OTHER INFORMATION: Synthetic

<400> SEQUENCE: 39

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Phe Ser Arg Tyr
                 20                  25                  30

Trp Met Ser Trp Val Arg Gln Ala Pro Gly Lys Gly Leu Glu Trp Ile
             35                  40                  45

Gly Glu Ile Asn Pro Asp Ser Ser Thr Ile Asn Tyr Ala Pro Ser Leu
 50                  55                  60

Lys Asp Lys Phe Ile Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Asp Gly Asn Tyr Trp Tyr Phe Asp Val Trp Gly Gln Gly
                100                 105                 110

Thr Leu Val Thr Val Ser Ser
            115
```

<210> SEQ ID NO 40
<211> LENGTH: 107
<212> TYPE: PRT
<213> ORGANISM: Artificial Sequence
<220> FEATURE:
<223> OTHER INFORMATION: Synthetic

<400> SEQUENCE: 40

```
Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
            100                 105
```

<210> SEQ ID NO 41
<211> LENGTH: 121
<212> TYPE: PRT
<213> ORGANISM: Artificial Sequence
<220> FEATURE:
<223> OTHER INFORMATION: Synthetic

<400> SEQUENCE: 41

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Val Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Asp Asp Thr Ala Val Tyr Tyr Cys
                85                  90                  95

Ala Arg Trp Asp Phe Tyr Asp Tyr Val Glu Ala Met Asp Tyr Trp Gly
            100                 105                 110

Gln Gly Thr Thr Val Thr Val Ser Ser
        115                 120
```

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
```

```
              20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys His Gln Tyr Tyr Thr Tyr Pro Leu
                    85                  90                  95

Phe Thr Phe Gly Gln Gly Thr Lys Val Glu Ile Lys
                100                 105
```

<210> SEQ ID NO 43
<211> LENGTH: 118
<212> TYPE: PRT
<213> ORGANISM: Artificial Sequence
<220> FEATURE:
<223> OTHER INFORMATION: Synthetic

<400> SEQUENCE: 43

```
Glu Val Lys Leu Asp Glu Thr Gly Gly Gly Leu Val Gln Pro Gly Arg
 1               5                  10                  15

Pro Met Lys Leu Ser Cys Val Ala Ser Gly Phe Thr Phe Ser Asp Tyr
                20                  25                  30

Trp Met Asn Trp Val Arg Gln Ser Pro Glu Lys Gly Leu Glu Trp Val
            35                  40                  45

Ala Gln Ile Arg Asn Lys Pro Tyr Asn Tyr Glu Thr Tyr Tyr Ser Asp
 50                  55                  60

Ser Val Lys Gly Arg Phe Thr Ile Ser Arg Asp Asp Ser Lys Ser Ser
 65                  70                  75                  80

Val Tyr Leu Gln Met Asn Asn Leu Arg Val Glu Asp Met Gly Ile Tyr
                85                  90                  95

Tyr Cys Thr Gly Ser Tyr Tyr Gly Met Asp Tyr Trp Gly Gln Gly Thr
                100                 105                 110

Ser Val Thr Val Ser Ser
        115
```

<210> SEQ ID NO 44
<211> LENGTH: 112
<212> TYPE: PRT
<213> ORGANISM: Artificial Sequence
<220> FEATURE:
<223> OTHER INFORMATION: Synthetic

<400> SEQUENCE: 44

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu Arg Trp Tyr Leu Gln Lys Pro Gly Gln Ser
            35                  40                  45

Pro Lys Val Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                85                  90                  95
```

```
Thr His Val Pro Trp Thr Phe Gly Gly Gly Thr Lys Leu Glu Ile Lys
            100                 105                 110
```

<210> SEQ ID NO 45
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid

<400> SEQUENCE: 45

```
Ser Ser Xaa Xaa
1
```

<210> SEQ ID NO 46
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: Xaa can be any naturally occurring amino acid

<400> SEQUENCE: 46

```
Ala Ser Xaa Xaa
1
```

<210> SEQ ID NO 47
<211> LENGTH: 5
<212> TYPE: PRT
<213> ORGANISM: Artificial Sequence
<220> FEATURE:
<223> OTHER INFORMATION: Synthetic

<400> SEQUENCE: 47

```
Gly Gly Gly Gly Ser
1               5
```

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

```
Gly Gly Gly Ser Ala Ala Ala
1               5
```

<210> SEQ ID NO 49
<211> LENGTH: 7
<212> TYPE: PRT
<213> ORGANISM: Artificial Sequence
<220> FEATURE:
<223> OTHER INFORMATION: Synthetic

<400> SEQUENCE: 49

```
Gly Gly Gly Gly Ser Ala Ser
1               5
```

<210> SEQ ID NO 50
<211> LENGTH: 10

```
<212> TYPE: PRT
<213> ORGANISM: Artificial Sequence
<220> FEATURE:
<223> OTHER INFORMATION: Synthetic

<400> SEQUENCE: 50

Gly Arg Pro Gly Ser Gly Arg Pro Gly Ser
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic

<400> SEQUENCE: 51

Gly Gly Gly Gly Ser Gly Gly Gly Gly Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic

<400> SEQUENCE: 52

Gly Lys Ser Ser Gly Ser Gly Ser Glu Ser Lys Ser
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetic

<400> SEQUENCE: 53

Gly Ser Thr Ser Gly Ser Gly Lys Ser Ser Glu Gly Lys Gly
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Synthetic

<400> SEQUENCE: 54

Gly Gly Gly Gly Ser Gly Gly Gly Ser Gly Gly Gly Gly Ser
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: Synthetic

<400> SEQUENCE: 55

Gly Gly Gly Gly Ser Asp Lys Thr His Thr Ser Pro Pro Ser
1               5                   10

<210> SEQ ID NO 56
<211> LENGTH: 14
<212> TYPE: PRT
```

```
<213> ORGANISM: Artificial Sequence
<220> FEATURE:
<223> OTHER INFORMATION: Synthetic

<400> SEQUENCE: 56

Glu Pro Lys Ser Ser Asp Lys Thr His Thr Ser Pro Pro Ser
1               5                   10

<210> SEQ ID NO 57
<211> LENGTH: 17
<212> TYPE: PRT
<213> ORGANISM: Artificial Sequence
<220> FEATURE:
<223> OTHER INFORMATION: Synthetic

<400> SEQUENCE: 57

Gly Gly Gly Gly Ser Gly Gly Gly Ser Gly Gly Gly Gly Ser Ala
1               5                   10                  15

Ser

<210> SEQ ID NO 58
<211> LENGTH: 18
<212> TYPE: PRT
<213> ORGANISM: Artificial Sequence
<220> FEATURE:
<223> OTHER INFORMATION: Synthetic

<400> SEQUENCE: 58

Gly Ser Thr Ser Gly Ser Gly Lys Ser Ser Glu Gly Ser Gly Ser Thr
1               5                   10                  15

Lys Gly

<210> SEQ ID NO 59
<211> LENGTH: 18
<212> TYPE: PRT
<213> ORGANISM: Artificial Sequence
<220> FEATURE:
<223> OTHER INFORMATION: Synthetic

<400> SEQUENCE: 59

Gly Ser Thr Ser Gly Ser Gly Lys Pro Gly Ser Gly Glu Gly Ser Thr
1               5                   10                  15

Lys Gly

<210> SEQ ID NO 60
<211> LENGTH: 20
<212> TYPE: PRT
<213> ORGANISM: Artificial Sequence
<220> FEATURE:
<223> OTHER INFORMATION: Synthetic

<400> SEQUENCE: 60

Gly Gly Gly Gly Ser Gly Gly Gly Gly Ser Gly Gly Gly Gly Ser Gly
1               5                   10                  15

Gly Gly Gly Ser
            20

<210> SEQ ID NO 61
<211> LENGTH: 19
<212> TYPE: PRT
<213> ORGANISM: Artificial Sequence
<220> FEATURE:
<223> OTHER INFORMATION: Synthetic

<400> SEQUENCE: 61
```

Asp Lys Thr His Thr Ser Pro Pro Ser Gly Gly Gly Ser Gly Gly
1               5                   10                  15

Gly Gly Ser

<210> SEQ ID NO 62
<211> LENGTH: 12
<212> TYPE: PRT
<213> ORGANISM: Artificial Sequence
<220> FEATURE:
<223> OTHER INFORMATION: Synthetic

<400> SEQUENCE: 62

Ala Pro Ala Pro Ala Pro Ala Pro Ala Pro Ala Pro
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic

<400> SEQUENCE: 63

Ala Glu Ala Ala Ala Lys Glu Ala Ala Ala Lys Ala
1               5                   10

<210> SEQ ID NO 64
<211> LENGTH: 32
<212> TYPE: PRT
<213> ORGANISM: Artificial Sequence
<220> FEATURE:
<223> OTHER INFORMATION: Synthetic

<400> SEQUENCE: 64

Gly Gly Gly Gly Ser Gly Gly Gly Ser Gly Gly Gly Ser Gly
1               5                   10                  15

Gly Gly Ser Gly Gly Gly Ser Gly Gly Gly Ser Ala Ser
        20                  25                  30

<210> SEQ ID NO 65
<211> LENGTH: 37
<212> TYPE: PRT
<213> ORGANISM: Artificial Sequence
<220> FEATURE:
<223> OTHER INFORMATION: Synthetic

<400> SEQUENCE: 65

Ala Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
        20                  25                  30

Gly Gly Ser Ala Ser
        35

<210> SEQ ID NO 66
<211> LENGTH: 7
<212> TYPE: PRT
<213> ORGANISM: Artificial Sequence
<220> FEATURE:
<223> OTHER INFORMATION: Synthetic

<400> SEQUENCE: 66

Asp Lys Thr His Thr Cys Pro
1               5

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Glu Pro Lys Ser Ser Asp Lys Thr His Thr Cys Pro
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic

<400> SEQUENCE: 68

Gly Gly Gly Gly Ser Asp Lys Thr His Thr Cys Pro
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic

<400> SEQUENCE: 69

Arg Gly Arg Gly Ser Asp Lys Thr His Thr Cys Pro
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic

<400> SEQUENCE: 70

Asp Gly Asp Gly Ser Asp Lys Thr His Thr Cys Pro
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetic

<400> SEQUENCE: 71

Gly Arg Gly Arg Gly Ser Asp Lys Thr His Thr Cys Pro
1               5                   10

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Ala Ser Thr Arg Gly Arg Gly Ser Asp Lys Thr His Thr Cys Pro
1               5                   10                  15

```
<210> SEQ ID NO 73
<211> LENGTH: 15
<212> TYPE: PRT
<213> ORGANISM: Artificial Sequence
<220> FEATURE:
<223> OTHER INFORMATION: Synthetic

<400> SEQUENCE: 73

Gly Gln Pro Asp Gly Asp Ala Ser Asp Lys Thr His Thr Cys Pro
1               5                   10                  15

<210> SEQ ID NO 74
<211> LENGTH: 5
<212> TYPE: PRT
<213> ORGANISM: Artificial Sequence
<220> FEATURE:
<223> OTHER INFORMATION: Synthetic

<400> SEQUENCE: 74

Asp Lys Thr His Thr
1               5

<210> SEQ ID NO 75
<211> LENGTH: 107
<212> TYPE: PRT
<213> ORGANISM: Artificial Sequence
<220> FEATURE:
<223> OTHER INFORMATION: Synthetic

<400> SEQUENCE: 75

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 76
<211> LENGTH: 106
<212> TYPE: PRT
<213> ORGANISM: Artificial Sequence
<220> FEATURE:
<223> OTHER INFORMATION: Synthetic

<400> SEQUENCE: 76

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60
```

```
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 77
<211> LENGTH: 106
<212> TYPE: PRT
<213> ORGANISM: Artificial Sequence
<220> FEATURE:
<223> OTHER INFORMATION: Synthetic

<400> SEQUENCE: 77

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 78
<211> LENGTH: 106
<212> TYPE: PRT
<213> ORGANISM: Artificial Sequence
<220> FEATURE:
<223> OTHER INFORMATION: Synthetic

<400> SEQUENCE: 78

```
Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
             35                  40                  45

Ala Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 79
<211> LENGTH: 106
<212> TYPE: PRT
<213> ORGANISM: Artificial Sequence
<220> FEATURE:
<223> OTHER INFORMATION: Synthetic

<400> SEQUENCE: 79

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 80
<211> LENGTH: 106
<212> TYPE: PRT
<213> ORGANISM: Artificial Sequence
<220> FEATURE:
<223> OTHER INFORMATION: Synthetic

<400> SEQUENCE: 80

Gly Gln Pro Lys Ala Ala Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Ser Ser Pro
        35                  40                  45

Ala Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 81
<211> LENGTH: 105
<212> TYPE: PRT
<213> ORGANISM: Artificial Sequence
<220> FEATURE:
<223> OTHER INFORMATION: Synthetic

<400> SEQUENCE: 81

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

```
Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 82
<211> LENGTH: 103
<212> TYPE: PRT
<213> ORGANISM: Artificial Sequence
<220> FEATURE:
<223> OTHER INFORMATION: Synthetic

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 83
<211> LENGTH: 113
<212> TYPE: PRT
<213> ORGANISM: Artificial Sequence
<220> FEATURE:
<223> OTHER INFORMATION: Synthetic

<400> SEQUENCE: 83

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 84
<211> LENGTH: 113
<212> TYPE: PRT
<213> ORGANISM: Artificial Sequence
<220> FEATURE:
<223> OTHER INFORMATION: Synthetic

<400> SEQUENCE: 84
```

-continued

```
Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Gly Ala Pro Ile Glu Lys Thr Ile Ser Lys Ala
            100                 105                 110

Lys
```

<210> SEQ ID NO 85
<211> LENGTH: 113
<212> TYPE: PRT
<213> ORGANISM: Artificial Sequence
<220> FEATURE:
<223> OTHER INFORMATION: Synthetic

<400> SEQUENCE: 85

```
Pro Cys Pro Ala Pro Glu Phe Glu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Ser Ile Glu Lys Thr Ile Ser Lys Ala
            100                 105                 110

Lys
```

<210> SEQ ID NO 86
<211> LENGTH: 113
<212> TYPE: PRT
<213> ORGANISM: Artificial Sequence
<220> FEATURE:
<223> OTHER INFORMATION: Synthetic

<400> SEQUENCE: 86

```
Pro Cys Pro Ala Pro Glu Phe Glu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60
```

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Gly Ile Glu Lys Thr Ile Ser Lys Ala
            100                 105                 110

Lys

<210> SEQ ID NO 87
<211> LENGTH: 113
<212> TYPE: PRT
<213> ORGANISM: Artificial Sequence
<220> FEATURE:
<223> OTHER INFORMATION: Synthetic

<400> SEQUENCE: 87

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Ala Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys

<210> SEQ ID NO 88
<211> LENGTH: 113
<212> TYPE: PRT
<213> ORGANISM: Artificial Sequence
<220> FEATURE:
<223> OTHER INFORMATION: Synthetic

<400> SEQUENCE: 88

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Gly Ser Thr Tyr Arg Val Val Ser Val Leu Thr
65                  70                  75                  80

Val Leu His Gln Asp Trp Leu Asn Gly Lys Glu Tyr Lys Cys Lys Val
            85                  90                  95

Ser Asn Lys Ala Leu Pro Ala Pro Ile Glu Lys Thr Ile Ser Lys Ala
            100                 105                 110

Lys

<210> SEQ ID NO 89

```
<211> LENGTH: 113
<212> TYPE: PRT
<213> ORGANISM: Artificial Sequence
<220> FEATURE:
<223> OTHER INFORMATION: Synthetic

<400> SEQUENCE: 89

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Gln Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 90
<211> LENGTH: 113
<212> TYPE: PRT
<213> ORGANISM: Artificial Sequence
<220> FEATURE:
<223> OTHER INFORMATION: Synthetic

<400> SEQUENCE: 90

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys

<210> SEQ ID NO 91
<211> LENGTH: 113
<212> TYPE: PRT
<213> ORGANISM: Artificial Sequence
<220> FEATURE:
<223> OTHER INFORMATION: Synthetic

<400> SEQUENCE: 91

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30
```

Thr Cys Val Val Asp Val Ser His Glu Asp Pro Glu Val Lys Phe
         35                  40                  45

Asn Trp Tyr Val Asp Gly Val Glu Val His Asn Ala Lys Thr Lys Pro
 50                  55                  60

Arg Glu Glu Gln Tyr Gln Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Ala Leu Pro Ala Pro Ile Glu Lys Thr Ile Ser Lys Ala
                100                 105                 110

Lys

<210> SEQ ID NO 92
<211> LENGTH: 113
<212> TYPE: PRT
<213> ORGANISM: Artificial Sequence
<220> FEATURE:
<223> OTHER INFORMATION: Synthetic

<400> SEQUENCE: 92

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Ala Val Ser His Glu Asp Pro Glu Val Lys Phe
         35                  40                  45

Asn Trp Tyr Val Asp Gly Val Glu Val His Asn Ala Lys Thr Lys Pro
 50                  55                  60

Arg Glu Glu Gln Tyr Ala Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Gln Leu Pro Ala Pro Ile Glu Lys Thr Ile Ser Lys Ala
                100                 105                 110

Lys

<210> SEQ ID NO 93
<211> LENGTH: 113
<212> TYPE: PRT
<213> ORGANISM: Artificial Sequence
<220> FEATURE:
<223> OTHER INFORMATION: Synthetic

<400> SEQUENCE: 93

Pro Cys Pro Ala Pro Glu Leu Leu Gly Gly Pro Ser Val Phe Leu Phe
 1               5                  10                  15

Pro Pro Lys Pro Lys Asp Thr Leu Met Ile Ser Arg Thr Pro Glu Val
                 20                  25                  30

Thr Cys Val Val Val Ala Val Ser His Glu Asp Pro Glu Val Lys Phe
         35                  40                  45

Asn Trp Tyr Val Asp Gly Val Glu Val His Asn Ala Lys Thr Lys Pro
 50                  55                  60

Arg Glu Glu Gln Tyr Gln Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Gln Leu Pro Ala Pro Ile Glu Lys Thr Ile Ser Lys Ala
             100                 105                 110
Lys

<210> SEQ ID NO 94
<211> LENGTH: 112
<212> TYPE: PRT
<213> ORGANISM: Artificial Sequence
<220> FEATURE:
<223> OTHER INFORMATION: Synthetic

<400> SEQUENCE: 94

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 95
<211> LENGTH: 112
<212> TYPE: PRT
<213> ORGANISM: Artificial Sequence
<220> FEATURE:
<223> OTHER INFORMATION: Synthetic

<400> SEQUENCE: 95

Pro Ser Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 96
<211> LENGTH: 112
<212> TYPE: PRT
<213> ORGANISM: Artificial Sequence
<220> FEATURE:
<223> OTHER INFORMATION: Synthetic

<400> SEQUENCE: 96

Pro Ala Pro Ala Pro Pro Val Ala Gly Pro Ser Val Phe Leu Phe Pro
1               5                   10                  15

```
Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
                100                 105                 110
```

<210> SEQ ID NO 97
<211> LENGTH: 112
<212> TYPE: PRT
<213> ORGANISM: Artificial Sequence
<220> FEATURE:
<223> OTHER INFORMATION: Synthetic

<400> SEQUENCE: 97

```
Pro Gly Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
                100                 105                 110
```

<210> SEQ ID NO 98
<211> LENGTH: 112
<212> TYPE: PRT
<213> ORGANISM: Artificial Sequence
<220> FEATURE:
<223> OTHER INFORMATION: Synthetic

<400> SEQUENCE: 98

```
Pro Pro Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
```

<210> SEQ ID NO 99
<211> LENGTH: 112
<212> TYPE: PRT
<213> ORGANISM: Artificial Sequence
<220> FEATURE:
<223> OTHER INFORMATION: Synthetic

<400> SEQUENCE: 99

```
Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Ala Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110
```

<210> SEQ ID NO 100
<211> LENGTH: 112
<212> TYPE: PRT
<213> ORGANISM: Artificial Sequence
<220> FEATURE:
<223> OTHER INFORMATION: Synthetic

<400> SEQUENCE: 100

```
Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Ala Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110
```

<210> SEQ ID NO 101
<211> LENGTH: 112
<212> TYPE: PRT
<213> ORGANISM: Artificial Sequence
<220> FEATURE:
<223> OTHER INFORMATION: Synthetic

<400> SEQUENCE: 101

```
Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30
```

```
Cys Val Val Ala Val Ser His Glu Ala Pro Glu Val Gln Phe Asn
        35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 102
<211> LENGTH: 107
<212> TYPE: PRT
<213> ORGANISM: Artificial Sequence
<220> FEATURE:
<223> OTHER INFORMATION: Synthetic

<400> SEQUENCE: 102

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 103
<211> LENGTH: 107
<212> TYPE: PRT
<213> ORGANISM: Artificial Sequence
<220> FEATURE:
<223> OTHER INFORMATION: Synthetic

<400> SEQUENCE: 103

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

```
<210> SEQ ID NO 104
<211> LENGTH: 107
<212> TYPE: PRT
<213> ORGANISM: Artificial Sequence
<220> FEATURE:
<223> OTHER INFORMATION: Synthetic

<400> SEQUENCE: 104

Gly Gln Pro Arg Glu Pro Gln Val Tyr Thr Leu Pro Pro Ser Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 105
<211> LENGTH: 107
<212> TYPE: PRT
<213> ORGANISM: Artificial Sequence
<220> FEATURE:
<223> OTHER INFORMATION: Synthetic

<400> SEQUENCE: 105

Gly Gln Pro Arg Glu Pro Gln Val Tyr Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45
```

Asn Asn Tyr Lys Thr Thr Pro Pro Val Leu Asp Ser Asp Gly Ser Phe
            50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 107
<211> LENGTH: 107
<212> TYPE: PRT
<213> ORGANISM: Artificial Sequence
<220> FEATURE:
<223> OTHER INFORMATION: Synthetic

<400> SEQUENCE: 107

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 108
<211> LENGTH: 107
<212> TYPE: PRT
<213> ORGANISM: Artificial Sequence
<220> FEATURE:
<223> OTHER INFORMATION: Synthetic

<400> SEQUENCE: 108

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 109
<211> LENGTH: 107
<212> TYPE: PRT

```
<213> ORGANISM: Artificial Sequence
<220> FEATURE:
<223> OTHER INFORMATION: Synthetic

<400> SEQUENCE: 109

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 110
<211> LENGTH: 107
<212> TYPE: PRT
<213> ORGANISM: Artificial Sequence
<220> FEATURE:
<223> OTHER INFORMATION: Synthetic

<400> SEQUENCE: 110

Gly Gln Pro Arg Glu Pro Gln Val Tyr Thr Leu Pro Pro Ser Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Asp Thr Thr Pro Pro Val Leu Asp Ser Asp Gly Ser Phe
    50                  55                  60

Phe Leu Tyr Ser Asp Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 111
<211> LENGTH: 107
<212> TYPE: PRT
<213> ORGANISM: Artificial Sequence
<220> FEATURE:
<223> OTHER INFORMATION: Synthetic

<400> SEQUENCE: 111

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Arg Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Lys Ser Asp Gly Ser Phe
    50                  55                  60
```

```
Phe Leu Ala Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 112
<211> LENGTH: 107
<212> TYPE: PRT
<213> ORGANISM: Artificial Sequence
<220> FEATURE:
<223> OTHER INFORMATION: Synthetic

<400> SEQUENCE: 112

Gly Gln Pro Arg Glu Pro Gln Val Tyr Thr Leu Pro Pro Ser Arg Asp
  1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Asp Thr Thr Pro Pro Val Leu Asp Ser Asp Gly Ser Phe
         50                  55                  60

Phe Leu Tyr Ser Asp Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Synthetic

<400> SEQUENCE: 113

Gly Gln Pro Arg Glu Pro Gln Val Tyr Thr Leu Pro Pro Ser Arg Lys
  1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Lys Ser Asp Gly Ser Phe
         50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 114
<211> LENGTH: 107
<212> TYPE: PRT
<213> ORGANISM: Artificial Sequence
<220> FEATURE:
<223> OTHER INFORMATION: Synthetic
```

<400> SEQUENCE: 114

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 115
<211> LENGTH: 107
<212> TYPE: PRT
<213> ORGANISM: Artificial Sequence
<220> FEATURE:
<223> OTHER INFORMATION: Synthetic

<400> SEQUENCE: 115

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 116
<211> LENGTH: 258
<212> TYPE: PRT
<213> ORGANISM: Artificial Sequence
<220> FEATURE:
<223> OTHER INFORMATION: Synthetic

<400> SEQUENCE: 116

Val Pro Arg Trp Arg Gln Gln Trp Ser Gly Pro Gly Thr Thr Lys Arg
1               5                   10                  15

Phe Pro Glu Thr Val Leu Ala Arg Cys Val Lys Tyr Thr Glu Ile His
            20                  25                  30

Pro Glu Met Arg His Val Asp Cys Gln Ser Val Trp Asp Ala Phe Lys
        35                  40                  45

Gly Ala Phe Ile Ser Lys His Pro Cys Asn Ile Thr Glu Glu Asp Tyr
    50                  55                  60

Gln Pro Leu Met Lys Leu Gly Thr Gln Thr Val Pro Cys Asn Lys Ile
65                  70                  75                  80

```
Leu Leu Trp Ser Arg Ile Lys Asp Leu Ala His Gln Phe Thr Gln Val
                85                  90                  95

Gln Arg Asp Met Phe Thr Leu Glu Asp Thr Leu Leu Gly Tyr Leu Ala
            100                 105                 110

Asp Asp Leu Thr Trp Cys Gly Glu Phe Asn Thr Ser Lys Ile Asn Tyr
            115                 120                 125

Gln Ser Cys Pro Asp Trp Arg Lys Asp Cys Ser Asn Asn Pro Val Ser
        130                 135                 140

Val Phe Trp Lys Thr Val Ser Arg Arg Phe Ala Glu Ala Ala Cys Asp
145                 150                 155                 160

Val Val His Val Met Leu Asn Gly Ser Arg Ser Lys Ile Phe Asp Lys
                165                 170                 175

Asn Ser Thr Phe Gly Ser Val Glu Val His Asn Leu Gln Pro Glu Lys
            180                 185                 190

Val Gln Thr Leu Glu Ala Trp Val Ile His Gly Gly Arg Glu Asp Ser
        195                 200                 205

Arg Asp Leu Cys Gln Asp Pro Thr Ile Lys Glu Leu Glu Ser Ile Ile
        210                 215                 220

Ser Lys Arg Asn Ile Gln Phe Ser Cys Lys Asn Ile Tyr Arg Pro Asp
225                 230                 235                 240

Lys Phe Leu Gln Cys Val Lys Asn Pro Glu Asp Ser Ser Cys Thr Ser
                245                 250                 255

Glu Ile

<210> SEQ ID NO 117
<211> LENGTH: 54
<212> TYPE: PRT
<213> ORGANISM: Artificial Sequence
<220> FEATURE:
<223> OTHER INFORMATION: Synthetic

<400> SEQUENCE: 117

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 118
<211> LENGTH: 220
<212> TYPE: PRT
<213> ORGANISM: Artificial Sequence
<220> FEATURE:
<223> OTHER INFORMATION: Synthetic

<400> SEQUENCE: 118

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60
```

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
            85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg
        210                 215                 220

<210> SEQ ID NO 119
<211> LENGTH: 204
<212> TYPE: PRT
<213> ORGANISM: Artificial Sequence
<220> FEATURE:
<223> OTHER INFORMATION: Synthetic

<400> SEQUENCE: 119

Ser Gly Pro Val Lys Glu Leu Val Gly Ser Val Gly Gly Ala Val Thr
1               5                   10                  15

Phe Pro Leu Lys Ser Lys Val Lys Gln Val Asp Ser Ile Val Trp Thr
            20                  25                  30

Phe Asn Thr Thr Pro Leu Val Thr Ile Gln Pro Glu Gly Gly Thr Ile
            35                  40                  45

Ile Val Thr Gln Asn Arg Asn Arg Glu Arg Val Asp Phe Pro Asp Gly
50                  55                  60

Gly Tyr Ser Leu Lys Leu Ser Lys Leu Lys Asn Asp Ser Gly Ile
65                  70                  75                  80

Tyr Tyr Val Gly Ile Tyr Ser Ser Leu Gln Gln Pro Ser Thr Gln
            85                  90                  95

Glu Tyr Val Leu His Val Tyr Glu His Leu Ser Lys Pro Lys Val Thr
            100                 105                 110

Met Gly Leu Gln Ser Asn Lys Asn Gly Thr Cys Val Thr Asn Leu Thr
            115                 120                 125

Cys Cys Met Glu His Gly Glu Glu Asp Val Ile Tyr Thr Trp Lys Ala
130                 135                 140

Leu Gly Gln Ala Ala Asn Glu Ser His Asn Gly Ser Ile Leu Pro Ile
145                 150                 155                 160

Ser Trp Arg Trp Gly Glu Ser Asp Met Thr Phe Ile Cys Val Ala Arg
            165                 170                 175

Asn Pro Val Ser Arg Asn Phe Ser Ser Pro Ile Leu Ala Arg Lys Leu
            180                 185                 190

Cys Glu Gly Ala Ala Asp Asp Pro Asp Ser Ser Met
            195                 200

-continued

<210> SEQ ID NO 120
<211> LENGTH: 651
<212> TYPE: PRT
<213> ORGANISM: Artificial Sequence
<220> FEATURE:
<223> OTHER INFORMATION: Synthetic

<400> SEQUENCE: 120

```
Lys Leu Thr Ile Glu Ser Thr Pro Phe Asn Val Ala Glu Gly Lys Glu
1               5                   10                  15

Val Leu Leu Val His Asn Leu Pro Gln His Leu Phe Gly Tyr Ser
            20                  25                  30

Trp Tyr Lys Gly Glu Arg Val Asp Gly Asn Arg Gln Ile Ile Gly Tyr
                35                  40                  45

Val Ile Gly Thr Gln Gln Ala Thr Pro Gly Pro Ala Tyr Ser Gly Arg
    50                  55                      60

Glu Ile Ile Tyr Pro Asn Ala Ser Leu Leu Ile Gln Asn Ile Ile Gln
65                  70                  75                  80

Asn Asp Thr Gly Phe Tyr Thr Leu His Val Ile Lys Ser Asp Leu Val
                85                  90                  95

Asn Glu Glu Ala Thr Gly Gln Phe Arg Val Tyr Pro Glu Leu Pro Lys
            100                 105                 110

Pro Ser Ile Ser Ser Asn Asn Ser Lys Pro Val Glu Asp Lys Asp Ala
        115                 120                 125

Val Ala Phe Thr Cys Glu Pro Glu Thr Gln Asp Ala Thr Tyr Leu Trp
    130                 135                 140

Trp Val Asn Asn Gln Ser Leu Pro Val Ser Pro Arg Leu Gln Leu Ser
145                 150                 155                 160

Asn Gly Asn Arg Thr Leu Thr Leu Phe Asn Val Thr Arg Asn Asp Thr
                165                 170                 175

Ala Ser Tyr Lys Cys Glu Thr Gln Asn Pro Val Ser Ala Arg Arg Ser
            180                 185                 190

Asp Ser Val Ile Leu Asn Val Leu Tyr Gly Pro Asp Ala Pro Thr Ile
        195                 200                 205

Ser Pro Leu Asn Thr Ser Tyr Arg Ser Gly Glu Asn Leu Asn Leu Ser
    210                 215                 220

Cys His Ala Ala Ser Asn Pro Pro Ala Gln Tyr Ser Trp Phe Val Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys Gln Ala His Asn Ser Asp Thr
            260                 265                 270

Gly Leu Asn Arg Thr Thr Val Thr Thr Ile Thr Val Tyr Ala Glu Pro
        275                 280                 285

Pro Lys Pro Phe Ile Thr Ser Asn Asn Ser Asn Pro Val Glu Asp Glu
    290                 295                 300

Asp Ala Val Ala Leu Thr Cys Glu Pro Glu Ile Gln Asn Thr Thr Tyr
305                 310                 315                 320

Leu Trp Trp Val Asn Asn Gln Ser Leu Pro Val Ser Pro Arg Leu Gln
                325                 330                 335

Leu Ser Asn Asp Asn Arg Thr Leu Thr Leu Leu Ser Val Thr Arg Asn
            340                 345                 350

Asp Val Gly Pro Tyr Glu Cys Gly Ile Gln Asn Lys Leu Ser Val Asp
        355                 360                 365
```

His Ser Asp Pro Val Ile Leu Asn Val Leu Tyr Gly Pro Asp Pro
    370                 375                 380

Thr Ile Ser Pro Ser Tyr Thr Tyr Arg Pro Gly Val Asn Leu Ser
385                 390                 395                 400

Leu Ser Cys His Ala Ala Ser Asn Pro Pro Ala Gln Tyr Ser Trp Leu
            405                 410                 415

Ile Asp Gly Asn Ile Gln Gln His Thr Gln Glu Leu Phe Ile Ser Asn
            420                 425                 430

Ile Thr Glu Lys Asn Ser Gly Leu Tyr Thr Cys Gln Ala Asn Asn Ser
            435                 440                 445

Ala Ser Gly His Ser Arg Thr Thr Val Lys Thr Ile Thr Val Ser Ala
            450                 455                 460

Glu Leu Pro Lys Pro Ser Ile Ser Ser Asn Asn Ser Lys Pro Val Glu
465                 470                 475                 480

Asp Lys Asp Ala Val Ala Phe Thr Cys Glu Pro Glu Ala Gln Asn Thr
            485                 490                 495

Thr Tyr Leu Trp Trp Val Asn Gly Gln Ser Leu Pro Val Ser Pro Arg
            500                 505                 510

Leu Gln Leu Ser Asn Gly Asn Arg Thr Leu Thr Leu Phe Asn Val Thr
            515                 520                 525

Arg Asn Asp Ala Arg Ala Tyr Val Cys Gly Ile Gln Asn Ser Val Ser
530                 535                 540

Ala Asn Arg Ser Asp Pro Val Thr Leu Asp Val Leu Tyr Gly Pro Asp
545                 550                 555                 560

Thr Pro Ile Ile Ser Pro Pro Asp Ser Ser Tyr Leu Ser Gly Ala Asn
            565                 570                 575

Leu Asn Leu Ser Cys His Ser Ala Ser Asn Pro Ser Pro Gln Tyr Ser
            580                 585                 590

Trp Arg Ile Asn Gly Ile Pro Gln Gln His Thr Gln Val Leu Phe Ile
            595                 600                 605

Ala Lys Ile Thr Pro Asn Asn Asn Gly Thr Tyr Ala Cys Phe Val Ser
            610                 615                 620

Asn Leu Ala Thr Gly Arg Asn Asn Ser Ile Val Lys Ser Ile Thr Val
625                 630                 635                 640

Ser Ala Ser Gly Thr Ser Pro Gly Leu Ser Ala
            645                 650

<210> SEQ ID NO 121
<211> LENGTH: 104
<212> TYPE: PRT
<213> ORGANISM: Artificial Sequence
<220> FEATURE:
<223> OTHER INFORMATION: Synthetic

<400> SEQUENCE: 121

Asp Gly Asn Glu Glu Met Gly Gly Ile Thr Gln Thr Pro Tyr Lys Val
1               5                   10                  15

Ser Ile Ser Gly Thr Thr Val Ile Leu Thr Cys Pro Gln Tyr Pro Gly
            20                  25                  30

Ser Glu Ile Leu Trp Gln His Asn Asp Lys Asn Ile Gly Gly Asp Glu
        35                  40                  45

Asp Asp Lys Asn Ile Gly Ser Asp Glu Asp His Leu Ser Leu Lys Glu
    50                  55                  60

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
            85                  90                  95

Cys Glu Asn Cys Met Glu Met Asp
            100

<210> SEQ ID NO 122
<211> LENGTH: 112
<212> TYPE: PRT
<213> ORGANISM: Artificial Sequence
<220> FEATURE:
<223> OTHER INFORMATION: Synthetic

<400> SEQUENCE: 122

Pro Pro Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Thr Lys
            100                 105                 110

<210> SEQ ID NO 123
<211> LENGTH: 112
<212> TYPE: PRT
<213> ORGANISM: Artificial Sequence
<220> FEATURE:
<223> OTHER INFORMATION: Synthetic

<400> SEQUENCE: 123

Pro Pro Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Ala Lys
            100                 105                 110

<210> SEQ ID NO 124
<211> LENGTH: 112
<212> TYPE: PRT
<213> ORGANISM: Artificial Sequence
<220> FEATURE:
<223> OTHER INFORMATION: Synthetic

<400> SEQUENCE: 124

```
Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Ala Pro Glu Val Gln Phe Asn
            35                  40                  45

Trp Tyr Val Asp Gly Val Glu Val His Asn Ala Lys Thr Lys Pro Arg
        50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Ala Leu Pro Ala Pro Ile Glu Lys Thr Ile Ser Lys Thr Lys
                100                 105                 110

<210> SEQ ID NO 125
<211> LENGTH: 112
<212> TYPE: PRT
<213> ORGANISM: Artificial Sequence
<220> FEATURE:
<223> OTHER INFORMATION: Synthetic

<400> SEQUENCE: 125

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Ala Pro Glu Val Gln Phe Asn
            35                  40                  45

Trp Tyr Val Asp Gly Val Glu Val His Asn Ala Lys Thr Lys Pro Arg
        50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Ala Lys
                100                 105                 110

<210> SEQ ID NO 126
<211> LENGTH: 112
<212> TYPE: PRT
<213> ORGANISM: Artificial Sequence
<220> FEATURE:
<223> OTHER INFORMATION: Synthetic

<400> SEQUENCE: 126

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Ala Pro Glu Val Gln Phe Asn
            35                  40                  45

Trp Tyr Val Asp Gly Val Glu Val His Asn Ala Lys Thr Lys Pro Arg
        50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95
```

```
Asn Lys Ala Leu Pro Ala Pro Ile Glu Lys Thr Ile Ser Lys Ala Lys
            100                 105                 110
```

<210> SEQ ID NO 127
<211> LENGTH: 112
<212> TYPE: PRT
<213> ORGANISM: Artificial Sequence
<220> FEATURE:
<223> OTHER INFORMATION: Synthetic

<400> SEQUENCE: 127

```
Pro Pro Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Ala Val Ser His Glu Ala Pro Glu Val Gln Phe Asn
                35                  40                  45

Trp Tyr Val Asp Gly Val Glu Val His Asn Ala Lys Thr Lys Pro Arg
            50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110
```

<210> SEQ ID NO 128
<211> LENGTH: 112
<212> TYPE: PRT
<213> ORGANISM: Artificial Sequence
<220> FEATURE:
<223> OTHER INFORMATION: Synthetic

<400> SEQUENCE: 128

```
Pro Leu Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Asp Pro Glu Val Gln Phe Asn
                35                  40                  45

Trp Tyr Val Asp Gly Val Glu Val His Asn Ala Lys Thr Lys Pro Arg
            50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110
```

<210> SEQ ID NO 129
<211> LENGTH: 112
<212> TYPE: PRT
<213> ORGANISM: Artificial Sequence
<220> FEATURE:
<223> OTHER INFORMATION: Synthetic

<400> SEQUENCE: 129

```
Pro Phe Pro Ala Pro Pro Val Ala Gly Pro Ser Val Phe Leu Phe Pro
1               5                   10                  15
```

```
Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 130
<211> LENGTH: 112
<212> TYPE: PRT
<213> ORGANISM: Artificial Sequence
<220> FEATURE:
<223> OTHER INFORMATION: Synthetic

<400> SEQUENCE: 130

Pro Arg Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 131
<211> LENGTH: 112
<212> TYPE: PRT
<213> ORGANISM: Artificial Sequence
<220> FEATURE:
<223> OTHER INFORMATION: Synthetic

<400> SEQUENCE: 131

Pro Val Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110
```

<210> SEQ ID NO 132
<211> LENGTH: 112
<212> TYPE: PRT
<213> ORGANISM: Artificial Sequence
<220> FEATURE:
<223> OTHER INFORMATION: Synthetic

<400> SEQUENCE: 132

Pro Gln Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 133
<211> LENGTH: 112
<212> TYPE: PRT
<213> ORGANISM: Artificial Sequence
<220> FEATURE:
<223> OTHER INFORMATION: Synthetic

<400> SEQUENCE: 133

Pro Lys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 134
<211> LENGTH: 112
<212> TYPE: PRT
<213> ORGANISM: Artificial Sequence
<220> FEATURE:
<223> OTHER INFORMATION: Synthetic

<400> SEQUENCE: 134

Pro Asp Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

```
Cys Val Val Asp Val Ser His Glu Asp Pro Glu Val Gln Phe Asn
         35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
            100                 105                 110

<210> SEQ ID NO 135
<211> LENGTH: 112
<212> TYPE: PRT
<213> ORGANISM: Artificial Sequence
<220> FEATURE:
<223> OTHER INFORMATION: Synthetic

<400> SEQUENCE: 135

Pro Ile Pro Ala Pro Pro Val Ala Gly Pro Ser Val Phe Leu Phe Pro
 1               5                  10                  15

Pro Lys Pro Lys Asp Thr Leu Met Ile Ser Arg Thr Pro Glu Val Thr
             20                  25                  30

Cys Val Val Val Asp Val Ser His Glu Asp Pro Glu Val Gln Phe Asn
         35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
            100                 105                 110

<210> SEQ ID NO 136
<211> LENGTH: 112
<212> TYPE: PRT
<213> ORGANISM: Artificial Sequence
<220> FEATURE:
<223> OTHER INFORMATION: Synthetic

<400> SEQUENCE: 136

Pro Tyr Pro Ala Pro Pro Val Ala Gly Pro Ser Val Phe Leu Phe Pro
 1               5                  10                  15

Pro Lys Pro Lys Asp Thr Leu Met Ile Ser Arg Thr Pro Glu Val Thr
             20                  25                  30

Cys Val Val Val Asp Val Ser His Glu Asp Pro Glu Val Gln Phe Asn
         35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
            100                 105                 110

<210> SEQ ID NO 137
```

<211> LENGTH: 112
<212> TYPE: PRT
<213> ORGANISM: Artificial Sequence
<220> FEATURE:
<223> OTHER INFORMATION: Synthetic

<400> SEQUENCE: 137

Pro Asn Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 138
<211> LENGTH: 112
<212> TYPE: PRT
<213> ORGANISM: Artificial Sequence
<220> FEATURE:
<223> OTHER INFORMATION: Synthetic

<400> SEQUENCE: 138

Pro Met Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 139
<211> LENGTH: 112
<212> TYPE: PRT
<213> ORGANISM: Artificial Sequence
<220> FEATURE:
<223> OTHER INFORMATION: Synthetic

<400> SEQUENCE: 139

Pro Thr Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

```
Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 140
<211> LENGTH: 112
<212> TYPE: PRT
<213> ORGANISM: Artificial Sequence
<220> FEATURE:
<223> OTHER INFORMATION: Synthetic

<400> SEQUENCE: 140

Pro His Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Asp Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 141
<211> LENGTH: 112
<212> TYPE: PRT
<213> ORGANISM: Artificial Sequence
<220> FEATURE:
<223> OTHER INFORMATION: Synthetic

<400> SEQUENCE: 141

Pro Glu Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Asp Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 142
<211> LENGTH: 112
<212> TYPE: PRT
<213> ORGANISM: Artificial Sequence
```

<220> FEATURE:
<223> OTHER INFORMATION: Synthetic

<400> SEQUENCE: 142

Pro Trp Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65              70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Synthetic

<400> SEQUENCE: 143

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Pro Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65              70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 144
<211> LENGTH: 112
<212> TYPE: PRT
<213> ORGANISM: Artificial Sequence
<220> FEATURE:
<223> OTHER INFORMATION: Synthetic

<400> SEQUENCE: 144

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Lys Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 145
<211> LENGTH: 112
<212> TYPE: PRT
<213> ORGANISM: Artificial Sequence
<220> FEATURE:
<223> OTHER INFORMATION: Synthetic

<400> SEQUENCE: 145

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Ser Val Ser His Glu Asp Pro Glu Val Gln Phe Asn
                35                  40                  45

Trp Tyr Val Asp Gly Val Glu Val His Asn Ala Lys Thr Lys Pro Arg
50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 146
<211> LENGTH: 112
<212> TYPE: PRT
<213> ORGANISM: Artificial Sequence
<220> FEATURE:
<223> OTHER INFORMATION: Synthetic

<400> SEQUENCE: 146

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Phe Val Ser His Glu Asp Pro Glu Val Gln Phe Asn
                35                  40                  45

Trp Tyr Val Asp Gly Val Glu Val His Asn Ala Lys Thr Lys Pro Arg
50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 147
<211> LENGTH: 112
<212> TYPE: PRT
<213> ORGANISM: Artificial Sequence
<220> FEATURE:
<223> OTHER INFORMATION: Synthetic

```
<400> SEQUENCE: 147

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Arg Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
            85                  90                  95

Asn Lys Gly Leu Pro Ala Pro Ile Glu Lys Thr Ile Ser Lys Thr Lys
            100                 105                 110

<210> SEQ ID NO 148
<211> LENGTH: 112
<212> TYPE: PRT
<213> ORGANISM: Artificial Sequence
<220> FEATURE:
<223> OTHER INFORMATION: Synthetic

<400> SEQUENCE: 148

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Leu Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
            85                  90                  95

Asn Lys Gly Leu Pro Ala Pro Ile Glu Lys Thr Ile Ser Lys Thr Lys
            100                 105                 110

<210> SEQ ID NO 149
<211> LENGTH: 112
<212> TYPE: PRT
<213> ORGANISM: Artificial Sequence
<220> FEATURE:
<223> OTHER INFORMATION: Synthetic

<400> SEQUENCE: 149

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Gly Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80
```

Val His Gln Asp Trp Leu Asn Gly Lys Glu Tyr Lys Cys Lys Val Ser
            85                  90                  95

Asn Lys Gly Leu Pro Ala Pro Ile Glu Lys Thr Ile Ser Lys Thr Lys
            100                 105                 110

<210> SEQ ID NO 150
<211> LENGTH: 112
<212> TYPE: PRT
<213> ORGANISM: Artificial Sequence
<220> FEATURE:
<223> OTHER INFORMATION: Synthetic

<400> SEQUENCE: 150

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Thr Val Ser His Glu Asp Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
            85                  90                  95

Asn Lys Gly Leu Pro Ala Pro Ile Glu Lys Thr Ile Ser Lys Thr Lys
            100                 105                 110

<210> SEQ ID NO 151
<211> LENGTH: 112
<212> TYPE: PRT
<213> ORGANISM: Artificial Sequence
<220> FEATURE:
<223> OTHER INFORMATION: Synthetic

<400> SEQUENCE: 151

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Tyr Val Ser His Glu Asp Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
            85                  90                  95

Asn Lys Gly Leu Pro Ala Pro Ile Glu Lys Thr Ile Ser Lys Thr Lys
            100                 105                 110

<210> SEQ ID NO 152
<211> LENGTH: 112
<212> TYPE: PRT
<213> ORGANISM: Artificial Sequence
<220> FEATURE:
<223> OTHER INFORMATION: Synthetic

<400> SEQUENCE: 152

Pro Cys Pro Ala Pro Pro Val Ala Gly Pro Ser Val Phe Leu Phe Pro

```
                 1               5                  10                 15
Pro Lys Pro Lys Asp Thr Leu Met Ile Ser Arg Thr Pro Glu Val Thr
                20                  25                 30

Cys Val Val Val Trp Val Ser His Glu Asp Pro Glu Val Gln Phe Asn
                35                  40                 45

Trp Tyr Val Asp Gly Val Glu Val His Asn Ala Lys Thr Lys Pro Arg
                50                  55                 60

Glu Glu Gln Phe Asn Ser Thr Phe Arg Val Val Ser Val Leu Thr Val
 65                 70                  75                 80

Val His Gln Asp Trp Leu Asn Gly Lys Glu Tyr Lys Cys Lys Val Ser
                85                  90                 95

Asn Lys Gly Leu Pro Ala Pro Ile Glu Lys Thr Ile Ser Lys Thr Lys
               100                 105                110
```

<210> SEQ ID NO 153
<211> LENGTH: 112
<212> TYPE: PRT
<213> ORGANISM: Artificial Sequence
<220> FEATURE:
<223> OTHER INFORMATION: Synthetic

<400> SEQUENCE: 153

```
Pro Cys Pro Ala Pro Pro Val Ala Gly Pro Ser Val Phe Leu Phe Pro
 1               5                  10                 15

Pro Lys Pro Lys Asp Thr Leu Met Ile Ser Arg Thr Pro Glu Val Thr
                20                  25                 30

Cys Val Val Val His Val Ser His Glu Asp Pro Glu Val Gln Phe Asn
                35                  40                 45

Trp Tyr Val Asp Gly Val Glu Val His Asn Ala Lys Thr Lys Pro Arg
                50                  55                 60

Glu Glu Gln Phe Asn Ser Thr Phe Arg Val Val Ser Val Leu Thr Val
 65                 70                  75                 80

Val His Gln Asp Trp Leu Asn Gly Lys Glu Tyr Lys Cys Lys Val Ser
                85                  90                 95

Asn Lys Gly Leu Pro Ala Pro Ile Glu Lys Thr Ile Ser Lys Thr Lys
               100                 105                110
```

<210> SEQ ID NO 154
<211> LENGTH: 112
<212> TYPE: PRT
<213> ORGANISM: Artificial Sequence
<220> FEATURE:
<223> OTHER INFORMATION: Synthetic

<400> SEQUENCE: 154

```
Pro Cys Pro Ala Pro Pro Val Ala Gly Pro Ser Val Phe Leu Phe Pro
 1               5                  10                 15

Pro Lys Pro Lys Asp Thr Leu Met Ile Ser Arg Thr Pro Glu Val Thr
                20                  25                 30

Cys Val Val Val Val Ser His Glu Asp Pro Glu Val Gln Phe Asn
                35                  40                 45

Trp Tyr Val Asp Gly Val Glu Val His Asn Ala Lys Thr Lys Pro Arg
                50                  55                 60

Glu Glu Gln Phe Asn Ser Thr Phe Arg Val Val Ser Val Leu Thr Val
 65                 70                  75                 80

Val His Gln Asp Trp Leu Asn Gly Lys Glu Tyr Lys Cys Lys Val Ser
                85                  90                 95
```

Asn Lys Gly Leu Pro Ala Pro Ile Glu Lys Thr Ile Ser Lys Thr Lys
            100                 105                 110

<210> SEQ ID NO 155
<211> LENGTH: 112
<212> TYPE: PRT
<213> ORGANISM: Artificial Sequence
<220> FEATURE:
<223> OTHER INFORMATION: Synthetic

<400> SEQUENCE: 155

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Gln Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 156
<211> LENGTH: 112
<212> TYPE: PRT
<213> ORGANISM: Artificial Sequence
<220> FEATURE:
<223> OTHER INFORMATION: Synthetic

<400> SEQUENCE: 156

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Glu Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 157
<211> LENGTH: 112
<212> TYPE: PRT
<213> ORGANISM: Artificial Sequence
<220> FEATURE:
<223> OTHER INFORMATION: Synthetic

<400> SEQUENCE: 157

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr

```
                20                  25                  30
Cys Val Val Val Met Val Ser His Glu Asp Pro Glu Val Gln Phe Asn
             35                  40                  45

Trp Tyr Val Asp Gly Val Glu Val His Asn Ala Lys Thr Lys Pro Arg
         50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110
```

<210> SEQ ID NO 158
<211> LENGTH: 112
<212> TYPE: PRT
<213> ORGANISM: Artificial Sequence
<220> FEATURE:
<223> OTHER INFORMATION: Synthetic

<400> SEQUENCE: 158

```
Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asn Val Ser His Glu Asp Pro Glu Val Gln Phe Asn
         35                     40                  45

Trp Tyr Val Asp Gly Val Glu Val His Asn Ala Lys Thr Lys Pro Arg
         50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
                100                 105                 110
```

<210> SEQ ID NO 159
<211> LENGTH: 112
<212> TYPE: PRT
<213> ORGANISM: Artificial Sequence
<220> FEATURE:
<223> OTHER INFORMATION: Synthetic

<400> SEQUENCE: 159

```
Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Ile Val Ser His Glu Asp Pro Glu Val Gln Phe Asn
         35                  40                  45

Trp Tyr Val Asp Gly Val Glu Val His Asn Ala Lys Thr Lys Pro Arg
         50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
                100                 105                 110
```

<210> SEQ ID NO 160
<211> LENGTH: 112
<212> TYPE: PRT
<213> ORGANISM: Artificial Sequence
<220> FEATURE:
<223> OTHER INFORMATION: Synthetic

<400> SEQUENCE: 160

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Leu Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 161
<211> LENGTH: 112
<212> TYPE: PRT
<213> ORGANISM: Artificial Sequence
<220> FEATURE:
<223> OTHER INFORMATION: Synthetic

<400> SEQUENCE: 161

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Arg Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 162
<211> LENGTH: 112
<212> TYPE: PRT
<213> ORGANISM: Artificial Sequence
<220> FEATURE:
<223> OTHER INFORMATION: Synthetic

<400> SEQUENCE: 162

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Pro Pro Glu Val Gln Phe Asn

```
                35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 163
<211> LENGTH: 112
<212> TYPE: PRT
<213> ORGANISM: Artificial Sequence
<220> FEATURE:
<223> OTHER INFORMATION: Synthetic

<400> SEQUENCE: 163

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Gly Pro Glu Val Gln Phe Asn
            35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 164
<211> LENGTH: 112
<212> TYPE: PRT
<213> ORGANISM: Artificial Sequence
<220> FEATURE:
<223> OTHER INFORMATION: Synthetic

<400> SEQUENCE: 164

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Val Pro Glu Val Gln Phe Asn
            35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 165
<211> LENGTH: 112
```

<212> TYPE: PRT
<213> ORGANISM: Artificial Sequence
<220> FEATURE:
<223> OTHER INFORMATION: Synthetic

<400> SEQUENCE: 165

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu His Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 166
<211> LENGTH: 112
<212> TYPE: PRT
<213> ORGANISM: Artificial Sequence
<220> FEATURE:
<223> OTHER INFORMATION: Synthetic

<400> SEQUENCE: 166

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Tyr Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 167
<211> LENGTH: 112
<212> TYPE: PRT
<213> ORGANISM: Artificial Sequence
<220> FEATURE:
<223> OTHER INFORMATION: Synthetic

<400> SEQUENCE: 167

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Ile Pro Glu Val Gln Phe Asn
        35                  40                  45

Trp Tyr Val Asp Gly Val Glu Val His Asn Ala Lys Thr Lys Pro Arg

```
                50             55                  60
Glu Glu Gln Phe Asn Ser Thr Phe Arg Val Val Ser Val Leu Thr Val
 65              70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 168
<211> LENGTH: 112
<212> TYPE: PRT
<213> ORGANISM: Artificial Sequence
<220> FEATURE:
<223> OTHER INFORMATION: Synthetic

<400> SEQUENCE: 168

Pro Cys Pro Ala Pro Val Ala Gly Pro Ser Val Phe Leu Phe Pro
 1               5                  10                  15

Pro Lys Pro Lys Asp Thr Leu Met Ile Ser Arg Thr Pro Glu Val Thr
                20                  25                  30

Cys Val Val Val Asp Val Ser His Glu Glu Pro Glu Val Gln Phe Asn
                35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65              70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 169
<211> LENGTH: 112
<212> TYPE: PRT
<213> ORGANISM: Artificial Sequence
<220> FEATURE:
<223> OTHER INFORMATION: Synthetic

<400> SEQUENCE: 169

Pro Cys Pro Ala Pro Val Ala Gly Pro Ser Val Phe Leu Phe Pro
 1               5                  10                  15

Pro Lys Pro Lys Asp Thr Leu Met Ile Ser Arg Thr Pro Glu Val Thr
                20                  25                  30

Cys Val Val Val Asp Val Ser His Glu Phe Pro Glu Val Gln Phe Asn
                35                  40                  45

Trp Tyr Val Asp Gly Val Glu Val His Asn Ala Lys Thr Lys Pro Arg
 50                  55                  60

Glu Glu Gln Phe Asn Ser Thr Phe Arg Val Val Ser Val Leu Thr Val
 65              70                  75                  80

Val His Gln Asp Trp Leu Asn Gly Lys Glu Tyr Lys Cys Lys Val Ser
                 85                  90                  95

Asn Lys Gly Leu Pro Ala Pro Ile Glu Lys Thr Ile Ser Lys Thr Lys
                100                 105                 110

<210> SEQ ID NO 170
<211> LENGTH: 112
<212> TYPE: PRT
<213> ORGANISM: Artificial Sequence
<220> FEATURE:
```

<223> OTHER INFORMATION: Synthetic

<400> SEQUENCE: 170

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Lys Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 171
<211> LENGTH: 112
<212> TYPE: PRT
<213> ORGANISM: Artificial Sequence
<220> FEATURE:
<223> OTHER INFORMATION: Synthetic

<400> SEQUENCE: 171

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Trp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

<210> SEQ ID NO 172
<211> LENGTH: 112
<212> TYPE: PRT
<213> ORGANISM: Artificial Sequence
<220> FEATURE:
<223> OTHER INFORMATION: Synthetic

<400> SEQUENCE: 172

Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Ser Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val

```
                65                  70                  75                  80
Val His Gln Asp Trp Leu Asn Gly Lys Glu Tyr Lys Cys Lys Val Ser
                    85                  90                  95

Asn Lys Gly Leu Pro Ala Pro Ile Glu Lys Thr Ile Ser Lys Thr Lys
                100                 105                 110
```

<210> SEQ ID NO 173
<211> LENGTH: 112
<212> TYPE: PRT
<213> ORGANISM: Artificial Sequence
<220> FEATURE:
<223> OTHER INFORMATION: Synthetic

<400> SEQUENCE: 173

```
Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Thr Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                    85                  90                  95

Asn Lys Gly Leu Pro Ala Pro Ile Glu Lys Thr Ile Ser Lys Thr Lys
                100                 105                 110
```

<210> SEQ ID NO 174
<211> LENGTH: 112
<212> TYPE: PRT
<213> ORGANISM: Artificial Sequence
<220> FEATURE:
<223> OTHER INFORMATION: Synthetic

<400> SEQUENCE: 174

```
Pro Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20                  25                  30

Cys Val Val Val Asp Val Ser His Glu Gln Pro Glu Val Gln Phe Asn
            35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                    85                  90                  95

Asn Lys Gly Leu Pro Ala Pro Ile Glu Lys Thr Ile Ser Lys Thr Lys
                100                 105                 110
```

<210> SEQ ID NO 175
<211> LENGTH: 112
<212> TYPE: PRT
<213> ORGANISM: Artificial Sequence
<220> FEATURE:
<223> OTHER INFORMATION: Synthetic

<400> SEQUENCE: 175

```
Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20              25              30

Cys Val Val Asp Val Ser His Glu Met Pro Glu Val Gln Phe Asn
        35              40              45

Trp Tyr Val Asp Gly Val Glu Val His Asn Ala Lys Thr Lys Pro Arg
        50              55              60

Glu Glu Gln Phe Asn Ser Thr Phe Arg Val Val Ser Val Leu Thr Val
65                  70              75                  80

Val His Gln Asp Trp Leu Asn Gly Lys Glu Tyr Lys Cys Lys Val Ser
                85              90              95

Asn Lys Gly Leu Pro Ala Pro Ile Glu Lys Thr Ile Ser Lys Thr Lys
                100             105             110

<210> SEQ ID NO 176
<211> LENGTH: 112
<212> TYPE: PRT
<213> ORGANISM: Artificial Sequence
<220> FEATURE:
<223> OTHER INFORMATION: Synthetic

<400> SEQUENCE: 176

Pro Cys Pro Ala Pro Pro Val Ala Gly Pro Ser Val Phe Leu Phe Pro
1               5                   10                  15

Pro Lys Pro Lys Asp Thr Leu Met Ile Ser Arg Thr Pro Glu Val Thr
                20              25              30

Cys Val Val Asp Val Ser His Glu Asn Pro Glu Val Gln Phe Asn
        35              40              45

Trp Tyr Val Asp Gly Val Glu Val His Asn Ala Lys Thr Lys Pro Arg
        50              55              60

Glu Glu Gln Phe Asn Ser Thr Phe Arg Val Val Ser Val Leu Thr Val
65                  70              75                  80

Val His Gln Asp Trp Leu Asn Gly Lys Glu Tyr Lys Cys Lys Val Ser
                85              90              95

Asn Lys Gly Leu Pro Ala Pro Ile Glu Lys Thr Ile Ser Lys Thr Lys
                100             105             110
```